United States Patent
Marconi et al.

(10) Patent No.: US 8,808,705 B2
(45) Date of Patent: Aug. 19, 2014

(54) POLYVALENT CHIMERIC OSPC VACCINOGEN AND DIAGNOSTIC ANTIGEN

(75) Inventors: Richard T. Marconi, Midlothian, VA (US); Christopher Earnhart, Spotsylvania, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 13/879,848

(22) PCT Filed: Oct. 19, 2011

(86) PCT No.: PCT/US2011/056854
§ 371 (c)(1),
(2), (4) Date: Jun. 13, 2013

(87) PCT Pub. No.: WO2012/054580
PCT Pub. Date: Apr. 26, 2012

(65) Prior Publication Data
US 2013/0266606 A1 Oct. 10, 2013

Related U.S. Application Data

(60) Provisional application No. 61/394,877, filed on Oct. 20, 2010.

(51) Int. Cl.
*C07K 14/20* (2006.01)
*G01N 33/68* (2006.01)
*C07K 16/12* (2006.01)

(52) U.S. Cl.
CPC ............ *C07K 14/20* (2013.01); *G01N 33/6854* (2013.01); *C07K 16/1207* (2013.01)
USPC ...................... 424/190.1; 530/350; 530/387.9

(58) Field of Classification Search
None
See application file for complete search history.

(56) References Cited

U.S. PATENT DOCUMENTS

2007/0178117 A1   8/2007   Marconi
2009/0297560 A1   12/2009  Dattwyler

FOREIGN PATENT DOCUMENTS

WO   WO 0078966 A1 * 12/2000
WO   2009/135118 A2   11/2009

OTHER PUBLICATIONS

Earnhart et al., "Construction and analysis of variants of a polyvalent Lyme disease vaccine: approaches for improving the immune response to chimeric vaccinogens", Vaccine, Apr. 20, 2007, pp. 3419-3427, vol. 25, No. 17.
Earnhart et al., "Development of an OspC-based tetravalent, recombinant, chimeric vaccinogen that elicits bactericidal antibody against diverse Lyme disease spirochete strains", Vaccine, Jan. 5, 2007, pp. 466-480, vol. 25, No. 3.

* cited by examiner

*Primary Examiner* — Robert A Zeman
(74) *Attorney, Agent, or Firm* — Whitham, Curtis, Christofferson & Cook, P.C.

(57) ABSTRACT

A chimeric polyvalent recombinant protein for use as a vaccine and diagnostic for Lyme disease is provided. The chimeric protein comprises epitopes of the loop 5 region and/or the alpha helix 5 region of outer surface protein C (OspC) types. The OspC types may be associated with mammalian *Borrelia* infections.

6 Claims, 48 Drawing Sheets

| OspC type | Loop 5 epitope Sequences aa136-150 | # of Sequences | SEQ ID NO: | Alpha 5 epitope(s) Sequences (aa168-203) | # of Sequences | SEQ ID NO: |
|---|---|---|---|---|---|---|
| A | NKLKEKHTD-LGKEG--V | 53 | 1 | KGAEELGKLFESVEVLSKAAKEMLANSVKELTSPVV | 42 | 33 |
|   | ..........R..--. | 3 | 2 |  ..........................N....... | 1 | 34 |
|   | ........SF...--. | 1 | 3 |  |  |  |
| B | TKLKDNHAQLG-IQG--V | 24 | 4 | KGVEELEKLSGSLESLSKAAKEMLANSVKELTSPVV | 17 | 35 |
|   | ....Q..R...--. | 1 | 5 |  |  |  |
| C | KKLKEKHTDLG-KKD--A | 4 | 6 | KGAAELEKLFESVENLAKAAKEMLSNSVKELTSPVV | 3 | 36 |
| D | KKLSDNQAELG-IEN--A | 7 | 7 | KGAEELVKLSESVAGLLKAAQATLANSVKELTSPVV | 5 | 37 |
| E | NKLKSEHAVLG-LDN--L | 13 | 8 | KGAAELEKLFKAVENLSKAAQDTLKNAVKELTSPIV | 13 | 38 |
| F | NKLKNGNAQLG-LAA--A | 11 | 9 | KGAKELKDLSDSVESLVKAAQVMLTNSVKELTSPVV | 9 | 39 |
| G | KKLADSNADLGVAAG-NA | 5 | 10 | KGGKELKELSEAVKSLLKAAQAALANSVQELTSPVV | 3 | 40 |
| H | GKLKNEHASLG-KKD--A | 7 | 11 | KGAKELKDLSDSVESLVKAAKEMLTNSVKELTSPVV | 3 | 41 |
| I | AKLKGEHTDLG-KEG--V | 12 | 12 | KGADELEKLFESVKNLSKAAKEMLTNSVKELTSPVV | 9 | 42 |
| J | KKLKDSRAELG-KKD--A | 2 | 13 | KGAKELKELFEAVESLSKAAKEML | 3 | 43 |
|   | .........H....--. | 1 | 14 |  |  |  |
| K | KKLEGEHAQLG-IEN--V | 20 | 15 | KGAAELEKLFKAVENLAKAAKEMLANSVKELTSPIV | 12 | 44 |
|   | .N.......--T..... | 3 | 16 |  .........................P........ | 6 | 45 |
|   |  |  |  | .....A...................PQ........ | 3 | 46 |
| L | DKLKSENVALG-KQD--A | 7 | 17 | KGAKELKELSESVETILKAAKEMLANSVKELTSPVV | 10 | 47 |
|   | ..........A...--. | 3 | 18 |  |  |  |
| M | DKLKSSHAELG-IANGAA | 5 | 19 | KGAQELEKLFESVKNLSKAAQETLNNSVKELTSPVV | 4 | 48 |
| N | KKLQSSHAQLG-VAGGAT | 8 | 20 | KGAEELEKLFKSVESLAKAAQDALANSVNELTSPVV | 7 | 49 |
|   | ...KD..QE....N..A | 2 | 21 |  .....E.....A......S........M.T..K.. | 2 | 50 |
|   |  |  |  | ....................G..E.......KEM. | 1 | 51 |
| O | TKLKSSNAQLN-QAN--A | 3 | 22 | KGAEELVKLAESVAGLFKVAQEMLNNSVKELTSPVV | 3 | 52 |
| P | NKLKNSHAELGVAGNGAT | 6 | 23 | KGAKELKELFESVESLAKAAKESLTNSVKELTSPVV | 3 | 53 |
|   | ..V.............. | 1 | 24 |  ....................A.S............ | 3 | 54 |
|   | .....N........... | 1 | 25 |  ...................L..Q.A.......T.. | 1 | 55 |
| Q | DKLKNEHASLG-KKD--A | 4 | 26 | KGADELIKLSGSLESLSKAAQAILANSVKELTSPVV | 1 | 56 |

*Figure 4A*

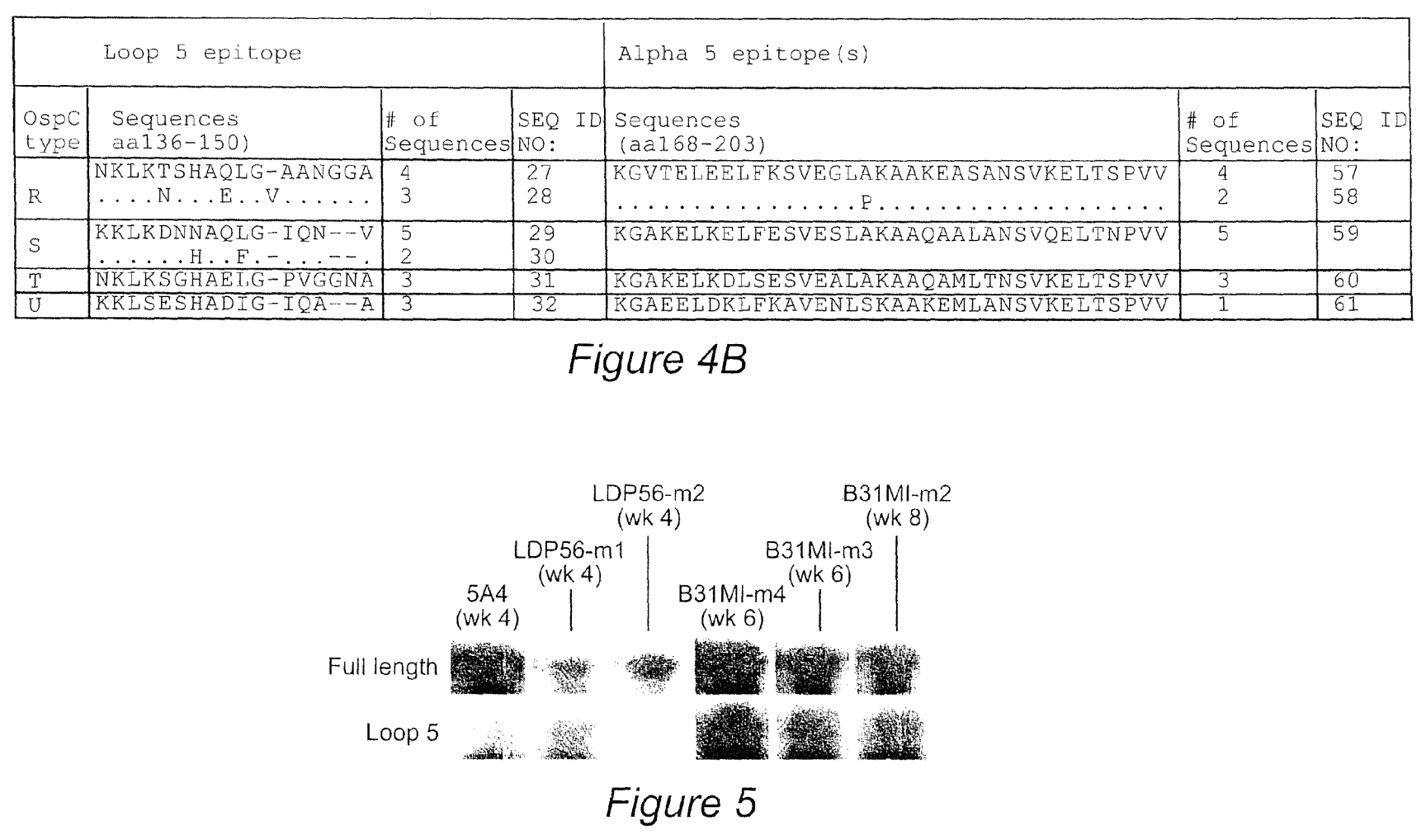

| OspC type | Loop 5 epitope Sequences aa136-150 | SEQ ID NO: | # of Sequences | Alpha Type A OspC loop 5 domain peptides
1 2 3 4 5 6 7 8 9 10 11 12

Mouse-α-B31MI infection serum #1

Mouse-α-B31MI infection serum #2

Human early serum #8

Human early serum #44

Figure 7A

```
     CSETFTNKLKEKHTDLGKEGVTDADAKEAILKTNG    SEQ ID NO: 62
 1   CSETFTNKLKEKH                          SEQ ID NO: 63
 2       ETFTNKLKEKHTD                      SEQ ID NO: 64
 3        FTNKLKEKHTDLG                     SEQ ID NO: 65
 4          NKLKEKHTDLGKE                   SEQ ID NO: 66
 5            LKEKHTDLGKEGV                 SEQ ID NO: 67
 6             EKHTDLGKEGVTD                SEQ ID NO: 68
 7               HTDLGKEGVTDAD              SEQ ID NO: 69
 8                DLGKEGVTDADAK             SEQ ID NO: 70
 9                  GKEGVTDADAKEA           SEQ ID NO: 71
10                   EGVTDADAKEAIL          SEQ ID NO: 72
11                      VTDADAKEAILKT       SEQ ID NO: 73
12                        DADAKEAILKTNG     SEQ ID NO: 74
```

Figure 7B r-type A loop 5
B. parkeri
B. burgdorferi       kDa
                     −37

−25
OspC→                −20

Figure 8

```
1           GSMGML                                      (SEQ ID NO: 76)
2           STNGNL                                      (SEQ ID NO: 77)
3           SSMSVL                                      (SEQ ID NO: 78)
4           SSSQGL                                      (SEQ ID NO: 79)
5           GAMSAL                                      (SEQ ID NO: 80)
Type A Loop 5  SETFTNKLKEKHTDLGKEG                      (SEQ ID NO: 81)
Type B Helix 5 LKANAAGKDKGVEELEKLSGSLESLSKAAKEMLANSVKELTS (SEQ ID NO: 82)
Type K Helix 5 LITDAAKDKGAAELEKLFKAVENLAKAAKEMLANSVKELTS  (SEQ ID NO: 83)
Type D Helix 5 LKTHNAKDKGAEELVKLSESVAGLLKAAQAILANSVKELTS  (SEQ ID NO: 84)
```

Figure 15B

| | ABKD* | ABKD | ABKD-ppa | ABKD-gg | ABKDD | ADBK | ADBKD |
|---|---|---|---|---|---|---|---|
| Titer | 14538 | 38233 | 29483 | 54617 | 54617 | 36100 | 42033 |
| | 7401 | 22767 | 19917 | 21250 | 31083 | 30717 | 40100 |
| | 2167 | 12367 | 9567 | 6033 | 6083 | 19367 | 19767 |
| | 326 | 10800 | 4717 | 6400 | 22150 | 1733 | 15067 |
| vs ABKD* | --- | 2.63 | 2.03 | 3.55 | 3.76 | 2.48 | 2.89 |
| | --- | 3.08 | 2.69 | 2.87 | 4.20 | 4.15 | 5.42 |
| | --- | 5.71 | 4.42 | 2.78 | 2.81 | 8.94 | 9.12 |
| | --- | 33.10 | 14.46 | 19.62 | 67.89 | 5.31 | 46.18 |
| vs ABKD | 0.38 | --- | 0.77 | 1.35 | 1.43 | 0.94 | 1.10 |
| | 0.33 | --- | 0.87 | 0.93 | 1.37 | 1.35 | 1.76 |
| | 0.18 | --- | 0.77 | 0.49 | 0.49 | 1.57 | 1.60 |
| | 0.03 | --- | 0.44 | 0.59 | 2.05 | 0.16 | 1.40 |

Type A, Type B, Type K, Type D

| OspC Type | Borrelia species | | | |
|---|---|---|---|---|
| | B. burgdorferi | B. garinii | B. afzelii | Other species |
| Assigned | | | | |
| A (B31)* | 38 | | | |
| B (LDP73) | 13 | | | |
| D (LDP116) | 3 | | | |
| E (N40) | 7 | | | |
| F (PAd) | 4 | | | |
| H (LDS101) | 3 | | | |
| I (HB19) | 7 | | | |
| K (LDP74) | 11 | | | |
| L (SI1) | 6 | | | |
| M (B356) | 3 | | | |
| N (LDP63) | 7 | | | |
| U (148) | 3 | | | |
| OspCt-Smar | | 4 | | |
| OspCt-PLi | | 9 | | |
| OspCt-H13 | | 3 | | |
| OspCt-PFiM | | 6 | | |
| OspCt-PMit | | 3 | | |
| OspCt-PKi | | 5 | | |
| OspCt-PBes | | 7 | | |
| OspCt-HT22 | | 4 | | |
| OspCt-Pko | | | 11 | |
| OspCt-PLj7 | | | 6 | |
| OspCt-VS461 | | | 3 | |
| OspCt-DK15 | | | 3 | |
| OspCt-HT25 | | | 4 | |
| OspCt-72a | 4 | | | |
| OspCt-Szid | 3 | | | |
| OspCt-PHez | | 5 | | |
| OspCt-PWa | | 17 | | |
| Unassigned | | | | |
| B. burgdorferi | 8 | | | |
| B. garinii | | 22 | | |
| B. afzelii | | | 21 | |
| B. bissettii | | | | 8 |
| B. japonica | | | | 1 |
| B. andersonii | | | | 6 |
| B. tanukii | | | | 1 |
| B. valaisiana | | | | 8 |
| B. species | | | | 3 |
| Totals | 120 | 85 | 48 | 27 |

\* - For letter-assigned OspC types, an example strain is given in parentheses.

*Figure 20A*

| OspC Type | Geographic Region | | | | |
|---|---|---|---|---|---|
| | North America | Europe | Russia | Asia | Not provided |
| Assigned | | | | | |
| A (B31)* | 25 | 9 | | 4 | |
| B (LDP73) | 6 | 5 | | | 2 |
| D (LDP116) | 3 | | | | |
| E (N40) | 7 | | | | |
| F (PAd) | 4 | | | | |
| H (LDS101) | 3 | | | | |
| I (HB19) | 7 | | | | |
| K (LDP74) | 11 | | | | |
| L (SI1) | 5 | 1 | | | |
| M (B356) | 3 | | | | |
| N (LDP63) | 7 | | | | |
| U (148) | 3 | | | | |
| OspCt-Smar | | 4 | | | |
| OspCt-PLi | | 9 | | | |
| OspCt-H13 | | 3 | | | |
| OspCt-PFiM | | 6 | | | |
| OspCt-PMit | | 3 | | | |
| OspCt-PKi | | 5 | | | |
| OspCt-PBes | | 6 | | 1 | |
| OspCt-HT22 | | | 3 | 1 | |
| OspCt-Pko | | 7 | | 4 | |
| OspCt-PLj7 | | 5 | | | 1 |
| OspCt-VS461 | | 2 | | | 1 |
| OspCt-DK15 | | 1 | | 2 | |
| OspCt-HT25 | | | 1 | 3 | |
| OspCt-72a | 4 | | | | |
| OspCt-Szid | | 3 | | | |
| OspCt-PHez | | 5 | | | |
| OspCt-PWa | | 17 | | | |
| Unassigned | | | | | |
| *B. burgdorferi* | 6 | 1 | 1 | | |
| *B. garinii* | | 7 | 4 | 10 | 1 |
| *B. afzelii* | | 10 | 9 | 1 | 1 |
| *B. bissettii* | 8 | | | | |
| *B. japonica* | | | | 1 | |
| *B. andersonii* | 6 | | | | |
| *B. tanukii* | | | | 1 | |
| *B. valaisiana* | | 4 | | 4 | |
| *B. species* | 3 | | | | |
| Totals | 111 | 113 | 18 | 32 | 6 |

* - For letter-assigned OspC types, an example strain is given in parentheses.

Figure 20B

|  | Isolated from | | | | | |
| --- | --- | --- | --- | --- | --- | --- |
| OspC Type | Human Skin | Human Blood | Human CSF | Other animal | Tick | Not provided |
| Assigned | | | | | | |
| A (B31)* | 7 | 9 | 6 | 6 | 7 | 3 |
| B (LDP73) | 5 | 1 | 1 |  | 4 | 2 |
| D (LDP116) |  | 1 |  |  | 2 |  |
| E (N40) | 3 |  |  |  | 4 |  |
| F (PAd) | 1 |  |  |  | 3 |  |
| H (LDS101) | 2 |  |  |  | 1 |  |
| I (HB19) | 3 | 2 | 1 |  | 1 |  |
| K (LDP74) | 3 | 2 | 1 |  | 5 |  |
| L (SI1) |  |  |  | 5 | 1 |  |
| M (B356) | 1 |  |  | 2 |  |  |
| N (LDP63) | 1 | 2 | 1 | 1 | 2 |  |
| U (148) | 1 |  |  |  | 2 |  |
| OspCt-Smar |  |  | 1 |  | 3 |  |
| OspCt-PLi | 5 | 1 | 3 |  |  |  |
| OspCt-H13 | 1 |  | 1 |  | 1 |  |
| OspCt-PFiM | 1 |  | 3 |  | 2 |  |
| OspCt-PMit | 1 |  | 1 |  | 1 |  |
| OspCt-PKi | 3 |  | 2 |  |  |  |
| OspCt-PBes | 3 |  | 3 |  | 1 |  |
| OspCt-HT22 |  |  |  |  | 4 |  |
| OspCt-Pko | 5 |  | 1 | 2 | 3 |  |
| OspCt-PLj7 | 3 | 1 |  |  | 1 | 1 |
| OspCt-VS461 | 1 |  |  |  | 1 | 1 |
| OspCt-DK15 | 1 |  |  |  | 2 |  |
| OspCt-HT25 |  |  |  |  | 4 |  |
| OspCt-72a | 1 |  |  | 1 | 2 |  |
| OspCt-Szid | 1 |  | 1 |  | 1 |  |
| OspCt-PHez |  |  | 4 |  | 1 |  |
| OspCt-PWa | 1 |  | 1 |  |  |  |
| Unassigned | | | | | | |
| *B. burgdorferi* | 1 | 1 |  | 1 | 5 |  |
| *B. garinii* | 4 |  | 2 |  | 15 | 1 |
| *B. afzelii* | 7 |  |  | 3 | 10 | 1 |
| *B. bissettii* |  |  |  | 6 | 2 |  |
| *B. japonica* |  |  |  |  |  | 1 |
| *B. andersonii* |  |  |  | 1 | 5 |  |
| *B. tanukii* |  |  |  | 1 |  |  |
| *B. valaisiana* |  |  |  | 3 | 5 |  |
| *B. species* |  |  |  | 1 | 2 |  |
| Totals | 66 | 20 | 48 | 33 | 103 | 10 |

\* - For letter-assigned OspC types, an example strain is given in parentheses.

```
B31MI  (type A)   NNSGKDGNTSANSADESVKGPNLTEISKKITDSNAVLLAVKEVEALLSSIDEIAAKAIGKKIHQNN
LDP73  (type B)   ..........................................L.-...........KNDG
LDP74  (type K)   ........................E...V...IT.A....L.T.........Q..G
LDP116 (type D)   .............................V......L.K.........D...

B31MI  (type A)   GLDTENNHNGSLLAGAYAISTLIKQKLDGLKN-EGLKEKIDAAKKCSETFTNKLKEKHTDLGKEGV
LDP73  (type B)   S..N.A.R.E......T......T..SK.NGS.....A......E.ST...DN.AQ..IQ..
LDP74  (type K)   ..AV.AG...T......T.K.T......S.K.....EN......D..K..EGE.AQ..I.N.
LDP116 (type D)   A.G.L...........A..TE...SSI.DSGE..AE.EK.....S..K..SDNQAE..I.NA B31MI  (type A)   TDADAKEAILKTNGT-KTKGAEELGKLFESVEVLSKAAKEMLANSVKELTSPVVAESPKKP   (SEQ ID NO: 119)
LDP73  (type B)   ..EN..K....A.AAG.D.V...E..SG.L.S.................I..........   (SEQ ID NO: 120)
LDP74  (type K)   ..EN..K....I.DAA-..D...A.E...KA.N.A.........................   (SEQ ID NO: 121)
LDP116 (type D)   ..DN..K....HNA-...D......V..S...AG.L..QAI...................   (SEQ ID NO: 122)
```

*Figure 24*

```
Construct 1: E-N-I-C-A-B-K-D
STEFTNKLKSEHAVLGLDNLTDDNAQRAILKKHANKDKGAAELEKLFKAVENLSKAAQDT
LKNAVKELTSXSDDFTKKLQSSHAQLGVAGGATTDEEAKKAILRTNAIKDKGADELEKLF
KSVESLAKAAQDALANSVNELTSXSEEFTAKLKGEHTDLGKEGVTDDNAKKAILKTNNDK
TKGADELEKLFESVKNLSKAAKEMLTNSVKELTSXSEEFTKKLKEKHTDLGKKDATDVHA
KEAILKTNGTKDKGAAELEKLFESVENLAKAAKEMLSNSVKELTSXSETFTNKLKEKHTD
LGKEGVTDADAKEAILKTNGTKTKGAEELGKLFESVEVLSKAAKEMLANSVKELTSXSEE
FSTKLKDNHAQLGIQGVTDENAKKAILKANAAGKDKGVEELEKLSGSLESLSKAAKEMLA
NSVKELTSXSEDFTKKLEGEHAQLGIENVTDENAKKAILITDAAKDKGAAELEKLFKAVE
NLAKAAKEMLANSVKELTSXSESFTKKLSDNQAELGIENATDDNAKKAILKTHNAKDKGA
EELVKLSESVAGLLKAAQAILANSVKELTSPVVAESPKKP     (SEQ ID NO: 123)

Construct 2: F-M-U-L-H-Szid-72a
SEDFTNKLKNGNAQLGLAAATDDNAKAAILKTNGTNDKGAKELKDLSDSVESLVKAAQVM
LTNSVKELTSXNKAFTDKLKSSHAELGIANGAATDANAKAAILKTNGTKDKGAQELEKLF
ESVKNLSKAAQETLNNSVKELTSXSEKFTKKLSESHADIGIQAATDANAKDAILKTNPTK
TKGAEELDKLFKAVENLSKAAKEMLANSVKDLQVXSEKFTDKLKSENAALGKQDASDDDA
KKAILKTHNDITKGAKELKELSESVETLLKAAKEMLANSVKELTSXSEKFAGKLKNEHAS
LGKKDATDDDAKKAILKTHGNTDKGAKELKDLSDSVESLVKAAKEMLTNSVKELTSXSEA
FTDKLKNEHASLGKKDATDDDAKKAILKTNVDKTKGADELIKLSGSLESLSKAAQAILAN
SVKELTSXSAAFTKKLADSNADLGVAAGNATDDNAKRAILKTHGHEDKGGKELKELSEAV
KSLLKAAQAALANSVQELTS     (SEQ ID NO: 124)

Construct 3: PHez-PWa-Smar-PLi-H13-PFiM-SL10-PMit
SEKFTTKLRDSHAELGIQNVQDDNAKRAILKTHGNKDKGAKELKELSESLEKLSKAAQAA
LANSVQELTSXSEKFTTKLKDSHAELGIQSVQDDNAKKAILKTHGTKDKGAKELEELFKS
LESLSKAAQAALTNSVKELTNXSEAFTNKLKEKHAELGVNGGDTTDDNAKAAIFKTHPTK
DKGVEDLEKLSESVKSLLKAAQAALSNSVKELTSXSDKFTKKLTDSHAQLGAVGGAINDD
RAKEAILKTHGTNDKGAKELKELSESVESLAKAAQAALANSVKELTSXSEAFTKKLKDNN
AQLGIQNVQDVEAKKAILKTNGDISKGAKELKELFESVESLAKAAQAALANSVQELTNXS
EAFTNRLKGSHAQLGVAAATDDHAKEAILKSNPTKDKGAKELKDLSESVESLAKAAQEAL
ANSVKELTNXSEAFTNRLTGSHAQHGVAAATDDHAKEAILKSNPTKDKGAKELKDLSESV
ESLAKAAQEALANSVKELTNXSEAFTNKLKEKTQELAVAAGAATDIDAKKAILKTNRDKD
LGADERGKLFKSVESLSKAAQEASANSVKELTS     (SEQ ID NO: 125)

Construct 4: PKi-PBes-HT22-Pko-PLj7-VS461-DK15-HT25
SVAFTSKLKSSNAQLGVANGNATDDDAKKAILKTNTPNDKGAKELKELFESVESLAKAAQ
AALVNSVQELTNXSEAFTKKLKDSNAQLGMQNGAATDAHAKAAILKTDATKDKGATELGE
LFKSVESLSKAAQEASANSVKELTSXSAAFTKKLQDGHVDLGKTDVTDDNAKEAILKTNP
TKTKGATELEELFKSVEGLVKAAKEASANSVKELTSXSEEFTNKLKSGHADLGKQDATDD
HAKAAILKTHATTDKGAKEFKDLFESVEGLLKAAQVALTNSVKELTSXSEEFTNKLKGGH
AELGLAAATDENAKKAILKTNGTKDKGAEELEKLFKSVESLAKAAKESLTNSVKELTNXS
EAFTKKLQDSNADLGKHNATADADSKEAILKTNGTKTKGAKELEELFKSVESLSKAAKEAL
SNSVKELTSXSEAFTKKLQDSNADLGKHDATDADAKKAILKTDATKDKGAKELEELFKSV
ESLSKAAKEALSNSVKELTSXSQDFINKLKGGHAELGLVAATDANAKAAILKTNGDKTKG
ADEFEKLFKSVEGLLKAAQEALTNSVKELTS     (SEQ ID NO: 126)
```

*Figure 25A*

```
Construct 5: M-PFiM-DK15-L-SL10-PBes-Szid-PLi
NKAFTDKLKSSHAELGIANGAATDANAKAAILKTNGTKDKGAQELEKLFESVKNLSKAAQ
ETLNNSVKELTSXSEAFTNRLKGSHAQLGVAAATDDHAKEAILKSNPTKDKGAKELKDLS
ESVESLAKAAQEALANSVKELTNXSEAFTKKLQDSNADLGKHDATDADAKKAILKTDATK
DKGAKELEELFKSVESLSKAAKEALSNSVKELTSXSEKFTDKLKSENAALGKQDASDDDA
KKAILKTHNDITKGAKELKELSESVETLLKAAKEMLANSVKELTSXSEAFTNRLTGSHAQ
HGVAAATDDHAKEAILKSNPTKDKGAKELKDLSESVESLAKAAQEALANSVKELTNXSEA
FTKKLKDSNAQLGMQNGAATDAHAKAAILKTDATKDKGATELGELFKSVESLSKAAQEAS
ANSVKELTSXSEAFTDKLKNEHASLGKKDATDDDAKKAILKTNVDKTKGADELIKLSGSL
ESLSKAAQAILANSVKELTSXSDKFTKKLTDSHAQLGAVGGAINDDRAKEAILKTHGTND
KGAKELKELSESVESLAKAAQAALANSVKELTS    (SEQ ID NO: 127)

Construct 6: Smar-VS461-H-PWa-HT25-HT22-H13-U
SEAFTNKLKEKHAELGVNGGDTTDDNAKAAIFKTHPTKDKGVEDLEKLSESVKSLLKAAQ
AALSNSVKELTSXSEAFTKKLQDSNADLGKHNATDADSKEAILKTNGTKTKGAKELEELF
KSVESLSKAAKEALSNSVKELTSXSEKFAGKLKNEHASLGKKDATDDDAKKAILKTHGNT
DKGAKELKDLSDSVESLVKAAKEMLTNSVKELTSXSEKFTTKLKDSHAELGIQSVQDDNA
KKAILKTHGTKDKGAKELEELFKSLESLSKAAQAALTNSVKELTNXSQDFINKLKGGHAE
LGLVAATDANAKAAILKTNGDKTKGADEFEKLFKSVEGLLKAAQEALTNSVKELTSXSAA
FTKKLQDGHVDLGKTDVTDDNAKEAILKTNPTKTKGATELEELFKSVEGLVKAAKEASAN
SVKELTSXSEAFTKKLKDNNAQLGIQNVQDVEAKKAILKTNGDISKGAKELKELFESVES
LAKAAQAALANSVQELTNXSEKFTKKLSESHADIGIQAATDANAKDAILKTNPTKTKGAE
ELDKLFKAVENLSKAAKEMLANSVKDLQV    (SEQ ID NO: 128)

Construct 7: PMit-PKi-Pko-PLj7-72a-F-PHez
SEAFTNKLKEKTQELAVAAGAATDIDAKKAILKTNRDKDLGADERGKLFKSVESLSKAAQ
EASANSVKELTSXSVAFTSKLKSSNAQLGVANGNATDDDAKKAILKTNTPNDKGAKELKE
LFESVESLAKAAQAALVNSVQELTNXSEEFTNKLKSGHADLGKQDATDDHAKAAILKTHA
TTDKGAKEFKDLFESVEGLLKAAQVALTNSVKELTSXSEEFTNKLKGGHAELGLAAATDE
NAKKAILKTNGTKDKGAEELEKLFKSVESLAKAAKESLTNSVKELTNXSAAFTKKLADSN
ADLGVAAGNATDDNAKRAILKTHGHEDKGGKELKELSEAVKSLLKAAQAALANSVQELTS
XSEDFTNKLKNGNAQLGLAAATDDNAKAAILKTNGTNDKGAKELKDLSDSVESLVKAAQV
MLTNSVKELTSXSEKFTTKLRDSHAELGIQNVQDDNAKRAILKTHGNKDKGAKELKELSE
SLEKLSKAAQAALANSVQELTS    (SEQ ID NO: 129)
```

Figure 25B

Construct 8: A-B-K-D-E-N-I-C
SETFTNKLKEKHTDLGKEGVTDADAKEAILKTNGTKTKGAEELGKLFESVEVLSKAAKEM
LANSVKELTSXSEEFSTKLKDNHAQLGIQGVTDENAKKAILKANAAGKDKGVEELEKLSG
SLESLSKAAKEMLANSVKELTSXSEDFTKKLEGEHAQLGIENVTDENAKKAILITDAAKD
KGAAELEKLFKAVENLAKAAKEMLANSVKELTSXSESFTKKLSDNQAELGIENATDDNAK
KAILKTHNAKDKGAEELVKLSESVAGLLKAAQAILANSVKELTSXSTEFTNKLKSEHAVL
GLDNLTDDNAQRAILKKHANKDKGAAELEKLFKAVENLSKAAQDTLKNAVKELTSXSDDF
TKKLQSSHAQLGVAGGATTDEEAKKAILRTNAIKDKGADELEKLFKSVESLAKAAQDALA
NSVNELTSXSEEFTAKLKGEHTDLGKEGVTDDNAKKAILKTNNDKTKGADELEKLFESVK
NLSKAAKEMLTNSVKELTSXSEEFTKKLKEKHTDLGKKDATDVHAKEAILKTNGTKDKGA
AELEKLFESVENLAKAAKEMLSNSVKELTSPVVAESPKKP  (SEQ ID NO: 130)

Construct 9: Smar-PWa-PLi-PHez-H13-Szid-PFiM-H
SEAFTNKLKEKHAELGVNGGDTTDDNAKAAIFKTHPTKDKGVEDLEKLSESVKSLLKAAQ
AALSNSVKELTSXSEKFTTKLKDSHAELGIQSVQDDNAKKAILKTHGTKDKGAKELEELF
KSLESLSKAAQAALTNSVKELTNXSDKFTKKLTDSHAQLGAVGGAINDDRAKEAILKTHG
TNDKGAKELKELSESVESLAKAAQAALANSVKELTSXSEKFTTKLRDSHAELGIQNVQDD
NAKRAILKTHGNKDKGAKELKELSESLEKLSKAAQAALANSVQELTSXSEAFTKKLKDNN
AQLGIQNVQDVEAKKAILKTNGDISKGAKELKELFESVESLAKAAQAALANSVQELTNXS
EAFTDKLKNEHASLGKKDATDDDAKKAILKTNVDKTKGADELIKLSGSLESLSKAAQAIL
ANSVKELTSXSEAFTNRLKGSHAQLGVAAATDDHAKEAILKSNPTKDKGAKELKDLSESV
ESLAKAAQEALANSVKELTNXSEKFAGKLKNEHASLGKKDATDDDAKKAILFTHGNTDKG
AKELKDLSDSVESLVKAAKEMLTNSVKELTS   (SEQ ID NO: 131)

Construct 10: SL10-L-PMit-U-PKi-M-PBes-F
SEAFTNRLTGSHAQHGVAAATDDHAKEAILKSNPTKDKGAKELKDLSESVESLAKAAQEA
LANSVKELTNXSEKFTDKLKSENAALGKQDASDDDAKKAILKTHNDITKGAKELKELSES
VETLLKAAKEMLANSVKELTSXSEAFTNKLKEKTQELAVAAGAATDIDAKKAILKTNRDK
DLGADERGKLFKSVESLSKAAQEASANSVKELTSXSEKFTKKLSESHADIGIQAATDANA
KDAILKTNPTKTKGAEELDKLFKAVENLSKAAKEMLANSVKDLQVXSVAFTSKLKSSNAQ
LGVANGNATDDDAKKAILKTNTPNDKGAKELKELFESVESLAKAAQAALVNSVQELTNXN
KAFTDKLKSSHAELGIANGAATDANAKAAILKTNGTKDKGAQELEKLFESVKNLSKAAQE
TLNNSVKELTSXSEAFTKKLKDSNAQLGMQNGAATDAHAKAAILKTDATKDKGATELGEL
FKSVESLSKAAQEASANSVKELTSXSEDFTNKLKNGNAQLGLAAATDDNAKAAILKTNGT
NDKGAKELKDLSDSVESLVKAAQVMLTNSVKELTS   (SEQ ID NO: 132)

Construct 11: HT22-72a-Pko-HT25-PLj7-DK15-VS461
SAAFTKKLQDGHVDLGKTDVTDDNAKEAILKTNPTKTKGATELEELFKSVEGLVKAAKEA
SANSVKELTSXSAAFTKKLADSNADLGVAAGNATDDNAKRAILKTHGHEDKGGKELKELS
EAVKSLLKAAQAALANSVQELTSXSEEFTNKLKSGHADLGKQDATDDHAKAAILKTHATT
DKGAKEFKDLFESVEGLLKAAQVALTNSVKELTSXSQDFINKLKGGHAELGLVAATDANA
KAAILKTNGDKTKGADEFEKLFKSVEGLLKAAQEALTNSVKELTSXSEEFTNKLKGGHAE
LGLAAATDENAKKAILKTNGTKDKGAEELEKLFKSVESLAKAAKESLTNSVKELTNXSEA
FTKKLQDSNADLGKHDATDADAKKAILKTDATKDKGAKELEELFKSVESLSKAAKEALSN
SVKELTSXSEAFTKKLQDSNADLGKHNATDADSKEAILKTNGTKTKGAKELEELFKSVES
LSKAAKEALSNSVKELTS   (SEQ ID NO: 132)

*Figure 25C*

Construct 12: I-C-A-B-K-D
SEEFTAKLKGEHTDLGKEGVTDDNAKKAILKTNNDKTKGADELEKLFESVKNLSKAAKEM
LTNSVKELTSXSEEFTKKLKEKHTDLGKKDATDVHAKEAILKTNGTKDKGAAELEKLFES
VENLAKAAKEMLSNSVKELTSXSETFTNKLKEKHTDLGKEGVTDADAKEAILKTNGTKTK
GAEELGKLFESVEVLSKAAKEMLANSVKELTSXSEEFSTKLKDNHAQLGIQGVTDENAKK
AILKANAAGKDKGVEELEKLSGSLESLSKAAKEMLANSVKELTSXSEDFTKKLEGEHAQL
GIENVTDENAKKAILITDAAKDKGAAELEKLFKAVENLAKAAKEMLANSVKELTSXSESF
TKKLSDNQAELGIENATDDNAKKAILKTHNAKDKGAEELVKLSESVAGLLKAAQAILANS
VKELTSPVVAESPKKP    (SEQ ID NO: 134)

Construct 13: E-N-M-L-F-H-U
STEFTNKLKSEHAVLGLDNLTDDNAQRAILKKHANKDKGAAELEKLFKAVENLSKAAQDT
LKNAVKELTSXSDDFTKKLQSSHAQLGVAGGATTDEEAKKAILRTNAIKDKGADELEKLF
KSVESLAKAAQDALANSVNELTSXNKAFTDKLKSSHAELGIANGAATDANAKAAILKTNG
TKDKGAQELEKLFESVKNLSKAAQETLNNSVKELTSXSEKFTDKLKSENAALGKQDASDD
DAKKAILKTHNDITKGAKELKELSESVETLLKAAKEMLANSVKELTSXSEDFTNKLKNGN
AQLGLAAATDDNAKAAILKTNGTNDKGAKELKDLSDSVESLVKAAQVMLTNSVKELTSXS
EKFAGKLKNEHASLGKKDATDDDAKKAILKTHGNTDKGAKELKDLSDSVESLVKAAKEML
TNSVKELTSXSEKFTKKLSESHADIGIQAATDANAKDAILKTNPTKTKGAEELDKLFKAV
ENLSKAAKEMLANSVKDLQV    (SEQ ID NO: 135)

Construct 14: 72a-Szid-PFiM-DK15-SL10-PBes
SAAFTKKLADSNADLGVAAGNATDDNAKRAILKTHGHEDKGGKELKELSEAVKSLLKAAQ
AALANSVQELTSXSEAFTDKLKNEHASLGKKDATDDDAKKAILKTNVDKTKGADELIKLS
GSLESLSKAAQAILANSVKELTSXSEAFTNRLKGSHAQLGVAAATDDHAKEAILKSNPTK
DKGAKELKDLSESVESLAKAAQEALANSVKELTNXSEAFTKKLQDSNADLGKHDATDADA
KKAILKTDATKDKGAKELEELFKSVESLSKAAKEALSNSVKELTSXSEAFTNRLTGSHAQ
HGVAAATDDHAKEAILKSNPTKDKGAKELKDLSESVESLAKAAQEALANSVKELTNXSEA
FTKKLKDSNAQLGMQNGAATDAHAKAAILKTDATKDKGATELGELFKSVESLSKAAQEAS
ANSVKELTS    (SEQ ID NO: 136)

Construct 15: PLi-Smar-VS461-PWa-HT25-HT22
SDKFTKKLTDSHAQLGAVGGAINDDRAKEAILKTHGTNDKGAKELKELSESVESLAKAAQ
AALANSVKELTSXSEAFTNKLKEKHAELGVNGGDTTDDNAKAAIFKTHPTKDKGVEDLEK
LSESVKSLLKAAQAALSNSVKELTSXSEAFTKKLQDSNADLGKHNATDADSKEAILKTNG
TKTKGAKELEELFKSVESLSKAAKEALSNSVKELTSXSEKFTTKLKDSHAELGIQSVQDD
NAKKAILKTHGTKDKGAKELEELFKSLESLSKAAQAALTNSVKELTNXSQDFINKLKGGH
AELGLVAATDANAKAAILKTNGDKTKGADEFEKLFKSVEGLLKAAQEALTNSVKELTSXS
AAFTKKLQDGHVDLGKTDVTDDNAKEAILKTNPTKTKGATELEELFKSVEGLVKAAKEAS
ANSVKELTS    (SEQ ID NO: 137)

Construct 16: H13-PMit-PKi-Pko-PLj7-PHez
SEAFTKKLKDNNAQLGIQNVQDVEAKKAILKTNGDISKGAKELKELFESVESLAKAAQAA
LANSVQELTNXSEAFTNKLKEKTQELAVAAGAATDIDAKKAILKTNRDKDLGADERGKLF
KSVESLSKAAQEASANSVKELTSXSVAFTSKLKSSNAQLGVANGNATDDDAKKAILKTNT
PNDKGAKELKELFESVESLAKAAQAALVNSVQELTNXSEEFTNKLKSGHADLGKQDATDD
HAKAAILKTHATTDKGAKEFKDLFESVEGLLKAAQVALTNSVKELTSXSEEFTNKLKGGH
AELGLAAATDENAKKAILKTNGTKDKGAEELEKLFKSVESLAKAAKESLTNSVKELTNXS
EKFTTKLRDSHAELGIQNVQDDNAKRAILKTHGNKDKGAKELKELSESLEKLSKAAQAAL
ANSVQELTS    (SEQ ID NO: 138)

*Figure 25D*

Construct 17: C-A-B-K-D
SEEFTKKLKEKHTDLGKKDATDVHAKEAILKTNGTKDKGAAELEKLFESVENLAKAAKEMLS
NSVKELTSXSETFTNKLKEKHTDLGKEGVTDADAKEAILKTNGTKTKGAEELGKLFESVEVL
SKAAKEMLANSVKELTSXSEEFSTKLKDNHAQLGIQGVTDENAKKAILKANAAGKDKGVEEL
EKLSGSLESLSKAAKEMLANSVKELTSXSEDFTKKLEGEHAQLGIENVTDENAKKAILITDA
AKDKGAAELEKLFKAVENLAKAAKEMLANSVKELTSXSESFTKKLSDNQAELGIENATDDNA
KKAILKTHNAKDKGAEELVKLSESVAGLLKAAQAILANSVKELTSPVVAESPKKP (SEQ ID NO: 139)

Construct 18: I-E-N-M-L
SEEFTAKLKGEHTDLGKEGVTDDNAKKAILKTNNDKTKGADELEKLFESVKNLSKAAKEMLT
NSVKELTSXSTEFTNKLKSEHAVLGLDNLTDDNAQRAILKKHANKDKGAAELEKLFKAVENL
SKAAQDTLKNAVKELTSXSDDFTKKLQSSHAQLGVAGGATTDEEAKKAILRTNAIKDKGADE
LEKLFKSVESLAKAAQDALANSVNELTSXNKAFTDKLKSSHAELGIANGAATDANAKAAILK
TNGTKDKGAQELEKLFESVKNLSKAAQETLNNSVKELTSXSEKFTDKLKSENAALGKQDASD
DDAKKAILKTHNDITKGAKELKELSESVETLLKAAKEMLANSVKELTS (SEQ ID NO: 140)

Construct 19: F-H-U-72a-Szid
SEDFTNKLKNGNAQLGLAAATDDNAKAAILKTNGTNDKGAKELKDLSDSVESLVKAAQVMLT
NSVKELTSXSEKFAGKLKNEHASLGKKDATDDDAKKAILKTHGNTDKGAKELKDLSDSVESL
VKAAKEMLTNSVKELTSXSEKFTKKLSESHADIGIQAATDANAKDAILKTNPTKTKGAEELD
KLFKAVENLSKAAKEMLANSVKDLQVXSAAFTKKLADSNADLGVAAGNATDDNAKRAILKTH
GHEDKGGKELKELSEAVKSLLKAAQAALANSVQELTSXSEAFTDKLKNEHASLGKKDATDDD
AKKAILKTNVDKTKGADELIKLSGSLESLSKAAQAILANSVKELTS (SEQ ID NO: 141)

Construct 20: PFiM-DK15-SL10-PBes-PLi
SEAFTNRLKGSHAQLGVAAATDDHAKEAILKSNPTKDKGAKELKDLSESVESLAKAAQEALA
NSVKELTNXSEAFTKKLQDSNADLGKHDATDADAKKAILKTDATKDKGAKELEELFKSVESL
SKAAKEALSNSVKELTSXSEAFTNRLTGSHAQHGVAAATDDHAKEAILKSNPTKDKGAKELK
DLSESVESLAKAAQEALANSVKELTNXSEAFTKKLKDSNAQLGMQNGAATDAHAKAAILKTD
ATKDKGATELGELFKSVESLSKAAQEASANSVKELTSXSDKFTKKLTDSHAQLGAVGGAIND
DRAKEAILKTHGTNDKGAKELKELSESVESLAKAAQAALANSVKELTS (SEQ ID NO: 142)

Construct 21: Smar-VS461-PWa-HT25-HT22
SEAFTNKLKEKHAELGVNGGDTTDDNAKAAIFKTHPTKDKGVEDLEKLSESVKSLLKAAQAA
LSNSVKELTSXSEAFTKKLQDSNADLGKHNATDADSKEAILKTNGTKTKGAKELEELFKSVE
SLSKAAKEALSNSVKELTSXSEKFTTKLKDSHAELGIQSVQDDNAKKAILKTHGTKDKGAKE
LEELFKSLESLSKAAQAALTNSVKELTNXSQDFINKLKGGHAELGLVAATDANAKAAILKTN
GDKTKGADEFEKLFKSVEGLLKAAQEALTNSVKELTSXSAAFTKKLQDGHVDLGKTDVTDDN
AKEAILKTNPTKTKGATELEELFKSVEGLVKAAKEASANSVKELTS (SEQ ID NO: 143)

Construct 22: H13-PMit-PKi-Pko-PLj7-PHez
SEAFTKKLKDNNAQLGIQNVQDVEAKKAILKTNGDISKGAKELKELFESVESLAKAAQAALA
NSVQELTNXSEAFTNKLKEKTQELAVAAGAATDIDAKKAILKTNRDKDLGADERGKLFKSVE
SLSKAAQEASANSVKELTSXSVAFTSKLKSSNAQLGVANGNATDDDAKKAILKTNTPNDKGA
KELKELFESVESLAKAAQAALVNSVQELTNXSEEFTNKLKSGHADLGKQDATDDHAKAAILK
THATTDKGAKEFKDLFESVEGLLKAAQVALTNSVKELTSXSEEFTNKLKGGHAELGLAAATD
ENAKKAILKTNGTKDKGAEELEKLFKSVESLAKAAKESLTNSVKELTNXSEKFTTKLRDSHA
ELGIQNVQDDNAKRAILKTHGNKDKGAKELKELSESLEKLSKAAQAALANSVQELTS (SEQ ID NO: 144)

Figure 25E

Construct 23: Smar-PLi-H13-PFiM-SL10-PMit-PKi-PBes
SEAFTNKLKEKHAELGVNGGDTTDDNAKAAIFKTHPTKDKGVEDLEKLSESVKSLLKAAQ
AALSNSVKELTSXSDKFTKKLTDSHAQLGAVGGAINDDRAKEAILKTHGTNDKGAKELKE
LSESVESLAKAAQAALANSVKELTSXSEAFTKKLKDNNAQLGIQNVQDVEAKKAILKTNG
DISKGAKELKELFESVESLAKAAQAALANSVQELTNXSEAFTNRLKGSHAQLGVAAATDD
HAKEAILKSNPTKDKGAKELKDLSESVESLAKAAQEALANSVKELTNXSEAFTNRLTGSH
AQHGVAAATDDHAKEAILKSNPTKDKGAKELKDLSESVESLAKAAQEALANSVKELTNXS
EAFTNKLKEKTQELAVAAGAATDIDAKKAILKTNRDKDLGADERGKLFKSVESLSKAAQE
ASANSVKELTSXSVAFTSKLKSSNAQLGVANGNATDDDAKKAILKTNTPNDKGAKELKEL
FESVESLAKAAQAALVNSVQELTNXSEAFTKKLKDSNAQLGMQNGAATDAHAKAAILKTD
ATKDKGATELGELFKSVESLSKAAQEASANSVKELTS      (SEQ ID NO: 145)

Construct 24: HT22-Pko-PLj7-VS461-DK15-HT25-72a-F
SAAFTKKLQDGHVDLGKTDVTDDNAKEAILKTNPTKTKGATELEELFKSVEGLVKAAKEA
SANSVKELTSXSEEFTNKLKSGHADLGKQDATDDHAKAAILKTHATTDKGAKEFKDLFES
VEGLLKAAQVALTNSVKELTSXSEEFTNKLKGGHAELGLAAATDENAKKAILKTNGTKDK
GAEELEKLFKSVESLAKAAKESLTNSVKELTNXSEAFTKKLQDSNADLGKHNATDADSKE
AILKTNGTKTKGAKELEELFKSVESLSKAAKEALSNSVKELTSXSEAFTKKLQDSNADLG
KHDATDADAKKAILKTDATKDKGAKELEELFKSVESLSKAAKEALSNSVKELTSXSQDFI
NKLKGGHAELGLVAATDANAKAAILKTNGDKTKGADEFEKLFKSVEGLLKAAQEALTNSV
KELTSXSAAFTKKLADSNADLGVAAGNATDDNAKRAILKTHGHEDKGGKELKELSEAVKS
LLKAAQAALANSVQELTSXSEDFTNKLKNGNAQLGLAAATDDNAKAAILKTNGTNDKGAK
ELKDLSDSVESLVKAAQVMLTNSVKELTS     (SEQ ID NO: 146)

Construct 25: M-U-L-H-Szid-PHez-PWa
NKAFTDKLKSSHAELGIANGAATDANAKAAILKTNGTKDKGAQELEKLFESVKNLSKAAQ
ETLNNSVKELTSXSEKFTKKLSESHADIGIQAATDANAKDAILKTNPTKTKGAEELDKLF
KAVENLSKAAKEMLANSVKDLQVXSEKFTDKLKSENAALGKQDASDDDAKKAILKTHNDI
TKGAKELKELSESVETLLKAAKEMLANSVKELTSXSEKFAGKLKNEHASLGKKDATDDDA
KKAILKTHGNTDKGAKELKDLSDSVESLVKAAKEMLTNSVKELTSXSEAFTDKLKNEHAS
LGKKDATDDDAKKAILKTNVDKTKGADELIKLSGSLESLSKAAQAILANSVKELTSXSEK
FTTKLRDSHAELGIQNVQDDNAKRAILKTHGNKDKGAKELKELSESLEKLSKAAQAALAN
SVQELTSXSEKFTTKLKDSHAELGIQSVQDDNAKKAILKTHGTKDKGAKELEELFKSLES
LSKAAQAALTNSVKELTN   (SEQ ID NO: 147)

*Figure 25F*

Construct 26: E-N-Smar-PBes-DK15-72a
STEFTNKLKSEHAVLGLDNLTDDNAQRAILKKHANKDKGAAELEKLFKAVENLSKAAQDT
LKNAVKELTSXSDDFTKKLQSSHAQLGVAGGATTDEEAKKAILRTNAIKDKGADELEKLF
KSVESLAKAAQDALANSVNELTSXSEAFTNKLKEKHAELGVNGGDTTDDNAKAAIFKTHP
TKDKGVEDLEKLSESVKSLLKAAQAALSNSVKELTSXSEAFTKKLKDSNAQLGMQNGAAT
DAHAKAAILKTDATKDKGATELGELFKSVESLSKAAQEASANSVKELTSXSEAFTKKLQD
SNADLGKHDATDADAKKAILKTDATKDKGAKELEELFKSVESLSKAAKEALSNSVKELTS
XSAAFTKKLADSNADLGVAAGNATDDNAKRAILKTHGHEDKGGKELKELSEAVKSLLKAA
QAALANSVQELTS   (SEQ ID NO: 148)

Construct 27: HT22-M-PHez-PFiM-PLj7-Szid
SAAFTKKLQDGHVDLGKTDVTDDNAKEAILKTNPTKTKGATELEELFKSVEGLVKAAKEA
SANSVKELTSXNKAFTDKLKSSHAELGIANGAATDANAKAAILKTNGTKDKGAQELEKLF
ESVKNLSKAAQETLNNSVKELTSXSEKFTTKLRDSHAELGIQNVQDDNAKRAILKTHGNK
DKGAKELKELSESLEKLSKAAQAALANSVQELTSXSEAFTNRLKGSHAQLGVAAATDDHA
KEAILKSNPTKDKGAKELKDLSESVESLAKAAQEALANSVKELTNXSEEFTNKLKGGHAE
LGLAAATDENAKKAILKTNGTKDKGAEELEKLFKSVESLAKAAKESLTNSVKELTNXSEA
FTDKLKNEHASLGKKDATDDDAKKAILKTNVDKTKGADELIKLSGSLESLSKAAQAILAN
SVKELTS   (SEQ ID NO: 149)

Construct 28: PLi-PMit-VS461-H-HT25-F
SDKFTKKLTDSHAQLGAVGGAINDDRAKEAILKTHGTNDKGAKELKELSESVESLAKAAQ
AALANSVKELTSXSEAFTNKLKEKTQELAVAAGAATDIDAKKAILKTNRDKDLGADERGK
LFKSVESLSKAAQEASANSVKELTSXSEAFTKKLQDSNADLGKHNATDADSKEAILKTNG
TKTKGAKELEELFKSVESLSKAAKEALSNSVKELTSXSEKFAGKLKNEHASLGKKDATDD
DAKKAILKTHGNTDKGAKELKDLSDSVESLVKAAKEMLTNSVKELTSXSQDFINKLKGGH
AELGLVAATDANAKAAILKTNGDKTKGADEFEKLFKSVEGLLKAAQEALTNSVKELTSXS
EDFTNKLKNGNAQLGLAAATDDNAKAAILKTNGTNDKGAKELKDLSDSVESLVKAAQVML
TNSVKELTS   (SEQ ID NO: 150)

Construct 29: H13-SL10-PKi-Pko-U-L-PWa
SEAFTKKLKDNNAQLGIQNVQDVEAKKAILKTNGDISKGAKELKELFESVESLAKAAQAA
LANSVQELTNXSEAFTNRLTGSHAQHGVAAATDDHAKEAILKSNPTKDKGAKELKDLSES
VESLAKAAQEALANSVKELTNXSVAFTSKLKSSNAQLGVANGNATDDDAKKAILKTNTPN
DKGAKELKELFESVESLAKAAQAALVNSVQELTNXSEEFTNKLKSGHADLGKQDATDDHA
KAAILKTHATTDKGAKEFKDLFESVEGLLKAAQVALTNSVKELTSXSEKFTKKLSESHAD
IGIQAATDANAKDAILKTNPTKTKGAEELDKLFKAVENLSKAAKEMLANSVKDLQVXSEK
FTDKLKSENAALGKQDASDDDAKKAILKTHNDITKGAKELKELSESVETLLKAAKEMLAN
SVKELTSXSEKFTTKLKDSHAELGIQSVQDDNAKKAILKTHGTKDKGAKELEELFKSLES
LSKAAQAALTNSVKELTN   (SEQ ID NO: 151)

*Figure 25G*

Construct 30: PLi-72a-VS461-Smar-SL10-DK15-PBes-H
SDKFTKKLTDSHAQLGAVGGAINDDRAKEAILKTHGTNDKGAKELKELSESVESLAKAAQ
AALANSVKELTSXSAAFTKKLADSNADLGVAAGNATDDNAKRAILKTHGHEDKGGKELKE
LSEAVKSLLKAAQAALANSVQELTSXSEAFTKKLQDSNADLGKHNATDADSKEAILKTNG
TKTKGAKELEELFKSVESLSKAAKEALSNSVKELTSXSEAFTNKLKEKHAELGVNGGDTT
DDNAKAAIFKTHPTKDKGVEDLEKLSESVKSLLKAAQAALSNSVKELTSXSEAFTNRLTG
SHAQHGVAAATDDHAKEAILKSNPTKDKGAKELKDLSESVESLAKAAQEALANSVKELTN
XSEAFTKKLQDSNADLGKHDATDADAKKAILKTDATKDKGAKELEELFKSVESLSKAAKE
ALSNSVKELTSXSEAFTKKLKDSNAQLGMQNGAATDAHAKAAILKTDATKDKGATELGEL
FKSVESLSKAAQEASANSVKELTSXSEKFAGKLKNEHASLGKKDATDDDAKKAILKTHGN
TDKGAKELKDLSDSVESLVKAAKEMLTNSVKELTS (SEQ ID NO: 152)

Construct 31: HT25-M-F-PWa-PLj7-PMit-PHez-PFiM
SQDFINKLKGGHAELGLVAATDANAKAAILKTNGDKTKGADEFEKLFKSVEGLLKAAQEA
LTNSVKELTSXNKAFTDKLKSSHAELGIANGAATDANAKAAILKTNGTKDKGAQELEKLF
ESVKNLSKAAQETLNNSVKELTSXSEDFTNKLKNGNAQLGLAAATDDNAKAAILKTNGTN
DKGAKELKDLSDSVESLVKAAQVMLTNSVKELTSXSEKFTTKLKDSHAELGIQSVQDDNA
KKAILKTHGTKDKGAKELEELFKSLESLSKAAQAALTNSVKELTNXSEEFTNKLKGGHAE
LGLAAATDENAKKAILKTNGTKDKGAEELEKLFKSVESLAKAAKESLTNSVKELTNXSEA
FTNKLKEKTQELAVAAGAATDIDAKKAILKTNRDKDLGADERGKLFKSVESLSKAAQEAS
ANSVKELTSXSEKFTTKLRDSHAELGIQNVQDDNAKRAILKTHGNKDKGAKELKELSESL
EKLSKAAQAALANSVQELTSXSEAFTNRLKGSHAQLGVAAATDDHAKEAILKSNPTKDKG
AKELKDLSESVESLAKAAQEALANSVKELTN (SEQ ID NO: 153)

Construct 32: L-H13-Pko-Szid-PKi-HT22-U
SEKFTDKLKSENAALGKQDASDDDAKKAILKTHNDITKGAKELKELSESVETLLKAAKEM
LANSVKELTSXSEAFTKKLKDNNAQLGIQNVQDVEAKKAILKTNGDISKGAKELKELFES
VESLAKAAQAALANSVQELTNXSEEFTNKLKSGHADLGKQDATDDHAKAAILKTHATTDK
GAKEFKDLFESVEGLLKAAQVALTNSVKELTSXSEAFTDKLKNEHASLGKKDATDDDAKK
AILKTNVDKTKGADELIKLSGSLESLSKAAQAILANSVKELTSXSVAFTSKLKSSNAQLG
VANGNATDDDAKKAILKTNTPNDKGAKELKELFESVESLAKAAQAALVNSVQELTNXSAA
FTKKLQDGHVDLGKTDVTDDNAKEAILKTNPTKTKGATELEELFKSVEGLVKAAKEASAN
SVKELTSXSEKFTKKLSESHADIGIQAATDANAKDAILKTNPTKTKGAEELDKLFKAVEN
LSKAAKEMLANSVKDLQV (SEQ ID NO: 154)

*Figure 25H*

Construct 33: E-N-PLi-72a-VS461-Smar
STEFTNKLKSEHAVLGLDNLTDDNAQRAILKKHANKDKGAAELEKLFKAVENLSKAAQDT
LKNAVKELTSXSDDFTKKLQSSHAQLGVAGGATTDEEAKKAILRTNAIKDKGADELEKLF
KSVESLAKAAQDALANSVNELTSXSDKFTKKLTDSHAQLGAVGGAINDDRAKEAILKTHG
TNDKGAKELKELSESVESLAKAAQAALANSVKELTSXSAAFTKKLADSNADLGVAAGNAT
DDDNAKRAILKTHGHEDKGGKELKELSEAVKSLLKAAQAALANSVQELTSXSEAFTKKLQD
SNADLGKHNATDADSKEAILKTNGTKTKGAKELEELFKSVESLSKAAKEALSNSVKELTS
XSEAFTNKLKEKHAELGVNGGDTTDDNAKAAIFKTHPTKDKGVEDLEKLSESVKSLLKAA
QAALSNSVKELTS    (SEQ ID NO: 155)

Construct 34: SL10-DK15-PBes-H-HT25-M
SEAFTNRLTGSHAQHGVAAATDDHAKEAILKSNPTKDKGAKELKDLSESVESLAKAAQEA
LANSVKELTNXSEAFTKKLQDSNADLGKHDATDADAKKAILKTDATKDKGAKELEELFKS
VESLSKAAKEALSNSVKELTSXSEAFTKKLKDSNAQLGMQNGAATDAHAKAAILKTDATK
DKGATELGELFKSVESLSKAAQEASANSVKELTSXSEKFAGKLKNEHASLGKKDATDDDA
KKAILKTHGNTDKGAKELKDLSDSVESLVKAAKEMLTNSVKELTSXSQDFINKLKGGHAE
LGLVAATDANAKAAILKTNGDKTKGADEFEKLFKSVEGLLKAAQEALTNSVKELTSXNKA
FTDKLKSSHAELGIANGAATDANAKAAILKTNGTKDKGAQELEKLFESVKNLSKAAQETL
NNSVKELTS    (SEQ ID NO: 156)

Construct 35: F-PWa-PLj7-PMit-PHez-PFiM-L
SEDFTNKLKNGNAQLGLAAATDDNAKAAILKTNGTNDKGAKELKDLSDSVESLVKAAQVM
LTNSVKELTSXSEKFTTKLKDSHAELGIQSVQDDNAKKAILKTHGTKDKGAKELEELFKS
LESLSKAAQAALTNSVKELTNXSEEFTNKLKGGHAELGLAAATDENAKKAILKTNGTKDK
GAEELEKLFKSVESLAKAAKESLTNSVKELTNXSEAFTNKLKEKTQELAVAAGAATDIDA
KKAILKTNRDKDLGADERGKLFKSVESLSKAAQEASANSVKELTSXSEKFTTKLRDSHAE
LGIQNVQDDNAKRAILKTHGNKDKGAKELKELSESLEKLSKAAQAALANSVQELTSXSEA
FTNRLKGSHAQLGVAAATDDHAKEAILKSNPTKDKGAKELKDLSESVESLAKAAQEALAN
SVKELTNXSEKFTDKLKSENAALGKQDASDDDAKKAILKTHNDITKGAKELKELSESVET
LLKAAKEMLANSVKELTS    (SEQ ID NO: 157)

Construct 36: H13-Pko-Szid-PKi-HT22-U
SEAFTKKLKDNNAQLGIQNVQDVEAKKAILKTNGDISKGAKELKELFESVESLAKAAQAA
LANSVQELTNXSEEFTNKLKSGHADLGKQDATDDHAKAAILKTHATTDKGAKEFKDLFES
VEGLLKAAQVALTNSVKELTSXSEAFTDKLKNEHASLGKKDATDDDAKKAILKTNVDKTK
GADELIKLSGSLESLSKAAQAILANSVKELTSXSVAFTSKLKSSNAQLGVANGNATDDDA
KKAILKTNTPNDKGAKELKELFESVESLAKAAQAALVNSVQELTNXSAAFTKKLQDGHVD
LGKTDVTDDNAKEAILKTNPTKTKGATELEELFKSVEGLVKAAKEASANSVKELTSXSEK
FTKKLSESHADIGIQAATDANAKDAILKTNPTKTKGAEELDKLFKAVENLSKAAKEMLAN
SVKDLQV    (SEQ ID NO: 158)

Figure 25I

Construct 37: Smar-PLi-H13-PFiM-SL10-PMit-PKi-PBes
SEAFTNKLKEKHAELGVNGGDTTDDNAKAAIFKTHPTKDKGVEDLEKLSESVKSLLKAAQ
AALSNSVKELTSXSDKFTKKLTDSHAQLGAVGGAINDDRAKEAILKTHGTNDKGAKELKE
LSESVESLAKAAQAALANSVKELTSXSEAFTKKLKDNNAQLGIQNVQDVEAKKAILKTNG
DISKGAKELKELFESVESLAKAAQAALANSVQELTNXSEAFTNRLKGSHAQLGVAAATDD
HAKEAILKSNPTKDKGAKELKDLSESVESLAKAAQEALANSVKELTNXSEAFTNRLTGSH
AQHGVAAATDDHAKEAILKSNPTKDKGAKELKDLSESVESLAKAAQEALANSVKELTNXS
EAFTNKLKEKTQELAVAAGAATDIDAKKAILKTNRDKDLGADERGKLFKSVESLSKAAQE
ASANSVKELTSXSVAFTSKLKSSNAQLGVANGNATDDDAKKAILKTNTPNDKGAKELKEL
FESVESLAKAAQAALVNSVQELTNXSEAFTKKLKDSNAQLGMQNGAATDAHAKAAILKTD
ATKDKGATELGELFKSVESLSKAAQEASANSVKELTS    (SEQ ID NO: 159)

Construct 38: HT22-Pko-PLj7-VS461-DK15-HT25-A-D
SAAFTKKLQDGHVDLGKTDVTDDNAKEAILKTNPTKTKGATELEELFKSVEGLVKAAKEA
SANSVKELTSXSEEFTNKLKSGHADLGKQDATDDHAKAAILKTHATTDKGAKEFKDLFES
VEGLLKAAQVALTNSVKELTSXSEEFTNKLKGGHAELGLAAATDENAKKAILKTNGTKDK
GAEELEKLFKSVESLAKAAKESLTNSVKELTNXSEAFTKKLQDSNADLGKHNATDADSKE
AILKTNGTKTKGAKELEELFKSVESLSKAAKEALSNSVKELTSXSEAFTKKLQDSNADLG
KHDATDADAKKAILKTDATKDKGAKELEELFKSVESLSKAAKEALSNSVKELTSXSQDFI
NKLKGGHAELGLVAATDANAKAAILKTNGDKTKGADEFEKLFKSVEGLLKAAQEALTNSV
KELTSXSETFTNKLKEKHTDLGKEGVTDADAKEAILKTNGTKTKGAEELGKLFESVEVLS
KAAKEMLANSVKELTSXSESFTKKLSDNQAELGIENATDDNAKKAILKTHNAKDKGAEEL
VKLSESVAGLLKAAQAILANSVKELTSPVVAESPKKP    (SEQ ID NO: 160)

Construct 39: 72a-F-E-M-U-I-L-H
SAAFTKKLADSNADLGVAAGNATDDNAKRAILKTHGHEDKGGKELKELSEAVKSLLKAAQ
AALANSVQELTSXSEDFTNKLKNGNAQLGLAAATDDNAKAAILKTNGTNDKGAKELKDLS
DSVESLVKAAQVMLTNSVKELTSXSTEFTNKLKSEHAVLGLDNLTDDNAQRAILKKHANK
DKGAAELEKLFKAVENLSKAAQDTLKNAVKELTSXNKAFTDKLKSSHAELGIANGAATDA
NAKAAILKTNGTKDKGAQELEKLFESVKNLSKAAQETLNNSVKELTSXSEKFTKKLSESH
ADIGIQAATDANAKDAILKTNPTKTKGAEELDKLFKAVENLSKAAKEMLANSVKDLQVXS
EEFTAKLKGEHTDLGKEGVTDDNAKKAILKTNNDKTKGADELEKLFESVKNLSKAAKEML
TNSVKELTSXSEKFTDKLKSENAALGKQDASDDDAKKAILKTHNDITKGAKELKELSESV
ETLLKAAKEMLANSVKELTSXSEKFAGKLKNEHASLGKKDATDDDAKKAILKTHGNTDKG
AKELKDLSDSVESLVKAAKEMLTNSVKELTS    (SEQ ID NO: 161)

Construct 40: Szid-PHez-PWa-B-K-N-C
SEAFTDKLKNEHASLGKKDATDDDAKKAILKTNVDKTKGADELIKLSGSLESLSKAAQAI
LANSVKELTSXSEKFTTKLRDSHAELGIQNVQDDNAKRAILKTHGNKDKGAKELKELSES
LEKLSKAAQAALANSVQELTSXSEKFTTKLKDSHAELGIQSVQDDNAKKAILKTHGTKDK
GAKELEELFKSLESLSKAAQAALTNSVKELTNXSEEFSTKLKDNHAQLGIQGVTDENAKK
AILKANAAGKDKGVEELEKLSGSLESLSKAAKEMLANSVKELTSXSEDFTKKLEGEHAQL
GIENVTDENAKKAILITDAAKDKGAAELEKLFKAVENLAKAAKEMLANSVKELTSXSDDF
TKKLQSSHAQLGVAGGATTDEEAKKAILRTNAIKDKGADELEKLFKSVESLAKAAQDALA
NSVNELTSXSEEFTKKLKEKHTDLGKKDATDVHAKEAILKTNGTKDKGAAELEKLFESVE
NLAKAAKEMLSNSVKELTS    (SEQ ID NO: 162)

*Figure 25J*

| Strain | Protein accession # | DNA accession # |
| --- | --- | --- |
| Smar | AAN87993 | AY150195 |
| Pli | CAH56461 | AJ841691 |
| H13 | AAB36997 | L42889 |
| PFim | CAG44493 | AJ749871 |
| SL10 | CAA59251 | X84780 |
| PMit | CAG44496 | AJ49874 |
| PKi | CAG44499 | AJ49877 |
| PBes | CAG44498 | AJ749876 |
| HT22 | BAA08464 | D49504 |
| Pko | CAA44093 | X62162 |
| KK5 | AAO17303 | AF334784 |
| PLj7 | CAA57243 | X81523 |
| VS461 | AAB37014 | L42871 |
| DK15 | BAA24124 | AB009894 |
| HT25 | BAA08462 | D49502 |
| 2398 | AAR97893 | AY491403 |
| B31 | AAC66329 | AE000792 |
| 72a | ABD95820 | DQ437456 |
| PAd | AAQ19283 | AY275225 |
| N40 | AAQ19279 | AY275221 |
| B356 | AAN37936 | AF467873 |
| LDP116 | ABK41068 | EF053527 |
| cs5 | ABD95831 | DQ437467 |
| 148 | AAQ19278 | AY275220 |
| HB19 | AAC43297 | U04281 |
| SI1 | AAK69466 | AF278593 |
| LDS101 | ABK41065 | EF053524 |
| Szid | AAN88007 | AY150209 |
| PHez | CAG44495 | AJ749873 |
| PWa | CAB46232 | AJ132794 |
| LDP73 | ABK41066 | EF053525 |
| DK7 | CAA52004 | X73625 |
| LDP74 | ABK41058 | EF053517 |
| LDP63 | ABK41056 | EF053515 |

*Figure 26*

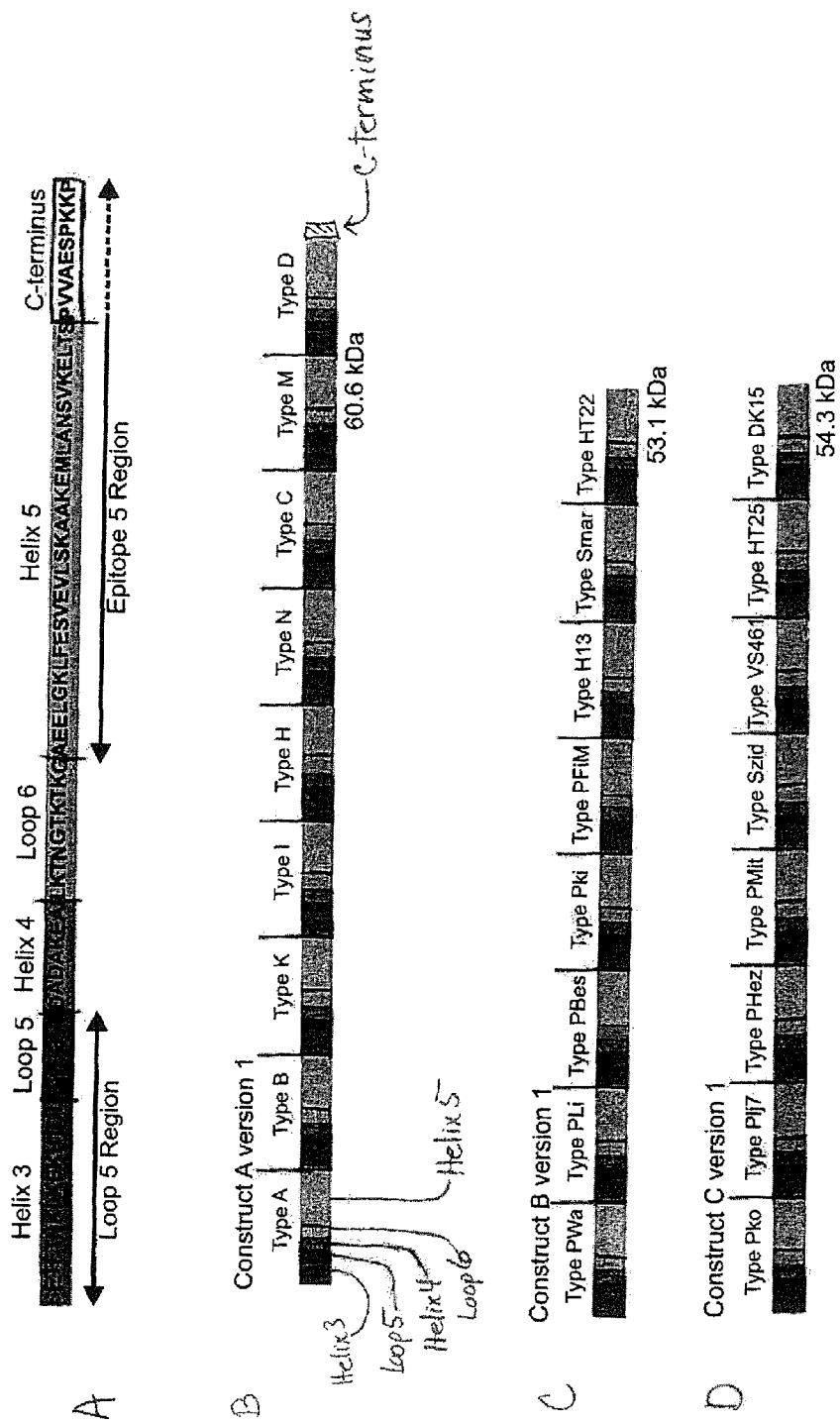
Figure 28A-D

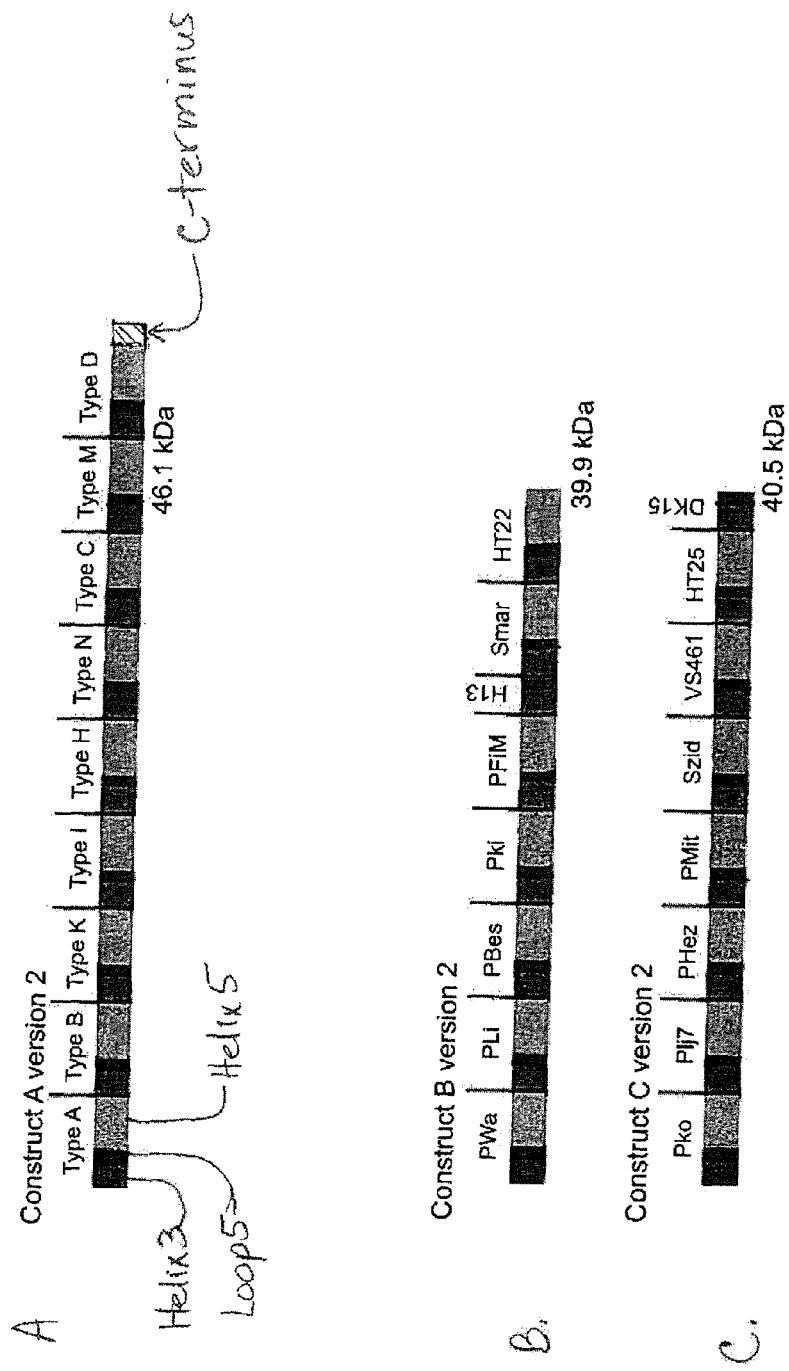
Figure 29 A-C

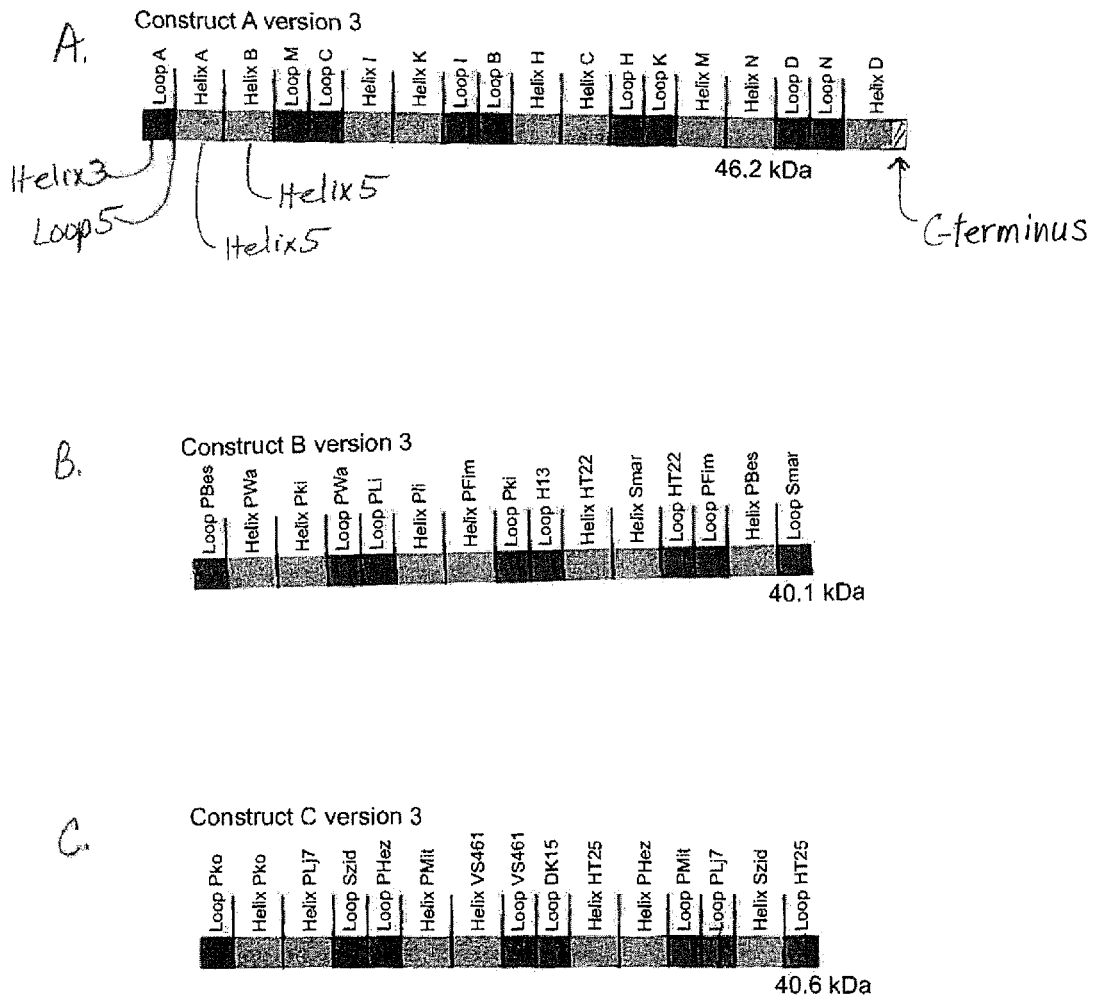
Figure 30A-C

POLYVALENT CHIMERIC OSPC VACCINOGEN AND DIAGNOSTIC ANTIGEN

BACKGROUND OF THE INVENTION

1. Field of the Invention

The invention generally relates to a vaccine and diagnostic for Lyme's disease. In particular, the invention provides a chimeric polyvalent recombinant protein comprising immunodominant epitopes of loop 5 and/or alpha helix 5 regions/domains of outer surface protein C (OspC) types associated with mammalian infections.

2. Background of the Invention

Lyme disease is the most common arthropod-borne disease in North America and Europe. It is caused by the spirochetes *Borrelia burgdorferi*, *B. garinii* and *B. afzelii*. Transmission to mammals occurs through the bite of infected *Ixodes* ticks [Burgdorfer et al, 1982, Benach et al., 1983]. Considerable morbidity is associated with Lyme disease and there are areas in the United States and Europe where up to 3% of the population is infected annually [Fahrer et al., 1991]. Infection results in a multi-systemic inflammatory disease with early stage symptoms that may include erythema migrans, low-grade fever, arthralgia, myalgia, and headache [Steere et al., 1977a]. Late stage clinical manifestations can be severe and may include in part, arthritis [Steere et al., 1977a; Eiffert et al., 1998; Steere et al., 2004], carditis [Asch et al., 1994; Nagi et al., 1996 Barthold et al., 1991] and neurological complications [Nachman and Pontrelli, 2003; Coyle and Schutzer 2002]. In addition, Lyme disease has significant socio-economic costs, manifested by reductions in outdoor recreational and social activities due to concerns about tick exposure.

Pharmacoeconomic studies indicate that a clear need exists for a Lyme disease vaccine, particularly in populations where the annual disease risk exceeds 1% [Meltzer et al., 1999; Shadick et al., 2001]. However, at the present time a vaccine is not commercially available. The first human Lyme disease vaccine was the OspA-based LYMErix (GlaxoSmithKline); however, its tenure was short and, citing a drop in sales, GSK voluntarily pulled it from the market in 2002. The decline in sales can be traced to concerns, real or perceived, of possible adverse effects including a chronic inflammatory arthritis that could theoretically develop in HLA-DR4-positive recipients [Kalish et al., 1993]. While new OspA-based vaccinogens are being developed to mitigate this potential complication [Koide et al., 2005; Willett et al., 2004], questions remain about the viability of an OspA-based vaccine. One concern is the frequency of boosts required to maintain long term protection. OspA is expressed in the tick midgut, is rapidly downregulated upon tick feeding, and is not expressed in mammals [Gilmore et al., 2001; Schwan et al., 1995]. The mechanism of action of OspA-based vaccines is to target spirochetes within the tick and prevent their transmission [de Silva et al., 1999]. Since transmission occurs within 48 hours of tick feeding, effective protection is dependent on high circulating titers of anti-OspA antibodies, necessitating frequent boosts. The inherent problems associated with OspA-based vaccines can be avoided by the use of antigens that are expressed at high levels during early infection and that elicit bactericidal antibody.

OspC has received considerable attention in Lyme disease vaccine development. It is a 22 kDa, surface exposed lipoprotein [Fuchs et al., 1992] encoded on a 26 kb circular plasmid that is universal among isolates of the *B. burgdorferi sensu lato* complex [Marconi et al., 1993; Sadziene et. al., 1993]. Its expression is induced upon tick feeding and is maintained during early mammalian infection [Schwan, 2004], and it is genetically stable during infection [Hodzic et al., 2000; Stevenson et al., 1994]. Anti-OspC antibodies have been demonstrated to protect against infection, but only against strains expressing OspC that is closely related in sequence to the vaccinogen [Gilmore et al., 1996; Bockenstedt et al., 1997; Gilmore and Mbow, 1999; Mathiesen et al., 1998; Scheiblhofer et al., 2003; Jobe et al., 2003; Rousselle et al., 1998; Wallich et al., 2001; Mbow et al., 1999; Probert et al., 1997; Brown et al., 2005; Probert and LeFebvre 1994]. Analyses of OspC sequences have delineated ~21 OspC phyletic clusters or types that are differentiated by letter designation (A through U) [Seinost et al., 1999; Wang et al., 1999]. While sequence variation within a cluster is generally less than 2%, between OspC types it can be as high as 22% [Wang et al., 1999; Theisen et al., 1995; Brisson and Dykhuizen, 2004]. Such inter-type variation of epitopes most likely explains the limited range of protection afforded by vaccination with a single OspC type.

U.S. Pat. No. 6,248,562 (Jun. 19, 2001) to Dunn and Luft describes chimeric *Borrelia* proteins that consist of at least two polypeptides from corresponding and/or non-corresponding proteins from the same and/or different species of *Borrelia*. The chimeric polypeptides incorporated in the chimeric proteins are derived from any *Borrelia* protein from any strain of *Borrelia* and include OspA, OspB, OspC, OspD, p12, p39, p41, p66, and p93. The chimeric proteins can be used as immunodiagnostic reagents and as vaccine immunogens against *Borrelia* infection. However, there is no reference to loop 5 and alpha 5 epitopes present in OspC proteins.

U.S. Pat. Nos. 6,872,550 and 6,486,130 (Mar. 29, 2005, and Nov. 26, 2002, respectively) both to Livey, describe constructs for use a vaccines against Lyme disease which contain OspC antigens. However, there is no mention of the characterization of loop 5 and alpha 5 epitopes in these patents.

U.S. Pat. No. 7,008,625 (Mar. 7, 2006) to Dattwyler et al. discloses antigenic polypeptides of a variety of *Borrelia* strains and/or proteins within a single protein. The chimeric *Borrelia* proteins are made up of polypeptide fragments of the outer surface protein OspA and the outer surface protein OspC. These proteins can be effective against Lyme borreliosis as well as for immunodiagnostic reagents. However, there is no mention of the characterization of loop 5 and alpha 5 epitopes.

The publication "Recombinant Chimeric *Borrelia* Proteins for Diagnosis of Lyme Disease" (Maria J. C. Gomes-Solecki et al. 2000. J. Clin. Microbiol., 38: 2530-2535) is related to the two above-identified patents. The authors engineered recombinant chimeras, each containing portions of the key antigenic proteins of *Borrelia burgdorferi*, OspA, OspB, OspC, flagellin (Fla or p41), and a protein p93. The paper is directed to diagnosis, but describes applications to vaccinogens in the closing paragraph. The authors mention that better chimeras can be created with further study of the genetic variability of the important epitopes but do not mention the loop 5 and alpha 5 epitopes of OspC.

The prior art has thus-far failed to provide a vaccine that affords broad protection against multiple OspC types for use in the prevention and/or treatment of Lyme disease.

SUMMARY OF THE INVENTION

The invention provides a chimeric polyvalent recombinant protein for use as a vaccine and diagnostic for Lyme disease. The invention is based in part on the discovery and characterization of novel protective, epitopes from several different OspC phyletic groups (types), each of which is associated with mammalian (e.g. human) Lyme disease infection. Identification of these epitopes made possible the construction of a chimeric protein or proteins that comprises a plurality of epitopes from different OspC infective types. Thus, when used as a vaccine, the chimeric recombinant protein elicits broad protection against a plurality of *Borrelia* strains that express those OspC types, and are associated with mammalian Lyme disease. In addition, the chimeric protein is useful as a diagnostic tool to identify individuals that have antibodies to the epitopes, and to thus determine if an individual has been exposed to or infected by the causative agent of Lyme disease. In some embodiments of the invention, the epitopes are B-cell epitopes and/or immunodominant epitopes.

It is an object of this invention to provide a chimeric recombinant protein comprising epitopes from loop 5 region or alpha helix 5 region, or both, of two or more outer surface protein C (OspC) types. In one embodiment, the OspC types are selected from the group consisting of Smar, PLi, H13, PFiM, SL10, PMit, PKi, Pbes, HT22, Pko, PLj7, VS461, DK15, HT25, A, 72a, F, E, M, D, U, I, L, H, Szid, PHez, PWa, B, K, N, C and T. In some embodiments, the chimeric protein has an amino acid sequence selected from the group consisting of SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, and SEQ ID NO: 267. In some embodiments, the OspC types are associated with invasive *Borrelia* infection.

The invention further provides a method for eliciting an immune response against *Borrelia* in an individual in need thereof. The method comprises the step of administering to the individual a chimeric recombinant protein comprising epitopes from loop 5 region or alpha helix 5 region, or both, of two or more outer surface protein C (OspC) types. In one embodiment of the invention, the OspC types are selected from the group consisting of Smar, PLi, H13, PFiM, SL10, PMit, PKi, Pbes, HT22, Pko, PLj7, VS461, DK15, HT25, A, 72a, F, E, M, D, U, I, L, H, Szid, PHez, PWa, B, K, N, C and T. In some embodiments, the chimeric protein has an amino acid sequence selected from the group consisting of SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, and SEQ ID NO: 267. In some embodiments, the OspC types are associated with invasive *Borrelia* infection.

The invention further provides a method for ascertaining whether an individual has been exposed to or infected with *Borrelia*. The method comprises the steps of 1) obtaining a biological sample from the individual; 2) exposing the biological sample to at least one recombinant chimeric protein, wherein the at least one chimeric protein comprises epitopes from loop 5 region or alpha helix 5 region, or both, of two or more outer surface protein C (OspC) types; and 3) determining whether antibodies in said biological sample bind to the at least one chimeric protein, wherein detection of antibody binding is indicative of prior exposure to or infection with *Borrelia*. In one embodiment of the invention, the OspC types are selected from the group consisting of Smar, PLi, H13, PFiM, SL10, PMit, PKi, Pbes, HT22, Pko, PLj7, VS461, DK15, HT25, A, 72a, F, E, M, D, U, I, L, H, Szid, PHez, PWa, B, K, N, C and T. In some embodiments, the chimeric protein has an amino acid sequence selected from the group consisting of SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, and SEQ ID NO: 267. In some embodiments of the invention, the OspC types are associated with invasive *Borrelia* infection.

The invention further provides antibodies to a chimeric recombinant protein comprising epitopes from loop 5 region or alpha helix 5 region, or both, of two or more outer surface protein C (OspC) types. In one embodiment of the invention, the OspC types are selected from the group consisting of Smar, PLi, H13, PFiM, SL10, PMit, PKi, Pbes, HT22, Pko, PLj7, VS461, DK15, HT25, A, 72a, F, E, M, D, U, I, L, H, Szid, PHez, PWa, B, K, N, C and T. In some embodiments, the chimeric protein has an amino acid sequence selected from the group consisting of SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, and SEQ ID NO: 267. In some embodiments, the OspC types are associated with invasive *Borrelia* infection. The antibodies may be either polyclonal or monoclonal. In one embodiment, the antibody is bactericidal for *Borrelia* spirochetes.

The invention further provides an immunogenic cocktail of chimeric recombinant proteins. Each chimeric recombinant protein in the cocktail comprises epitopes from loop 5 region or alpha helix 5 region, or both, of two or more outer surface protein C (OspC) types.

BRIEF DESCRIPTION OF THE DRAWINGS

FIGS. 4A and B. Comparative analysis of segments of the loop 5 and alpha 5 epitopes at the inter- and intratype levels, shown in tabular form.

FIG. 5. Demonstration of a loop 5 antibody response in multiple animals infected with different type A OspC producing strains. Immunoblots of either 1) full length type A OspC or 2) a fragment containing amino acids 130-150 (which includes loop 5) were screened with infection sera. The strain used to generate the infection sera and the specific mouse (m) from which the sera were collected is indicated above each panel. The timepoint during infection when the sera were collected is also indicated. An equal amount of protein was immunoblotted for each and all were exposed to film for the same amount of time.

FIGS. 7A and B. Identification of the specific residues that comprise the type A OspC loop 5 epitopes through PepSpot analysis. Overlapping peptides that span the loop 5 domain were generated and spotted onto nitrocellulose. The immobilized peptides were then screened with serum from mice infected with a clonal population of a type A OspC-producing strain (B31 MI) or with serum from human Lyme disease patients (as indicated). (A) Immunoblotting results for loop 5 domain; (B) peptide sequences.

FIG. 8. Demonstration that loop 5 is surface exposed and that antibody to loop 5 is bactericidal. The IFAs and bactericidal assays were conducted with antiserum generated against type A loop 5. (A) The results demonstrate the specificity of the anti-loop 5 antiserum. Whole-cell lysates of B. burgdorferi B31 MI, B. parkeri, and r-type A loop 5 fragment were separated by sodium dodecyl sulfatepolyacrylamide gel electrophoresis, immunoblotted, and screened with anti-type A loop 5 antiserum (1:1,000). Molecular masses of the protein markers are to the right of the figure.

FIGS. 18A and B. Assessment of the antibody response to the ABKD vaccinogen administered in Freund's adjuvants or alum. In panel A are the results of a quantitative ELISA titration of IgG in mouse sera generated against the ABKD vaccine emulsified in Freund's adjuvants (solid bars) or adsorbed to alum (hatched bars). The sera were titrated against immobilized ABKD vaccinogen or full length, r-OspC of types A, B, K, and D. In panel B is shown the isotype profile of the sera bound to immobilized ABKD vaccinogen. The bound Ig isotypes were detected with biotinylated isotype-specific secondary antibodies and peroxidase-conjugated streptavidin.

FIG. 20A-C. Species, geographical and biological isolation data for assigned OspC types.

FIG. 23. Alignment of the epitope-containing region of OspC protein sequences from all OspC types defined in this study. All sequences within OspC types that differ by more than one amino acid are indicated by a representative sequence. Identity threshold for shading is 80%. Secondary structural alpha helices and loops (corresponding to the B31 structure) are shown below the alignment (Kumaran et al, 2001).

FIG. 24. Clustal X alignment of the parental OspC sequences used in the construction of the ABKD chimeric vaccinogen and physical location of epitope-containing regions included in the vaccinogen. The locations of the epitope-containing region of OspC type A (loop 5 region, light grey box) and types B, K, and D (alpha helix 5 region) dark grey box) are highlighted within a ClustalX alignment of the parent sequences.

FIG. 25A-J. Exemplary chimeric vaccinogens of the invention. The construct title indicates the OspC type-specific loop 5 and helix 5 epitopes incorporated in the construct, as well their order. The bold X represents the position of optional linker sequences.

FIG. 26. Protein and DNA accession numbers of OspC from several *Borrelia* strains.

FIG. 28A-D. A, general epitope locations within a representative sequence of OspC from *B. burgdorferi*; B, epitope pattern in A9.1 construct; C, epitope pattern in B9.1 construct; D, epitope pattern in C9.1 construct.

FIG. 29A-C. A, epitope pattern in A9.2 construct; B, epitope pattern in B9.2 construct; C, epitope pattern in C9.2 construct.

FIG. 30A-C. A, epitope pattern in A9.3 construct; B, epitope pattern in B9.3 construct; C, epitope pattern in C9.3 construct. "Loop" indicates the loop 5 region which includes helix 3.

DETAILED DESCRIPTION OF THE PREFERRED EMBODIMENTS OF THE INVENTION

Figure 1:
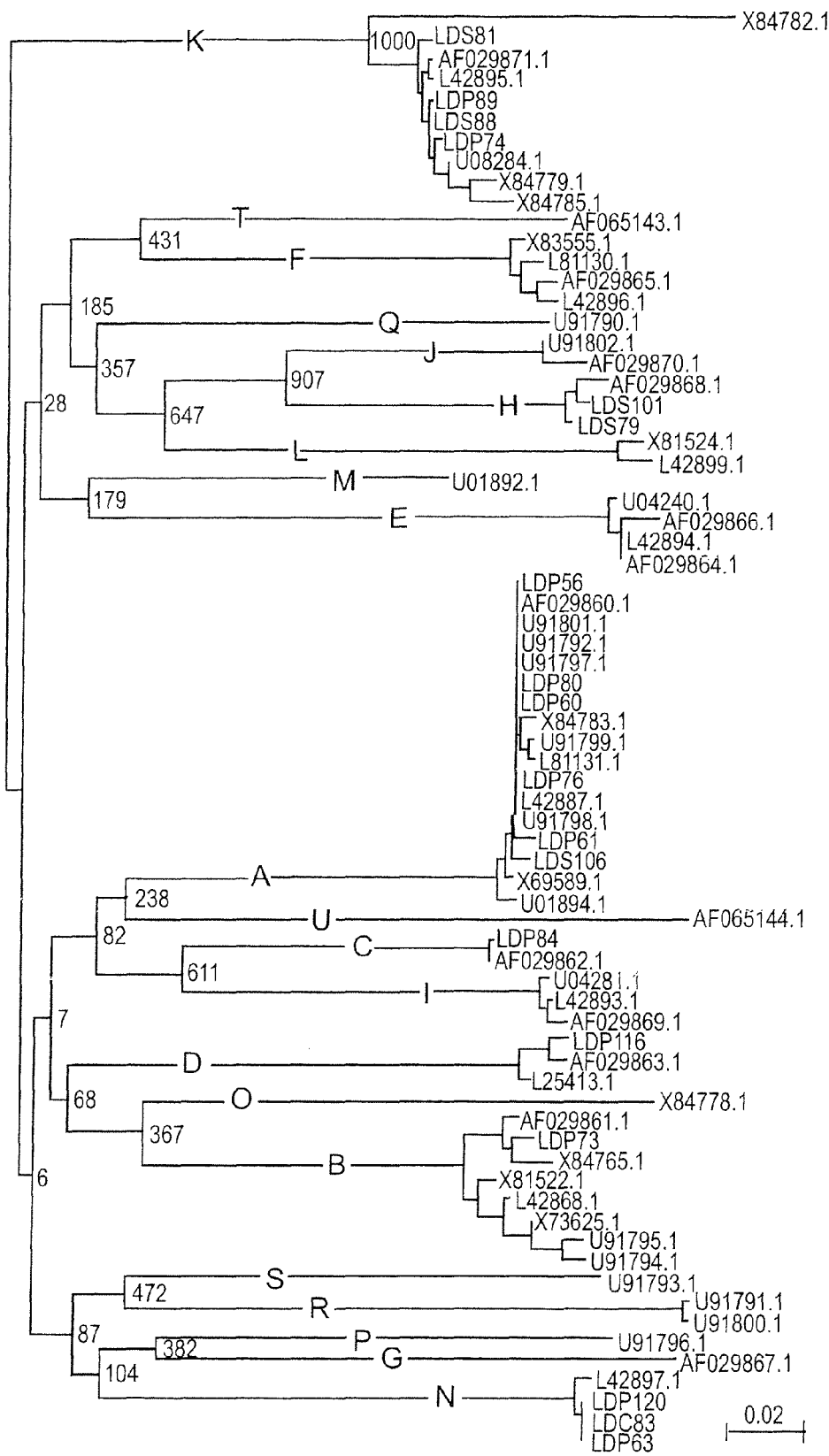
FIG. 1. Evolutionary relationships of OspC sequences derived from human patients in Maryland: OspC type identification. OspC genes were PCR amplified, sequenced, and a phylogram was constructed. Database sequences representative of the 22 ospC types were included in the analysis (accession numbers are indicated). The type designation (capital letters) assigned to each phyletic group is indicated by the capital letters on each branch. Bootstrap values (1000 trials) are displayed at each node critical for group differentiation.

The present invention is based on the identification and characterization of novel protective, type-specific epitopes of OspC types that are associated with human Lyme disease infection. The novel epitopes are located within two domains (regions) in the carboxyl-terminal half of OspC. Neither domain was previously identified as highly immunogenic. The first domain (referred to as "alpha helix 5 region/domain" or "alpha 5 region/domain" or "helix 5 region/domain" herein) is located between residues 160 and 200, and contains secondary structural elements including a portion of loop 6, alpha helix 5, and the unstructured C-terminal domain (Kumaran et al., 2001). The second domain ("loop 5 region/domain" herein) is located between residues 131 and 159 and contains secondary structural elements including a portion of alpha helix 3, loop 5 and alpha helix 4 (Kumaran et al., 2001). Each of these regions contains at least one epitope that may be used in the practice of the present invention. Epitopes from these two domains, or antigenic peptides or polypeptides from within these two regions, may be used in the practice of the present invention, either alone or preferably in combination with other epitopes in a chimeric immunogen. In some embodiments of the invention, the epitopes are immunodominant epitopes. Typically, the epitopes are B-cell epitopes, although T-cell epitopes are not excluded.

Discovery of the novel epitopes, and mapping of the epitopes to different OspC types, has made possible the construction of multivalent chimeric proteins that contain a plurality of linear, type-specific immunodominant epitopes from multiple OspC types. When used as a vaccine, the multivalent (polyvalent) recombinant chimeric protein elicits broad protection against infection with Borrelia spirochetes expressing the OspC types that correspond to those in the chimeric protein, i.e. those Borrelia that are highly infective. In addition, the chimeric protein is useful as a diagnostic tool to identify individuals that have antibodies to the epitopes contained in the chimeric protein, and to thus determine if an individual has been exposed to and/or infected by a causative agent of Lyme disease.

In order to facilitate the understanding of the present invention, the following definitions are provided:

Antigen: term used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, reference to it as either an immunogen or antigen will typically be made according to its intended utility. The terms "antigen", "immunogen" and "epitope" may be used interchangeably herein.

B-cell Epitope: a specific chemical domain on an antigen that is recognized by a B-cell receptor, and which can be bound by secreted antibody. The term is interchangeable with "antigenic determinant".

Immunodominant epitope: The epitope on a molecule that induces the dominant, or most intense, immune response.

Linear epitope: An epitope comprising a single, non-interrupted, contiguous chain of amino acids joined together by peptide bonds to form a peptide or polypeptide. Such an epitope can be described by its primary structure, i.e. the linear sequence of amino acids in the chain.

Conformational epitope: an epitope comprised of at least some amino acids that are not part of an uninterrupted, linear sequence of amino acids, but which are brought into proximity to other residues in the epitope by secondary, tertiary and/or quaternary interactions of the protein. Such residues may be located far from other resides in the epitope with respect to primary sequence, but may be spatially located near other residues in the conformational epitope due to protein folding.

Loop 5 region/domain: The region of OspC that includes residues that align with residues 131 to 159 of the type A OspC sequences as denoted in FIG. 23. Strain B31 OspC secondary structural elements included in the region are a portion of alpha helix 3, loop 5, and alpha helix 4, as defined by Kumaran et al. (2001).

Figure 23:
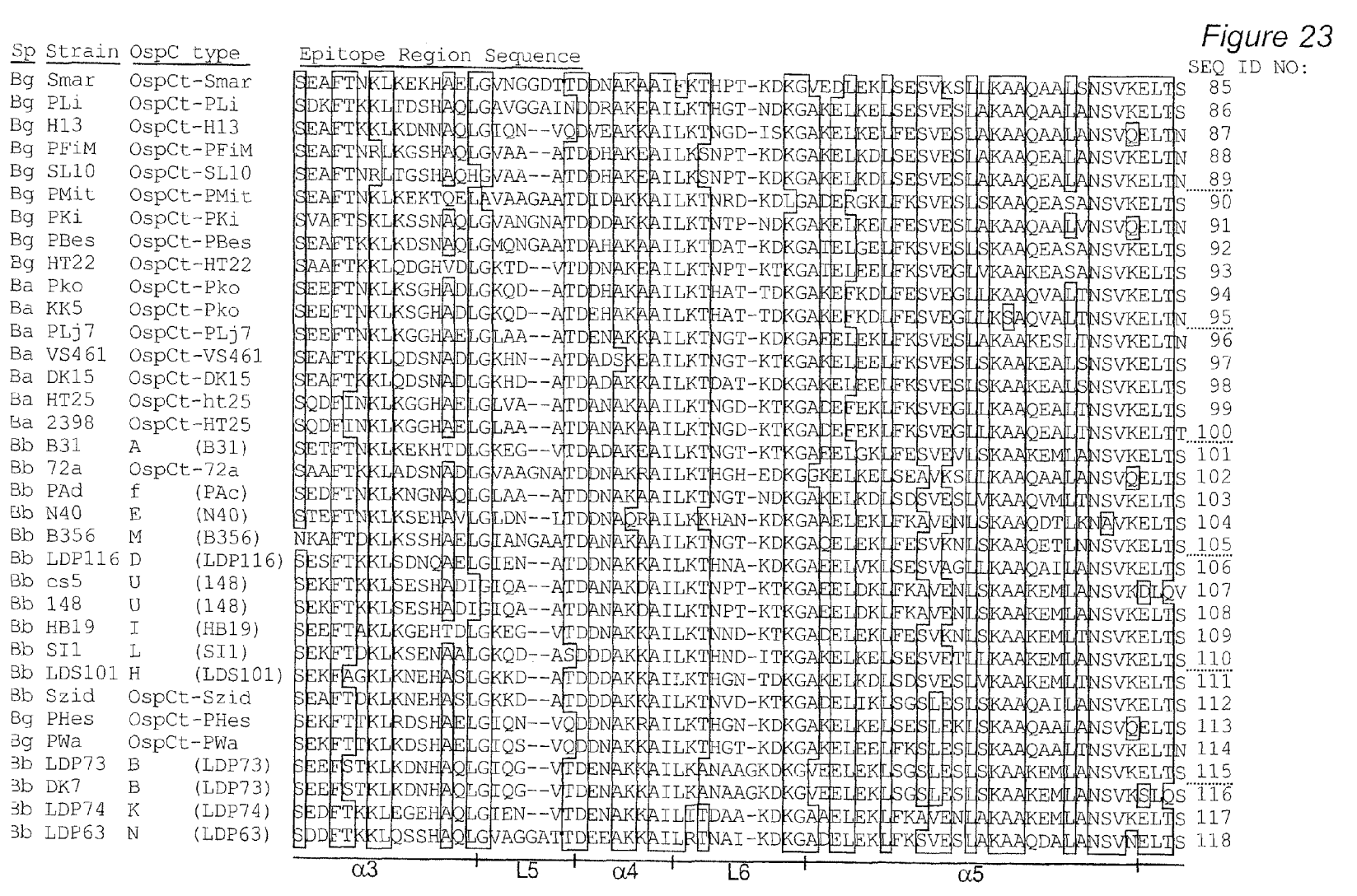

Alpha helix 5 region/domain: The region of OspC that includes residues that align with amino acids 160 to 200 of the strain B31 (OspC type A) sequence as shown in FIG. 23, as well as the C-terminal portion of the protein (amino acids 201-210 of the B31 sequence) not shown in FIG. 23. Strain B31 OspC secondary structural elements included in this region are a portion of loop 6, alpha helix 5, and the unstructured C-terminal domain, as defined by Kumaran et al. (2001).

Protein. A linear sequence of from about 100 or more amino acids covalently joined by peptide bonds.

Polypeptide: A linear sequence of from about 20 to about 100 amino acids covalently joined by peptide bonds.

Peptide: A linear sequence of about 20 or fewer amino acids covalently joined by peptide bonds.

The terms "protein", "polypeptide" and "peptide" may be used interchangeably herein.

Chimeric protein: a recombinant protein whose primary sequence comprises multiple peptide, polypeptide, and/or protein sequences which do not occur together in a single molecule in nature.

Valency of a chimeric protein (e.g. "multivalent" or "polyvalent") refers to the number of OspC type-specific epitope-bearing polypeptides included in the chimeric vaccinogen. For example, a divalent chimera may be composed of alpha helix 5 of type A and alpha helix 5 of type B, or, alpha helix 5 of type A and loop 5 of type A. There may be multiple distinct epitopes in each polypeptide epitope-bearing region.

Original or native or wild type sequence: The sequence of a peptide, polypeptide, protein or nucleic acid as found in nature.

Recombinant peptide, polypeptide, protein or nucleic acid: peptide, polypeptide, protein or nucleic acid that has been produced and/or manipulated using molecular biology techniques such as cloning, polymerase chain reaction (PCR), etc.

Type-specific: associated primarily with a single phyletic group.

Invasive infection: An OspC protein is said to be "associated with invasive infection" if Borrelia bearing the OspC type have been isolated during human infection from locations other than the skin surrounding the initial inoculation by tick bite (e.g. from plasma, cerebrospinal fluid, etc.).

The invention thus provides recombinant chimeric proteins that comprise multiple linear epitopes from the loop 5 and/or alpha helix 5 regions, at least two of which are from different OspC types that are associated with invasive infection. Preferably, antigenic epitopes representing from about 2 to about 20, and preferably from about 5 to about 13, different OspC types are included in a single chimeric protein. In some embodiments, the chimeric recombinant protein comprises epitopes from 5 OspC types, or from 6 OspC types, or from 7 OspC types, or from 8 OspC types, or from 9 OspC types, or from 13 OspC types. While typically at least two of the epitopes are different from one another in primary sequence and originate from different OspC types, it is also possible to include multiple copies of a single type of epitope in a chimera, or to include several sequences that are based on or derived from the original sequence of the same OspC type. While the total number of linear epitopes in a chimera may vary somewhat, in general, the range will be from about 10 to 30. In one embodiment of the invention, the immunodominant epitopes are selected from two or more of OspC types Smar, PLi, H13, PFiM, SL10, PMit, PKi, Pbes, HT22, Pko, PLj7, VS461, DK15, HT25, A, 72a, F, E, M, D, U, I, L, H, Szid, PHez, PWa, B, K, N, C and T. In one embodiment, the chimeric protein is tetravalent and contains epitopes from types A, B, K and D. In another, embodiment, the chimeric protein is octavalent and contains epitopes from OspC types E, N, I, C, A, B, K and D. However, those of skill in the art will recognize that epitopes from other combinations of OspC types may also be used, so long as the resulting chimera produces a suitable immune response and/or is effective as a vaccine in preventing Lyme disease. Examples of other suitable combinations, as demonstrated by the numerous examples disclosed herein, include but are not limited to: 1) A, B, K, D, E, N, C; 2) I, C, A, B, K, D; and 3) C, A, B, K, D.

In some embodiments, the chimeric protein has an amino acid sequence selected from the group consisting of SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267; or is an amino acid sequence with at least 95%, 96%, 97%, 98%, 99% or more identity to any one of the amino acid sequences set forth in SEQ ID NOS: 250-267.

In further embodiments, at least one of the OspC types in the chimeric recombinant protein is associated with invasive *Borrelia* infection in humans.

The invention further comprises a method for eliciting an immune response against *Borrelia* in an individual in need thereof using these chimeric recombinant proteins.

In a further embodiment, the invention provides diagnostic methods for ascertaining whether an individual has been exposed to or infected with *Borrelia*. The methods comprise the steps of 1) obtaining a biological sample from said individual, 2) exposing the biological sample to at least one recombinant chimeric protein as described herein; and 3) determining whether antibodies in the biological sample bind to the at least one chimeric protein. Detection of antibody binding is indicative of prior exposure to or infection with *Borrelia*.

In yet other embodiments, the invention provides antibodies to the chimeric recombinant proteins described herein; and immunogenic cocktails which include the chimeric recombinant proteins described herein.

In some embodiments, both the loop 5 and alpha helix 5 regions will be included. For example, an "E, N, I, C, A, B, K, D" construct may contain both the loop 5 and helix 5 regions of each of OspC types E, N, I, C, A, B, K, and D. However, this need not be the case. For example, the loop 5 region of type A and the alpha helix 5 regions of E, N, I, C, B, K, and D may be included; or only the loop 5 region for each OspC type may be included; or only the alpha helix 5 region; or other combinations may be included (e.g. loop 5 region of types E, N, I, and C and the alpha helix 5 region of types A, B, K, and D. Many such combinations will occur to those of skill in the art, and all such variations are intended to be encompassed herein.

Further, the linear order of the epitopes within a chimera may vary. In general, the order, from amino to carboxyl terminus, will be "loop 5 region, alpha helix 5 region, loop 5 region, alpha helix 5 region . . . " etc. For example, in the case of the E, N, I, C, A, B, K, D construct, a preferred order is "E-type loop 5 region, E-type alpha helix 5 region; N-type loop 5 region, N-type alpha helix 5 region; 1-type loop 5 region, 1-type alpha helix 5 region . . . ", etc. along the length of the chimera, with the different OspC types and/or the different domains optionally separated by neutral linker sequences. However, this order may vary, depending, for example, on the elements that are chosen for inclusion in the chimera. Any order of OspC types and domains may be used, so long as the resulting chimera produces a suitable immune response and/or is effective as a vaccine in preventing Lyme disease, or can be effectively used in a diagnostic. Examples of exemplary chimera sequences are given in FIG. 25A-J. A key to the protein and DNA accession numbers for OspC from several strains of *Borrelia* is presented in tabular form in FIG. 26.

The amino acid sequences that are included in the chimeric protein may comprise the alpha helix 5 and/or the loop 5 regions, or antigenic fragments thereof. By "antigenic fragment" we mean a segment of the primary OspC sequence that contains at least one linear epitope recognized during infection. Such an epitope, when expressed in a recombinant protein subunit of OspC, retains the ability to bind infection-induced antibodies in a manner similar to the binding of wild-type protein expressed at the cell surface. An individual antigenic fragment may contain more than one distinct epitope. Those of skill in the art will recognize that measurement of the affinity or avidity of antibodies for an epitope is somewhat imprecise, and that the affinity/avidity can change significantly during the immune response, e.g. by affinity maturations/somatic hypermutataiton. In general, however, the affinity/avidity of binding of antibodies to the chimeric protein is in the range of at least about 50%, preferably about 60%, more preferably about 70%, even more preferably about 80%, and most preferably about 90-100% or even greater, than the affinity exhibited by native, intact alpha 5 or loop 5. In general, the antigenic sequences that are included in the chimeric proteins will contain from about 20 to about 100 amino acids, and preferably from about 30 to about 70 amino acids, and the chimeric proteins themselves will contain a total of from about 160 to about 800 amino acids, and preferably from about 240 to about 560 amino acids. Further, the antigenic sequences may be referred to herein as "epitopes", whether or not they include an entire "natural" epitope, so long as they possess the antibody binding characteristics described herein.

Alternatively, appropriate antigen fragments or antigenic sequences or epitopes may be identified by their ability, when included in a chimeric protein, to elicit suitable antibody production to the epitope in a host to which the chimeric protein is administered. Those of skill in the art will recognize that definitions of antibody titer may vary. Herein, "titer" is taken to be the inverse dilution of antiserum that will bind one half of the available binding sites on an ELISA well coated with 100 ng of test protein. In general, suitable antibody production is characterized by an antibody titer in the range of from about 100 to about 100,000, and preferably in the range of from about 10,000 to about 10,000,000. Alternatively, and particularly in diagnostic assays, the "titer" should be about three times the background level of binding. For example, to be considered "positive", reactivity in a test should be at least three times greater than reactivity detected in serum from uninfected individuals. Preferably, the antibody response is protective, i.e. prevents or lessens the development of symptoms of disease in a vaccinated host that is later exposed to *Borrelia*, compared to an unvaccinated host.

Figure 9A:
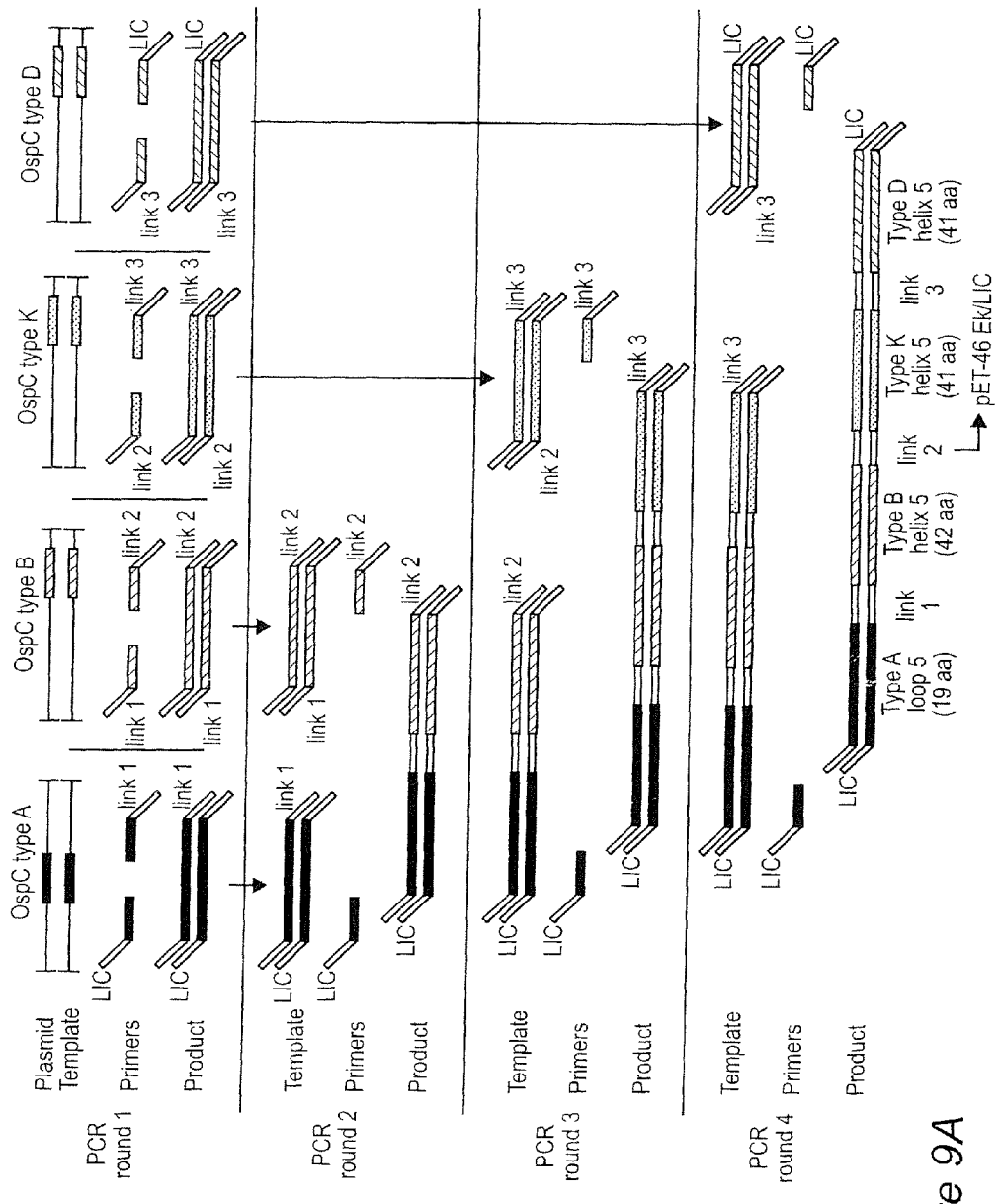
FIGS. 9A and B. Generation of a tetravalent chimeric OspC test construct. A, A flow chart for the generation of the tetravalent ABKD chimeric vaccinogen constructs is shown in panel A. The type-specific OspC epitopes used in the ABKD chimeric vaccinogen are represented by different bar shading. The loop 5 epitope of OspC type A and the alpha helix 5 epitope of types B, K and D were amplified in PCR round 1 and gel purified. These initial amplicons were then joined in subsequent rounds of PCR to produce the full chimeric construct. Since the termini (linker sequences) of the amplicons are complementary, after denaturation they can anneal to allow overlap extension followed by PCR amplification. The final amplicon was annealed into the pET46 Ek/LIC vector. B, In panel B, the final protein sequence of the ABKD chimeric vaccinogen construct is shown with constituent epitope-containing regions and linker sequences noted.
Figure 9B:
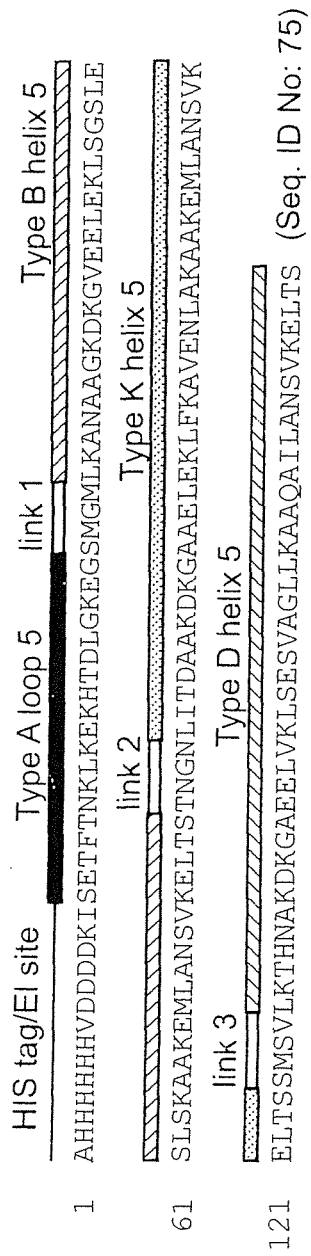

The amino acid sequence of one exemplary chimeric protein according to the invention is presented in FIG. 9B. In this illustrative embodiment, the chimera contains loop 5 region amino acid sequences from Type A OspC, and alpha helix 5 regions sequences from OspC types B, K and D. In this case, the Type A OspC sequence is from strain LDP56, with nucleotide accession number EF053513 and protein accession number ABK41054; the Type B OspC is from strain LDP73, with nucleotide accession number EF053525 and protein accession number ABK41066; the Type K OspC is from strain LDP89, with nucleotide accession number EF053523 and protein accession number ABK41064; and the Type D OspC is from strain LDP116, with nucleotide accession number EF053527 and protein accession number ABK41068. Those of skill in the art will recognize that OspC from many strains of *Borrelia* are known or may be discovered, and may be used in the practice of the present invention. The sequences of exemplary chimeric constructs are set forth in or represented by the SEQ ID NOS: disclosed herein.

Those of skill in the art will recognize that, while in some embodiments of the invention, the amino acid sequences that are chosen for inclusion in the chimeric protein of the invention correspond directly to the primary amino acid sequence of the original or native sequence of the OspC protein, this need not be the case. The amino acid sequence of an epitope that is included in the chimeric protein of the invention may be altered somewhat and still be suitable for use in the present invention. For example, certain conservative amino acid substitutions may be made without having a deleterious effect on the ability of the epitope to elicit an immune response. Those of skill in the art will recognize the nature of such conservative substitutions, for example, substitution of a positively charged amino acid for another positively charged amino acid; substitution of a negatively charged amino acid for another negatively charged amino acid; substitution of a hydrophobic amino acid for another hydrophobic amino acid; etc. All such substitutions or alterations of the sequence of an epitope that is contained in the chimeric protein of the invention are intended to be encompassed by the present invention, so long as the resulting epitope still functions to elicit a suitable immune response. In addition, the amino acid sequences that are included in the chimeric proteins of the invention need not encompass a full length native epitope or epitope-containing domain. Those of skill in the art will recognize that truncated versions of amino acid sequences that are known to be or to contain epitopes may, for a variety or reasons, be preferable for use in the present invention, so long as the criteria set forth for an epitope is fulfilled by the sequence. Amino acid sequences that are so substituted or otherwise altered may be referred to herein as "based on" or "derived from" the original wild type or native sequence. In general, the OspC proteins from which the linear epitopes are "derived" or on which the linear epitopes are "based" are the OspC proteins as they occur in nature. These natural OspC proteins may alternatively be referred to as native or wildtype proteins.

Such changes to the primary sequence may be introduced for any of a variety of reasons, for example, to eliminate or introduce a protease cleavage site, to increase or decrease solubility, to promote or discourage intra- or inter-molecular interactions such a folding, ionic interactions, salt bridges, etc, which might otherwise interfere with the presentation and accessibility of the individual epitopes along the length of the chimera. All such changes are intended to be encompassed by the present invention, so long as the resulting amino acid sequence functions to elicit a protective antibody reaction to the OspC type from which the epitope originates. In general, such substituted sequences will be at least about 50% identical to the corresponding sequence in the native protein, preferably about 60 to 70, or even 70 to 80, or 80 to 90% identical to the wild type sequence, and preferably about 95 to about 100% identical.

In some embodiments of the invention, the individual linear epitopes in the chimeric vaccinogen are separated from one another by intervening sequences that are more or less neutral in character, i.e. they do not in and of themselves elicit an immune response to *Borrelia*. Such sequences may or may not be present between the epitopes of a chimera. If present, they may, for example, serve to separate the epitopes and contribute to the steric isolation of the epitopes from each other. Alternatively, such sequences may be simply artifacts of recombinant processing procedures, e.g. cloning procedures. Such sequences are typically known as linker or space peptides, many examples of which are known to those of skill in the art. See, for example, Crasto, C. J. and J. A. Feng. 2000. LINKER: a program to generate linker sequences for fusion proteins. Protein Engineering 13(5): 309-312, which is a reference that describes unstructured linkers. Structured (e.g. helical) sequence linkers may also be designed using, for example, existing sequences that are known to have that secondary structure, or using basic known biochemical principles to design the linkers. In addition, other elements may be present in the chimeric proteins, for example leader sequences or sequences that "tag" the protein to facilitate purification or detection of the protein, examples of which include but are not limited to histidine tags, detection tags (e.g. S-tag, or Flag-tag), other antigenic amino acid sequences such as known T-cell epitope containing sequences and protein stabilizing motifs, etc. In addition, the chimeric proteins may be chemically modified, e.g. by amidation, sulfonylation, lipidation, or other techniques that are known to those of skill in the art.

The invention further provides nucleic acid sequences that encode the chimeric proteins of the invention. Such nucleic acids include DNA, RNA, and hybrids thereof, and the like. Further, the invention comprehends vectors which contain or house such coding sequences. Examples of suitable vectors include but are not limited to plasmids, cosmids, viral based vectors, expression vectors, etc. In a preferred embodiment, the vector will be a plasmid expression vector.

The chimeric proteins of the invention may be produced by any suitable method, many of which are known to those of skill in the art. For example, the proteins may be chemically synthesized, or produced using recombinant DNA technology (e.g. in bacterial cells, in cell culture (mammalian, yeast or insect cells), in plants or plant cells, or by cell-free prokaryotic or eukaryotic-based expression systems, by other in vitro systems, etc.).

The present invention also provides compositions for use in eliciting an immune response which may be utilized as a vaccine to prevent or treat *Borrelia* infection, particularly when manifested as Lyme disease (Lyme borreliosis). By eliciting an immune response, we mean that administration of the antigen causes the synthesis of specific antibodies (at a titer as described above) and/or cellular proliferation, as measured, e.g. by $^{3}H$ thymidine incorporation. By "vaccine" we mean a chimeric protein that elicits an immune response which results protection against challenge with *Borrelia*, either wholly or partially preventing or arresting the development of symptoms related to *Borrelia* infection (i.e. the symptoms of Lyme disease), in comparison to a non-vaccinated (e.g. adjunct alone) control organisms. The compositions include one or more substantially purified recombinant chimeric proteins as described herein, and a pharmacologically suitable carrier. The plurality of chimeric proteins in the composition may be the same or different, i.e. the composition may be a "cocktail" of different chimeras, or a composition containing only a single type of chimera. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. The vaccine preparations of the present invention may further comprise an adjuvant, suitable examples of which include but are not limited to Seppic, Quil A, Alhydrogel, etc. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of chimeric protein in the formulations may vary. However, in general, the amount in the formulations will be from about 0.01-99%, weight/volume.

The methods involve administering a composition comprising a chimeric recombinant protein in a pharmacologically acceptable carrier to a mammal. The vaccine preparations of the present invention may be administered by any of the many suitable means which are well known to those of skill in the art, including but not limited to by injection, inhalation, orally, intranasally, by ingestion of a food product containing the chimeric protein, etc. In preferred embodiments, the mode of administration is subcutaneous or intramuscular. In addition, the compositions may be administered in conjunction with other treatment modalities such as substances that boost the immune system, chemotherapeutic agents, and the like.

The present invention provides methods to elicit an immune response to *Borrelia* and to vaccinate against *Borrelia* infection in mammals. In one embodiment, the mammal is a human. However, those of skill in the art will recognize that other mammals exist for which such vaccinations would also be desirable, e.g. the preparations may also be used for veterinary purposes. Examples include but are not limited to companion "pets" such as dogs, cats, etc.; food source, work and recreational animals such as cattle, horses, oxen, sheep, pigs, goats, and the like; or even wild animals that serve as a reservoir of *Borrelia* (e.g. mice, deer). The invention also provides a diagnostic and a method for using the diagnostic to identify individuals who have antibodies to the epitopes contained within the chimeric proteins of the invention. A biological sample from an individual (e.g. a human, a deer, or other mammals susceptible to infection by *Borrelia* spirochetes) suspected of having been exposed to *Borrelia*, or at risk for being exposed to *Borrelia*, is contacted with the chimeric proteins of the invention. Using known methodology, the presence or absence of a binding reaction between the chimeric protein and antibodies in the biological sample is detected. A positive result (binding occurs, thus antibodies are present) indicates that the individual has been exposed to and/or is infected with *Borrelia*. In this connection, depending on the goal of the analysis, chimeras specific for any subset of interest of OspC types may be constructed, i.e. all possible OspC types may or may not be included in the diagnostic chimera.

Further, the diagnostic aspects of the invention are not confined to clinical use or home use, but may also be valuable for use in the laboratory as a research tool, e.g. to identify *Borrelia* spirochetes isolated from ticks, to investigate the geographical distribution of OspC types, etc.

The present invention also encompasses antibodies to the epitopes and/or to the chimeric proteins disclosed herein. Such antibodies may be polyclonal, monoclonal or chimeric, and may be generated in any manner known to those of skill in the art. In a preferred embodiment of the invention, the antibodies are bactericidal (borreliacidal), i.e. exposure of *Borrelia* spirochetes to the antibodies causes death of the spirochetes. Such antibodies may be used in a variety of ways, e.g. as detection reagents to diagnose prior exposure to *Borrelia*, as a reagent in a kit for the investigation of *Borrelia*, to treat *Borrelia* infections, etc.

The following Examples are provided to illustrate various embodiments of the invention, but should not be considered as limiting in any way.

EXAMPLES

Example 1

Demonstration of OspC Type Diversity in Invasive Human Lyme Disease Isolates and Identification of Previously Uncharacterized Epitopes that Define the Specificity of the OspC Antibody Response Introduction Lyme disease is transmitted to humans through the bite of *Ixodes* ticks infected with *Borrelia burgdorferi, B. garinii* or *B. afzelii*. Outer surface protein C (OspC) is thought to be an important virulence factor involved in the transmission process and possibly in the establishment of early infection in mammals (Grimm et al, 2004; Parl et al, 2004; Schwan et al., 1995). OspC is a variable, ~22 kDa, surface exposed, plasmid-encoded lipoprotein (Fuchs et al., 1992; Marconi et al., 1993; Sadziene et al., 1993). Crystal structures have been determined for three OspC proteins (Eicken et al, 2001; Kumaran et al, 2001). The protein is largely helical with 5 alpha helices connected by variable loops. The loops have been postulated to form ligand binding domains (Eicken et al, 2001; Kumaran et al, 2001). Evidence suggests that OspC may facilitate translocation of spirochetes from the tick midgut by serving as an adhesin that binds to unidentified receptors in the salivary gland (Pal et al, 2004). Orthologs of OspC have been identified in several species of the relapsing fever group raising the possibility that the OspC related proteins carry out a similar role in other *Borrelia* species (Marconi et al, 1993; Margolis et al, 1994). OspC expression is environmentally regulated, induced by tick feeding, and OspC is a dominant antigen during early infection in mammals (Alverson et al, 2003; Schwan et al, 1998; Stevenson et al, 1995). Transcription is regulated, at least in part, by the RpoN/S regulatory network (Hubner et al, 2001). It should be noted that there are conflicting reports regarding the precise details of the temporal nature of OspC expression during transmission and during early infection (Ohnishi et al., 2001; Schwan et al, 1995).

OspC exhibits significant genetic and antigenic diversity (Theisen et al, 1995; Theisen et al, 1993). Twenty one OspC phyletic groups (henceforth referred to as OspC types) have been delineated (Seinost et al., 1999; Wang et al, 1999). OspC types are differentiated by letter designations (A through U). Analysis of several hundred OspC amino acid sequences that are in the databases indicates that divergence between OspC types can be as high as 30% while within a type it is generally less than 6%. Seinost et al. have hypothesized a correlation between OspC types A, B, I and K and invasive infections in humans (Seinost et al., 1999). Lagal et al. also reported that specific ospC variants, as defined by single-strand conformation polymorphism analysis, correlate with invasive human infections (Lagal et al, 2003). However, a recent study by Alghaferi and colleagues has called into question the strength of this correlation (Alghaferi et al., 2005). The influence of OspC type or sequence on function and the host-pathogen interaction represents an important and fertile area of investigation. OspC has been investigated for use in Lyme disease vaccine development (Bockenstedt et al. 1997; Gilmore et al., 2003; Gilmore et al., 1999a; Probert et al., 1994; Theisen et al, 1993; Wilske et al, 1996). However, OspC variation and limited knowledge of the antigenic structure of OspC have complicated these efforts. OspC has protective capability, but only against the same strain (Bockenstedt et al. 1997; Gilmore et al., 1999; Gilmore et al., 1999b; Probert and LeFebvre, 1994; Wilske et al, 1996). This suggests that the protective epitopes reside within regions of the protein that are highly variable in sequence.

The goals of this study were several fold. First, further assessment of the putative correlation between OspC type and invasive infections was sought by determining the OspC type of invasive and non-invasive isolates recovered from a defined patient population in Maryland. Second, in an attempt to better understand the antibody response to OspC, determination of whether or not that response is type specific was sought. Finally, definition of the antigenic structure of OspC was sought by identifying epitopes that elicit an antibody response during infection in mice. The data presented here indicate that the number of OspC types associated with invasive infection is greater than previously postulated (Seinost et al., 1999). In addition, we have identified two previously uncharacterized epitopes and have demonstrated that the antibody response to OspC appears to be type specific. These analyses provide important information that enhance our understanding of the role of OspC in Lyme disease pathogenesis and that will facilitate the construction of an OspC based vaccine.

EXPERIMENTAL PROCEDURES

Bacterial Isolates, Cultivation and Generation of Infection Serum.

Lyme disease isolates recovered from human patients in Maryland were employed in these analyses (Table 1). Patients provided informed consent prior to the study as approved by the John Hopkins Medicine Institutional Review Board. The spirochetes were cultivated in BSK-H complete media (Sigma) at 33° C., monitored by dark-field microscopy and harvested by centrifugation. Clonal populations were generated for some isolates by sub-surface plating as previously described (Sung et al., 2000). To determine the OspC type of individual colonies, the ospC gene was PCR amplified, sequenced and comparative sequence analyses were performed (as described below). To generate antisera against a series of clonal populations expressing OspC proteins of known type, $10^3$ spirochetes were washed in phosphate buffered saline (PBS) and needle inoculated into C3H-HeJ mice (sub-cutaneous, between the shoulder blades; Jackson Labs). Infection of the mice was confirmed by real time PCR of ear punch biopsies at wk 2 or 4 post-inoculation using primers targeting the flaB gene as previously described (Zhang et al., 2005). Blood was collected from each mouse at 0, 2, 4 and 8 wks by tail snip and the infection serum was harvested. Additional antisera and infection serum used in these analyses have been described previously (McDowell et l., 2002).

TABLE 1

Bacterial isolates, source information and OspC type.

| B. burgdorferi Isolate | Source | OspC type |
|---|---|---|
| B31MI | Tick | A |
| 5A4 | Clone derived from B31MI | A |

TABLE 1-continued

Bacterial isolates, source information and OspC type.

| B. burgdorferi Isolate | Source | OspC type |
|---|---|---|
| LDP56 | Human blood | A |
| LDP61 | Human blood | A |
| LDP60 | Human blood | A |
| LDP80 | Human blood | A |
| LDP76 | Human blood | A |
| LDS106 | Human skin | A |
| LDP73 | Human blood | B |
| LDS79 | Human skin | H |
| LDS101 | Human skin | H |
| LDP84 | Human blood | C |
| LDP63 | Human blood | N |
| LDC83 | Human CSF | N |
| LDP120 | Human blood | N |
| LDP74 | Human blood | K |
| LDS81 | Human skin | K |
| LDS88 | Human skin | K |
| LDP89 | Human blood | K |
| LDP116 | Human blood | D |

DNA Isolation, OspC Typing and Computer Assisted Structural Analyses.

To determine the OspC type, total DNA was isolated from each strain as previously described (Marconi et al., 2003) and used as template for PCR with the OspC20(+)LIC and OspC210(−)LIC primers (Table 2). PCR was performed using Expand High Fidelity polymerase (Roche) with the following cycling conditions: Initial denaturation at 94° C. for 2 minutes; 94° C. for 15 s, 50° C. for 30 s, 68° C. for 60 s for 10 cycles; 94° C. for 15 s, 50° C. for 30 s, 68° C. for 60 s with an additional 5 s added to each of the last 20 cycles; final elongation at 68° C. for 7 minutes. The amplicons were recovered using QiaQuick PCR Purification kit (Qiagen), treated with T4 DNA polymerase to generate single strand overhangs, annealed into the pET-32 Ek/LIC vector (Novagen) and transformed into *E. coli* NovaBlue (DE3) cells (Novagen). The methods for these procedures were as described by the manufacturer. Colonies were selected for ampicillin resistance (50 μml-1) and screened for the ospC insert by PCR. Selected colonies were transferred into LB broth (Fisher), cultivated at 37° C. with shaking (300 rpm) and the plasmids isolated using QiaFilter Midi Plasmid Isolation Kits (Qiagen). The ospC inserts were sequenced on a fee for service basis (MWG Biotech). The determined sequences were translated and aligned using ClustalX (35) with default parameters. To determine OspC type, a neighbor joining tree was created, and bootstrap values calculated (1000 trials). The resultant phylogram was visualized with N-J Plotter. Additional OspC sequences available in the databases were included in the analysis. Structural models for OspC were generated using the NCBI molecular modeling database files 1GGQ, 1F1M, and 1G5Z (4, 15) and CN3D software available at the website at ncbi.nlm.nih.gov/Structure/CN3D/cn3d.shtml.

TABLE 2

Polymerase Chain Reaction Primers employed in this study.

| Primer | Sequence [a] | SEQ ID NO: |
|---|---|---|
| ospC 20(+) LIC | GACGACGACAAGATTAATAATTCAGGGAAAGATGGG | 163 |
| ospC 40(+) LIC | GACGACGACAAGATTCCTAATCTTACAGAAATAAGTAAAAAAAT | 165 |

TABLE 2 -continued

Polymerase Chain Reaction Primers employed in this study.

| Primer | Sequence [a] | SEQ ID NO: |
|---|---|---|
| ospC 60(+) LIC | GACGACGACAAGATTAAAGAGGTTGAAGCGTTGCT | 165 |
| ospC 80(+) LIC | GACGACGACAAGATTAAAATACACCAAAATAATGGTTTG | 166 |
| ospC 100(+) LIC | GACGACGACAAGATTGGAGCTTATGCAATATCAACCC | 167 |
| ospC 130(+) LIC | GACGACGACAAGATTTGTTCTGAAACATTTACTAATAAATTAAAAG | 168 |
| ospC 136(+) LIC | GACGACGACAAGATTAATAAATTAAAAGAAAAACACACAGATCTTG | 169 |
| ospC 142(+) LIC | GACGACGACAAGATTCACACAGATCTTGGTAAAGAAGG | 170 |
| ospC 151(+) LIC | GACGACGACAAGATTACTGATGCTGATGCAAAAGAAG | 171 |
| ospC 171(+) LIC | GACGACGACAAGATTGAAGAACTTGGAAAATTATTTGAATC | 172 |
| ospC 191(+) LIC | GACGACGACAAGATTCTTGCTAATTCAGTTAAAGAGCTTAC | 173 |
| ospC 130(-) LIC | GACGACAAGCCCGGTTTAACATTTCTTAGCCGCATCAATTTTTC | 174 |
| ospC 150(-) LIC | GACGACAAGCCCGGTTTAAACACCTTCTTTACCAAGATCTGT | 175 |
| ospC 170(-) LIC | GACGACAAGCCCGGTTTAAGCACCTTTAGTTTTAGTACCATT | 176 |
| ospC 190(-) LIC | GACGACAAGCCCGGTTTACATCTCTTTAGCTGCTTTTGACA | 177 |
| ospC 200(-) LIC | GACGACAAGCCCGGTTTAGCTTGTAAGCTCTTTAACTGAATTAGC | 178 |
| ospC 210(-) LIC | GACGACAAGCCCGGTTTAAGGTTTTTTGGACTTTCTGC | 179 |

[a] LIC tail sequences are underlined

Generation of Recombinant Proteins.

To generate full length and truncations of OspC, primers were designed based on the type A ospC sequence of *B. burgdorferi* B31MI (Fraser et al., 1997). The primers possess tail sequences that allow for annealing into the pET-32 Ek/LIC vector (Novagen), a ligase independent cloning (LIC) and expression vector. All LIC procedures were as previously described (Hovis et al, 2004). To verify the sequence of all constructs, recombinant plasmids were purified from *E. coli* NovaBlue (DE3) cells using QiaFilter Midi Plasmid Purification kits (Qiagen), and the inserts were sequenced (MWG Biotech).

SDS-PAGE and Immunoblot Analyses.

Proteins were separated in 12.5% Criterion Precast Gels (Biorad) by SDS-PAGE and immunoblotted onto PVDF membranes (Millipore) as previously described (Roberts et al, 2002). Expression of recombinant proteins was confirmed using S-Protein horseradish peroxidase (HRP) conjugate (Novagen), which detects the N-terminal S-Tag fusion that is carried by all recombinant proteins employed in this study. The HRP conjugated S-Protein was used at a dilution of 1:10,000. For immunoblot analyses, serum collected from infected mice was used at a dilution of 1:1000. HRP conjugated goat anti-mouse IgG served as the secondary (Pierce) and was used at a dilution of 1:10,000. General immunoblot methods were as previously described (Metts et al, 2003).

Results ospC Typing Analysis of Isolates Recovered from Human Lyme Disease Patients in Maryland.

ospC was successfully amplified from each of the isolates analyzed that were recovered from the human Lyme disease patients from Maryland. The sequence of each amplicon was determined and comparative sequence analyses were performed to determine OspC type (FIG. 1). Representatives of several different OspC types including A (n=6), B (n=1), C (n=1), D (n=1), H (n=2), K (n=4) and N (n=3) were identified. It had been previously reported that only OspC types A, B, I and K are associated with invasive infections in humans (Seinost et al., 1999). In that study, invasive isolates were defined as those that were recovered from blood, organs or cerebrospinal fluid whereas non-invasive isolates were those that were recovered from the skin but not found at other body sites (Seinost et al, 1999). However, here it is demonstrated that some isolates expressing OspC types C, D, and N were recovered from blood (LDP84, LDP63, LDP116, and LDP120) or cerebrospinal fluid (LDC83) and hence are invasive. This observation suggests that the correlation of specific OspC types with invasive infection may not be a strict one and that the strength of the correlation requires re-evaluation.

Analysis of the Type Specificity of the Antibody Response to OspC During Infection in Mice.

Figure 2:
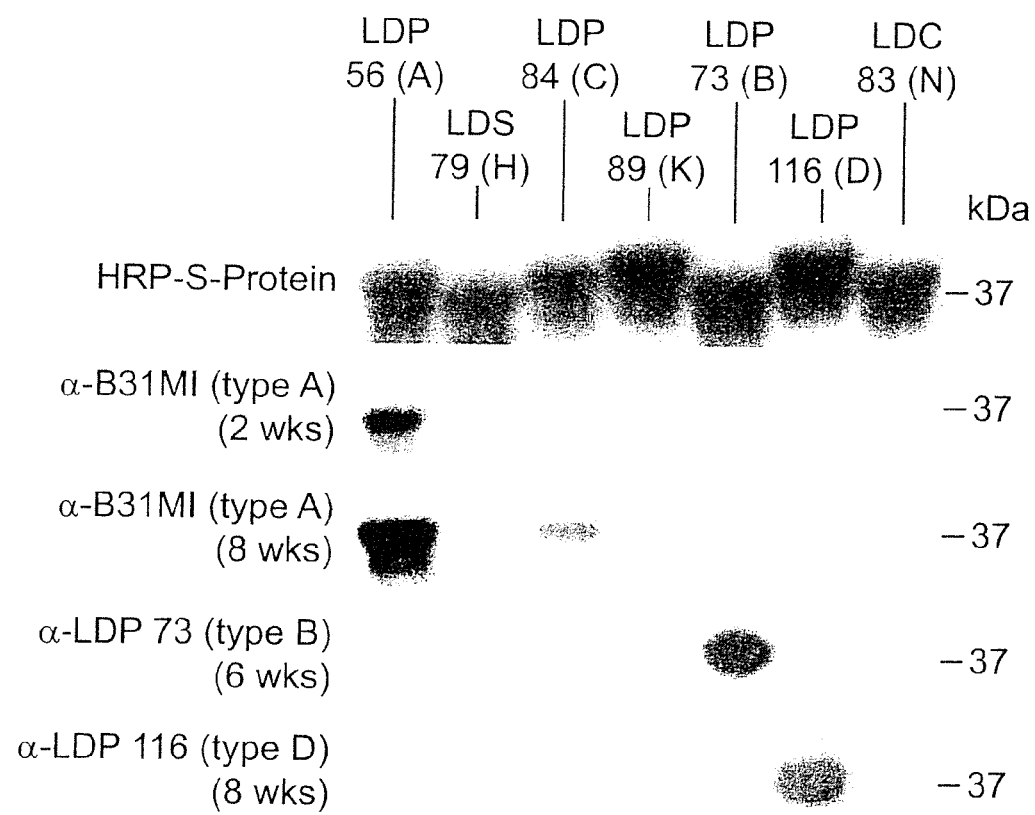
FIG. 2. Demonstration that the antibody response to OspC during infection is predominantly OspC type specific. Recombinant OspC proteins of several OspC types (indicated in the figure) were generated, separated by SDS-PAGE, immunoblotted and screened with HRP conjugated S-Protein or serum collected from mice infected with clonal isolates of known OspC type as indicated.

To determine if the antibody response elicited to OspC during infection is type specific, type A, B, C, D, H, K and N recombinant OspC proteins were generated for use as test antigens. The recombinant proteins were immunoblotted and screened with serum collected from mice infected with *B. burgdorferi* isolates of the A, B, or D OspC type (as determined above) (FIG. 2). Expression of the recombinant proteins in *E. coli* and the equal loading of protein was confirmed by screening one immunoblot with HRP conjugated S-Protein which recognizes the S-Tag in the N-terminal fusion. When screened with anti-*B. burgdorferi* B31 MI antiserum (type A OspC) collected at wk 2 of infection, strong reactivity was detected only with the type A protein. The strong and early IgG response to OspC is consistent with earlier reports (Theisen et al, 1995; Wilske et al, 1993). Sera collected at wk 8 of infection also reacted predominantly with type A OspC but weak cross immunoreactivity with other OspC types was observed. The Ab response to OspC in mice infected with LDP116 and LDP73 (OspC type D and B isolates respectively) was also type specific. It can be concluded that there is a significant degree of type specificity in the antibody response to OspC and that this specificity implies that the in vivo immunodominant epitopes are located within the type specific domains of the protein.

Localization of the OspC Linear Epitopes that Elicit an Antibody Response During Infection in Mice.

Figure 3A:
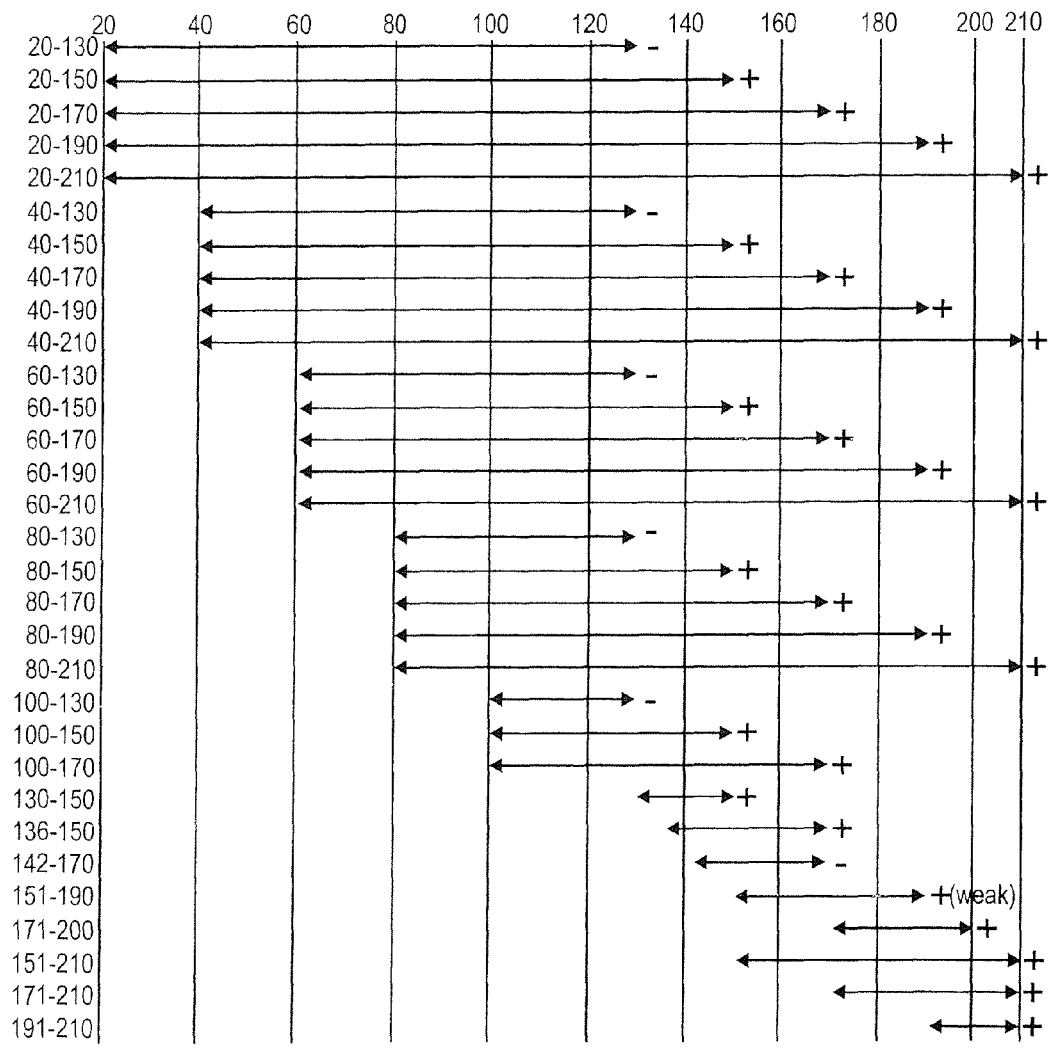
FIG. 3A-C. Localization of the immunodominant epitopes of type A OspC. Truncations of type A OspC were generated as S-Tag fusion proteins and expressed in *E. coli*. Panel A presents a schematic of the OspC truncations. The numbering reflects the residue numbering of *B. burgdorferi* B31MI OspC. In panel A, the ability of each truncated protein to bind infection antibody is indicated to the right by a (+) or (−). The numbers to the left indicate the amino acid residues that comprise each truncation. In panels B and C immunoblots of the recombinant proteins were screened with HRP-conjugated S-Protein to verify expression and loading or with serum from a mouse infected with *B. burgdorferi* B31MI (α-B31MI infection serum), a type A OspC producing strain. For reference, the arrows in panels b and c indicate the migration position of recombinants that were not immunoreactive with the α-B31MI infection serum are indicated. Molecular mass markers are indicate to the right of each immunoblot.
Figure 3B:
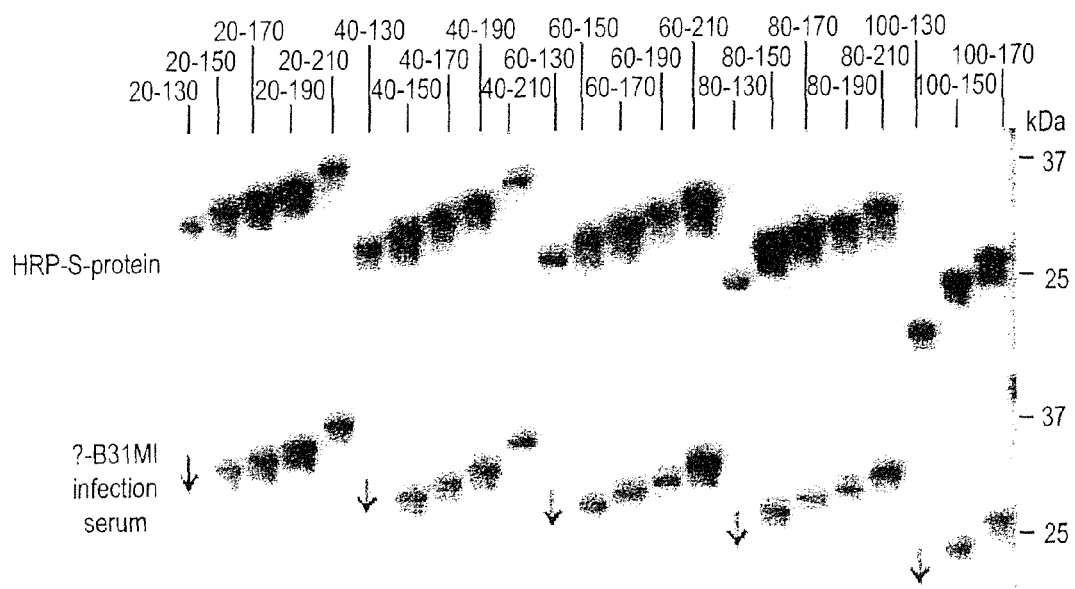
Figure 3C:
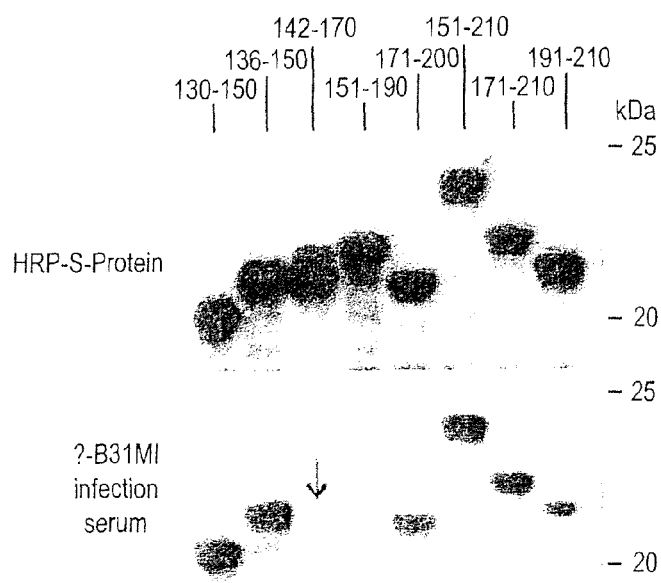

To identify the linear epitopes of type A OspC that elicit an antibody response during infection, several recombinant OspC fragments were generated and screened with α-*B. burgdorferi* B31MI infection serum (wk 8) (FIG. 3). B31MI is an OspC type A producing strain. The expression of the recombinant proteins was confirmed by immunoblotting with the HRP conjugated S-Protein. To localize the linear epitopes of OspC, immunoblots of the OspC fragments were screened with infection serum. Two domains containing one or more epitopes were localized, one within the C-terminal half of the protein between residues 168 and 203 of alpha helix 5 and the other between residues 136 and 150 of helix 3 and loop 5 (henceforth, referred to as the alpha 5 and loop 5 epitopes, respectively). These epitopes have not been previously characterized in the literature.

ospC Sequence Analyses and Computer Modeling of OspC Structure.

To determine where the loop 5 and alpha 5 epitopes spatially reside on the OspC protein, the coordinates determined by X-ray crystallographic analyses (Eicken et al., 2001; Kumaran et al, 2001) were accessed and ribbon and space fill models were generated for monomeric and or dimeric forms of type A OspC (data not shown). Monomeric forms of type I and E OspC proteins were also modeled. These analyses revealed that the loop 5 epitope is surface exposed on both the monomeric and dimeric forms of type A, E and I OspC proteins. In the original X-ray crystallographic analyses, portions of both the N- and C-termini were either not part of the recombinant protein or could not be modeled. In any event, the determined structures indicate that both the N- and C-termini reside in close proximity to one another and are proximal to the cell membrane.

To assess sequence variation within the loop 5 and alpha 5 epitopes at the intra-type level, 227 OspC sequences were aligned. These analyses revealed that both the loop 5 and alpha 5 epitopes are highly variable at the inter-type level but remarkably highly conserved within a type. FIG. 4 provides (in tabular form) the loop 5 and alpha 5 domain sequences for each OspC type and indicates the frequency with which each specific sequence was detected in the OspC sequences analyzed. As evidence for the conservation of loop 5 at the intra-type level, comparison of 57 type A loop 5 epitopes sequences revealed that 53 were identical with the outlying sequences differing at only one or two residues. A similar observation was noted for the alpha 5 epitopes. Of 43 type A OspC sequences, 42 were identical between residues 168 and 203. Note that fewer alpha 5 epitope sequences were analyzed since in many cases the sequences available in the databases were partial and lacked varying amounts of the C-terminus.

Demonstration that the Antibody Response to the Loop 5 Epitope is not Unique to an Individual Mouse.

In view of the intra-type conservation of loop 5 and its relatively short length, the loop 5 epitope might be an excellent candidate for use in the development of a chimeric OspC loop 5 based vaccinogen. To verify that the antibody response to the loop 5 epitope occurs commonly during infection and was not unique to an individual mouse, immunoblots of the loop 5 containing 130-150 fragment were screened with serum from several additional mice infected with the type A OspC producing strains, B31MI, LDP56 and 5A4. In all cases, antibody was detected that recognized this epitope (FIG. 5). While the response to loop 5 was weaker in the infection serum from the LDP56 infected mouse 2, longer exposure clearly revealed that loop 5 was antigenic in this animal. This demonstrates that the immune response mounted to these epitopes is not unique to an individual animal and provides further support for its possible use in vaccine development.

Discussion.

OspC is clearly established as an important contributor to Lyme disease pathogenesis (Grimm et al, 2004; Pal et al, 2004; Schwan et al, 1995). There is strong evidence that it plays an important role during the transit of the Lyme disease spirochetes from the midgut to the salivary gland (Pal et al, 2004). In addition, it is selectively expressed during early infection, is an immunodominant antigen (Fingerle et al, 1995; Schwan et al, 1998; Wilske et al, 1993) and has been hypothesized by others to be a key determinant in the dissemination capability of Lyme disease isolates (Seinost et al., 1999). The goals of this study were to test the potential correlation between OspC type and invasive infection, determine if the antibody response to OspC is type specific and further define the antigenic structure of OspC by localizing the linear epitopes that are presented during infection.

Sequence analyses of OspC have delineated 21 distinct OspC types (Seinost et al., 1999) and it has been postulated that only four of these (types A, B, I and K) are associated with invasive infections in humans (Seinost et al., 1999). However, a recent study has called into question this putative correlation (Alghaferi et al., 2005). To address this further, the OspC type of invasive and non-invasive Lyme disease isolates recovered from human patients in Maryland was determined. To accomplish this the full length ospC gene was PCR amplified, sequenced and comparative sequence analyses were performed. These analyses revealed that the OspC types associated with invasive human infections in this patient population also includes types C, D, and N. While type I OspC producing strains have been suggested to be a dominant type associated with invasive human infections (Seinost et al., 1999), none of the invasive isolates identified in the Maryland patient population carried a type I ospC. Similarly, Alghaferi et al. also did not detect type I OspC producing strains (Alghaferi et al., 2005). Collectively, these two studies have identified 18 invasive isolates in the greater Baltimore area with the following breakdown: A, n=5; B, n=2; C, n=1; D, n=1; H, n=1; K, n=3 and N, n=7. Hence, in this geographic area it appears that OspC type A and N producing invasive isolates predominate. These data argue against the hypothesis that only 4 OspC types are associated with invasive infections in humans. Additional analyses of isolates recovered from larger patient populations from different geographic regions will be required to further assess the validity of OspC type—invasive infection correlation and to determine if differences exist in the prevalence of specific OspC types in defined geographic regions.

The variable protection offered by vaccination with OspC in conjunction with the delineation of distinct OspC types (Seinost et al., 1999), raises the possibility that the antibody response could be type specific. This hypothesis is supported by the fact that vaccination with OspC has been found to provide protection only against the same strain (Bockenstadt et al., 1997; Gilmore et al, 1999a; Probert and LeFebvre, 1994). Until this report, the type specificity of the antibody response to OspC during infection had not been directly assessed. To address this, a series of full length recombinant OspC proteins of types A, B, C, D, H, K and N were screened with infection serum generated in mice with clonal populations expressing known OspC types. The use of infection serum is important as it allows for a focused assessment of the antibody response to epitopes that are specifically presented by the bacterium in vivo. These analyses revealed that in spite of strong sequence conservation within the N and C-terminal domains of OspC, the antibody response to the OspC types analyzed was type specific. For example, serum from mice infected with type A or D strains was immunoreactive in a type specific manner with little or no cross-immunoreactivity with other OspC types. Although the antibody response to all 21 OspC types was not analyzed, the data presented above suggest that the conserved domains are not immunodominant and that the linear epitopes of OspC presented by the bacterium during infection are contained within the variable domains (i.e., type specific domains) of the protein.

Only a few studies have been published to date that have sought to localize or identify the epitopes of OspC. Both linear and conformational epitopes have been identified. Gilmore and Mbow demonstrated that independent N terminal deletions beyond the leader peptide as short as 6 residues and C-terminal truncations of 13 residues abolish the binding of the monoclonal antibody B5 (Gilmore et al, 1999a; Gilmore, 1998). From this it was concluded that the B5 monoclonal antibody recognizes a conformationally defined epitope (Gilmore et al, 1999b). The precise residues that comprise the antibody recognition site within this conformationally defined epitope were not identified. In contrast to that observed with monoclonal antibody B5, this analysis of the polyclonal antibody response to cell associated, native OspC revealed that deletion of the last 10 C-terminal residues of OspC or of extended regions of the N-terminus did not abolish recognition of OspC by IgG elicited during infection. This difference in results is presumably a reflection of the focus on polyclonal versus monclonal antibodies. This data, which certainly do not preclude the existence of conformational epitopes, clearly demonstrate that there are linear epitopes in OspC as well. In an earlier study, Mathieson et al. also reported on a linear epitope in OspC (Mathieson et al, 1998). They found that the C-terminal 7 residues of OspC constitute a linear epitope that is recognized by IgM in serum collected from European neuroborreliosis patients. While IgM binding was not assessed in this report, deletion of the C-terminal 10 residues of OspC did not abolish IgG binding. Epitopes that are recognized by infection induced IgG appear to be localized at several sites in the protein. However, this does not suggest that a C-terminal epitope does not exist or is not recognized by antibody elicited during infection but rather that there are additional epitopes located elsewhere in OspC.

Immunoblot analysis of shorter OspC fragments allowed for more precise localization of OspC epitopes. The antigenic regions of OspC were localized to two regions. One spans residues 136-150 and the other spans residues 168 to 210. Structural models generated using coordinates from X-ray diffraction analyses place residues 136-150 largely within a surface exposed loop, termed loop 5 (Kumaran et al., 2001). Loop 5 is surface exposed in both the mono- and dimeric models of OspC and is located within a prominent bend. While it has been demonstrated that recombinant OspC does in fact form dimers, it has not yet been determined if native OspC forms dimer or larger oligomers in vivo. The dimeric model for OspC indicates a significant buried interface that comprises greater than >30% of the protein. A buried interface of this extent suggests a tight interaction between the monomers and is considered to be an indication that the dimeric form of the protein is the biologically active form [Kumaran et al., 2001; Eicken et al., 2001; Zuckert et al., 2001]. In the OspC dimer, residues within loop 5 are predicted to be a part of a putative conformationally defined ligand binding pocket that may be of biological significance. This charged pocket is lined by amino acids containing carbonyl groups such as glutamate and aspartate residues. Crystal structures have been determined for three OspC proteins of types A, I (Kumaran et al., 2001) and E (Eicken et al., 2001). In all of these proteins the solvent structures of this putative binding pocket are remarkably well conserved. The accessibility of loop 5 to antibody in infection serum supports the postulate that this domain may be surface exposed and potentially available for ligand binding. In spite of strong inter-type structural conservation of loop 5 and the putative ligand binding pocket, the sequence of this domain is highly variable at the inter-type level. The sequence of the alpha 5 domain spanning residues 168 to 210 is also variable at the inter-type level with the exception of the last 20 residues which are highly conserved. To determine if sufficient conservation exists at the intra-type level to allow for the construction of a chimeric OspC vaccine consisting of a series of type specific epitopes, OspC sequences were aligned and a dendogram was constructed. Through these analyses the OspC type was determined for 227 sequences (data not shown). Both the loop 5 and alpha 5 epitopes were found to be well conserved at the intra-type level. For example, the loop 5 epitope of type A OspC proteins were identical in 54 of 57 sequences while the alpha 5 epitope was conserved in 42 of 43 type A sequences. Significant conservation of these domains in the other OspC types was noted as well with types C through I, M, N and O exhibiting absolute intra-type conservation within the loop 5 and alpha 5 epitopes.

This study demonstrates that there is greater OspC diversity among invasive isolates than previously recognized. This study also demonstrates that the antibody response to OspC in mice is largely type specific and is defined by previously uncharacterized loop 5 and alpha 5 epitopes. Earlier studies and the data presented here clearly demonstrate that a single OspC protein will not convey protection against diverse strains (Bockenstedt et al., 1997). One possible vaccination approach is to exploit the epitopes identified in this report in the development of a recombinant chimeric OspC vaccinogen. The loop 5 epitope or a combination of loop 5 and alpha 5 epitopes may offer the most promise if they also prove to be consistently antigenic in humans. These epitopes are relatively short in length, linear, and highly conserved at the intra-type level. In light of these features it should prove technically feasible to construct a loop 5-alpha 5 chimeric vaccinogen that can convey protection against highly diverse Lyme disease isolates.

Example 2

Analysis of Antibody Response in Humans to the Type A OspC Loop 5 Domain and Assessment of the Potential Utility of the Loop 5 Epitope in Lyme Disease Vaccine Development Outer surface protein C (OspC) of the Lyme disease spirochetes is a 22-kDa immunodominant (Fuchs et al, 1992) antigen that is expressed upon tick feeding and during early stages of infection (Schwan et al, 1995). Although a strong antibody response to OspC is mounted during natural infection, the response does not lead to bacterial clearance because OspC production is turned off shortly after the establishment of infection (Schwan et al, 1995). OspC has emerged as an important virulence factor and a potential candidate for Lyme disease vaccine development. However, efforts to develop an OspC-based vaccine have been hampered by its heterogeneity among strains (Theisen et al, 1993; Wilske et al, 1996; Wilske et al, 1993). Although vaccination with OspC elicits a highly protective response, most studies have reported only strain-specific protection (Bockenstedt et al, 1997; Gilmore et al, 1996; Mbow et al, 1999; Probert et al, 1997; Rousselle et al, 1998; Scheiblhofer et al., 2003). Recent analyses have provided significant insight into our understanding of the antigenic structure of OspC and the basis of strain-specific protection. Twenty-one OspC types, designated A through U, have been defined (Lagal et al, 2003; Seinost et al, 1999; Wang et al, 1999). By infecting mice with clonal populations of *Borrelia burgdorferi* that produce specific OspC types, is has been demonstrated that the antibody response during early infection is largely OspC type specific (see Example 1). This suggests that the dominant epitopes presented during early infection are likely to reside within the type-specific domains of OspC. While earlier studies suggested that only 4 of the 21 OspC types are associated with invasive infection (Seinost et al, 1999), recent studies have demonstrated that isolates producing additional OspC types can also establish invasive infection (Alghaferi et al, 2005; Example 1). However, type A OspC appears to predominate in strains that cause invasive infections in humans. Epitope-mapping analyses of type A OspC revealed that one of the dominant linear epitopes that elicits a response in mice resides within the loop 5 domain (see Example 1). The loop 5 domain is highly variable at the intertype level but conserved within sequences of a given type (see Example 1). In the present study, we refine the location of the epitope, demonstrate its surface exposure on intact bacteria, and demonstrate that it elicits bactericidal antibody.

Figure 6:
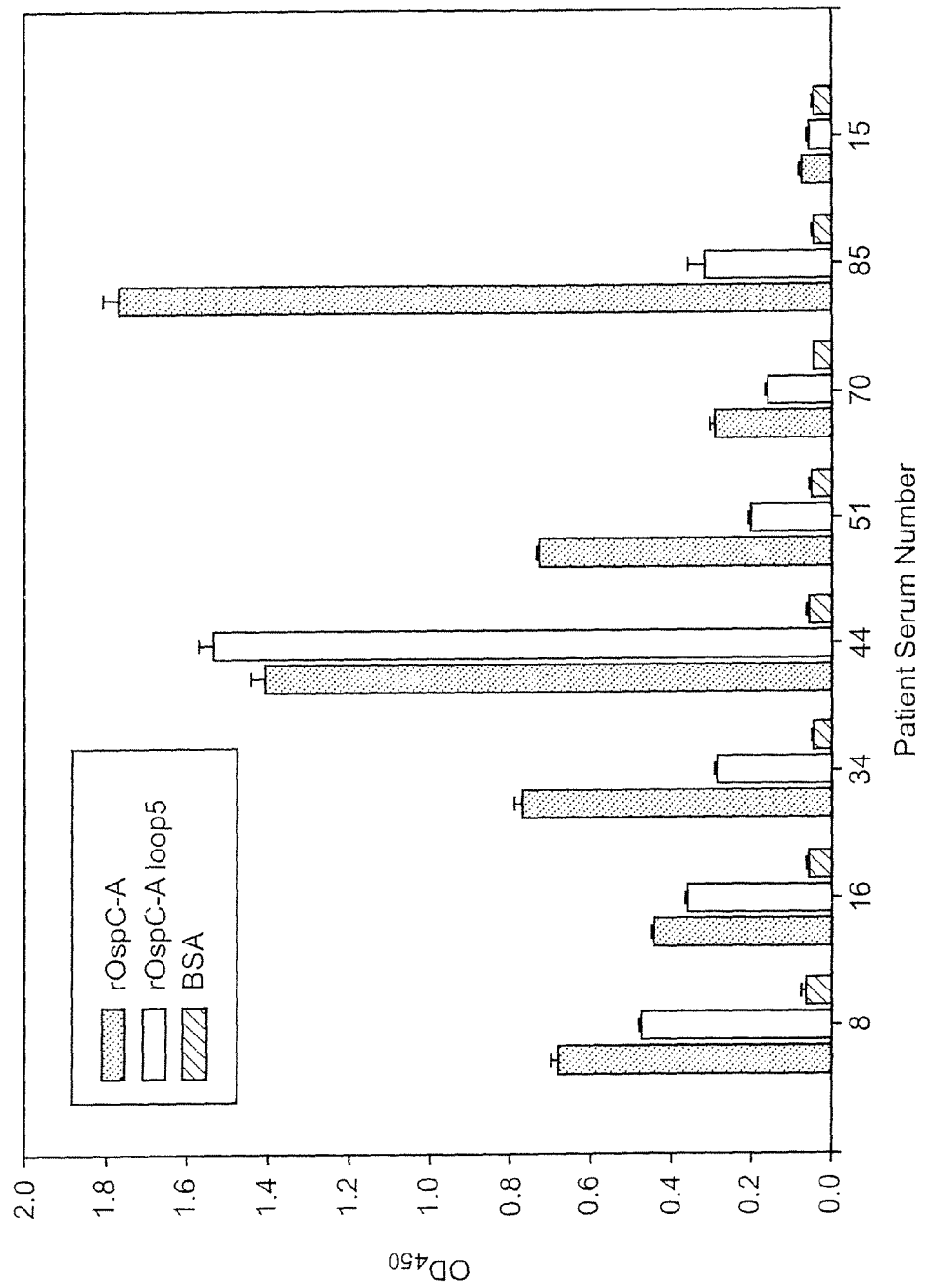
FIG. 6. ELISAs: identification of serum samples harboring type A OspC targeting antibody. r-type A full-length OspC, r-type A loop 5, and bovine serum albumin were used to coat the wells of ELISA plates. The wells were screened with serum from human Lyme disease patients. All assays were performed in triplicate, and the mean is presented along with the standard deviation. All methods were as described in the text. Serum from patient 15 which was determined to be IgG negative for antibody to B. burgdorferi B31MI served as a negative control.

Most studies that have sought to define the immunodominant epitopes of OspC have been conducted with mice (Bockenstedt et al, 1997; Gilmore et al, 1996; Mbow et al, 1999; Probert et al, 1994). However, it has been demonstrated that the antibody responses to some epitopes differ for humans versus mice and other mammals (Lovrich et al, 2005). The first objective of the present study was to determine whether the loop 5 domain of OspC is recognized by antibody elicited during infection in humans. Ideally, these analyses would be conducted with serum collected from individuals infected with a clonal population of a type A-producing strain. Since one cannot determine with absolute certainty whether an individual is infected with a heterogenous or a homogenous population, we sought to identify patient sera that exhibit a response to type A-specific sequences. To accomplish this, a panel of serum samples collected from patients with erythema migrans (early-stage Lyme disease) were screened by enzyme-linked immunosorbent assay (ELISA). Recombinant type (r-type) A OspC and an r-type A OspC subfragment containing loop 5 residues 130 to 150 were used to coat 96-well plates (250 ng of r-protein/well; 0.1 M $Na_2HPO_4$; 4° C. overnight). The plates were blocked (10% nonfat dry milk in phosphate-buffered saline, 0.5% Tween 20; 37° C. for 2 h) and washed, and human Lyme disease patient serum (diluted 1:400) was added to each well (37° C.; 1 h). Horseradish peroxidase-conjugated goat anti-human immunoglobulin G (IgG; Sigma) (50 µl of a 1:40,000 dilution) was added (1 h; 37° C.), followed by TMB substrate (3,3,5,5-tetramethylbenzidine) as instructed by the supplier (Sigma). The optical density values at 450 nm were determined by using a plate reader. Additional wells were coated with bovine serum albumin to serve as negative controls. All assays were performed in triplicate. The mean A450 value is presented with standard deviations. As shown in FIG. 6, several serum samples were found to have a strong IgG response to both the full-length type A OspC and the loop 5 fragment. Serum samples 8 and 44 displayed the strongest immunoreactivity with the loop 5 fragment and hence were selected for further analysis.

To more accurately define the residues within the loop 5 domain that are recognized by infection-induced antibody, PepSpot arrays were screened with the sera from patients 8 and 44 and with serum from mice infected with a clonal population of the type A OspC-producing strain B31MI (see Example 1). The PepSpot arrays consisted of 12- to 13-residue overlapping peptides (two-amino-acid step) spanning the loop 5 domain of type A OspC spotted onto Whatman 50 cellulose membrane (150 nmol/$cm^2$; JPT Peptide Technologies GmbH, Berlin, Germany). The PepSpot membranes were blocked (5% nonfat dry milk in Tris-buffered saline-0.5% Tween 20), washed, and screened with mouse and human serum samples (diluted 1:1,000 and 1:400 in blocking solution, respectively), and antibody binding was detected with species-specific anti-IgG antiserum. Although the specific residues that make up the immunoreactive domain differed slightly in mice and humans, the major epitopes localized within residues 130 to 146 (FIG. 7). In type A OspC sequences, this region encompasses the C-terminal region of alpha helix 3 and the N-terminal portion of loop 5.

The crystal structures of OspC spatially place loop 5 on a prominent bend of the protein (Eicken et al, 2005; Kumaran et al, 2001; FIG. 24). This loop has been postulated to be part of a potential ligand-binding pocket (Kumaran et al, 2001). To determine whether loop 5 is displayed at the cell surface and is accessible to antibody in in vitro grown spirochetes, immunofluorescence assays (IFAs) were performed by using anti-loop 5 antiserum. Immunoblot analyses with whole-cell lysates of *B. burgdorferi* B31 MI (type A OspC), *B. parkeri*, and S-tagged r-type A loop 5 demonstrated that the loop 5 antiserum is specific, establishing the suitability of this antiserum for IFAs. The strains analyzed by IFA consisted of *B. burgdorferi* B31MI (type A OspC) and LDP74 (type K OspC). The spirochetes were grown at 33° C. and transferred to 37° C. for 3 days to stimulate OspC expression. IFAs were conducted with permeabilized cells (acetone fixed), nonpermeabilized cells (air dried), and standard methods as previously described (Roberts et al, 2002). The slides were screened with a 1:1,000 dilution of mouse-loop 5 antiserum, mouse preimmune serum, or rabbit-flagellin antiserum. Detection was achieved by using Alexa Fluor 568-conjugated goat α-mouse IgG or Alexa Fluor 488-conjugated goat α-rabbit IgG (10 µml$^{-1}$ in blocking buffer). Slides were visualized on an Olympus BX51 fluorescence scope using a rhodamine or fluorescein filter set, as appropriate, or by dark-field microscopy, and photographed by using an Olympus MagnaFIRE camera. The labeling observed by IFA was highly specific and consistent with the immunoblot analyses; the type A-producing isolate was surface labeled, while the *B. burgdorferi* LDP74 type K OspC was not (data not shown). In addition, consistent with the upregulation of OspC at elevated temperature, IFAs revealed markedly greater surface labeling of spirochetes grown at 37° C. than cells grown at 33° C. The α-FlaB antiserum, which recognizes an inner-membrane anchored, periplasmic protein, did not label nonpermeabilized cells but readily labeled cells permeabilized with acetone (data not shown). This control demonstrates that the loop 5 epitope is in fact surface exposed and that the experimental conditions used in the IFA did not disrupt cell integrity and thereby artificially expose epitopes that are not naturally presented on the surface of the bacteria.

The ability of the loop 5 antiserum to efficiently bind to OspC at the cell surface raised the possibility that the interaction could be bactericidal, as has been demonstrated for antibody to full-length OspC (Bockenstedt et al, 1997; Ikushima et al, 2000; Jobe et al, 2003; Lovrich et al, 2005; Rousselle et al, 1998). To determine whether antibody targeting loop 5 also exhibits bactericidal activity, killing assays were conducted with *B. burgdorferi* isolates B31MI and LDP74 cultivated at 33° C. or temperature shifted to 37° C. The spirochetes were harvested by centrifugation, washed, and adjusted to 5×10$^5$ cells per 500 l (in BSK-H medium), and 12.5 µl was transferred into a sterile 0.65-ml microcentrifuge tube. Then, 10 µl of heat-inactivated (56° C.; 30 min) loop 5 serum was added with or without guinea pig complement (7.5 µl; Sigma Chemical, St. Louis, Mo.), the components were mixed and incubated at 33 or 37° C. for 8 h. A total of 70 µl of H$_2$O was added, and spirochetes were stained with the Live/Dead BacLight stain (Molecular Probes, Eugene, Oreg.) according to the manufacturer's instructions. In brief, two stains are added to the cells; SYTO 9 and propidium iodide. These dyes can distinguish live bacteria (i.e., with intact membranes) from bacteria with compromised membranes. Live bacteria fluoresce green due to staining with SYTO 9, whereas dead or damaged bacteria fluoresce red due to staining with propidium iodide. The baseline level of cells with disrupted membranes observed upon treatment with preimmune heat inactivated serum (with or without complement) was 25%. In contrast, ~70% of the cells exposed to the α-loop 5 antiserum displayed membrane disruption. The bactericidal activity was determined to be complement dependent. The blebbing effect seen here upon treatment with anti-loop 5 antibody is consistent with that reported with other anti-OspC antibodies (Bockenstedt et al, 1997; Escudero et al, 1997). It is also important to note that, consistent with the upregulation of OspC at elevated temperature, the percentage of dead cells was consistently higher in spirochetes grown at 37° C. than that in bacteria grown at 33° C. (data not shown). It is clear from the data presented that anti-loop 5 antibody is bactericidal.

Several reports have outlined the clear and strong justification for the development of Lyme disease vaccines (reviewed in Hanson and Edelman, 2004). However, at the present time, no vaccine is commercially available. In an effort to develop a broadly protective Lyme disease vaccine, Baxter pursued a strategy of generating a vaccine cocktail of 14 different full-length r-OspC proteins (Hanson and Edelman, 2004). However, the cocktail was deemed unacceptably reactigenic. The reactigenicity may have resulted from the large amount of protein that was required to elicit a sufficient response to the unique protective epitopes of each OspC type protein in the cocktail. A potential problem with cocktail vaccines that use multiple full-length proteins is the potential for misdirection of the antibody response to conserved, irrelevant, nonprotective epitopes. It may be possible to overcome this problem through the development of a chimeric, r-vaccinogen composed of the naturally presented immunodominant linear epitopes of each of the dominant OspC types. This general concept has its origins in efforts to develop malarial vaccines using epitopes from proteins expressed at different stages of infection (Hanson and Edelman, 2004). The same concept has been applied in the development of a hexavalent M protein vaccine for group A streptococci (Dale, 1999) and in the development of vaccines against several other pathogens with excellent success (Apta et al, 2006; Caro-Aguilar et al, 2005; Fan et al, 2005; Horvath et al, 2005; Kotloff et al, 2005; McNeil et al, 2005; Wang et al, 2005). With new insights into the physical and antigenic structure of OspC, it may now be possible to develop an effective, r-polyvalent, chimeric, OspC vaccine. The newly identified loop 5 domain is ideally suited for inclusion in such a vaccine.

Example 3

Development of an OspC-Based Tetravalent, Recombinant, Chimeric Vacinogen

Lyme disease is the most common arthropod-borne disease in North America and Europe. At present, there is no commercially available vaccine for use in humans. Outer surface protein C (OspC) has antigenic and expression characteristics that make it an attractive vaccine candidate; however, sequence heterogeneity has impeded its use as a vaccinogen. Sequence analyses have identified 21 well defined OspC phyletic groups or "types" (designated A through U). This study reports mapping of the linear epitopes presented by OspC types B, K and D during human and murine infection and exploitation of these epitopes (along with the previously identified type A OspC linear epitopes) in the development of a recombinant, tetravalent, chimeric vaccinogen. The construct was found to be highly immunogenic in mice and the induced antibodies surface labeled in vitro cultivated spirochetes. Importantly, vaccination induced complement-dependent bactericidal antibodies against strains expressing each of the OspC types that were incorporated into the construct. These results suggest that an effective and broadly protective polyvalent OspC-based Lyme disease vaccine can be produced as a recombinant, chimeric protein.

Materials and Methods

*Borrelia Burgdorferi* Isolates and Cultivation.

Clonal populations of *Borrelia burgdorferi* isolates B31MI (type A OspC), LDP73 (type B), LDP116 (type D) and LDP74 (type K) [see Example 1] were obtained by subsurface plating as previously described [Sung et al, 2000]. The OspC type of individual clones was determined by PCR amplification (Taq Polymerase, Promega) and DNA sequencing of ospC, with assignment to type by phylogenetic analysis [see Example 1]. Spirochetes were cultivated at 33 or 37° C., as indicated, in complete BSK-H medium (Sigma).

Ligase Independent Cloning and Production of Recombinant (r-) OspC Proteins.

Full length type B, K and D OspC and a series of truncations and fragments were generated by PCR amplification of the corresponding gene from each isolate. The primers were designed with 5' overhangs to allow ligase-independent cloning (LIC) in the pET-32 Ek/LIC vector (Table 3) [Example 1]. All LIC methods were performed essentially as directed by the manufacturer (Novagen). In brief, after amplification and regeneration of single stranded tails, the amplicons were annealed with the pET-32 Ek/LIC vector, which was transformed into and propagated in NovaBlue (DE3) *E. coli* cells. The plasmids were recovered and the insert sequences confirmed by DNA sequencing. For protein purification, purified plasmid was used to transform *E. coli* BL21 (DE3) cells and protein expression was induced by addition of IPTG (1 mM) to the cultures during the logarithmic growth phase followed by a three hour incubation. The N-terminal fusion added by expression from the pET-32 Ek/LIC vector contains a Trx-tag, S-tag, and a hexahistidine (His-tag) motif. The His-tag was exploited to allow purification of the r-proteins by nickel affinity chromatography. Briefly, cells were lysed and nucleic acid and cell wall peptidoglycan were degraded by benzonase nuclease and r-lysozyme, respectively. The soluble proteins were clarified by centrifugation (16000×g for 15 min), passed over an immobilized nickel column, washed, and eluted as per the manufacturer's protocol (Novagen). The eluted proteins were dialyzed extensively against phosphate buffered saline (PBS; pH 7.4) across a 10 kDa molecular weight cut-off membrane (Slid-a-lyzer, Pierce), the final protein concentration was quantified by the BCA assay (Pierce), and the purity of the preparation assessed by SDS-PAGE.

TABLE 3

PCR primers used in the generation of various OspC type fragments.

| Primer | Sequence | Description | SEQ ID NO: |
| --- | --- | --- | --- |
| ospC20(+)LIC | GACGACGACAAGATTAAT AATTCAGGGAAAGATGGG | Amplifies OspC from aa 20 and adds LIC tail | 180 |
| ospC210(+)LIC | GACGACAAGCCCGGTTT AAGGTTTTTTTGGACTTTC TGC | Amplifies OspC up to aa 210 and adds LIC tail | 181 |
| OCB110LIC(-) | GAGGAGAAGCCCGGTTT ATTGTGTTATTAAGGTTGA TATTG | Amplifies type B up to aa 110 and adds LIC tail | 182 |
| OCB131LIC(+) | GACGACGACAAGATCTTC TGAAGAGTTTAGTACTAAA CTAAAA | Amplifies type B from aa 131 and adds LIC tail | 183 |
| OCB140LIC(-) | GAGGAGAAGCCCGGTTT ATTTTAGTTTAGTACTAAA CTCTTCAG | Amplifies type B up to aa 140 and adds LIC tail | 184 |
| OCB140LIC(+) | GACGACGACAAGATAGAT AATCATGCACAGCTTGGTA TACAG | Amplifies type B from aa 140 and adds LIC tail | 185 |
| OCB148LIC(+) | GACGACGACAAGATTATA CAGGGCGTTACTGATGAA AATGC | Amplifies type B from aa 148 and adds LIC tail | 186 |
| OCB153LIC(+) | GACGACGACAAGATTGA AAATGCAAAAAAAGCTAT TTTAAAA | Amplifies type B from aa 153 and adds LIC tail | 187 |
| OCB155LIC(-) | GAGGAGAAGCCCGGTTT ATGCATTTTCATCAGTAAC GCCCTG | Amplifies type B up to aa 155 and adds LIC tail | 188 |
| OCB164LIC(+) | GACGACGACAAGATTGCA GCGGGTAAAGATAAGGGC GTTGAAG | Amplifies type B from aa 164 and adds LIC tail | 189 |
| OCB169LIC(-) | GAGGAGAAGCCCGGTTT ACTTATCTTTACCCGCTGC | Amplifies type B up to aa 169 and adds LIC tail | 190 |
| OCB175LIC(+) | GACGACGACAAGATTGA AAAGTTGTCCGGATCATTA GAAAGC | Amplifies type B from aa 175 and adds LIC tail | 191 |
| OCB180LIC(-) | GAGGAGAAGCCCGGTTT ATGATCCGGACAACTTTTC AAGTTCTTC | Amplifies type B up to aa 180 and adds LIC tail | 192 |
| OCB181LIC(+) | GACGACGACAAGATCTTA GAAAGCTTATCGAAAGCA GCTAAAGAG | Amplifies type B from aa 181 and adds LIC tail | 193 |
| OCB185LIC(-) | GAGGAGAAGCCCGGTTT ATGATTAAGCTTTCTAATG ATCCGGAC | Amplifies type B up to aa 185 and adds LIC tail | 194 |

TABLE 3 -continued

PCR primers used in the generation of various OspC type fragments.

| Primer | Sequence | Description | SEQ ID NO: |
|---|---|---|---|
| OCB190LIC(-) | GAGGAGAAGCCCGGTTTACTCTTTAGCTGCTTTTGATAAGCTTC | Amplifies type B up to aa 190 and adds LIC tail | 195 |
| OCB200LIC(-) | GAGGAGAAGCCCGGTTTATGTAAGCTCTTTAACTGAATTAGCAAG | Amplifies type B and K up to aa 200 and adds LIC tail | 196 |
| OCB49LIC(-) | GAGGAGAAGCCCGGTTTAAATTTTTTACTTATTTCTGTAAG | Amplifies type B and D up to aa 49 and adds LIC tail | 197 |
| OCB80LIC(-) | GAGGAGAAGCCCGGTTTATTTTTTACCAATAGCTTTAGCAAGCTC | Amplifies type B up to aa 80 and adds LIC tail | 198 |
| OCD112LIC(-) | GAGGAGAAGCCCGGTTTATAATTTTTCTGTTATTAGAGCTG | Amplifies type D up to aa 112 and adds LIC tail | 199 |
| OCD130LIC(+) | GACGACGACAAGATTAAATGTTCTGAAAGCTTTAC | Amplifies type D from aa 130 and adds LIC tail | 200 |
| OCD135LIC(-) | GAGGAGAAGCCCGGTTTAAAAGCTTTCAGAAACATTTCTTAGC | Amplifies type D up to aa 135 and adds LIC tail | 201 |
| OCD135LIC(+) | GACGACGACAAGATTACTAAAAAACTATCAGATAATCAAGCAG | Amplifies type D from aa 135 and adds LIC tail | 202 |
| OCD144LIC(+) | GACGACGACAAGATTGAGCTTGGTATAGAGAATGCTACTGATG | Amplifies type D from aa 144 and adds LIC tail | 203 |
| OCD151LIC(+) | GACGACGACAAGATTGCTACTGATGATAATGCAAAAAAGGC | Amplifies type D from aa 151 and adds LIC tail | 204 |
| OCD155LIC(-) | GAGGAGAAGCCCGGTTTAATTATCATCAGTAGCATTCTCTATACC | Amplifies type D up to aa 155 and adds LIC tail | 205 |
| OCD166LIC(-) | GAGGAGAAGCCCGGTTTAAGCATTATGTGTTTTTAAAATAGCC | Amplifies type D up to aa 166 and adds LIC tail | 206 |
| OCD167LIC(+) | GACGACGACAAGATTAAAGACAAGGGTGCTGAAGAACTTG | Amplifies type D from aa 167 and adds LIC tail | 207 |
| OCD180LIC(-) | GAGGAGAAGCCCGGTTTATGATTCAGATAACTTTACAAGTTC | Amplifies type D up to aa 180 and adds LIC tail | 208 |
| OCD180LIC(-) | GACGACGACAAGATTTCAGTAGCAGGCTTATTAAAAGCAGCTC | Amplifies type D from aa 180 and adds LIC tail | 209 |
| OCD195LIC(-) | GAGGAGAAGCCCGGTTTATGAATTAGCCAGTATGGCTTGAGCTGC | Amplifies type D up to aa 195 and adds LIC tail | 210 |
| OCD195LIC(+) | GACGACGACAAGATTTCAGTTAAAGAGCTTACAAGTCCTG | Amplifies type D from aa 195 and adds LIC tail | 211 |
| OCD80LIC(-) | GAGGAGAAGCCCGGTTTAATCTATTTTTTTACCAATA | Amplifies type D up to aa 80 and adds LIC tail | 212 |
| OCK110LIC(-) | GAGGAGAAGCCCGGTTTATTGTGTTATTAGTTTTGATATTG | Amplifies type K up to aa 110 and adds LIC tail | 213 |

TABLE 3 -continued

PCR primers used in the generation of various OspC type fragments.

| Primer | Sequence | Description | SEQ ID NO: |
|---|---|---|---|
| OCK130LICH | GATGACGACGACAAGATTAAATGTTCTGAAGATTTTAC | Amplifies type K from aa 130 and adds LIC tail | 214 |
| OCK135LIC(-) | GAGGAGAAGCCCGGTTTAAAAATCTTCAGAACATTTCTTAGC | Amplifies type K up to aa 135 and adds LIC tail | 215 |
| OCK148LIC(+) | GATGACGACGACAAGATAATTGAAAATGTTACTGATGAGAATGC | Amplifies type K from aa 148 and adds LIC tail | 216 |
| OCK150LIC(-) | GAGGAGAAGCCCGGTTTAATTTTCAATTCCAAGTTGCGCATGTTC | Amplifies type K up to aa 150 and adds LIC tail | 217 |
| OCK160LIC(-) | GATGACGACGACAAGATTATTTTAATAACAGATGCAGCTAAAG | Amplifies type K from aa 160 and adds LIC tail | 218 |
| OCK166LIC(-) | GAGGAGAAGCCCGGTTTAAGCTGCATCTGTTATTAAAATAGC | Amplifies type K up to aa 166 and adds LIC tail | 219 |
| OCK175LIC(-) | GAGGAGAAGCCCGGTTTATTCAAGCTCTGCAGCGCCCTTATC | Amplifies type K up to aa 175 and adds LIC tail | 220 |
| OCK180LIC(-) | GAGGAGAAGCCCGGTTTATGCTTTAAATAGCTTTTCAAGCTCTGC | Amplifies type K up to aa 180 and adds LIC tail | 221 |
| OCK180LIC(+) | GATGACGACGACAAGATTGCAGTAGAAACTTGGCAAAAGCAGC | Amplifies type K from aa 180 and adds LIC tail | 222 |
| OCK190LIC(-) | GAGGAGAAGCCCGGTTTACTCTTTAGCTGCMTGCCTTGTTTTC | Amplifies type K up to aa 190 and adds LIC tail | 223 |
| OCK191LIC(-) | GAGGAGAAGCCCGGTTTACATCTCTTTAGCTGCTTTTGCCAAG | Amplifies type K up to aa 191 and adds LIC tail | 224 |
| OCK80LIC(-) | GAGGAGAAGCCCGGTTTATTTTTTACCAATAGCTTTAGTAGC | Amplifies type K up to aa 80 and adds LIC tail | 225 |

LIC tails are in bold.

Immunoblot Analyses: Epitope Mapping of OspC Types B, D, and K.

To allow for the mapping of epitopes relevant during infection, C3H/HeJ mice were infected with 10⁴ spirochetes of clonal populations expressing OspC types B, K, or D and blood was collected at weeks 2, 4, 6, 8 and 12 by tail bleed. These sera were used to screen purified OspC proteins and truncations as described in Example 1. The r-proteins were subjected to SDS-PAGE, transferred to PVDF, and screened with a 1:1000 dilution of the type-specific murine infection sera (collected at wk 6). Similarly, the r-proteins were screened with serum (1:400) from patients known to have been infected with a *B. burgdorferi* strain expressing OspC types B, K, or D (kindly provided by Dr. Allen Steere). The appropriate IgG-specific, horseradish peroxidase (HRP)-conjugated secondary antibodies were utilized, and the results were visualized by chemiluminescence.

Construction and Expression of a Tetravalent Chimeric Vaccinogen.

The loop 5 region (aa 131 to 149) of type A and the alpha helix 5 region of types B (aa 160-201), K (aa 161-201), and D (aa 161-201) were chosen for inclusion in the tetravalent test vaccinogen. Each epitope-containing region was PCR amplified from the r-plasmids described above and primers listed in Table 4. PCR conditions were standard with an initial 2 min 94° C. denaturation step, followed by 35 cycles of denaturation at 94° C. for 15 sec, primer annealing at 50° C. for 30 sec, and extension at 72° C. for 60 sec, with a final 72° C. extension for 7 min. The primers were designed with vector-specific LIC tails or with unstructured, protease-resistant linker sequences as 5' overhangs (FIG. 9A) [Crasto and Feng, 2000]. All amplicons were analyzed by electrophoresis in agarose gels using TAE buffer and were gel purified (QiaQuick Gel Extraction, Qiagen). The purified products were then used as templates in subsequent rounds of PCR. In the second round, the amplicons of type A loop 5 and type B alpha helix 5 were combined as templates. After denaturation, the amplicons annealed via their complementary linker sequences allowing for overlap extension and subsequent amplification using the forward type A loop 5 and reverse type B alpha helix 5 primers. The types K and D alpha helix 5 sequences were added to the construct in a similar manner, except that the annealing temperature was increased to 60° C. after the first 10 cycles to increase the annealing specificity. The final product was annealed to the pET-46 Ek/LIC expression vector, which encodes an N-terminal hexahistidine tag fusion (Novagen), and NovaBlue (DE3) E. coli cells were transformed. The vaccinogen sequence was confirmed by DNA sequencing of purified plasmid. Protein expression and purification were completed as described above.

protein family 163) served as the negative control. To verify equal protein loading, one blot was screened with anti-His tag monoclonal Ab (mAb) (1:2000; Novagen). To assess the response to vaccination, identical blots were screened with a 1:500 dilution of the mouse anti-ABKD antiserum. HRP-conjugated goat-anti-mouse IgG (1:40000 dilution) served as the secondary antibody and binding was visualized by chemiluminescence. ELISA analyses were conducted using 96 well

TABLE 4

PCR primers used in the generation of the ABKD chimeric vaccinogen.

| Primer | Sequence | Description | SEQ ID NO: |
|---|---|---|---|
| OCAL5LIC(+) | GACGACGACAAGATTTCTGAAACATTTACTAATAAATTAAAAGAAAAAC | Amplifies type A from aa 131 and adds LIC tail | 226 |
| OCAL5L1(−) | <u>TAACATACCCATGCTACCTT</u>CTTTACCAAGATCTGTGTG | Amplifies type A up to aa 149 and adds linker 1 (GSMGML; SEQ ID 76) | 227 |
| OCBH5L1(+) | <u>GGTAGCATGGGTATGTTAAA</u>AGCAAATGCAGCGGG | Amplifies type B from aa 160 and adds linker 1 (GSMGML; SEQ ID 76) | 228 |
| OCBH5L2(−) | <u>TAAGTTACCGTTTGTGCTTG</u>TAAGCTCTTTAACTGAATTAG | Amplifies type B up to aa 201 and adds linker 2 (STNGNL; SEQ ID 77) | 229 |
| OCKH5L2(+) | <u>AGCACAAACGGTAACTTAAT</u>AACAGATGCAGCTAAAGATAAGG | Amplifies type K from aa 161 and adds linker 2 (STNGNL; SEQ ID 77) | 230 |
| OCKH5L3(−) | <u>TAAAACGCTCATGCTACTTG</u>TAAGCTCTTTAACTGAATTAGC | Amplifies type K up to aa 201 and adds linker 3 (SSMSVL; SEQ ID 78) | 231 |
| OCDH5L3(+) | <u>AGTAGCATGAGCGTTTTAAA</u>AACACATAATGCTAAAGACAAG | Amplifies type D from aa 161 and adds linker 3 (SSMSVL; SEQ ID 78) | 232 |
| OCDH5LIC(−) | GAGGAGAAGCCCGGTTTAACTTGTAAGCTCTTTAACTGAATTAG | Amplifies type D up to aa 201 and adds an LIC tail | 233 |

LIC tails are in bold, and linker sequences are underlined.

Immunization of Mice with the Tetravalent ABKD Chimeric Vaccinogen.

Twelve six-week-old, male, C3H/HeJ strain mice were immunized with 50 µg of and blocked as described above. Anti-ABKD antisera collected from the 12 vaccinated mice were analyzed in duplicate (100 µL; 1:10000; 1 hr). Bound vaccinogen-specific Ig was detected by incubation with isotype specific, biotinylated secondary antibodies (1 hr; Mouse isotyping kit; Zymed). Bound biotinylated antibody was detected by HRP-conjugated streptavidin (30 min) and the chromogenic substrate, ABTS. All incubations were completed at room temperature.

Indirect Immunofluorescence Assays (IFA).

To determine if epitopes included in the ABKD chimeric vaccinogen are presented on the surface of in vitro cultivated *B. burgdorferi*, IFA analyses were conducted. To maximize OspC production, cultures of clonal populations producing type A, B, K, or D OspC were temperature shifted from 33 to 37° C. The spirochetes from 5 mL of dense culture ($\sim 10^7$-$10^8$ cells mL$^{-1}$) were collected by centrifugation (7000×g for 15 min), washed 3 times with PBS, resuspended in 5 mL of PBS, and 100 µL spread over a 2 cm$^2$ area on charged slides (Superfrost Plus, Fisher Scientific). One set of slides was air dried and a second was acetone fixed. The slides were blocked (1 hr; 3% BSA in PBS-T) and then screened with a 1:100 dilution of anti-ABKD antiserum, pre-immune serum, or a 1:1000 dilution of rabbit-anti-flagellin antiserum (1 hr). Bound antibody was detected by Alexafluor 568-conjugated goat-anti-mouse IgG or Alexafluor 488-conjugated goat-anti-rabbit IgG (10 µg mL$^{-1}$ blocking buffer). Slides were washed three times in PBS-T between each step, and all incubations were for one hour at room temperature in a darkened, humidified chamber. Slides were mounted with Fluoromount-G (Electron Microscopy Sciences), visualized on an Olympus BX51 fluorescence scope using a rhodamine or fluorescein filter set, as appropriate, or by darkfield microscopy, and photographed using an Olympus MagnaFire digital camera.

Assessment of Bactericidal Activity.

The ability of the anti-ABKD antisera to kill *B. burgdorferi* was assessed in vitro. Spirochetes that had been temperature shifted from 33 to 37° C., as described above, were washed 3 times with BSK-H medium and the cell density adjusted to $\sim 10^6$ cells mL$^{-1}$. Eight µL of cells were combined with 8 µL of guinea pig complement (Sigma) and 4 µL of each test serum (heat inactivated at 56° C.; 30 min). Controls included heat inactivated anti-ABKD antisera without complement, complement only, and pooled heat-inactivated preimmune sera with complement. The total reaction volume was brought to 20 µL by the addition of BSK-H medium, as needed, and the samples were incubated at 37° C. for 18 hr. Killing was assessed using the BacLight LIVE/DEAD assay (Molecular Probes) and manual counts of live and dead/damaged cells in five high power fields using an Olympus BX51 fluorescence microscope with fluorescein and rhodamine filter sets.

Results

Identification of the Epitopes of OspC Types B, D, and K that are Presented During Infection in Mice and Humans.

To date, OspC types A, B, C, D, H, I, K and N have been recovered from patients determined to have invasive infections [Seinost et al, 1999; Example 1; Alghaferi et al, 2005]. Four of these OspC types (A, B, K, and D) were selected to establish proof of principle of the utility of a polyvalent chimeric OspC vaccine. Since the epitopes presented during infection had only been identified for type A OspC, the first step in this study was to identify the infection-relevant epitopes of OspC types B, K and D. To accomplish this, immunoblots of truncations and fragments of each type were screened with sera from mice infected with clonal populations of *B. burgdorferi* (OspC types B, K or D) or with sera from human Lyme disease patients determined to have been infected, at least in part, with *B. burgdorferi* strains producing OspC of types B, K, or D (personal communication, Dr. Allen Steere and Kathryn Jones). The antibody response in mice at week 6 was type-specific; however, some of the human sera displayed cross-immunoreactivity between types (data not shown) suggesting that these patients were possibly infected with mixed spirochete populations. For OspC type B, the epitopes localized in alpha helix 5 (between aa 175 and 200) for mouse infection sera. Human infection sera reacted with a similarly located fragment (aa 164-185), indicating that the alpha helix 5 region of type B is antigenic. In type K OspC, epitopes were mapped between aa 148 and 160 in the mouse, and to the alpha helix 5 region (between aa 160 and 175) in the human. OspC type D epitopes were mapped to the alpha helix 5 region (between aa 167 and 180) in the mouse and in the human, though there were multiple additional epitopes recognized by the human serum. These data indicate that the alpha helix 5 region of OspC types B, K, and D are appropriate selections for inclusion in the tetravalent ABKD vaccinogen construct.

Construction, Expression and Purification of a Tetravalent Chimeric OspC Vaccinogen.

Using the alpha helix 5 epitopes defined above for types B, K and D and the type A loop 5 epitope defined in an earlier study [Example 1] a polyvalent, chimeric r-vaccinogen was produced that is composed of the four epitope-containing regions. The epitopes were joined by short, unstructured, protease-resistant linker sequences (FIG. 9B). The recombinant vaccinogen is 169 aa in length with a molecular mass of 18.0 kDa and an isoelectric point of 6.49. Its structure is predicted to be predominantly helical [Gasteiger et al, 2005; Kneller et al, 1990] and to have a high stability index [Guruprasad et al, 1990]. Following dialysis with PBS, there was some precipitation of recombinant vaccinogen; however, approximately 500 µg mL$^{-1}$ remained soluble, and this soluble protein was used for all experiments. Analysis of the purified vaccinogen protein by SDS-PAGE demonstrated a single band of 18 kDa molecular mass and no contaminating proteins.

Immunogenicity of the ABKD Chimeric Vaccinogen in Mice.

Figure 10:
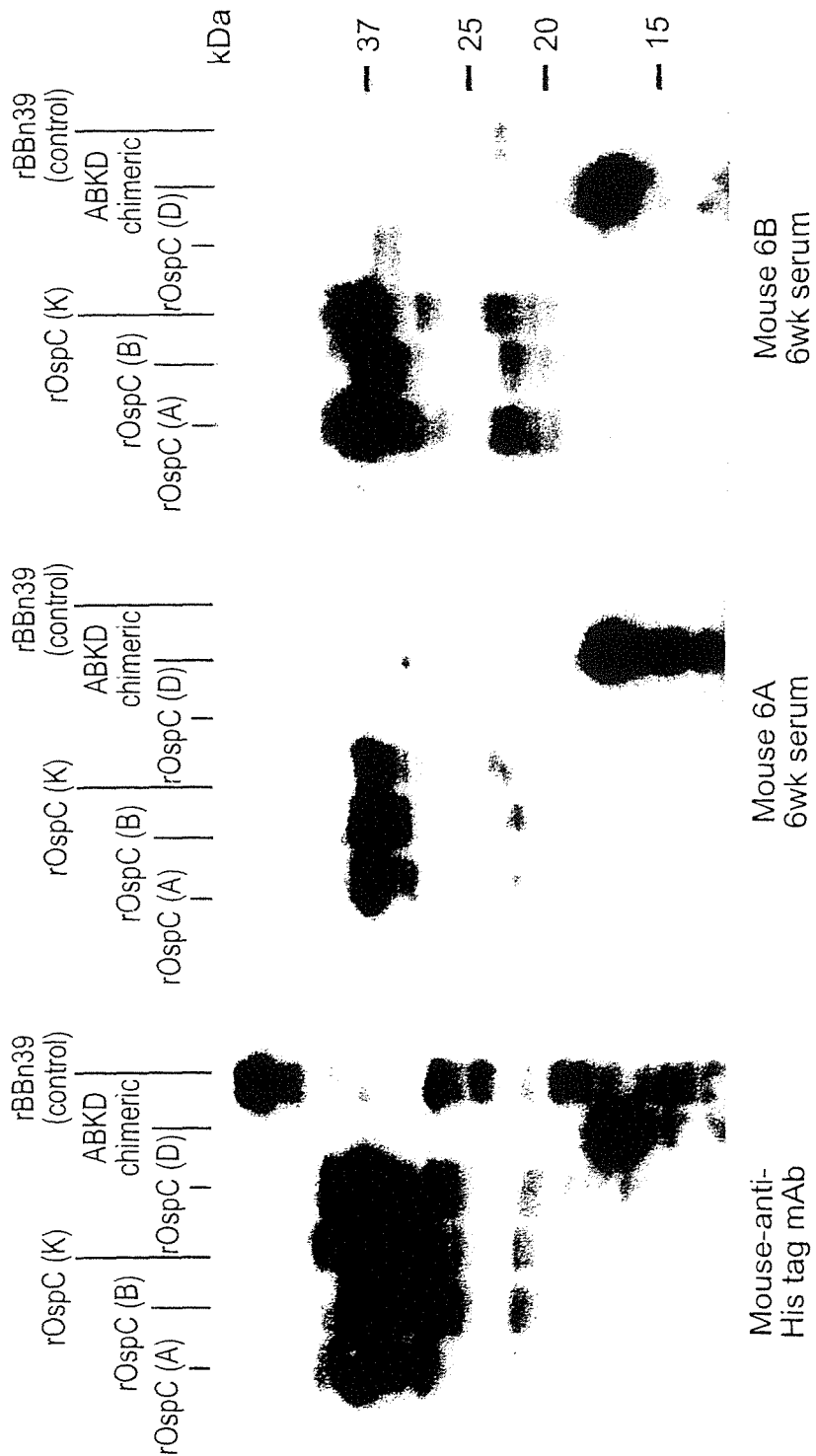
FIG. 10. Western blot demonstrating immunoreactivity of anti-ABKD antiserum with the ABKD chimeric vaccinogen and full length OspC. Immunogenicity was evaluated by immunoblotting the ABKD chimeric vaccinogen, full length r-OspC proteins of types A, B, K and D (as indicated), and rBBN39 (negative control). The blots were screened with anti-His tag mAb to demonstrate approximately equal loading, or with representative anti-ABKD antisera (indicated below). Molecular mass is shown on the right. A strong IgG response to A, B and K (but not D) was observed.
Figure 11A:
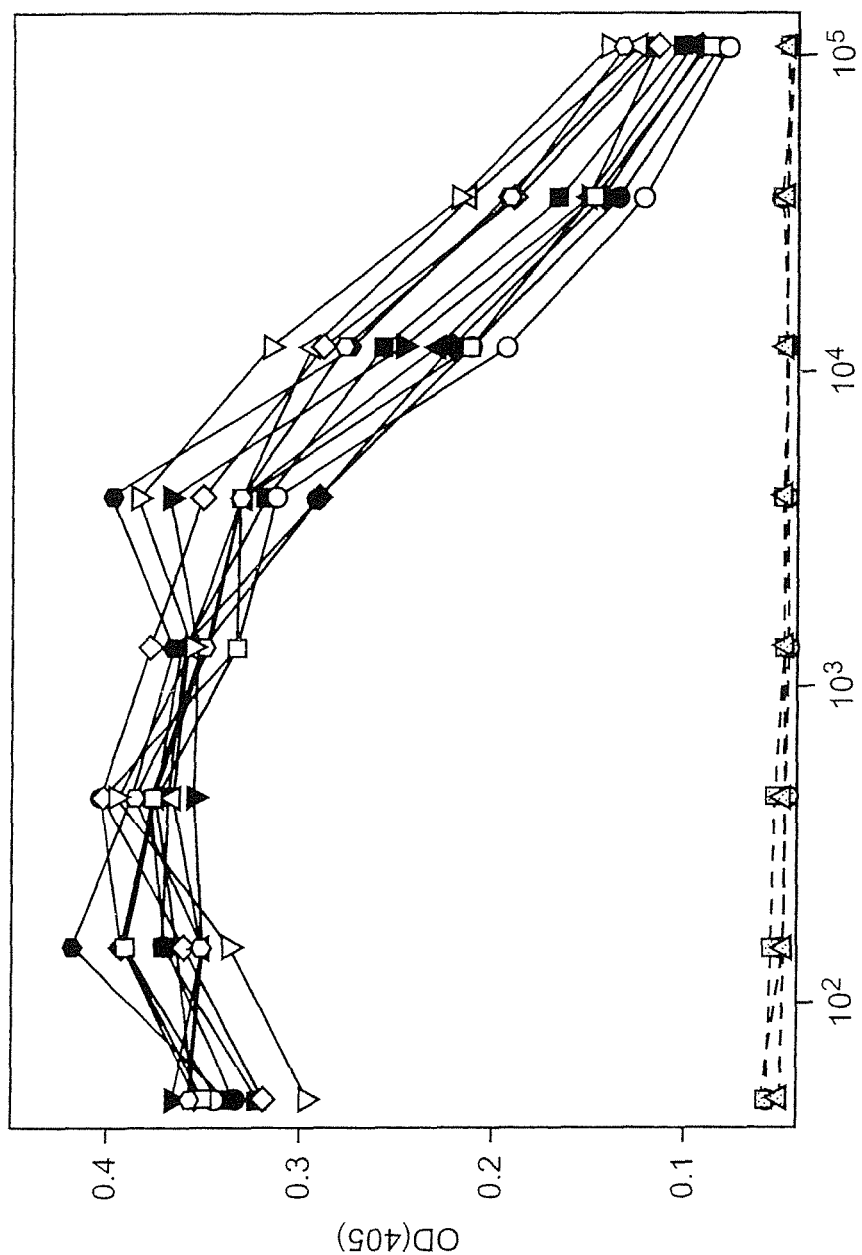
FIGS. 11A and B. ELISA titration of the reactivity of sera from mice immunized with the ABKD chimeric vaccinogen. A, Sera from mice vaccinated with the ABKD chimeric vaccinogen (n=12) or sham immunized with PBS/adjuvant (n=3) were titrated for reactivity with the ABKD chimeric vaccinogen or rOspC protein of types A, B, K, and D. Panel A demonstrates the titration of immunoreactivity of all sera to the ABKD chimeric vaccinogen construct (solid lines with a different symbol for each mouse). No Ab response was observed in the sham vaccinated mice (dashed lines). B, Titrations of the specific response to each OspC type were also completed (curves not shown), and the titers determined at ½ max OD405 are shown in panel B (one point per mouse, horizontal line at the mean titer). Control mice had no titer, and were not plotted.
Figure 11B:
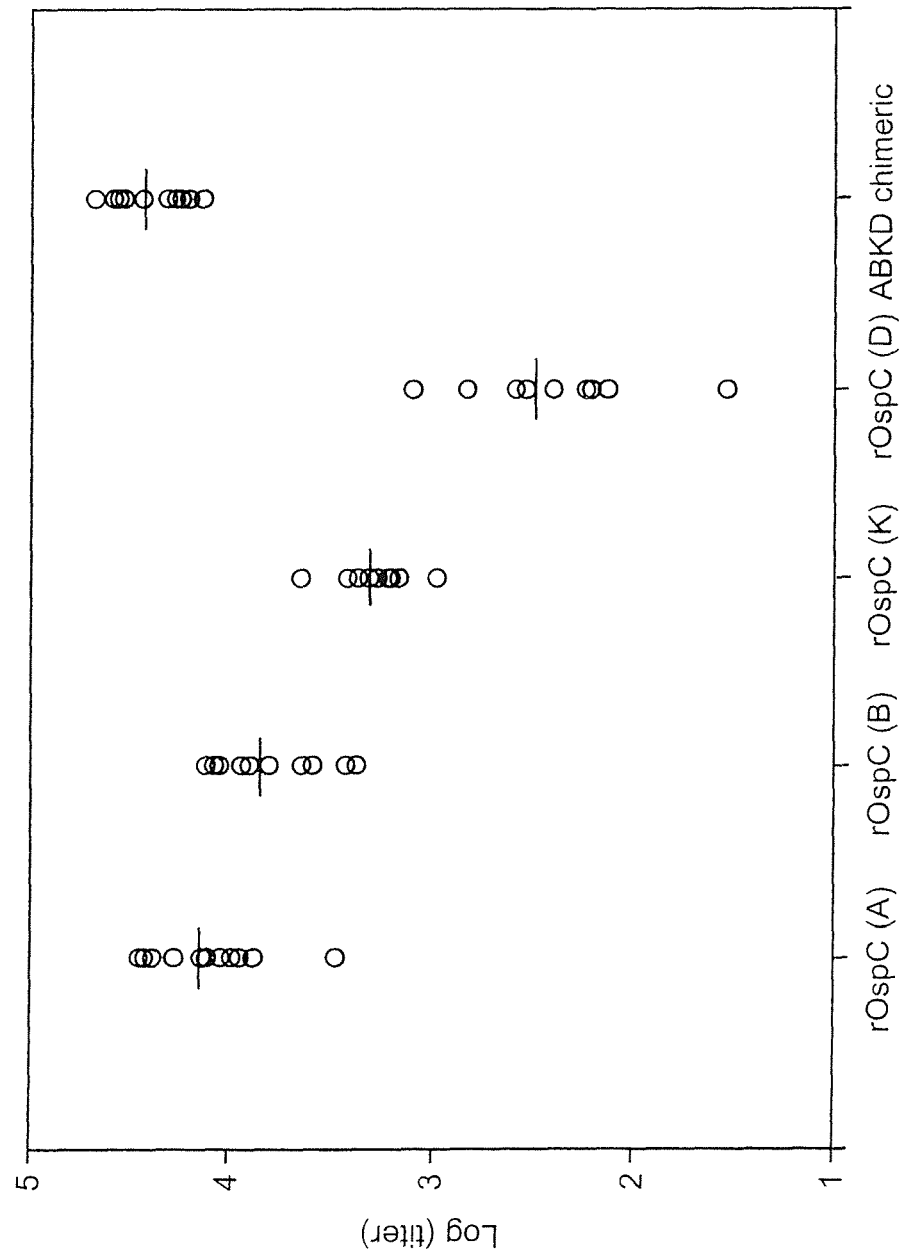

To assess the antibody response to the ABKD chimeric vaccinogen and its individual component epitopes, C3H/HeJ mice were administered the vaccinogen in Freund's adjuvants. Serum was collected from the vaccinated (n=12) and sham (PBS+adjuvant) immunized mice (n=3) and assessed for reactivity with the ABKD chimeric vaccinogen and full length r-OspC proteins of types A, B, K, and D. Western blot analysis demonstrated that the anti-ABKD antisera reacted strongly with the vaccinogen protein and with r-OspC of types A, B, and K. In contrast, reactivity with the C-terminal OspC type D epitope of the chimeric construct was considerably weaker (FIG. 10). There was no reactivity of any of the sera with the negative control protein (r-BBN39) and sera from sham-vaccinated mice did not react with any of the proteins. Quantitative ELISA-based titration of serum reactivity demonstrated a high-titered IgG response against the ABKD chimeric vaccinogen protein, with a mean titer of 27,800 (FIG. 11A). Titration of reactivity against type-specific epitopes was accomplished by assessing binding with immobilized full length r-OspC proteins. Significant differences in the antibody titer to the individual epitopes were observed (FIG. 11B). It is notable that the epitope-specific titer decreases with its proximity to the C-terminus of the vaccinogen.

Immunoglobulin Isotype Profile of the Anti-ABKD Antisera.

Figure 12:
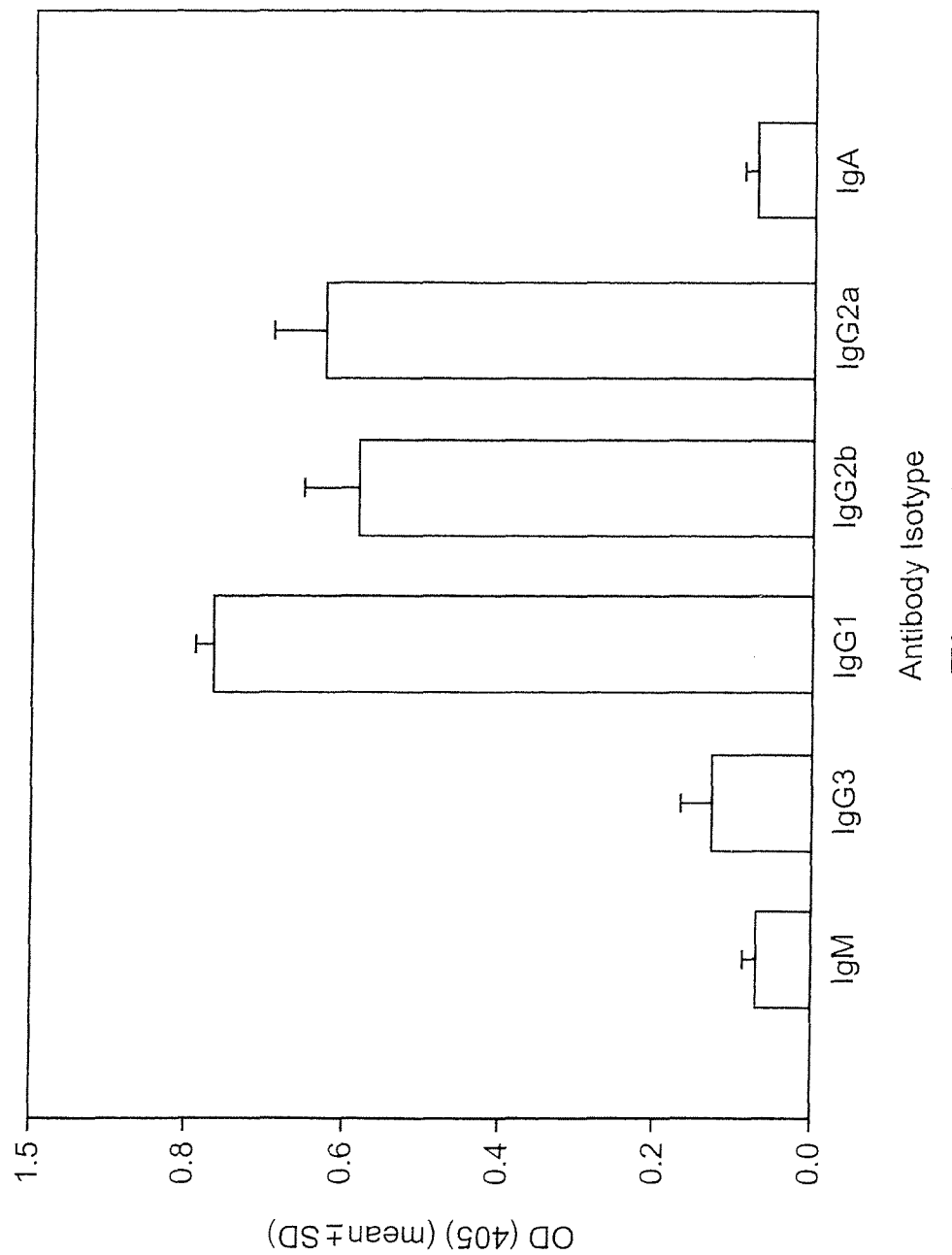
FIG. 12. Immunoglobulin isotype profile of anti-ABKD antiserum. ELISA wells were coated with the ABKD chimeric vaccinogen construct (100 ng/well) and probed with anti-ABKD antisera in duplicate (1:10000; n=12). Bound Ig was detected by biotinylated isotype-specific secondary Ab (Mouse Isotyping Kit; Zymed Laboratories) and HRP-conjugated streptavidin. Reactivity was quantified by measurement of the colored product created by the HRP-mediated conversion of ABTS substrate.

The immunoglobulin isotype profile is critical for the assessment of potential effector functions of vaccine-specific antibodies. To assess immunoglobulin heavy chain class switching induced by the ABKD chimeric vaccinogen, the isotype profile was determined by ELISA. The predominant isotype was IgG1, with marginally lower levels of IgG2a and IgG2b. The six-week sera showed only limited levels of IgM, IgG3, or IgA (FIG. 12).

Indirect Immunofluorescence Assays.

The ability of antibody elicited to each epitope of the ABKD chimeric vaccinogen to bind OspC on the *Borrelia* cell surface was assessed by indirect immunofluorescent microscopy. Specific surface labeling was observed with cells producing OspC of types A, B, K, and D (data not shown). The intensity of the fluorescent signal was consistent with the type-specific titer, with the most intense fluorescence seen with cells bearing OspC types A or B. Fluorescence of cells of bearing types K or D was less intense, and the staining was patchy, giving the cells a stippled appearance. No reactivity was noted in cells probed with matched preimmune sera. The lack of surface labeling by anti-flagellin antibody to air fixed cells served to verify that the outer membrane of the cells was intact and that the epitopes detected are naturally presented at the cell surface. As expected, cells permeabilized with acetone were labeled by anti-flagellin antibody (data not shown).

Demonstration that Vaccination with the ABKD Chimeric Vaccinogen Induces Bactericidal Antibody.

The bactericidal activity of the anti-ABKD antisera was assessed using the LIVE/DEAD BacLight assay [Tily et al, 2001; Ledin et al, 2005; Elias et al, 2000; Montgomaery et al, 2006; Elias et al, 2002; Shin et al, 2004]. Bactericidal activity was detected against strains bearing OspC of all types included in the chimeric vaccine construct. Incubation with the anti-ABKD antiserum induced significant cell aggregation. Both live and dead cells were present within the aggregates. Due to the inherent difficulty of counting cells within aggregates, the percentage of live and dead cells were determined by counting only non-aggregated, free cells. For all four OspC types, the background level of dead cells in the cultures used for the bactericidal assay was approximately 20-30%. This background level of dead cells has been consistently observed in our laboratory following transfer of the cultures from 33 to 37° C. to upregulate OspC expression. In the bactericidal assay, killing occurred in a complement dependent fashion, with the percentage of dead cells increasing significantly above background to 56 to 90%. The number of dead cells was in all cases at least twice that of the number of dead cells seen in any of the controls. Complement alone did not elicit killing. There was no bactericidal activity elicited by pooled preimmune serum, indicating that the specific immune response to the vaccinogen was necessary for bactericidal activity.

Discussion

Several studies have explored the potential utility of OspC of the Lyme disease spirochetes as a potential vaccinogen. Although vaccination with OspC elicits a protective antibody response, protection has been reported to be largely strain specific [Gilmore et al, 1996; Scheiblhofer et al, 2003; Wallich et al, 2001; Brown et al, 2005; Probert and LeFebvre, 1994; Gilmore 3t al, 2003]. Attempts to elicit broader protection using cocktails of multiple OspC proteins have not proven successful. Baxter tested an OspC cocktail consisting of 14 different full length OspC variants; however, they were not able to elicit sufficient antibody titers directed against the unique domains of each variant—a requirement if broad protection is to be conveyed. In addition, unacceptable reactigenicity was reported [Hanson et al, 2004]. A general concern with cocktail vaccines is the potential misdirection of the antibody response to epitopes that are not naturally presented during infection and that do not elicit protective antibody. The generation of chimeric vaccines offers an alternative approach that can circumvent the problems encountered using simple cocktails of r-proteins. Chimeric vaccines consisting of a series of immunodominant epitopes have been explored in the development of vaccines against malaria [Hanson et al, 2004; Caro-Aguilar et al, 2005;], group A streptococci [McNeil et al, 2005; Dale et al, 2005; Hu et al, 2002; Dale, 1999; Kotloff et al, 2005; Horvath et al, 2005], and several viruses [Apt et al, 2006; Fan and Mei, 2005; Wang et al, 2005; Bouche et al, 2005]. If a polyvalent OspC vaccine is to be broadly protective it will be necessary to incorporate into the vaccinogen a sufficient array of epitopes to elicit a protective response against diverse strains. The ability to move forward with the construction of such a vaccinogen has been greatly facilitated by phylogenetic analyses which have delineated 21 distinct OspC types designated A through U [Seinost et al, 1999], of which only a subset have been correlated with invasive infection in humans [Seinost et al, 1999; Example 1; Alghaferi et al, n 2005].

A detailed understanding of the epitope structure of OspC is required for the development of a chimeric vaccinogen. There have been several previous descriptions of OspC epitope locations [Gilmore et al, 1996; Jobe et al, 2003; Lovrich et al, 2005]. Two studies have reported that the epitope responsible for eliciting bactericidal antibodies resides within the C-terminal domain of OspC [Jobe et al, 2003; Lovrich et al, 2005]; however, since this domain is relatively conserved it is not clear why antibodies against the C-terminus are not broadly protective. Matheisen et al. also suggested that the C-terminus was the predominant target of the antibody response, noting greater reactivity of sera from European neuroborreliosis patients with full length OspC than with a 10 amino acid C-terminal truncated form [Mathiesen et al, 1998]. From this they concluded that there must be a C-terminal epitope; however, since the test antigen consisted of a single OspC variant of unknown type, the more widespread recognition of the C-terminus may be due to the greater conservation of this domain and not necessarily indicate that the C-terminus is immunodominant. Gilmore et al. demonstrated that immunization of mice with a non-denatured, but not with a denatured, r-OspC conferred protection to challenge with the homologous isolate [Gilmore et al, 1996; Gilmore and Mbow, 1999], indicating that protective epitopes may be conformationally defined. In a separate analysis, Gilmore et al. analyzed the immunoreactivity of a limited number of OspC truncations derived from a single OspC type (type A) with an anti-OspC monoclonal antibody that confers passive immunity [Gilmore and Mbow, 1999]. Deletion of either the N- or C-terminus eliminated detection of the r-proteins by the mAb, further suggesting the existence of a conformational or discontinuous epitope. It is not clear if the epitope recognized by the mAb is immunodominant, relevant during natural infection or conserved among the different OspC types. Linear immunodominant epitopes of type A OspC have recently been mapped and found to reside within the loop 5 and alpha helix 5 regions [Example 1]. A r-protein containing the type A loop 5 epitope elicited bactericidal antibodies in mice, raising the possibility that individual type-specific epitopes can be exploited in vaccine development [see Example 2]. In this report, the epitopes of OspC types B, K, and D that are presented during early infection are mapped, and a tetravalent chimeric vaccinogen based on these epitopes has been constructed. This ABKD chimeric vaccinogen was highly immunogenic in mice and elicited antibodies that bind OspC at the cell surface and effectively kill strains producing types A, B, K, and D OspC in a complement-dependent manner.

The first step in our efforts to develop a tetravalent chimeric test vaccinogen was to identify the linear epitopes of OspC types B, K and D presented during infection in mice and humans. These analyses were conducted essentially as described in Example 1 that identified the loop 5 and alpha helix 5 epitopes of type A OspC. In brief, extensive panels of type B, K and D OspC truncations and fragments were screened with serum from mice infected with clonal isolates and from humans infected with, at least in part, a strain expressing the corresponding OspC type. Precise epitope mapping was possible using sera from the experimentally infected mice; however, in naturally infected humans the antibody response was to a broader epitope array. This is not surprising and presumably reflects the expansion of the antibody response to OspC epitopes that are not normally presented at the bacterial cell surface during early infection. New epitopes, some of which may be from conserved domains of OspC (e.g. alpha helix 1), may become accessible upon bacterial cell death and release of OspC from the membrane. This illustrates the caveats that accompany the use of human serum samples in epitope mapping; namely that the exact duration of infection is typically not known and the clonality of the infecting population is doubtful [Wang et al, 1999; Ruzic-Sabljic et al, 2006; Hofmeister et al, 1999; Guttman et al, 1996; Rijpkema et al, 1997]. In any event, it is clear from the analyses of the human serum samples that epitopes within the alpha helix 5 region are recognized during infection by strains producing OspC types A, B, K or D. In addition, the consistency of the response to alpha helix 5 among several different OspC type producing strains may be an indication of functional relevance of this OspC domain.

Although the alpha helix 5 and loop 5 region sequences are variable between OspC types, these regions are highly conserved within each type [see Examples 1]. This suggests that, in the context of a chimeric vaccine, only a limited number of OspC epitopes will be required to effect broad protection. As a first step in the development of a broadly protective vaccinogen, the type A loop 5 epitope and the alpha helix 5 epitopes from OspC types B, K and D were employed in the development of a test vaccinogen. The region containing these epitopes was PCR amplified with primers designed to encode linker sequences. This allowed the use of PCR overlap extension in the creation of the chimeric construct, and provided a means to separate the epitopes with short, unstructured, protease-resistant amino acid sequences [Crasto and Feng, 2000]. The experimental OspC-based, tetravalent, ABKD chimeric vaccinogen developed in this study elicited a consistent, high titered IgG antibody response in all mice tested (n=12). Furthermore, the vaccinogen elicited antibody to each incorporated epitope. Interestingly, the epitope-specific titer appears to be influenced by the epitope position within the construct. There was a progressive decrease in titer from the N-terminal epitope (loop 5 of type A) through the C-terminal epitope (alpha helix 5 of type D). The phenomenon of decreased titer to C-terminal epitopes was also reported in early studies of a streptococcal M-protein based chimeric vaccine [Dale et al, 1993; Dale et al, 1996]. The basis for the location-specific effect on titer is not clear, but may be due to in vivo degradation or alteration of the structure of the C-terminus [Dale et al, 1999].

Although the Th cytokine response and related immunoglobulin isotype pattern necessary for protection against *Borrelia* infection have not been completely resolved [Kraiczy et al, n 2000; Widhe et al, 2004; Keane-Myers et al, 1995; Keane-Myers et al, 1996; Keane-Myers and Nickell, 1995], determination of this pattern is an important step in vaccinogen development and may provide important information regarding the potential protective capability of different constructions of the vaccinogen. The isotype profile of the response was determined by ELISA, and heavy chain Ig isotypes associated with a mixed Th1 and Th2 cytokine response were observed. The class switching noted in this study implies adequate T-cell help, even in the absence of a defined T-cell epitope incorporated into the vaccinogen. Analysis of the vaccinogen sequence using predictive peptide binding algorithms for a subset of the murine (H2Ak/H2Ek) and human (HLA-DRB1) type II MHC, revealed potential T-cell epitopes in the vaccinogen predicted to bind all available alleles [Rammensee et al, 1999; Zhang et al, 2005]. One of the predicted binding peptides, LANSVKELT is repeated three times within the construct, and this repetition may be important in eliciting a Th response [Jiang et al, 1999; Ahlborg et al, 1998; Kjerrulf et al, 1997; Theisen et al, 2000]. While the analysis of potential T-cell epitopes was not exhaustive, the predictions support our data that indicate the chimeric vaccinogen can elicit T-lymphocyte help in the mouse. Further, it implies that this construct would likely do so in humans without the need to incorporate a promiscuous T-cell epitope sequence. The importance of Freund's adjuvants in the generation of this isotype profile is not known, but the responses and isotype profiles will need to be assessed in the context of alum or other adjuvants appropriate for use in humans [ten Hagen et al, 1993; Lindblad, 2004; Petrovsky and Aguilar, 2004; Brewer et al, 1999; McNeela and Mills, 2001]. Additionally, alteration of the epitope order or structure of the chimeric vaccinogen may provide a mechanism by which the immune response can be tailored to maximize in vivo protection [Tongren et al, 2005; Cai et al, 2004].

For the response to the vaccinogen to be productive in terms of vaccine development, the elicited antibody must be able to bind to the surface of intact *B. burgdorferi* cells and cause bacterial killing. IFA analyses revealed strong labeling of the cell surface of strains producing OspC types A, B, K and D. Even though the antibody titer to the type D epitope was of significantly lower titer than that elicited to the more N-terminal epitopes, surface labeling of type D producing strains was readily apparent. A subset of cells in each of the OspC type cultures were observed not to label with the anti-ABKD antisera, implying that those cells were not expressing OspC. However, in vivo, it has been demonstrated that most if not all cells are expressing OspC during transmission from the tick to mammal and during early mammalian infection [Gilmore et al, 2001; Zhong et al, 1997]. The ability of anti-ABKD antibody to effect cell killing was also assessed. Serum from vaccinated mice efficiently killed spirochetes expressing types A, B, K and D OspC proteins in a complement dependent manner. While there was less than 100% killing for all of the OspC types, this is likely a function of the heterogeneity of in vitro OspC expression among cells of a population, a phenomenon that has been well documented in vivo [Schwan et al., 1995; Schwan and Piesman, 2000; Hu et al., 1996].

This Example describes the construction and proof of principle of a novel r-chimeric polyvalent OspC-based Lyme disease vaccinogen. The use of an epitope-based r-chimeric protein allows coverage of multiple OspC types in the same construct, and circumvents the potential problem of immune responses misdirected against irrelevant protein domains. The mapping of linear epitopes recognized during active infection is a crucial component of chimeric vaccine development, and this has been successfully completed for four OspC types associated with invasive infection in humans. The epitopes included in the vaccinogen have elicited type-specific IgG antibodies capable of binding OspC at the *Borrelia* cell surface, and effecting complement-mediated bacterial killing.

Example 4

Immune Responses to Variants of a Chimeric Polyvalent Lyme Disease Vaccine Intended to Improve Immunogenicity In this study, we sought to improve the solubility of the construct and assess the potential impact of epitope placement, epitope reiteration, and the inclusion of putative C-terminal stabilizing tags on the immune response. These analyses provide new insight into design strategies for a broadly protective OspC vaccine, and for construction of chimeric vaccines in general.

Materials and Methods

Expression and Purification of Recombinant OspC

Recombinant full length OspC proteins of types A, B, K and D were generated as previously described [see Examples 1 and 2]. Briefly, the ospC gene from clonal populations of *B. burgdorferi* isolates B31MI (type A OspC), LDP73 (type B), LDP74 (type K), and LDP116 (type D) were amplified by PCR using primers with 5' overhangs to allow ligase-independent cloning (LIC) in the pET-32 Ek/LIC vector (Novagen) [Example 1]. After amplification and regeneration of single stranded tails, the amplicons were annealed with the pET-32 Ek/LIC vector, which was transformed into and propagated in NovaBlue (DE3) *E. coli* cells. Following confirmation of the insert sequence by DNA sequencing (MWG-Biotech), protein expression was induced with IPTG (1 mM). Proteins were purified by nickel affinity chromatography using the pET-32 Ek/LIC expression tag-encoded hexahistidine motif (Novagen). The imidazole-eluted proteins were dialyzed extensively against phosphate buffered saline (PBS; pH 7.4) across a 10 kDa molecular weight cut-off membrane (Slid-a-lyzer, Pierce), the protein concentration was quantified by the BCA assay (Pierce), and the purity of the preparation was assessed by SDS-PAGE.

Construction, Expression, and Purification of ABKD Vaccine Variants

Figure 13B:
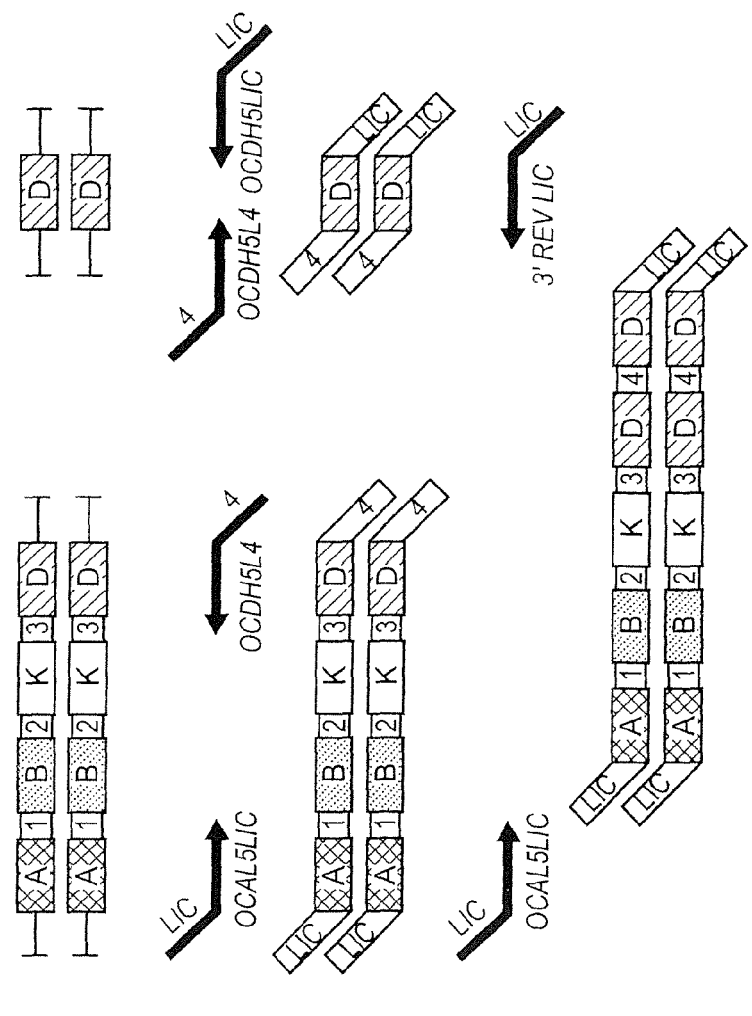
FIG. 13A-E. Schematic representation of the construction of the ABKD vaccine variants. ABKDppa (Panel A) was constructed by amplification of the original construct using a reverse primer with a 5' overhang to add the C-terminal amino acids. ABKDgg (not shown) was made in an identical manner, but using the OCDH5ggLIC primer. ABKDD (Panel B), ADBK (Panel C), and ADBKD (Panel D) were all made by PCR amplification of constituent sequences using primers that added tails encoding linker sequences. The resultant PCR products were gel purified, and joined by overlap annealing and extension. The final products were cloned into the pET-46 Ek/LIC vector. OspC type-specific epitope containing regions are denoted by letter, and linker sequences by number (see inset for encoded amino acid sequences). Arrows denote primers, and 5' overhanging LIC tails or linker sequences are noted on the tail of each primer arrow.
Figure 13A:
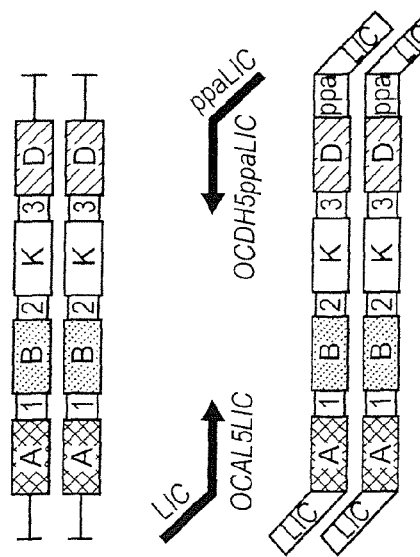
Figure 13C:
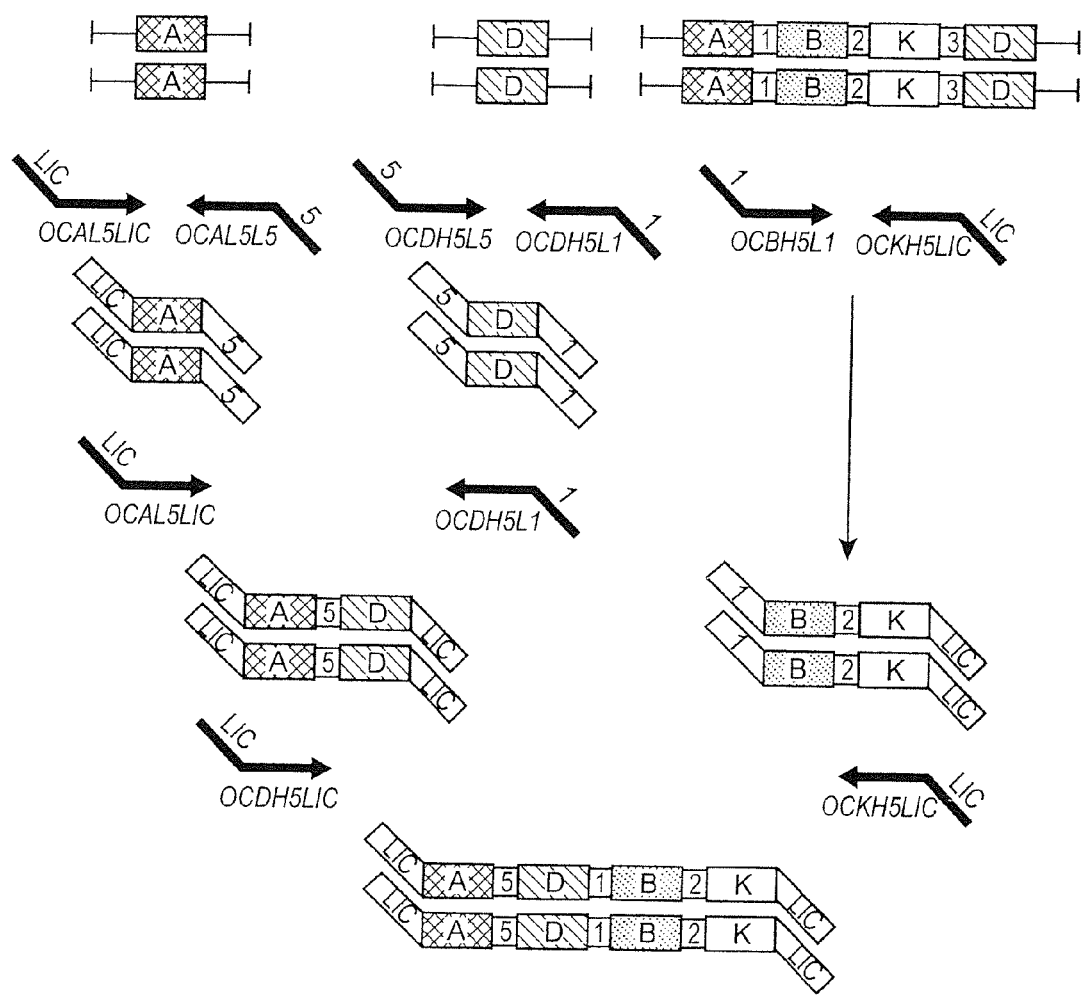
Figures 13D, 13E:
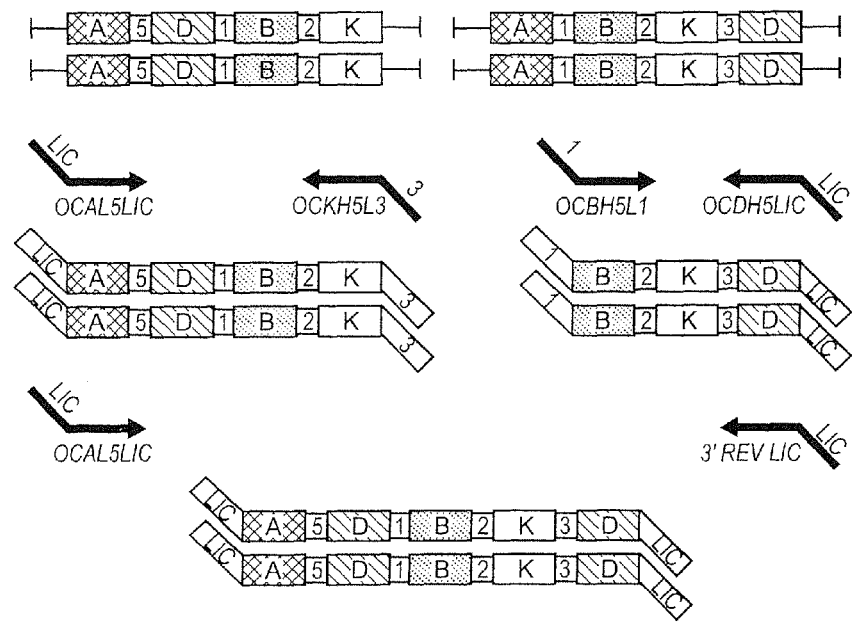

In order to investigate potential mechanisms of, and solutions to, the decreasing IgG titer to specific epitopes across the vaccine construct, multiple variants of the original vaccine were constructed. All vaccine variants were based on the sequence of the ABKD vaccinogen previously described [Example 3] and contain the same epitope-containing sequences. These include the loop 5 region of type A (amino acids (aa) 131 to 149) and the alpha helix 5 regions of types B (aa 160-201), K (aa 161-201), and D (aa 161-201) (FIG. 13 inset). The ABKDppa and ABKDgg added a Pro-Pro-Ala or Gly-Gly motif, respectively, to the C-terminus of the original ABKD construct. Both of these constructs were made by amplifying the original ABKD construct using reverse primers (Table 5) that added the motif via a 5' overhang encoding the appropriate amino acids (FIG. 13A). The other vaccine variants were made by overlap annealing and extension techniques similar to those used in construction of the original ABKD vaccinogen [Example 3]. The ABKDD construct was made by re-amplifying the ABKD construct using a reverse primer bearing a 3' tail sequencing encoding an unstructured, protease-resistant linker. This allowed the PCR product to anneal to the type D OspC epitope-containing sequence that had been amplified with the complementary linker-encoding sequence at the 5' end, with subsequent overlap extension and amplification of the annealed construct (FIG. 13B). The ADBK construct was made by annealing separately amplified type A and D epitope-containing regions with each other and subsequently with the type B and K helix 5 epitope regions amplified from the original ABKD construct (FIG. 13C). The ADBKD construct was made by annealing amplicons from the ABKD and ADBK sequences (FIG. 13D). In all cases, the PCR amplification was completed with GoTaq Green (Promega) using an initial 2 min 94° C. denaturation step, followed by 35 cycles of denaturation at 94° C. for 15 sec, primer annealing at 50° C. for 30 sec, and extension at 72° C. for 60 sec, with a final 72° C. extension for 7 min. All primers use in construction of these vaccinogens are listed in Table 5. All PCR products were gel purified (Qiagen) prior to use as templates in subsequent PCR reactions. Final amplicons were annealed to the pET-46 Ek/LIC vector by ligase independent cloning, and transformed into Novablue (DE3) *E. coli* cells. Colonies were screened for inserts using T7 primers, and plasmids were recovered (Qiafilter Midi, Qiagen) for confirmation of the insert by DNA sequencing. Recombinant proteins were expressed and purified as described above. Following purification, the vaccine proteins were dialyzed across a 10 kDa molecular weight cutoff membrane (Slide-a-Lyzer, Pierce) against three changes of either PBS (pH 7.4) or a pH 8 buffer containing 100 mM phosphate, 100 mM NaCl, 50 mM arginine, 50 mM glutamic acid (Arg/Glu buffer) [Golovanov et al, 2004]. The purity of the constructs was assessed by SDS-PAGE.

TABLE 5

Primers used in construction of the chimeric vaccinogens.

| Primer | Sequence | Description | SEQ ID NO: |
|---|---|---|---|
| OCAL5LIC(+) | GACGACGACAAGATTTCTGAAACATTTACTAATAAATTAAAAGAAAAAC | Amplifies type A from aa 131 and adds LIC tail | 234 |
| OCAL5L5(-) | TAAAGCTGACATAGCACCTTCTTTACCAAGATCTGTGTG | Amplifies type A up to aa 149 and adds linker 5 (GAMSAL; SEQ ID 80) | 235 |
| OCBH5L1(+) | GGTAGCATGGGTATGTTAAAAGCAAATGCAGCGGG | Amplifies type B from aa 160 and adds linker 1 (GSMGML; SEQ ID 76) | 236 |

TABLE 5 -continued

Primers used in construction of the chimeric vaccinogens.

| Primer | Sequence | Description | SEQ ID NO: |
|---|---|---|---|
| OCKH5L3(-) | TAAAACGCTCATGCTA CTTGTAAGCTCTTTAA CTGAATTAGC | Amplifies type K up to aa 201 and adds linker 3 (SSMSVL; SEQ ID 78) | 237 |
| OCKH5LIC(-) | GAGGAGAAGCCCGGT TTAACTTGTAAGCTCT TTAACTGAATTAGC | Amplifies type K up to aa 201 and adds an LIC tail | 238 |
| OCDHSLIC(-) | GAGGAGAAGCCCGGT TTAACTTGTAAGCTCT TTAACTGAATTAG | Amplifies type D up to aa 201 and adds an LIC tail | 239 |
| OCDH5ppaLIC(-) | GAGGAGAAGCCCGGT TTATGCAGGAGGACTT GTAAGCTCTTTAACTG AATTAG | Amplifies type D up to aa 201 and adds TPA' and an LIC tail | 240 |
| OCDH5ggLIC(-) | GAGGAGAAGCCCGGT TTATCCTCCACTTGTA AGCTCTTTAACTGAAT TAG | Amplifies type D up to aa 201 and adds 'GG' and an LIC tail | 241 |
| OCDH5L1(-) | TAACATACCCATGCTA CCACTTGTAAGCTCTT TAACTGAATTAG | Amplifies type D up to aa 201 and adds linker 1 (GSMGML; SEQ ID 76) | 242 |
| OCDH5L4(+) | AGTTCAAGCCAAGGCT TAAAAACACATAATGC TAAAGACAAG | Amplifies type D from aa 161 and adds linker 4 (SSSQGL; SEQ ID 79) | 243 |
| OCDH5L4(-) | TAAGCCTTGGCTTGAA CTTGTAAGCTCTTTAA CTGAATTAGC | Amplifies type D up to aa 201 and adds linker 4 (SSSQGL; SEQ ID 79) | 244 |
| OCDH5L5(+) | GGTGCTATGTCAGCTT TAAAAACACATAATGC TAAAGACAAG | Amplifies type D from aa 161 and adds linker 5 (GAMSAL; SEQ ID 80) | 245 |
| 3'REVLIC(-) | GAGGAGAAGCCCGGT | Amplifies up to the 3' LIC tail | 246 |
| pET46 T7(+) | CGAAATTAATACGACT CACTATAGGGG | Amplifies from pET46, 123 bases upstream of cloning site | 247 |
| pET46 T7(-) | GCTAGTTATTGCTCAG CGG | Amplifies up to pET46, 117 bases downstream of the cloning site | 248 |

LIC tails are in bold, and linker sequences are underlined.

Immunization of Mice with Vaccine Variants

Six week old male C3H/HeJ mice were immunized (3 mice per construct) with each of the six vaccinogen variants. Since the immunogenicity of the variants were to be compared with each other, it was desirable to administer the protein on a molar basis, to compensate for differences in the number of epitopes per unit of vaccinogen mass. Each mouse received approximately 2.8 nanomoles of protein per immunization, which is 50 μg of constructs ABKD, ABKDppa, ABKDgg, and ADBK or 62.5 μg of constructs ABKDD and ADBKD. Mice were immunized with vaccine in complete Freund's adjuvant, then boosted with Freund's incomplete adjuvant on weeks 2 and 4. Serum was collected from all mice by tail nick prior to the first immunization and at week 6. To determine the effect of adjuvant on the total and epitope-specific antibody titers, as well as on isotype profiles, mice (6 per adjuvant) were immunized with the ABKD vaccinogen emulsified in Freund's adjuvants as described above, or adsorbed onto alum (Imject Alum, Pierce), and serum was collected by tail nick at week 6.

Assessment of Epitope-Specific IgG Titer Induced by Vaccine Variants

The immunogenicity of each vaccinogen was assessed both by Western blot and ELISA. For the western blots, r-OspC of types A, B, K, D were loaded at 500 ng per lane in reducing sample buffer, electrophoresed in a 12.5% SDS-PAGE gel (Criterion, Biorad), and electroblotted to PVDF (Immobilon-P, Millipore). The blots were blocked with 1% BSA in phosphate buffered saline with 0.2% Tween-20 (PBS-T). The blots were probed with a 1:2500 dilution of each antiserum in PBS-T for one hour, and then washed three times. To verify equal protein loading, one blot was screened with anti-His tag monoclonal antibody (1:2000; Novagen). Secondary detection was by a 1:40000 dilution of peroxidase-conjugated goat-a-mouse IgG and chemiluminescence (SuperSignal Pico, Pierce). For quantitative analysis, OspC type-specific IgG titers were determined by ELISA analyses. r-OspC of types A, B, K, or D were coated onto 96 well plates (Costar 3590; Corning) at 100 ng well-1 for 16 hr at 4° C. in carbonate buffer (pH 9.6). The plates were blocked (1% BSA in PBS with 0.2% Tween-20 (PBS-T); 2 hr), washed 3 times with PBS-T, and serially diluted anti-vaccinogen antiserum (100 µL) was added to the wells of duplicate plates (1 hr). HRP-conjugated goat-a-mouse IgG (1:20000) served as the secondary antibody and ABTS as the chromogenic substrate. The absorbance was read at 405 nm in an ELISA plate reader (ELx 808; Biotek) while the reaction rate was linear, and titers were calculated by fitting a sigmoidal curve to the absorbance curve by a four parameter logistic equation (SigmaPlot). The titer is reported as the inverse dilution corresponding to 50% of the maximum absorbance plateau.

Determination of Epitope-Specific Immunoglobulin Isotype Profiles

The isotype profiles of the antibody response to the ABKD, ABKDD, and ADBKD vaccine variant constructs were assessed by ELISA. 96 well plates were coated with 100 ng well-1 of r-OspC of type A, B, K, and D. The plates were blocked and washed as described above. Anti-vaccinogen antisera were added to the plate and analyzed in duplicate (100 µL; 1:10000; 1 hr). Bound epitope-specific Ig was detected by incubation with isotype specific, biotinylated secondary antibodies (1 hr; Mouse isotyping kit; Zymed). The secondary antibodies were detected by peroxidase-conjugated streptavidin (30 min) and the chromogenic substrate, ABTS. All incubations were completed at room temperature.

Determination of IFN-γ and IL-4 Production by Vaccine-Specific T-Lymphocytes

The cytokine response of splenocytes from immunized mice was assessed by in vitro restimulation with vaccinogen using modifications of the methods of Abuodeh et al. [1999]. Vaccinated mice were euthanized by $CO_2$ narcosis, and spleens were aseptically removed and placed into RPMI media (Sigma). Spleens from the three mice immunized with each vaccine construct were pooled, and the cells were harvested by repeated injection of RPMI into the splenic capsule using 22 gauge needles. The cell suspensions were transferred to 50 mL centrifuge tubes and the cells harvested at 200×g for 5 minutes. Erythrocytes were lysed by exposure to 3 mL of 8.3 mg/mL ammonium chloride (R-7757, Sigma) for 1 minute. The ammonium chloride was then diluted with 20 mL of RPMI (Sigma), and the cells were centrifuged and washed three times. The cells were resuspended in 10 mL RPMI containing 10% FCS, 100 µg mL$^{-1}$ streptomycin, 100 U mL$^{-1}$ penicillin, 2.5 µg mL$^{-1}$ amphotericin B. The cells were stained with trypan blue to assess viability, enumerated with a hemacytometer, and all cell suspensions adjusted to 107 cells mL$^{-1}$. Cells were aliquoted into 24 well plates (Costar 3526) at $10^7$ cells per well (12 wells per vaccinogen type). Triplicate wells were stimulated with the immunizing vaccinogen at 5 or 10 µg mL$^{-1}$. Controls included triplicate wells stimulated with an irrelevant protein, bovine serum albumin at 10 µg mL$^{-1}$, and unstimulated wells (no protein). All plates were incubated at 37° C., 5% $CO_2$ for 96 hours, then supernatants were harvested and frozen at −80° C. pending ELISA quantification of cytokines.

To quantify the levels of the Th1/Th2 cytokines IFN-γ and IL-4, an ELISA-based assay (ELISA-Max; Biolegend) was used according to the manufacturer's instructions. Briefly, a capture antibody was coated onto 96-well ELISA plates, the plates were blocked, and 100 uL of each culture supernatant, in duplicate, was incubated for 2 hr in the plates. For IL-4 detection, undiluted culture supernatant was used, whereas for IFN-γ, the supernatant was tested undiluted and diluted 1:20 in PBS. A standard curve was generated using samples containing known concentrations of each of the cytokines. Detection of bound cytokines was by a biotinylated secondary antibody followed by HRP-conjugated streptavidin and colorimetric detection using TMB substrate.

Results

Construction, Expression and Purification of Variant Vaccine Constructs

Figure 14:
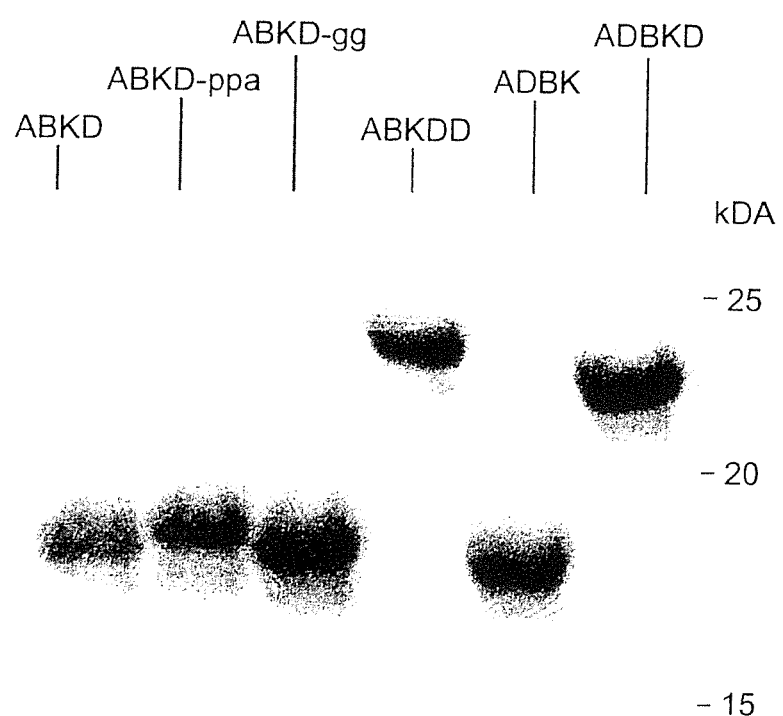
FIG. 14. Coomassie stained SDS-PAGE gel of the chimeric vaccinogen test constructs. Vaccinogen r-proteins were expressed in E. coli, affinity purified by nickel chromatography, and quantified by the BCA method. Two µg of the purified proteins were electrophoesed on a 15% SDS-PAGE gel (Criterion; Biorad) and stained with Coomassie G-250. No contaminating proteins were noted, and there was minimal or no degradation of the recombinant proteins.

Using primers with 5' overhangs and overlap annealing and extension PCR techniques, five variants of the original ABKD vaccine were produced (FIG. 13). The DNA sequences of all of the constructs were confirmed. Select physicochemical properties of the vaccinogens are presented in Table 6 [Gasteiger et al, 2005]. Following purification of the recombinant vaccinogens by nickel chromatography, it was noted that a significant proportion of the r-protein precipitated during dialysis against PBS. This was also noted in the initial report of the ABKD vaccinogen [Example 3]. While the higher molecular weight constructs, ABKDD and ADBKD, had higher solubility in PBS, r-protein precipitation was still significant. For that reason, a modified dialysis buffer (Arg/Glu buffer) was developed based on the work of Golovanov et al. [2004]. The pH of the buffer was increased from that of PBS (pH 7.4) to pH 8.0 to increase the difference between the buffer pH and the pI of the r-proteins (pI 6.49 or 6.85). In addition, the salt concentration was decreased from 150 mM to 100 mM and 50 mM arginine and 50 mM glutamic acid was added. Using this buffer, no precipitation of any of the r-proteins was noted, and there was a marked increase in the concentrations of soluble protein. As visualized by SDS-PAGE, the r-proteins were pure and free of degradation products (FIG. 14).

TABLE 6

Physicochemical properties of the vaccinogens.

| Construct | Amino acids | Molecular mass (Da) | Isoelectric point | Instability index |
|---|---|---|---|---|
| ABKD | 169 | 18014.4 | 6.49 | 10.14 |
| ABKDppa | 172 | 18279.7 | 6.49 | 14.93 |
| ABKDgg | 171 | 18128.5 | 6.49 | 10.86 |
| ABKDD | 214 | 22632.7 | 6.85 | 15.49 |
| ADBK | 170 | 18027.4 | 6.49 | 8.51 |
| ADBKD | 215 | 22645.7 | 6.85 | 14.18 |

Immunogenicity of Vaccine Variants

Figure 15A:
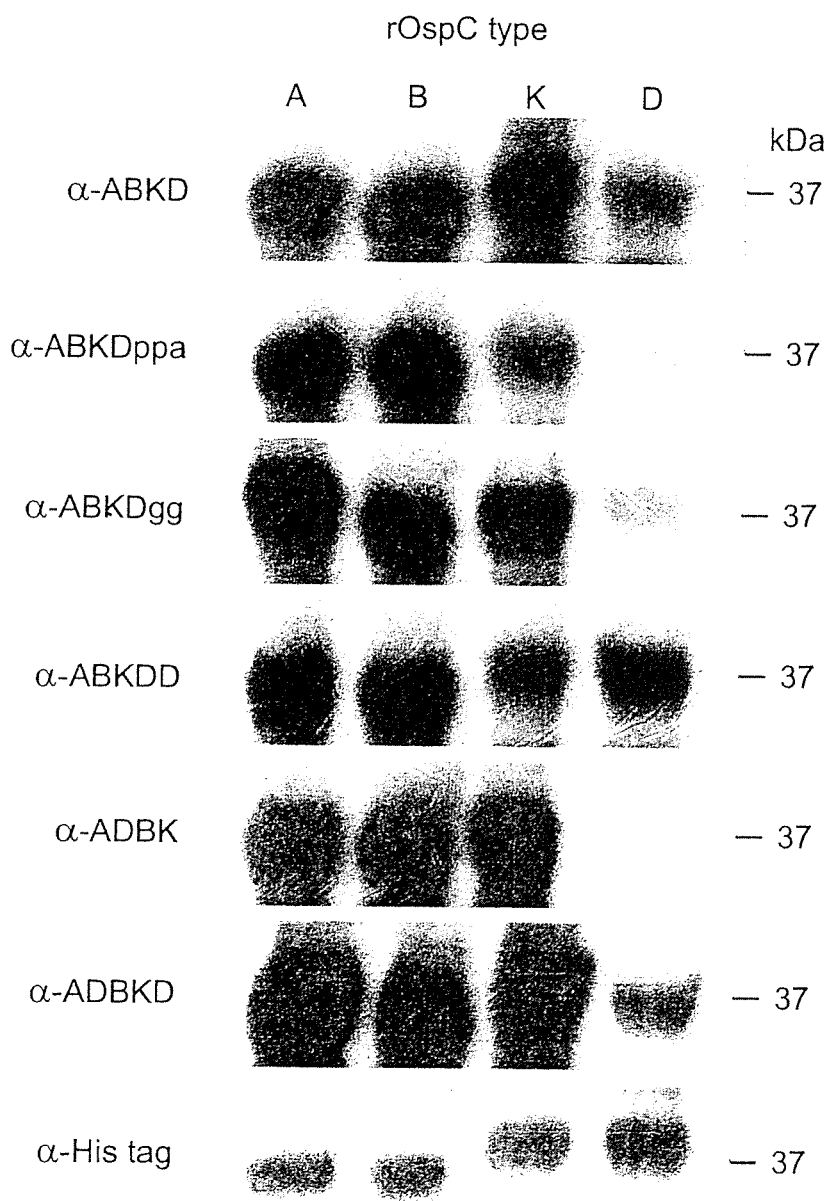
FIGS. 15 A and B. Assessment of mouse vaccine serum recognition of full length r-OspC. In panel A, r-OspC of types A, B, K, and D were electrophoresed and blotted to PVDF (type indicated at top; 500 ng/lane), and were probed with a 1:2500 dilution of representative sera from mice vaccinated with each of the variant constructs (indicated at left). Secondary detection was by peroxidase-conjugated goat-anti-mouse IgG (1:40000) and chemiluminescence. Molecular masses are indicted at the right. In panel B are the results of a quantitative ELISA titration of mouse vaccine serum reactivity with full length r-OspC. Sera generated against each vaccine construct (noted at bottom) were titrated against immobilized, full length, r-OspC of types A, B, K, and D. Also included are the titers from the ABKD construct dialyzed against PBS (ABKD*) [17]. Bars denote the mean titer against OspC types A (black), B (grey), K (open), and D (hatched). Titers from individual mice are denoted by open triangles. Listed below are the mean numerical titers, as well as the titers indexed either to the corresponding titer of the ABKD construct dialyzed against PBS (ABKD*) or against Arg/Glu buffer (ABKD).

To assess the relative immunogenicity of the ABKD vaccine variants, mice were immunized with each of the variants in Freund's adjuvants. Epitope-specific reactivity of the sera was assessed by western blot, in which the sera were used to probe PVDF-immobilized r-OspC of each of the four types. The proteins were confirmed to be equally loaded on the blot, as assessed by reactivity with the tag-specific mouse-a-His tag monoclonal antibody. The sera from immunized mice demonstrated vaccinogen-dependent differences in the levels of reactivity with each of the r-OspC proteins (FIG. 15A). Notably, there was diminished reactivity with the type D helix 5 epitope in mice vaccinated with the ABKDppa and ABKDgg variants, and most markedly with the ADBK variant. In order to assess these variations in a quantitative way, titration of IgG reactivity with each of the OspC type-specific epitopes included in the constructs was accomplished by ELISA, again by using full length r-OspC of each of the four types as the immobilized antigens. The titers largely mimicked the qualitative western blot findings, demonstrating vaccine-specific differences in the reactivity of immune serum to individual epitopes (FIG. 15B). The most marked differences were seen in reactivity with the type D epitope, with particularly low titers seen for the ABKDppa, ABKDgg and ADBK variants.

Isotype Profiles of Vaccine Variant-Specific Immunoglobulins

Figure 16A:
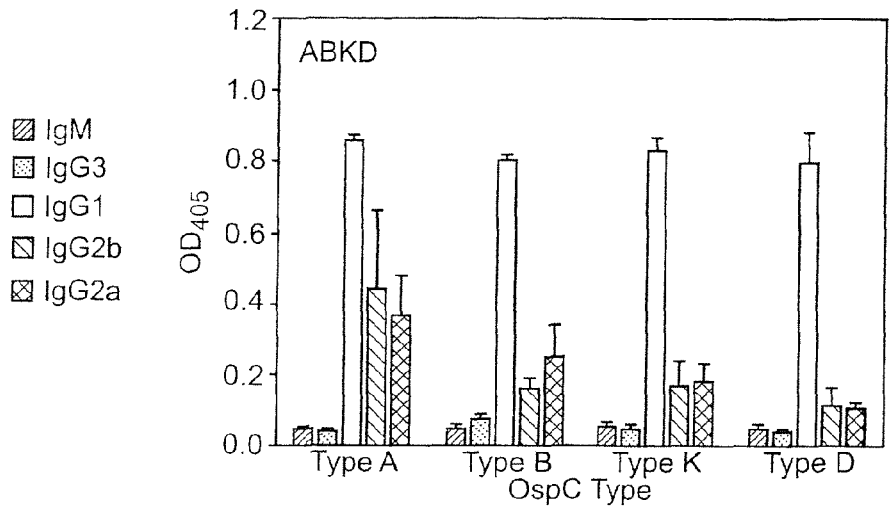
FIG. 16A-C. Epitope-specific isotype responses to three vaccine constructs. OspC types A, B, K, and D were immobilized on ELISA plates and probed with immune sera from mice vaccinated with the ABKD, ABKDD, or ADBKD constructs in duplicate. Bound Ig isotypes were detected with biotinylated isotype-specific secondary antibodies and peroxidase-conjugated streptavidin.
Figure 16B:
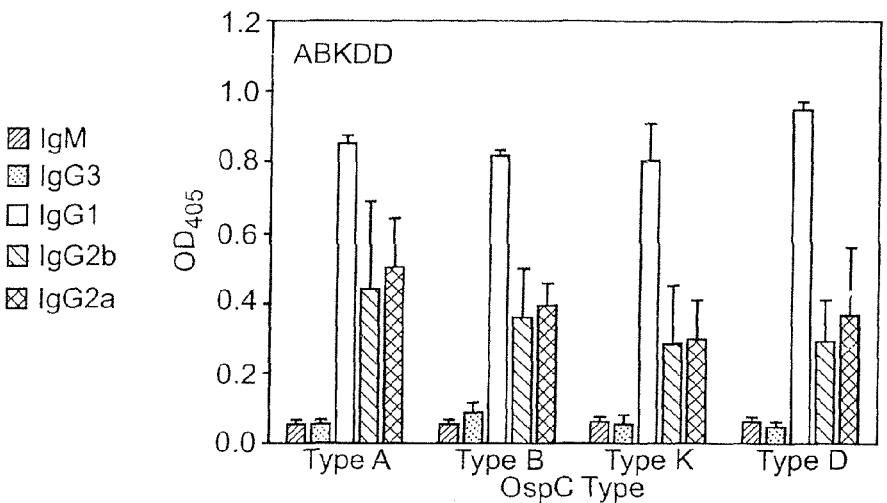
Figure 16C:
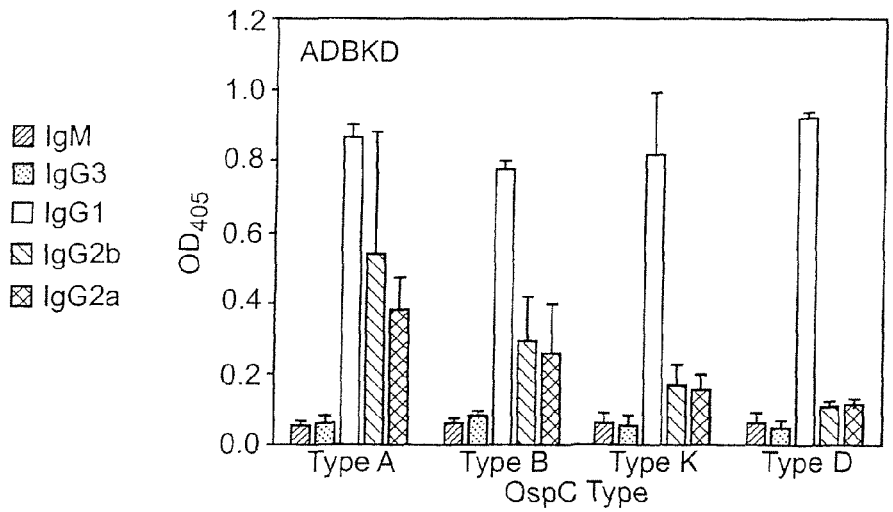

To understand in greater detail the immune response induced by the variant vaccinogens, epitope-specific immunoglobulin isotype profiles were completed for the three variants with the best vaccine potential (ABKD, ABKDD, ADBKD), as determined by epitope-specific titers. In general, there was a preponderance of IgG1 in the antigen-specific immunoglobulins, smaller amounts of IgG2a and IgG2b, and very little IgG3 or IgM, a pattern which has been previously noted [Example 3] (FIG. 16). For all epitopes and all vaccine variants, the pattern of Ig isotype was similar, with one exception. There was a greater reactivity of type K and D epitope-specific IgG2a and IgG2b in mice immunized with the ABKDD than with the ABKD or the ADBKD variants.

Th1/Th2 Cytokine Production by Vaccine-Specific T-Lymphocytes

Figure 17:
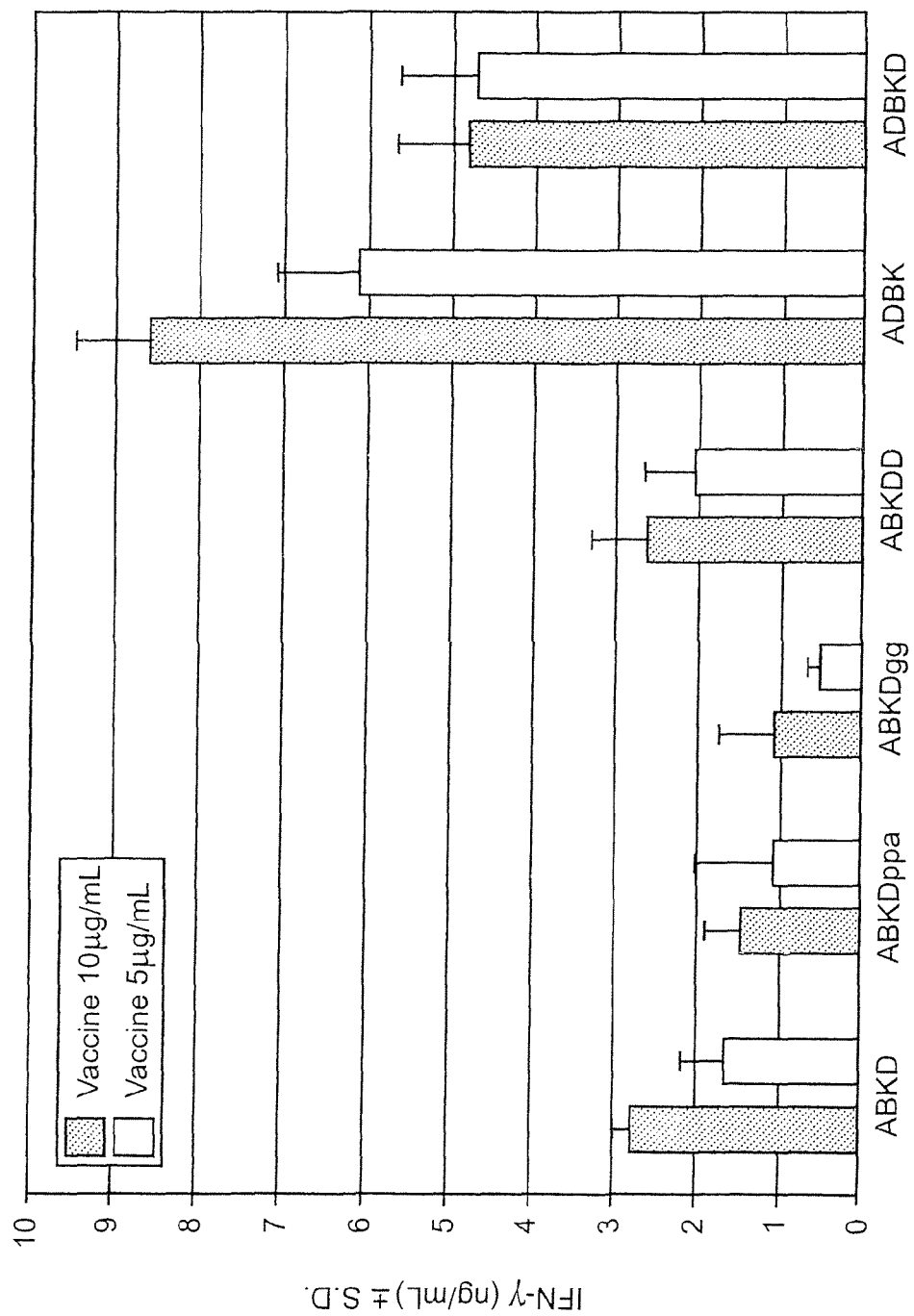
FIG. 17. IFN-γ response of splenocytes from immunized mice to in vitro restimulation with the immunizing antigen. Erythrocyte-free splenocytes from three mice immunized with each of the six vaccine constructs were collected, pooled, and restimulated in triplicate with the original immunizing antigen ($10^7$ cells $mL^{-1}$ in 24 well plates, antigen at 10 or 5 $\mu mL^{-1}$). Triplicate control wells were administered 10 mg $mL^{-1}$ BSA or no protein. After incubation (37° C., 5% $CO_2$) for 96 hours, cell free supernatants were collected, and IFN-γ concentrations were determined by ELISA. In all cases, the concentration of IFN-γ in the BSA and no protein wells was below the detection limit of the assay.

To assess the potential impact of the cytokine environment and Th1/Th2 balance induced by the variations in the ABKD vaccinogen, mouse splenocytes were re-stimulated in vitro with the vaccinogen with which the mice had been immunized. Marked differences in the induced levels of IFN-γ were noted between the differently immunized mice. All vaccine variants were associated with increased levels of IFN-γ in the culture supernatant, though ADBK and ADBKD had levels two to three times higher than that induced by the other vaccinogens (FIG. 17). In all cases, both the 5 μg mL$^{-1}$ and 10 μg mL$^{-1}$ concentrations of antigen induced IFN-γ, with levels ranging from 0.5 to 8.6 ng/mL. Cell culture supernatants from unstimulated splenocytes or from splenocytes stimulated with bovine serum albumin all had IFN-γ levels that were below the 15.6 pg/mL detection limit of the assay. In neither the vaccine-stimulated nor the control culture supernatants was IL-4 detected, indicating that the concentration was below the 2.0 pg/mL detection limit of the assay.

Effect of Adjuvant Type on Antibody Titer and Isotype Profile

Figures 18A, 18B:
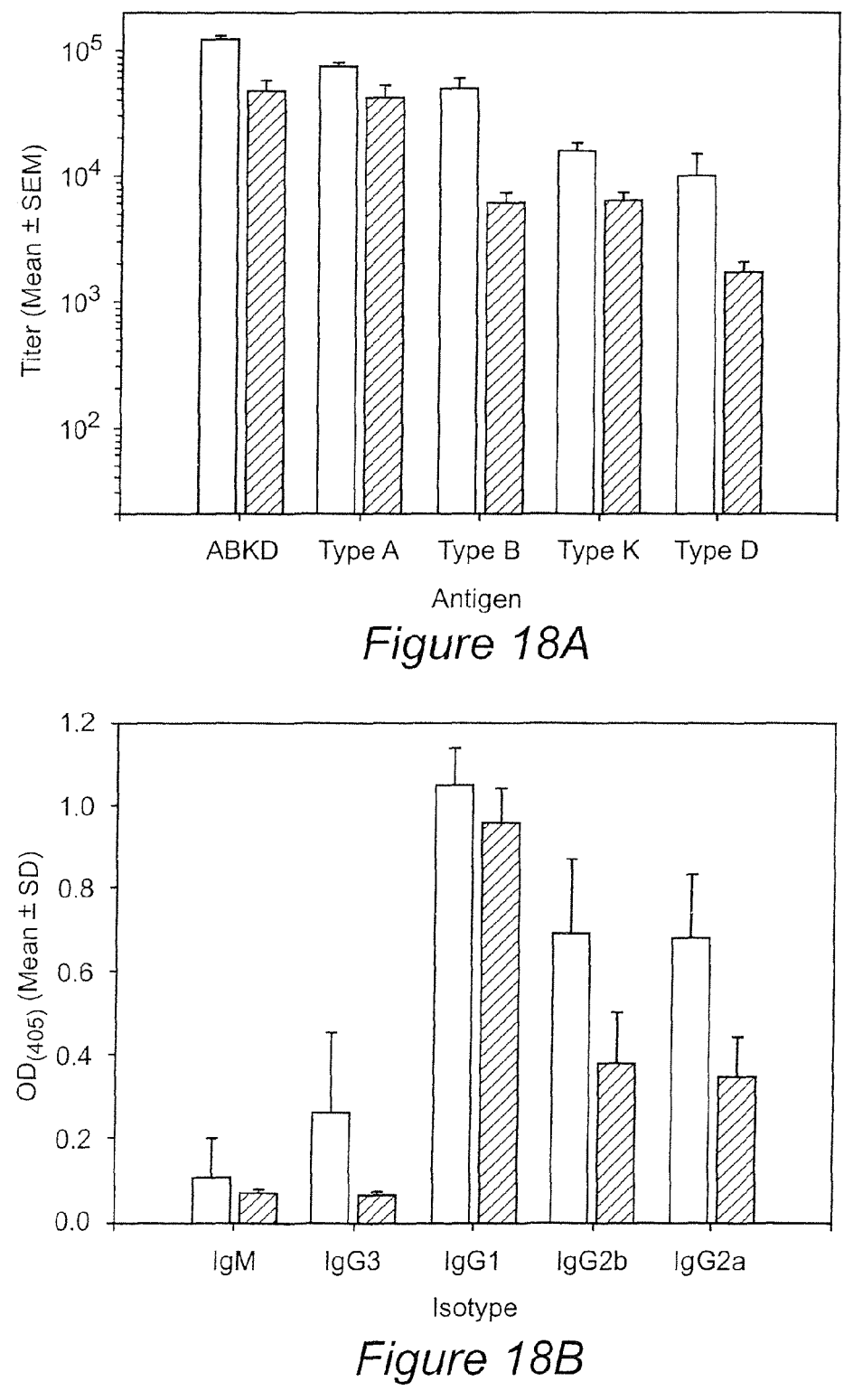

To determine the effect of adjuvant type on the response to the vaccinogen, mice were immunized with the ABKD protein emulsified in Freund's adjuvants or adsorbed to alum. The IgG titer against the whole vaccinogen, as well as against each component epitope was slightly lower in mice immunized with alum adjuvant, though the general pattern of the response was similar between the two adjuvants (FIG. 18A). Despite similar levels of IgG1, mice immunized with alum had reduced vaccinogen-specific IgG3, IgG2a, and IgG2b (FIG. 18B). The epitope-specific isotype profiles were very similar to the profile seen using the whole vaccinogen (data not shown).

Discussion

The use of chimeric proteins containing multiple B-cell epitopes has potential advantages over whole-protein polyvalent vaccinogens and peptide conjugates in vaccine development. The inclusion of only protective epitope sequences reduces the potential for misdirection of the response against irrelevant epitopes either in the parent molecule or on a peptide carrier. This is important if, as with OspC, there are large conserved domains that are immunodominant in the recombinant vaccinogen, but are not presented by the bacteria during infection [Example 1; Kumaran et al, 2001; Eicken et al, 2001]. Such epitopes are irrelevant to the generation of a protective immune response. The creation of novel proteins, however, requires consideration of inter- and intramolecular interactions that can occlude epitopes or impact protein stability and solubility. In this Example, we have extended the investigation of a recombinant, polyvalent chimeric Lyme disease vaccinogen based on OspC. The original ABKD vaccine was highly immunogenic in mice, and the induced IgG bound native OspC at the bacterial cell surface and elicited complement-dependent killing [Example 3]. Despite this success, the ABKD construct had two factors that required improvement, its poor solubility in PBS, which interfered with production of r-protein and could impact storage stability, and differences in the IgG titer against individual epitopes in the protein. Specifically, titer decreased in relation to the proximity of the epitope to the vaccine C-terminus. The goals of this study were to improve vaccinogen solubility, and use modified vaccinogens that differed in epitope placement, epitope reiteration, and the inclusion of stabilizing motifs to improve the total and the epitope-specific immune response.

In an earlier study, it was noted that there was significant precipitation of recombinant vaccinogen following dialysis against PBS [Example 3]. This poor solubility not only limited vaccinogen production but may also have impacted vaccine immunogenicity. The maximum concentration of the ABKD construct achieved following dialysis against PBS was 0.5 mg/mL, and was frequently much less. The OspC crystal structure suggests that the helix 5 epitope regions participate in intramonomeric 4-helical bundles in the native OspC proteins [Kumaran et al, 2001; Eicken et al, 2001]. This may lead to interactions between exposed hydrophobic helical faces within and between vaccinogen proteins, in turn leading to precipitation. The addition of Arg and Glu to the dialysis buffer was found to increase the solubility of all of the recombinant vaccinogen proteins by 4 to 100-fold (Table 7). The basis for this increased solubility may be an interaction of Arg and Glu with both with exposed residues of opposite charge, and with hydrophobic residues by interaction with the aliphatic portion of the Arg and Glu side chains [Golovanov et al, 2004]. Mice immunized with the ABKD construct dialyzed in the Arg/Glu buffer had markedly higher titers than those immunized with the ABKD vaccinogen dialyzed against PBS [Example 3]. The Arg/Glu buffer may cause a more advantageous folding pattern or fewer inter- or intramolecular interactions, thereby providing better access of epitopes to B-cell receptors. Adsorption of Arg or Glu to the r-protein apparently did not interfere with epitope recognition. The Arg/Glu buffer has been reported to protect against the activity of proteases in vitro [Golovanov et al, 2004]. While there is no apparent proteolytic degradation in either the PBS- or Arg/Glu-dialyzed samples, in vivo protection against proteolytic cleavage cannot be excluded. Dialysis against buffers containing Arg and Glu may be a useful tool that can be applied to other novel chimeric proteins that have significant intermolecular interactions.

TABLE 7

Concentration of soluble protein for vaccinogens dialyzed against PBS or Arg/Glu buffer.

| Construct | Protein concentration (mg mL$^{-1}$) | |
|---|---|---|
| | PBS | Arg/Glu buffer |
| ABKD | 0.15 | 3.04 |
| ABKDppa | 0.20 | 3.78 |
| ABKDgg | 0.22 | 5.99 |
| ABKDD | 0.80 | 4.66 |
| ADBK | 0.04 | 4.37 |
| ADBKD | 1.12 | 4.66 |

The association of poor immune response with the C-terminal epitope location has been previously reported in a chimeric streptococcal M-protein vaccinogen, potentially due to structural issues associated with the C-terminus, or proteolytic degradation by carboxypeptidases [Dale et al, 1993; Dale et al, 1996; Dale et al, 1999]. Numerous methods have been proposed for protection of peptides and recombinant proteins from protease activity, including amidation or PEGylation of the C-terminus, acetylation of the amino (N)-terminus, and addition of protective amino acid motifs [Brickerhoff et al, 1999; Powell et al, 1992; Lee et al, 2005; Alvarez et al, 2004; Kawarasaki et al, 2003; Walker et al, 2003]. Amino acid motifs have also been reported to stabilize the C-terminus of proteins by inhibiting the action of carboxypeptidases; however, their ability to protect has only been assessed with a few proteins. Two stabilizing motifs were assessed for their ability to enhance antibody responses to the ABKD vaccinogen. The addition of two neutral, hydrophilic Gly residues may reduce the activity of carboxypeptidases C and D, which have specificity for hydrophobic and basic C-terminal amino acids, respectively [Alvarez et al, 2004; Kawarasaki et al, 2003; Remington and bredam, 1994]. Addition of a Pro-Pro-Ala motif may sterically hinder carboxypeptidase progression through the juxtaposed, bulky proline residues [Walker et al, 2003].

To assess the impact of addition of these motifs on the antibody response to the ABKD chimeric vaccinogen, mice were immunized with the ABKDgg or ABKDppa constructs. In both cases, the sera had lower mean IgG titers against one of more epitopes, compared with those immunized with the unmodified ABKD construct. The ABKDppa construct had a reduction in the titer of type D specific IgG, though this was primarily due to a single outlier. The ABKDgg construct had reduced titers against the types K and D epitopes. On the basis of IgG titers, there was no advantage to the use of either of these motifs. The reduction in the titer to the C-terminal epitopes does not appear to be mediated by the action of those carboxypeptidases to which these motifs should confer resistance, though it is possible that any advantage due to protease protection may have been masked by similar protection provided by the Arg/Glu buffer [Golovanov et al, 2004].

To investigate possible structural factors involved in the poor immune response to the C-terminal epitope, several additional constructs were created. In the chimeric streptococcal vaccine, reiterating the N-terminal epitope at the C-terminus 'protected' the former C-terminal epitope by an unknown mechanism [Dale et al, 1999; Dale et al, 2005; Hu et al, 2002; McNeil et al, 2005]. Based on that success, similar variants of the ABKD vaccinogen were developed. The ABKDD construct was created to assess whether the response to the type D epitope could be protected by a second C-terminal type D epitope. To assess whether the decreased titer was due primarily to the C-terminal epitope location, the type D epitope was moved to the second-most N-terminal location (ADBK). Finally, the ADBKD construct was used to assess protection by a reiterated C-terminal epitope and, with ABKDD, the effect of a repeated epitope on the specific immune response. Epitope reiteration in the ABKDD vaccinogen doubled the type D-specific IgG titer, but simultaneously caused a decrease in the titer against the adjacent type K epitope. When the type D epitope was placed in a more N-terminal location in the ADBK construct, the type-D specific IgG titer was significantly reduced. Furthermore, the reactivity against the C-terminal type K epitope in the ADBK construct was improved over that in the ABKD. Adding a C-terminal type D epitope (ADBKD) did not improve the type K-specific titer; however, it yielded a significantly improved, though not doubled, titer against the type D epitope. These results indicate that the C-terminal location of the type D epitope is preferable to an internal location, and that there is no apparent protection of a C-terminal epitope by an additional 'protective' C-terminal epitope. The primary determinant of epitope-specific titer in this vaccinogen is not its proximity to the C-terminus, but is more likely the tertiary structure of the chimeric protein.

Vaccinogen-induced Ig isotypes may have consequences on in vivo protective efficacy. By altering the epitopes or their order, it may be possible to alter the isotype profile [Tongren et al, 2005], and thus antibody effector functions. To measure epitope-specific isotype profiles, antisera against the most promising vaccinogens (ABKD, ABKDD, ADBKD) were bound to immobilized rOspC of types A, B, K or D, and the bound antibody detected with isotype-specific antisera. As previously reported for the ABKD vaccinogen [Example 3], the predominant isotype was IgG1, with somewhat lower levels of IgG2a and IgG2b, dependent on the construct, and low levels of IgM and IgG3. The epitope specific Ig isotype profiles were similar between the ABKD and ADBKD antisera, with a decrease in the levels of IgG2a and IgG2b from the N- to the C-terminal epitope, mimicking the total IgG titer. The ABKDD had a consistent level of IgG2a and IgG2b across all of the epitopes, despite the lower type K-specific total IgG titer.

The ABKD vaccinogen elicits complement-dependent bactericidal antibodies [Example 3]. In the mouse, IgG1 does not activate complement [Dangl et al, 1988; Miletic and Frank, 1995], indicating that the major induced isotype may not be protective. While it has been reported that OspA-specific IgG1 can be borreliacidal by a complement-independent mechanism [Munson et al, 2000], bacterial killing by ABKD vaccinogen-induced antibodies is complement dependent [Example 3]. The elicited isotype profile may be influenced by the use of C3H/HeJ mice, a standard animal model for Lyme disease research. Humoral immune differences between C3H/HeJ and BALB/c strain mice have been noted during *B. burgdorferi* infection, especially in the levels of total IgG and especially in the levels of IgG2a, both of which are higher in C3H/HeJ mice [Yang et al, 1992; Keane-Myers and Nickell, 1995]. Additionally, the C3H/HeJ mouse line is deficient in TLR-4, though this is not expected to be critical for protection against Lyme disease by vaccination or during infection, as *Borrelia* do not make lipopolysaccharide [Takayama et al, 1987; Barthold et al, 1990].

Since it is generally accepted that humoral borreliacidal activity is complement-dependent, the elicitation of a Th1 cytokine response may be advantageous, as it is in many bacterial diseases (reviewed in [Spellberg and Edwards, 2001]). During active infection, Th cytokines have been implicated in the development and resolution of Lyme disease and its sequelae. Several studies have found that IL-4 is not a critical cytokine for the development of a borreliacidal antibody response [Munson et al, 2000; Potter et al, 2000; Christie et al, 2000; Satoskar et al, 2000-64], implying that a Th1-type response may be associated with protection. Additionally, IFN-γ secreting Th1 cells promote the resolution of carditis associated with Lyme disease [Bockenstedt et al, 2001; Kelleher et al, 1998]. Conversely, arthritis severity and the skin spirochete load are reduced by administration of r-IL-4, and increased by administration of an α-IL-4 antibody during infection [Keane-Myers and Nickell, 1995; Keane-Myers et al, 1996]. The production of IFN-γ has been associated with the development of chronic Lyme disease during natural infection [Widhe et al, 2004], as well as with the degree of joint swelling in Lyme arthritis [Gross et al, 1998]. IFN-γ has also been associated with inhibited production of borreliacidal anti-OspA antibodies induced from in vitro lymph node cultures [Munson et al, 2002]. To investigate the Th cytokine environment induced by vaccination, mouse splenocytes were re-stimulated with vaccinogen in vitro, and Th1 (IFN-γ) and Th2 (IL-4) cytokines and were quantified by ELISA. IFN-γ was detected in the supernatants of cells re-stimulated with vaccinogen, though in differing concentrations depending on the construct. In contrast, IL-4 was not detected in any of the splenocyte supernatants. The ABKD, ABKDppa, and ABKDD constructs all had similar concentrations of IFN-γ. The ADBKD had approximately double the concentration of IFN-γ, and the ADBK had an even higher level. There was no apparent correlation between the level of IFN-γ in the supernatant of re-stimulated cells and the total epitope-specific serum IgG titers or isotype profiles.

The cytokine and associated Ig isotype profiles could be altered by the choice of immunological adjuvant. Freund's complete adjuvant has been associated with a Th1 cytokine response [Cribbs et al, 2003; Shibaki and Katz, 2002], which may increase the level of IgG2a. The only adjuvant currently approved for human use is alum, which is known to increase secretion of Th2 cytokines [Cribbs et al, 2003; Brewer et al, 1999; Lindblad, 2004; Petrovsky and Aguilar, 2004]. In mice immunized with alum, the expected moderate decrease in IgG titer to the vaccinogen and its component epitopes was noted, in comparison with Freund's adjuvant. Additionally, there was a proportionally greater decrease in the IgG3, IgG2a, and IgG2b isotypes, as compared with IgG1. This conforms with the expectation of lower Th1 cytokine response with this adjuvant. The vaccinogen does, however, continue to elicit antibodies capable of complement fixation, indicating that significant changes to the construct or modifications of the adjuvant may not be necessary for an effective response.

In this Example, we have investigated alterations to a potential chimeric polyvalent Lyme disease vaccinogen that were intended to optimize the induced humoral immune response. A significant improvement to the immunogenicity of the construct was effected by increasing its solubility by dialysis against Arg/Glu buffer. This may have reduced protein interactions, allowing greater epitope exposure in vivo [Theisen et al, 2000]. Neither the addition of protease-protective C-terminal motifs nor addition of 'protective' C-terminal epitopes improved the immune response to the vaccinogen. Reordering of epitopes caused a substantial decline in the immune response to the epitope that was moved. Differences in the immune response toward component epitopes in this vaccine construct appear to be primarily dependent on the structure of the protein, rather than on the resistance of the protein to protease digestion. Furthermore, there is evidence that Th cytokines and IgG isotypes elicited by a vaccinogen can be altered by the structure of the chimeric construct and by the adjuvant formulation. This study provides important information regarding the basis for suboptimal immune responses to chimeric vaccinogens, as well as methods by which those responses can be improved.

Example 5

Figure 19:
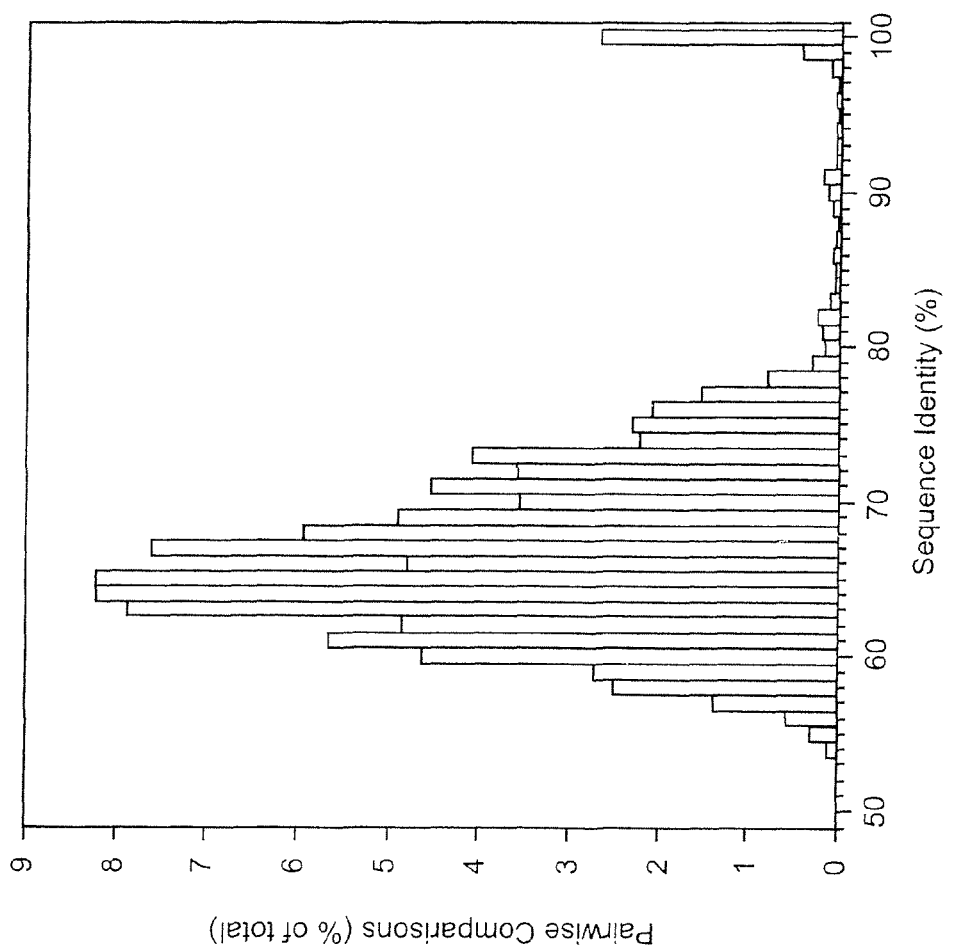
FIG. 19. Distribution of pairwise comparisons of OspC protein sequence identity. OspC protein sequences from 280 Borrelia isolates were Clustal aligned using a PAM40 scoring matrix, and pairwise percent identities were calculated. The histogram interval is 1% and there were no percent identities <50%.

Analyses of Available OspC Sequences Demonstrate the Feasibility of a Broadly Protective Polyvalent Chimeric Lyme Disease Vaccine To facilitate the further development of a broadly protective chimeric construct we have conducted phylogenetic analyses of OspC sequences available in the databases. The segment of OspC analyzed spanned residues 20 through 200 (using numbering for the B31MI sequence). Shorter sequences in the databases were excluded from these analyses, leaving sequences from 280 *Borrelia* strains available for analysis. The OspC type designation of each sequence was determined through alignment (PAM40 scoring matrix) and pairwise identity matrix analysis. Consistent with earlier studies, sequences that exhibited 95% or greater sequence identity were considered to belong to the same OspC type (Attie et al, 2006; Wang et al, 1999) (FIG. 19). A clear bimodal distribution of sequence comparisons, with a mean sequence identity of 65% between differing OspC type sequences, and >97% identity within types was observed. In addition to the 21 types described by Wang et al (1999), 17 additional clusters were defined. We did not assign OspC type designation to clusters that included less than 3 sequences. In naming new OspC types, we chose to maintain the existing OspC type designations A through U (Wang et al, 1999), with additional types named based on a prototype strain contained within each cluster. Of 280 analyzed sequences, 202 were assigned to OspC types, all of which were from Lyme disease-causing species. The 78 sequences not assigned to an OspC type included both Lyme disease-causing spirochetes (51 isolates) and other *Borrelia* species (27 isolates). The geographic and biological origin of the isolate from which each OspC sequence was obtained is indicated in FIG. 20 in tabular form. The majority of *B. burgdorferi* isolates were from North America (80%) with lesser numbers from Europe (16%) and Asia (4%). Fifty three percent of the *B. burgdorferi*, 48% of the *B. afzelii* and 79% of the *B. garinii* OspC sequences originated from isolates collected from humans. It is noteworthy that *B. garinii* OspC sequences from human isolates were predominantly of cerebrospinal fluid (CSF) origin (68%) whereas *B. afzelii* isolates were predominantly from the skin (83%). In contrast, *B. burgdorferi* derived OspC sequences were from isolates recovered from human skin (51%), plasma (30%), and CSF (19%). These findings are in agreement with the known patterns of disease caused by these organisms and indicate that the sample of OspC sequences assessed in this report is representative of the true population of Lyme disease spirochetes.

Figure 21A:
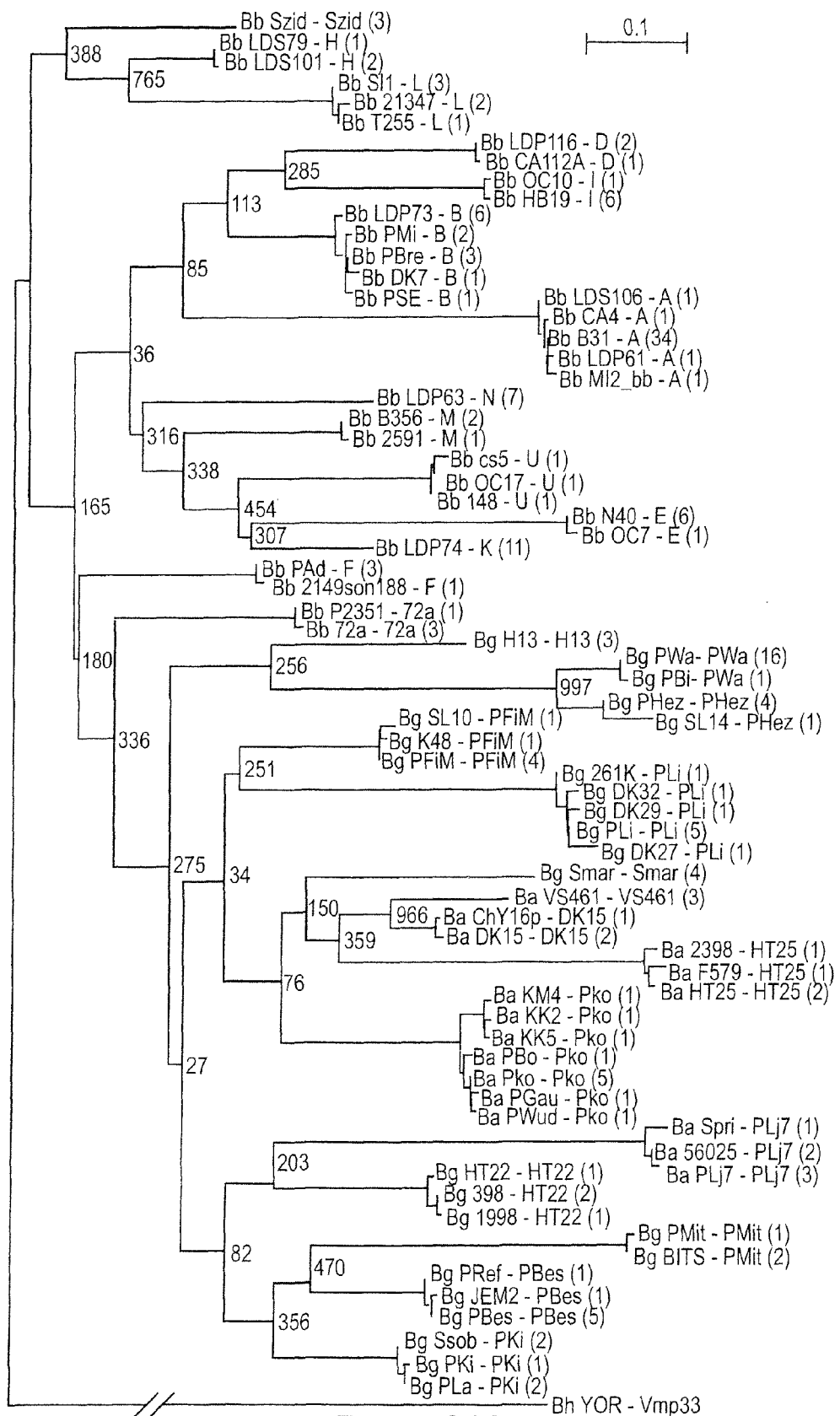
FIG. 21A-C. Consensus phylogenetic trees of representative OspC protein sequences. OspC sequences including amino acids 20-200 (A), 20-130 (B), and 131-200 (C) were bootstrapped (n=1000), distances calculated, and neighbor joining trees created and reconciled to a consensus tree. The Vmp33 sequence of *B. hermsii* was used as an outgroup. Labels indicate the species as *B. burgdorferi* (Bb), *B. garinii* (Bg), or *B. afzelii* (Ba), the isolate strain designation, the assigned OspC type (bold), and the number of identical OspC sequences from other strains represented by this single sequence (in parentheses). Bootstrap support is shown at all nodes that differentiate between OspC types.
Figure 21B:
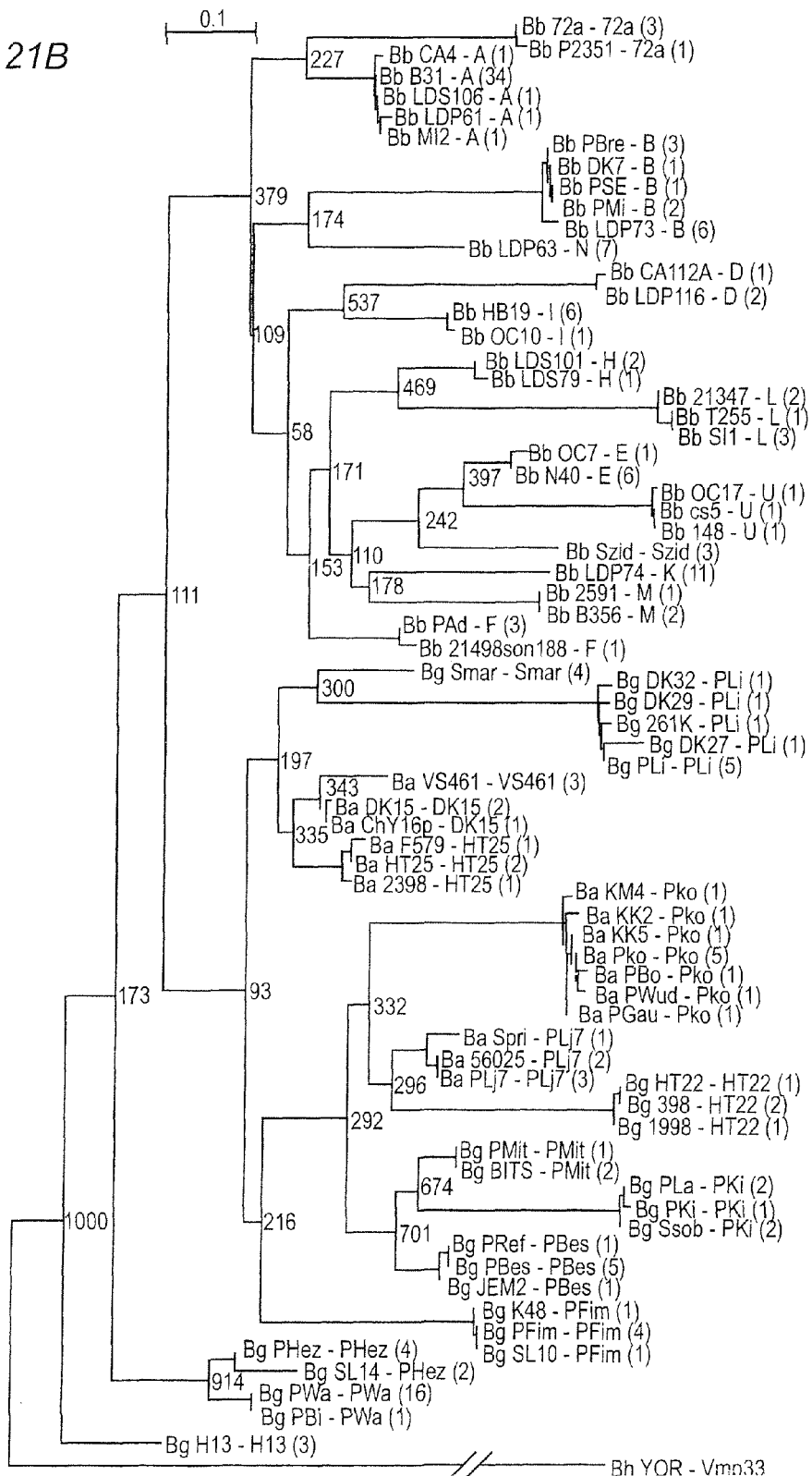
Figure 21C:
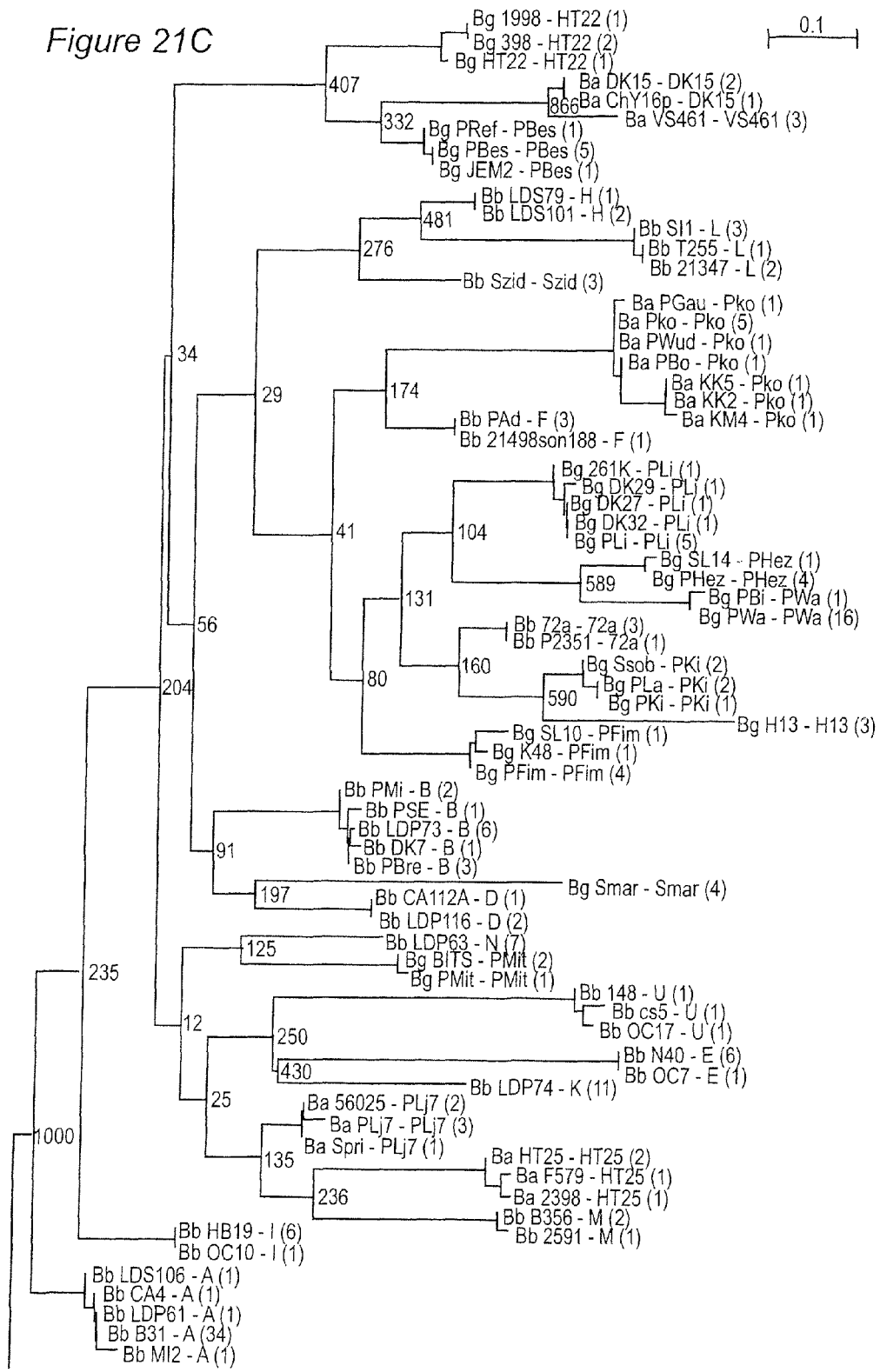
Figure 22:
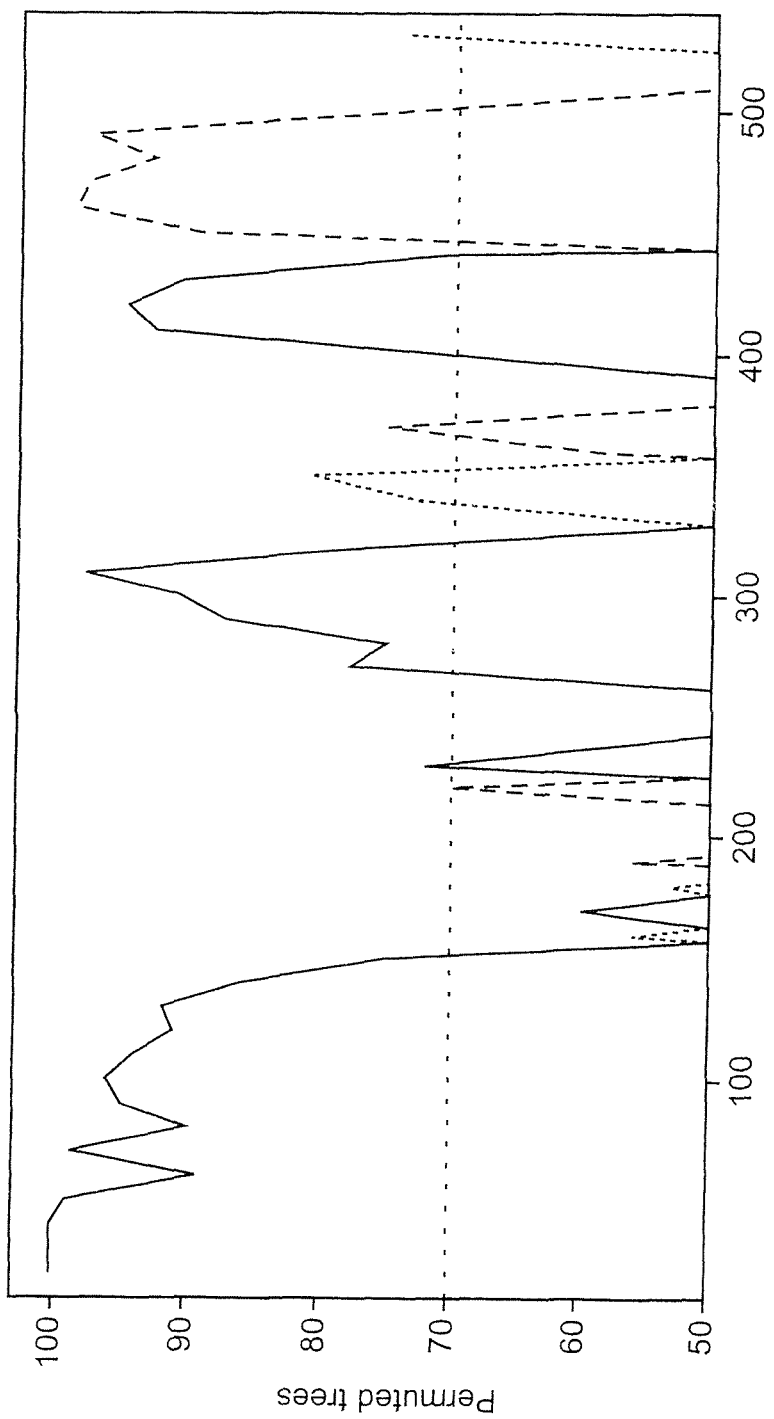
FIG. 22. Bootscan analysis of the OspC type PLj7 (*B. afzelii*) ospC sequence in comparison with OspC types Pki (*B. garinii*; solid black line), F (*B. burgdorferi*; solid grey line), and M (*B. burgdorferi*; dashed black line). The bootscan window was 40 bases, with a 10 base step. Comparison was by strict consensus with 100 bootstrap replicates. The graph has been simplified by showing only those peaks where the % permuted trees exceeds 50%, and the 70% level considered to represent possible recombination is indicated.

To facilitate further phylogenetic analyses, the set of sequences analyzed was reduced to 74 by eliminating identical sequences. These sequences were then aligned and analyzed using the Phylip (v.3.66) phylogenetics package with bootstrapping (n=1000). Distances were calculated for the regions spanning 20 to 200, 20 to 130 and 131 to 200 using the Dayhoff PAM matrix, and trees were created by neighbor joining. The *B. hermsii* OspC ortholog (Vmp33) sequence served as an outgroup (Margolis et al, 1994). A consensus tree was generated by majority rule (50% cutoff for group inclusion). Distances were re-calculated for the consensus tree by the maximum likelihood method under the Dayhoff PAM model (FIG. 21).

The consensus trees generated with the 20-200 aa segment of OspC were well supported at the terminal nodes, with all determined OspC types clustering as expected. While several of the deeper branches were less supported by the bootstrap analyses (FIG. 21A) this is not unexpected since the extended regions of identity among the sequences makes their phylogenetic differentiation subtle. Consensus trees generated using the 20-200 and 20-130 amino acid segments of OspC exhibited similar phylogenetic clustering (FIGS. 21A, 21B), based largely on species identity. However, the consensus tree generated using amino acids 131-200 (FIG. 21C) yielded significantly different clustering patterns that were not strongly supported by bootstrap analyses. This observation is consistent with the hypothesis that recombination between short segments of the ospC gene has occurred between strains of differing OspC types. Evidence for recombination of short segments of OspC between OspC types can be seen in specific sequences. For example, sequences of the *B. afzelii* OspC type, PLj7, have regions within the amino acid 20-130 domain that are identical to that seen in *B. garinii* OspC sequences that form the Pki cluster. In the 131-200 region of PLj7, the hypervariable loop 5 and loop 6 regions have motifs identical to those seen in *B. burgdorferi* OspC types F and M, respectively. Further evidence for recombination came from bootscanning using SimPlot (v. 3.5.1) (Lole et al, 1999). In bootscanning, potential recombination is assessed by generation of phlylogenetic trees (Kimura model, Ts/Tv ratio=2.0, Neighbor joining) of sequence segments within a sliding window (40 base window, 10 base step interval). The trees are bootstrapped (n=100) and the number of permuted trees supporting sequence grouping within that window is reported. Evidence of recombination is typically considered to be supported when >70% of permuted trees cluster the sequences together within a window. Evidence was found of possible recombination in the types described above (FIG. 22), as well as in numerous other OspC types (data not shown).

The evidence that OspC variability occurs by exchange between existing OspC types rather than by hypermutation provides evidence that there is a limit to the absolute number of OspC type-specific epitopes required for inclusion in a broadly protective vaccinogen. Since currently mapped linear epitopes are all contained in the C-terminal region of OspC (aa 131-200), it is possible to define a theoretical number of epitopes required for a chimeric vaccinogen. By inspecting this region in the 74 representative sequences described above, the number of unique epitope-containing regions can be reduced to 34 by elimination of sequences that are either identical or have only a single amino acid change (FIG. 22). It is likely that this number can be further restricted by epitope mapping since some epitopes may convey protection against two or more OspC types. Further reduction in the required number of epitopes could also come from consideration of only those OspC types associated with human disease or, more specifically, with invasive human disease (see Example 1). One theoretical concern with vaccination against a subset of OspC epitopes is the potential to drive selection toward types not included in the vaccinogen, thus increasing the fraction of the population bearing those rare alleles. However, as humans are only incidental hosts, it is unlikely that vaccination will significantly alter the population distribution of strains expressing specific OspC types in the tick vector or mammalian reservoirs.

In summary, the extensive nature of the OspC database has allowed thorough analyses to be conducted which have defined new OspC types and provided information regarding their frequency of isolation and association with human disease. The data suggest that the number of OspC epitope-containing sequences required for inclusion in a broadly protective chimeric vaccinogen is limited and that the development of a chimeric vaccinogen is feasible.

Example 6

Construction of an Octavalent Chimera

The ENICABKD octavalent construct (also referred to as construct A8.1 herein, e.g. in Example 7) is shown below, and several properties of the construct are presented as calculated by the PROTPARAM program. In this representation, "TAG" represents a histidine tag on the amino terminus of the protein. "RS" indicates an amino acid sequence that is encoded by a DNA sequence bearing a restriction site; such sequences basically function as linkers in the protein. "L" (e.g. L1, L2, L3, L6, L7, L8, etc.) indicates a linker sequence, e.g. an unstructured linker sequence) used to join the type specific sequences together.

```
A8.1
                                                    (SEQ ID NO: 249)
    <----TAG----->RS<----------------------Type E--------------
  1 AHHHHHHVDDDDKITGLKSEHAVLGLDNLTDDNAQRAILKKHANKDKGAAELEKLFKAVE ------------<L9>-----------------Type N------------------><L
 61 NLSKAAQDTLKNAPGVGATTDEEAKKAILRTNAIKDKGADELEKLFKSVESLAKAAQDAT 6><----------------Type I----------------><L7><-------------
121 QMLKTNNDKTKGADELEKLFESVKNLSKAAKEMLTNSVKELTSTEPSEEFTKKLKEKHTD ------Type C---------------------><L8RS<------Type A-----><-
181 LGKKDATDVHAKEAILKTNGTKDKGAAELEKLFESGEDVSETFTNKLKEKHTDLGKEGSM L1><----------------Type B-----------------><L2><-----------
241 GMLKANAAGKDKGVEELEKLSGSLESLSKAAKEMLANSVKELTSTNGNLITDAAKDKGAA ----Type K------------------><L3><---------------Type D-----
301 ELEKLFKAVENLAKAAKEMLANSVKELTSSMSVLKTHNAKDKGAEELVKLSESVAGLLKA

----------------------->
361 AQAILANSVKELTSPVVAESPKKP
```

Number of amino acids: 384

Molecular weight: 41263.7

Theoretical isoelectric point: 6.52

Amino Acid Composition:

| | | |
|---|---|---|
| Ala (A) | 51 | 13.3% |
| Arg (R) | 2 | 0.5% |
| Asn (N) | 20 | 5.2% |
| Asp (D) | 25 | 6.5% |
| Cys (C) | 0 | 0.0% |
| Gln (Q) | 5 | 1.3% |
| Glu (E) | 42 | 10.9% |
| Gly (G) | 21 | 5.5% |
| His (H) | 12 | 3.1% |
| Ile (I) | 7 | 1.8% |
| Leu (L) | 46 | 12.0% |
| Lys (K) | 62 | 16.1% |
| Met (M) | 7 | 1.8% |
| Phe (F) | 7 | 1.8% |
| Pro (P) | 5 | 1.3% |
| Ser (S) | 27 | 7.0% |
| Thr (T) | 26 | 6.8% |
| Trp (W) | 0 | 0.0% |
| Tyr (Y) | 0 | 0.0% |
| Val (V) | 19 | 4.9% |

Total number of negatively charged residues (Asp + Glu): 67

Total number of positively charged residues (Arg + Lys): 64

Atomic Composition:

|   |   |   |
|---|---|---|
| Carbon | C | 1787 |
| Hydrogen | H | 2983 |
| Nitrogen | N | 501 |
| Oxygen | O | 597 |
| Sulfur | S | 7 |

Formula: C1787H2983N501O597S7
Total number of atoms: 5875

Estimated Half-Life:
The N-terminal of the sequence considered is A (Ala).
The estimated half-life is: 4.4 hours (mammalian reticulocytes, in vitro).
>20 hours (yeast, in vivo).
>10 hours (*Escherichia coli*, in vivo).
Instability Index:
The instability index (II) is computed to be 12.58
This classifies the protein as stable.
Aliphatic index: 81.46
Grand average of hydropathicity (GRAVY): −0.668
When administered to test mammals, this chimeric protein construct is found to elicit a robust immune response, and to provide protection from the development of Lyme disease.

Example 7

Constructs for Use as Early Diagnostic Agents and Vaccine Antigens

Several chimeric proteins have shown promise for the development of early diagnostic assays, as well as vaccine candidates, for Lyme disease. Early detection (e.g. within about 3 weeks) is important because disease symptoms may be more treatable then and irreversible, chronic damage might not yet have occurred, and can be prevented. However, the diagnostics can be used at later times, e.g. within 6 weeks, or even longer, if necessary. As for vaccines, they can be administered prophylactically or therapeutically. Generally, the proteins are chimeric constructs formed by linking full length and/or antigenic subfragments of outer surface protein C (OspC) or outer surface protein A (OspA) from several different *Borrelia* phylogenetic types.

Figure 27:
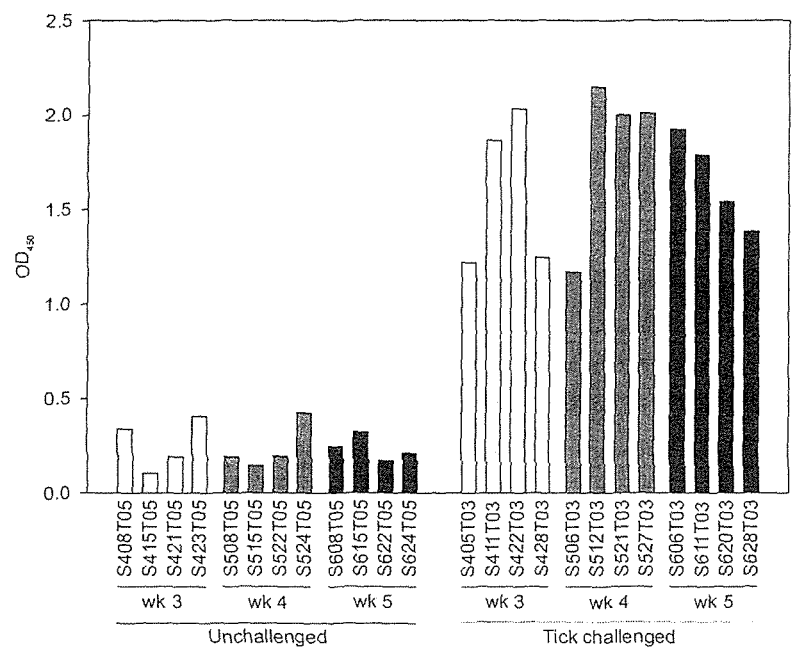
FIG. 27. Assessment of Lyme disease seroconversion in tick-challenged dogs using the chimeric A8.1 protein in an ELISA format. ELISA plates were coated with 100 ng/well of A8.1 protein in carbonate buffer. Sera from unchallenged (control) and tick-challenged dogs collected at weeks 3, 4, and 5 post-challenge were diluted (1:250) and applied in duplicate to the ELISA plates. Following incubation, the bound dog Ig was detected with an IgG-specific, peroxidase-conjugated secondary antibody (1:20000). Reactivity was quantified using a TMB-based chromogen. Each bar represents the mean data for an individual animal.

Exemplary data generated using the A8.1 construct are presented in FIG. 27. The data presented in this figure demonstrate that in an experimentally infected canine model, seroconversion can be detected specifically and at early time points following infection. The dogs were infected by wild-caught ticks that were confirmed to contain spirochetes expressing, in aggregate, a majority of described OspC types. This assay demonstrates that the chimeric protein is capable of detecting a broad array of OspC serotype-specific IgG antibodies, which is critical for the sensitivity of an OspC-based Lyme diagnostic. It also demonstrates detection of OspC seroconversion at early time points following infection. Since OspC is the dominant protein expressed at the *Borrelia* cell surface during early infection, it has definite advantages in early detection of seroconversion as compared with other potential diagnostic antigens. For these same reasons, it also has significant potential as a vaccine antigen.

The A9 series of proteins may also be used as the basis for diagnostic assays, or alternatively, as vaccines. The A9 proteins contain antigenic fragments from the OspC phylogenetic types predominantly found in North American strains of *Borrelia burgdorferi*. The A9.1, A9.2, and A9.3 vaccine proteins each contain sequences from the same OspC types, but differ in the precise subfragment and/or order in which the subfragments are assembled in the protein. A9.1 includes sequences from loop 5 through helix 5 plus the native intervening sequences for each indicated type. FIG. 28A depicts the general location of epitopes of the OspC protein and the arrangement or pattern of epitopes in construct A9.1. FIG. 28 B shows the precise patterns in A9.1. In A9.1, the N- and C-termini are truncated to eliminate redundant sequences; the epitopes of various types are linked without linker sequences; and the conserved C-terminal motif is present at the end. For all of the "A" constructs, including the A10, A11 and A12 series described in this Example, the epitopes include those of *B. burgdorferi* types A, B, C, D, E, F, H, I, K, M, N, T, and U.

```
Construct A9.1
                                                    (SEQ ID NO: 250)
SETFTNKLKEKHTDLGKEGVTDADAKEAILKTNGTKTKGAEELGKLFESVEVLSKAAKEM
<---------------------------Type A------------------------

LANSVKELTSSEEFSTKLKDNHAQLGIQGVTDENAKKAILKANAAGKDKGVEELEKLSGS
---------<>---------------------Type B---------------------

LESLSSEDFTKKLEGEHAQLGIENVTDENAKKAILITDAAKDKGAAELEKLFKAVENLAA
----><---------------------Type K------------------------><

KLKGEHTDLGKEGVTDDNAKKAILKTNNDKTKGADELEKLFESVKNLSKAAKEMLTNSSE
--------------------Type I--------------------------------><-

KFAGKLKNEHASLGKKDATDDDAKKAILKTHGNTDKGAKELKDLSDSVESLVSDDFTKKL
-------------------Type H-------------------------><-------

QSSHAQLGVAGGATTDEEAKKAILRTNAIKDKGADELEKLFKSVESLAKAAQDALANSVN
--------------------Type N---------------------------------

ELTSKKLKEKHTDLGKKDATDVHAKEAILKTNGTKDKGAAELEKLFESVENLAKAAKEML
---><-----------------------Type C------------------------

SNSNKAFTDKLKSSHAELGIANGAATDANAKAAILKTNGTKDKGAQELEKLFESVKNLSK
--><--------------------------Type M-----------------------

AAQETLNNSSESFTKKLSDNQAELGIENATDDNAKKAILKTHNAKDKGAEELVKLSESVA
--------><------------------------------Type D-------------

GLLKAAQAILANSVKELTSPVVAESPKKP
---------------------------->
```

For construct A9.1, the number of amino acids is 569, the molecular weight is 60657.2, and the theoretical pI is 6.35.

The sequence of the A9.2 construct is provided below (where "Lp" indicates "loop" and "Hx" indicates "helix") and depicted schematically in FIG. 29A. In this construct, the N- and C-termini are truncated to eliminate redundant sequences; the epitopes of various types are linked without linker sequences; intervening sequences (helix 4 and loop 6) are not present, and the conserved C-terminal motif is present. For this construct, the epitope order is the same as that of A9.1 (above).

```
Construct A9.2
                                              (SEQ ID NO: 251)
SETFTNKLKEKHTDLGKEGVTKGAEELGKLFESVEVLSKAAKEMLANSVKELTSSEEFST
<-----Lp A-----------><--------------Hx A---------------><---

KLKDNHAQLGIQGVTKGVEELEKLSGSLESLSSEDFTKKLEGEHAQLGIENVTAAELEKL
---Lp B--------><------Hx B------><--------Lp K--------><---

FKAVENLAKAAKEMAKLKGEHTDLGKEGVTKGADELEKLFESVKNLSKAAKEMLTNSKES
--Hx K--------><------Lp I-----><-----------Hx I----------><

EKFAGKLKNEHASLGKKDATKGAKELKDLSDSVESLVKASDDFTKKLQSSHAQLGVAGGA
-------Lp H--------><-------Hx H-------><--------Lp N-------

TTADELEKLFKSVESLAKAAQDALANSVNELTSKKLKEKHTDLGKKDATAAELEKLFESV
-><------------Hx N-------------><-----Lp C------><---------

ENLAKAAKEMLSNSNKAFTDKLKSSHAELGIANGAATKGAQELEKLFESVKNLSKAAQET
-Hx C--------><---------Lp M---------><-----------Hx M-----

LNNSVKESESFTKKLSDNQAELGIENATKGAEELVKLSESVAGLLKAAQAILANSVKELT
------><--------Lp D--------><-----------------Hx D--------

SPVVAESPKKP
---------->
```

For construct A9.2, the number of amino acids is 431, the molecular weight is 46088.0, and the theoretical pI: 5.85.

The sequence of the A9.3 construct is provided below (where "Lp" indicates "loop" and "Hx" indicates "helix") and depicted schematically in FIG. 30A. In this construct, the N- and C-termini are truncated to eliminate redundant sequences; the epitopes of various types are linked without linker sequences; intervening sequences (helix 4 and loop 6) are not present, and the conserved C-terminal motif is present. For this construct, the epitope order differs from that of A9.1 and A9.2 and, instead, epitopes are ordered as "helix-helix-loop-loop". The protein is designed to orient hydrophobic faces of the helices toward one another and between linked helices. Without being bound by theory, it is believed that this arrangement may promote orientation of the helix 5 epitopes in a manner similar to that found in native OspC.

```
Construct A9.3
                                              (SEQ ID NO: 252)
SETFTNKLKEKHTDLGKEGVTKGAEELGKLFESVEVLSKAAKEMLANSVKELTSKGVEEL
<--------Lp A-------><--------------Hx A---------------><-----

EKLSGSLESLSNKAFTDKLKSSHAELGIANGAATKKLKEKHTDLGKKDATKGADELEKLF
--Hx B----><---------Lp M---------><-----Lp C------><-------

ESVKNLSKAAKEMLTNSKEIAAELEKLFKAVENLAKAAKEMAKLKGEHTDLGKEGVTSEE
----Hx I-------------><--------Hx K--------><------Lp I----->

FSTKLKDNHAQLGIQGVTKGAKELKDLSDSVESLVKAAAELEKLFESVENLAKAAKEMLS
<------Lp B-------><-------Hx H-------><---------Hx C-------

NSSEKFAGKLKNEHASLGKKDATSEDFTKKLEGEHAQLGIENVTKGAQELEKLFESVKNL
-><---------Lp H--------><---------Lp K---------><---------Hx M-

SKAAQETLNNSVKEADELEKLFKSVESLAKAAQDALANSVNELTSSESFTKKLSDNQAEL
--------------><-------------Hx N--------------><-------Lp D---

GIENATSDDFTKKLQSSHAQLGVAGGATTKGAEELVKLSESVAGLLKAAQAILANSVKEL
-----><--------Lp N---------><--------------------Hx D------

TSPVVAESPKKP
----------->
```

For construct A9.3, the number of amino acids is 432, the molecular weight is 46201.2, and the theoretical pI is 5.85.

In addition to the A9 series, similarly constructed proteins have been developed which cover *Borrelia* OspC types that are not commonly found in North America, but which are more prevalent in Europe and Asia. Many of these OspC types are found in *Borrelia garinii* or *Borrelia afzelii*. These proteins are designated as the B9 and C9 series. For the B9 series, epitopes from *B. garinii* types Pwa, Pli, Pbes, Pki, PfiM, H13, Smar and HT22 are included (with some exceptions described below). For the C9 series, epitopes from *B. afzelii* types Pko, PLj7, pHez, Pmit, Szid, VS461, HT25 and DK15 are present (with some exceptions described below).

B9.1 and C9.1 contain loop 5 and helix 5 plus intervening sequences from the indicated type (as described above for A9.1, and as depicted in FIGS. 28C and D).

Constructs B9.2 and C9.2 contain epitopes (as described for A9.2 above, and as depicted in FIGS. 29B an C), except that the H13 helix 5 is identical to Pki helix 5, so it is excluded (i.e. the sequence is present only once) and the Dk15 helix 5 is identical to VS461 helix 5, so that sequence is also present only once. In addition, the C-terminus motif is not present.

Constructs B9.3 and C9.3 contain epitopes (as described for A9.3 above and as depicted in FIGS. 30B and C), except that the H13 helix is identical to that of Pki, so it is excluded (i.e. the sequence is present only once) and the Dk15 helix is identical to the VS461 helix, so that sequence is also present only once. In addition, the C-terminus motif is not present.

```
Construct B9.1
                                            (SEQ ID NO: 253)
SEKFTTKLKDSHAELGIQSVQDDNAKKAILKTHGTKDKGAKELEELFKSLESLSKAAQAA
<----------------------------------PWa--------------------

LTNSVKELTNSDKFTKKLTDSHAQLGAVGGAINDDRAKEAILKTHGTNDKGAKELKELSE
---------><------------------------PLi----------------------

SVESLAKAAQAALANSSEAFTKKLKDSNAQLGMQNGAATDAHAKAAILKTDATKDKGATE
----------------><------------------------PBes--------------

LGELFKSVESLSKAAQEASVAFTSKLKSSNAQLGVANGNATDDDAKKAILKTNTPNDKGA
------------------><------------------------Pki-----------

KELKELFESVESLAKAAQAALVNSVQELTNSEAFTNRLKGSHAQLGVAAATDDHAKEAIL
----------------------------><-----------------PFiM--------

KSNPTKDKGAKELKDLSESVESLAKAAQEALANSVKELTNSEAFTKKLKDNNAQLGIQNV
-----------------------------------------><----------H13------

QDVEAKKAILKTNGDISKSEAFTNKLKEKHAELGVNGGDTTDDNAKAAIFKTHPTKDKGV
------------------><------------------Smar-------------------

EDLEKLSESVKSLLKAAQAALSNSAAFTKKLQDGHVDLGKTDVTDDNAKEAILKTNPTKT
--------------------><-------------------------HT22-------

KGATELEELFKSVEGLVKAAKEA
---------------------->
                40
```

For construct B9.1, the number of amino acids is 503, the molecular weight is 53102.4, and the theoretical pI is 7.16.

```
Construct B9.2
                                            (SEQ ID NO: 254)
SEKFTTKLKDSHAELGIQSVQDKGAKELEELFKSLESLSKAAQAALTNSVKELTNSDKFT
<-----Lp PWa-----><--------------Hx PWa---------------><----

KKLTDSHAQLGAVGGAINDKGAKELKELSESVESLAKAAQAALANSSEAFTKKLKDSNAQ
-----Lp Pli------><-----------Hx Pli----------><-------Lp PBes

LGMQNGAATDKGATELGELFKSVESLSKAAQEASVAFTSKLKSSNAQLGVANGNATDKGA
--------><---------Hx PBes--------><---------Lp Pki--------><---

KELKELFESVESLAKAAQAALVNSVQELTNSEAFTNRLKGSHAQLGVAAATDKGAKELKD
-------Hx Pki----------------><-------Lp PFim------><---------

LSESVESLAKAAQEALANSVKELTNSEAFTKKLKDNNAQLGIQNVQSEAFTNKLKEKHAE
---Hx PFim--------------><-----Lp H13---------><----Lp Smar---

LGVNGGDTTDKGVEDLEKLSESVKSLLKAAQAALSNSAAFTKKLQDGHVDLGKTDVTTKG
--------><---------Hx Smar---------><------Lp HT22------><--

ATELEELFKSVEGLVKAAKEA
------Hx HT22------->
```

For construct B9.2, the number of amino acids is 381, the
molecular weight is 39928.6, and the theoretical pI is 5.79.

```
Construct B9.3
                                             (SEQ ID NO: 255)
SEAFTKKLKDSNAQLGMQNGAATDKGAKELEELFKSLESLSKAAQAALTNSVKELTNKDK
<----------Lp PBes----><--------------Hx PWa-------------><--

GAKELKELFESVESLAKAAQAALVNSVQELTNSEKFTTKLKDSHAELGIQSVQSDKFTKK
--------Hx PKi----------------><------Lp PWa-------><------

LTDSHAQLGAVGGAINDKGAKELKELSESVESLAKAAQAALANSDKGAKELKDLSESVES
-Lp Pli--------><----------Hx Pli----------><-------------Hx

LAKAAQEALANSVKELTNSVAFTSKLKSSNAQLGVANGNATSEAFTKKLKDNNAQLGIQN
PFim--------------><------Lp PKi----------><------Lp H13------

VQTKGATELEELFKSVEGLVKAAKEADKGVEDLEKLSESVKSLLKAAQAALSNSAAFTKK
-><--------Hx HT22-------><----------Hx Smar--------><------

LQDGHVDLGKTDVTSEAFTNRLKGSHAQLGVAAATDKGATELGELFKSVESLSKAAQEAS
Lp HT22------><-----Lp PFim--------><-------Hx PBes--------><

EAFTNKLKEKHAELGVNGGDTT
-------Lp Smar------->
```

For construct B9.3, the number of amino acids is 382, the
molecular weight is 40056.8, and the theoretical pI is 5.93.

```
Construct C9.1
                                             (SEQ ID NO: 256)
SEEFTNKLKSGHADLGKQDATDDHAKAAILKTHATTDKGAKEFKDLFESVEGLLKAAQVA
<-----------------------------------Pko-------------------

LTNSVKELTSKLKGGHAELGLAAATDENAKKAILKTNGTKDKGAEELEKLFKSVESLAKA
----------><-----------------------------PLj7--------------

AKESLTNSVKELTNTKLRDSHAELGIQNVQDDNAKRAILKTHGNKDKGAKELKELSESLE
--------------><------------------PHez----------------------

KLSKAAQAALANSVQELTSSEAFTNKLKEKTQELAVAAGAATDIDAKKAILKTNRDKDLG
------------------><---------------PMit---------------------

ADERGKLFKSVESLSKAAQEASANSVKELTSSEAFTDKLKNEHASLGKKDATDDDAKKAI
------------------------------><-----------------Szid-------

LKTNVDKTKGADELIKLSGSLESLSKAAQAILANSEAFTKKLQDSNADLGKHNATDADSK
------------------------------------><---------------VS461------

EAILKTNGTKTKGAKELEELFKSVESLSKAAKEALSNSVKELTSSQDFINKLKGGHAELG
----------------------------------------------><---------------

LVAATDANAKAAILKTNGDKTKGADEFEKLFKSVEGLLKAAQEALTNSVKELTSSEAFTK
-------HT25---------------------------------------------><-----

KLQDSNADLGKHDATDADAKKAILKTDATKDK
-----------DK15---------------->
                                                 50
```

For construct C9.1, the number of amino acids is 512; the
molecular weight is 54372.0; and the theoretical pI is 8.14.

```
Construct C9.2
                                             (SEQ ID NO: 257)
SEEFTNKLKSGHADLGKQDATKGAKEFKDLFESVEGLLKAAQVALTNSVKELTSKLKGGH
<-----Lp PKo--------><---------Hx PKo----------------><---Lp AELGLAAATKGAEELEKLFKSVESLAKAAKESLTNSVKELTNTKLRDSHAELGIQNVQKG
PLj7----><--------------Hx PLj7-----------><----Lp PHez---><-

AKELKELSESLEKLSKAAQAALANSVQELTSSEAFTNKLKEKTQELAVAAGAATLGADER
---------Hx PHez--------------><-------Lp PMit-------><-----

GKLFKSVESLSKAAQEASANSVKELTSSEAFTDKLKNEHASLGKKDATKGADELIKLSGS
------Hx PMit--------------><------Lp Szid------><-----------
```

```
                                 -continued
LESLSKAAQAILANSEAFTKKLQDSNADLGKHNATKGAKELEELFKSVESLSKAAKEALS
Hx Szid------><------Lp VS461-----><-------------Hx VS461---

NSVKELTSSQDFINKLKGGHAELGLVAATKGADEFEKLFKSVEGLLKAAQEALTNSVKEL
--------><------Lp HT25------><-------------Hx HT25----------

TSSEAFTKKLQDSNADLGKHDAT
-><------Lp DK15------>
```

For construct C9.2, the number of amino acids is 383, the molecular weight is 40492.5, and the theoretical pI: 6.45.

```
Construct C9.3
                                                 (SEQ ID NO: 258)
SEEFTNKLKSGHADLGKQDATKGAKEFKDLFESVEGLLKAAQVALTNSVKELTSKEKGAE
<------Lp PKo-------><-------------Hx PKo-------------><-----

ELEKLFKSVESLAKAAKESLTNSVKELTNSEAFTDKLKNEHASLGKKDATTKLRDSHAEL
----Hx PLj7-----------------><-----Lp Szid--------><-------Lp GIQNVQLGADERGKLFKSVESLSKAAQEASANSVKELTSKEKGAKELEELFKSVESLSKA
PHez-><------------Hx PMit-------------><----------Hx VS461-

AKEALSNSVKELTSSEAFTKKLQDSNADLGKHNATSEAFTKKLQDSNADLGKHDATKGAD
--------------><------Lp VS461-----><-------Lp DK15-----><---

EFEKLFKSVEGLLKAAQEALTNSVKELTSELKELSESLEKLSKAAQAALANSVQELTSSE
-------Hx HT25--------------><-----------Hx PHez---------><-

AFTNKLKEKTQELAVAAGAATKLKGGHAELGLAAATKGADELIKLSGSLESLSKAAQAIL
-----Lp PMit--------><---Lp PLj7---><---------Hx Szid-------

ANSQDFINKLKGGHAELGLVAAT
-><-----Lp HT25------->
```

For construct C9.3, the number of amino acids is 383, the molecular weight is 40622.6; and the theoretical pI is 6.10

The A10, A11, and A12 series proteins were also developed as proteins for vaccines and/or as diagnostic antigens, as follows:

```
A10CF
                                                 (SEQ ID NO: 259)
SEDFTNKLKNGNAQLGLAAATKGAKELKDLSDSVESLVKAAQVMLTNSSTGFTNKLKSGH
<--------lpF---------><------------hxF------------><------lpT-

AELGPVGGNATKGAKELKDLSESVEALAKAAQAMLTNSSEKFTKKLSESHADIGIQAATK
----------><----------hxT-------------><---------lpU--------><

GAEELDKLFKAVENLSKSTEFTNKLKSEHAVLGLDNLTKGAAELEKLFKAVENLSKAAQD
------hxU-------><---------lpE--------><----------------hxE--

TLKNAVKELTSPIVAESPKKPSETFTNKLKEKHTDLGKEGVTKGAEELGKLFESVEVLSK
--------------------><-------lpA---------><----------hxA----

AAKEMLANSVKELTSSEEFSTKLKDNHAQLGIQGVTKGVEELEKLSGSLESLSSEDFTKK
---------------><------lpB-----------><-------hxB------><------

LEGEHAQLGIENVTAAELEKLFKAVENLAKAAKEMAKLKGEHTDLGKEGVTKGADELEKL
--lpK--------><---------hxK--------><-----lpI-------><--------

FESVKNLSKAAKEMLTNSVKESEKFAGKLKNEHASLGKKDATKGAKELKDLSDSVESLVK
---hxI--------------><--------lpH--------><-------hxH-------

ASDDFTKKLQSSHAQLGVAGGATTADELEKLFKSVESLAKAAQDALANSVNELTSKKLKE
><---------lpN----------><-------------hxN-------------><----

KHTDLGKKDATAAELEKLFESVENLAKAAKEMLSNSNKAFTDKLKSSHAELGIANGAATK
--lpC-----><-----------hxC----------><---------lpM----------><

GAQELEKLFESVKNLSKAAQETLNNSVKESESFTKKLSDNQAELGIENATKGAEELVKLS
------------hxM-------------><---------lpD---------><---------

ESVAGLLKAAQAILANSVKELTSPVVAESPKKPNNSGKDGNTSANSADESVKGPNLTEIS
----------hxD-------------------><-------------------------
```

```
KKITESNAVVLAVKEIETLLSSIDELATKAIGQKIDANGLGVQANQNGSLLAGAYAISTL
-----------------------------OsPc Type F-----------------

ITQKLSALNSEDLKEKVAKVKKCSEDFTNKLKNGNAQLGLAAATDDNAKAAILKTNGTND
------------------------------------------------------------

KGAKELKDLSDSVESLVKAAQVMLTNSVKELTSPVVAESPKKP
------------------------------------------>
```

For construct A10CF, the number of amino acids is 823, the molecular weight is 87013.4 and the theoretical pI is 6.28. The estimated half-life (the N-terminal of the sequence considered is S (Ser)) is: 1.9 hours (mammalian reticulocytes, in vitro); >20 hours (yeast, in vivo); and >10 hours (*Escherichia coli*, in vivo). The instability index (II) is computed to be 17.53. This classifies the protein as stable. The aliphatic index is 86.18. The grand average of hydropathicity (GRAVY) is −0.487.

```
A11
                                               (SEQ ID NO: 260)
SEDFTNKLKNGNAQLGLAAATKGAKELKDLSDSVESLVKAAQVMLTNSSTGFTNKLKSGH
<-------lpF---------><-----------hxF------------><------lpT--

AELGPVGGNATKGAKELKDLSESVEALAKAAQAMLTNSSEKFTKKLSESHADIGIQAATK
----------><----------hxT-------------><--------lpU--------><

GAEELDKLFKAVENLSKSTEFTNKLKSEHAVLGLDNLTKGAAELEKLFKAVENLSKAAQD
------hxU-------><--------lpE---------><---------------hxE--

TLKNAVKELTSPIVAESPKKPSETFTNKLKEKHTDLGKEGVTKGAEELGKLFESVEVLSK
--------------------><-------lpA---------><----------hxA----

AAKEMLANSVKELTSSEEFSTKLKDNHAQLGIQGVTKGVEELEKLSGSLESLSSEDFTKK
---------------><------lpB----------><------hxB------><------

LEGEHAQLGIENVTAAELEKLFKAVENLAKAAKEM
--lpK--------><---------hxK-------->
```

For construct A11, the number of amino acids: 335; the molecular weight is 35688.4; and the theoretical pI is 5.87. The estimated half-life (the N-terminal of the sequence considered is S (Ser)) is: 1.9 hours (mammalian reticulocytes, in vitro); >20 hours (yeast, in vivo); and >10 hours (*Escherichia coli*, in vivo). The instability index (II) is computed to be 17.08. This classifies the protein as stable. The aliphatic index: is 84.57. The grand average of hydropathicity (GRAVY) is −0.478

```
A12
                                               (SEQ ID NO: 261)
AKLKGEHTDLGKEGVTKGADELEKLFESVKNLSKAAKEMLTNSVKESEKFAGKLKNEHAS
<-----lpI------><-----------hxI---------------><--------lpH--

LGKKDATKGAKELKDLSDSVESLVKASDDFTKKLQSSHAQLGVAGGATTADELEKLFKSV
-------><-------hxH-------><---------lpN---------><-----------

ESLAKAAQDALANSVNELTSKKLKEKHTDLGKKDATAAELEKLFESVENLAKAAKEMLSN
---hxN-------------><------lpC-----><----------hxC----------

SNKAFTDKLKSSHAELGIANGAATKGAQELEKLFESVKNLSKAAQETLNNSVKESESFTK
><--------lpM----------><------------hxM-------------><-----

KLSDNQAELGIENATKGAEELVKLSESVAGLLKAAQAILANSVKELTSPVVAESPKKP
---lpD--------><------------------hxD------------------>
```

For construct A12, the number of amino acids is 298; the molecular weight is 31637.7; and the theoretical pI is 7.19 Estimated half-life (the N-terminal of the sequence considered is A (Ala) is: 4.4 hours (mammalian reticulocytes, in vitro); >20 hours (yeast, in vivo); and >10 hours (*Escherichia coli*, in vivo). The instability index (II) is computed to be 17.79; this classifies the protein as stable. The aliphatic index is 82.99 and the grand average of hydropathicity (GRAVY) is −0.573

```
A12A
                                             (SEQ ID NO: 262)
AKLKGEHTDLGKEGVTKGADELEKLFESVKNLSKAAKEMLTNSVKESEKFAGKLKNEHAS
<-----lpI------><-----------hxI-------------><--------lpH--

LGKKDATKGAKELKDLSDSVESLVKASDDFTKKLQSSHAQLGVAGGATTADELEKLFKSV
------><-------hxH-------><---------lpN---------><----------

ESLAKAAQDALANSVNELTSKKLKEKHTDLGKKDATAAELEKLFESVENLAKAAKEMLSN
---hxN------------><------lpC-----><----------hxC---------

SNKAFTDKLKSSHAELGIANGAATKGAQELEKLFESVKNLSKAAQETLNNSVKESESFTK
><--------lpM---------><------------hxM------------><-----

KLSDNQAELGIENATKGAEELVKLSESVAGLLKAAQAILANSVKELTSPVVAESPKKPST
---lpD--------><------------------hxD------------------><-

EEKFNEKGEVSEKIITRADGTRLEYTGIKSDGSGKAKEVLKGYVLEGTLTAEKTTLVVKE
-------------------------------------OspA121273-----------

GTVTLSKNISKSGEVSVELNDTDSSAATKKTAAWNSGTSTLTITVNSKKTKDLVFTKENT
------------------------------------------------------------

ITVQQYDSNGTKLEGSAVEITKLDEIKNALK
------------------------------>
```

For construct A12A, the number of amino acids is 451; the molecular weight is 48061.1; and the theoretical pI is 7.19 The estimated half-life (the N-terminal of the sequence considered is A (Ala) is: 4.4 hours (mammalian reticulocytes, in vitro); >20 hours (yeast, in vivo); and >10 hours (*Escherichia coli*, in vivo). The instability index (II) is computed to be 16.121; this classifies the protein as stable. The aliphatic index is 81.84. The grand average of hydropathicity (GRAVY) is −0.579.

```
A12CF
                                             (SEQ ID NO: 263)
AKLKGEHTDLGKEGVTKGADELEKLFESVKNLSKAAKEMLTNSVKESEKFAGKLKNEHAS
<-----lpI------><-----------hxI-------------><--------lpH--

LGKKDATKGAKELKDLSDSVESLVKASDDFTKKLQSSHAQLGVAGGATTADELEKLFKSV
------><-------hxH-------><---------lpN---------><----------

ESLAKAAQDALANSVNELTSKKLKEKHTDLGKKDATAAELEKLFESVENLAKAAKEMLSN
---hxN------------><------lpC-----><----------hxC---------

SNKAFTDKLKSSHAELGIANGAATKGAQELEKLFESVKNLSKAAQETLNNSVKESESFTK
><--------lpM---------><------------hxM------------><-----

KLSDNQAELGIENATKGAEELVKLSESVAGLLKAAQAILANSVKELTSPVVAESPKKPNN
---lpD--------><------------------hxD------------------><-

SGKDGNTSANSADESVKGPNLTEISKKITESNAVVLAVKEIETLLSSIDELATKAIGQKI
------------------------------------------------------------

DANGLGVQANQNGSLLAGAYAISTLITQKLSALNSEDLKEKVAKVKKCSEDFTNKLKNGN
-----------------------OspC Type F------------------------

AQLGLAAATDDNAKAAILKTNGTNDKGAKELKDLSDSVESLVKAAQVMLTNSVKELTSPV
------------------------------------------------------------

VAESPKKP
------->
```

For construct A12CF, the number of amino acids is 488; the molecular weight is 51342.9; and the theoretical pI is 7.18. The estimated half-life (the N-terminal of the sequence considered is A (Ala)) is: 4.4 hours (mammalian reticulocytes, in vitro); >20 hours (yeast, in vivo); and >10 hours (*Escherichia coli*, in vivo). The instability index (II) is computed to be 17.56; this classifies the protein as stable. The aliphatic index is 87.30. The grand average of hydropathicity (GRAVY) is −0.492.

Further exemplary chimeric proteins which may be used as diagnostic antigens, designated as LDX1, LDX2, LDX3, and LDX4, are presented below. These sequences may also be used in vaccine compositions. In these sequences, "ECR" represents "epitope containing regions." The ECRs contain the regions from (and including) loop 5 to (and including) helix 5, as well as the C-terminal motif from the indicated type.

LDX1
(SEQ ID NO: 264)
NNSGKDGNTSANSADESVKGPNLTEISKKITDSNAVLLAVKEVEALLSSIDEIAAKAIGK
<------------------------------------------------------------

KIHQNNGLDTENNHNGSLLAGAYAISTLIKQKLDGLKNEGLKEKIDAAKKCSETFTNKLK
------------------------Type A full length------------------

EKHTDLGKEGVTDADAKEAILKTNGTKTKGAEELGKLFESVEVLSKAAKEMLANSVKELT
------------------------------------------------------------

SPVVAESPKKPSEDFTKKLEGEHAQLGIENVTDENAKKAILITDAAKDKGAAELEKLFKA
----------><--------------------Type K ECR-----------------

VENLAAKLKGEHTDLGKEGVTDDNAKKAILKTNNDKTKGADELEKLFESVKNLSKAAKEM
----><---------------------------Type I ECR-----------------

LTNSSEEFSTKLKDNHAQLGIQGVTDENAKKAILKANAAGKDKGVEELEKLSGSLESLSS
---><----------------------------Type B ECR----------------><

DDFTKKLQSSHAQLGVAGGATTDEEAKKAILRTNAIKDKGADELEKLFKSVESLAKAAQD
---------------------------------Type N ECR-----------------

ALANSVNELTSSESFTKKLSDNQAELGIENATDDNAKKAILKTHNAKDKGAEELVKLSES
----------><--------------------Type D ECR-----------------

VAGLLKAAQAILANSVKELTSPVVAESPKKP
------------------------------>

LDX2
(SEQ ID NO: 265)
SETFTNKLKEKHTDLGKEGVTDADAKEAILKTNGTKTKGAEELGKLFESVEVLSKAAKEM
<-------------------------------Type A ECR------------------

LANSVKELTSSEDFTKKLEGEHAQLGIENVTDENAKKAILITDAAKDKGAAELEKLFKAV
----------><--------------------Type K ECR------------------

ENLAAKLKGEHTDLGKEGVTDDNAKKAILKTNNDKTKGADELEKLFESVKNLSKAAKEML
---><---------------------------Type I ECR------------------

TNSSEEFSTKLKDNHAQLGIQGVTDENAKKAILKANAAGKDKGVEELEKLSGSLESLSSD
---><----------------------------Type B ECR---------------><-

DFTKKLQSSHAQLGVAGGATTDEEAKKAILRTNAIKDKGADELEKLFKSVESLAKAAQDA
---------------------------------Type N ECR------------------

LANSVNELTSSESFTKKLSDNQAELGIENATDDNAKKAILKTHNAKDKGAEELVKLSESV
----------><--------------------Type D ECR------------------

AGLLKAAQAILANSVKELTSPVVAESPKKP
----------------------------->

LDX3
(SEQ ID NO: 266)
NNSGKDGNTSANSADESVKGPNLTEISKKITESNAVVLAVKEIETLLSSIDELATKAIGQ
<------------------------------------------------------------

KIDANGLGVQANQNGSLLAGAYAISTLITQKLSALNSEDLKEKVAKVKKCSEDFTNKLKN
------------------------Type F full length------------------

GNAQLGLAAATDDNAKAAILKTNGTNDKGAKELKDLSDSVESLVKAAQVMLTNSVKELTS
------------------------------------------------------------

PVVAESPKKPSEKFAGKLKNEHASLGKKDATDDDAKKAILKTHGNTDKGAKELKDLSDSV
----------><--------------------Type H ECR------------------

ESLVSTGFTNKLKSGHAELGPVGGNATDENAKQAILKTHGNVTKGAKELKDLSESVEALA
---><----------------------------Type T ECR------------------

KAAQAMSEKFTKKLSESHADIGIQAATDANAKDAILKTNPTKTKGAEELDKLFKAVENLS
------><-------------------------Type U ECR------------------

KAAKKLKEKHTDLGKKDATDVHAKEAILKTNGTKDKGAAELEKLFESVENLAKAAKEMLS
--><-----------------------------Type C ECR------------------

NSNKAFTDKLKSSHAELGIANGAATDANAKAAILKTNGTKDKGAQELEKLFESVKNLSKA
-><------------------------------Type M ECR------------------

```
                              -continued
AQETLNNSSTEFTNKLKSEHAVLGLDNLTDDNAQRAILKKHANKDKGAAELEKLFKAVEN
-------><----------------------Type E ECR-----------------

LSKAAQDTLKNAVKELTSPIVAESPKKP
---------------------------->

LDX4
                                                   (SEQ ID NO: 267)
NKLKNGNAQLGLAAATDDNAKAAILKTNGTNDKGAKELKDLSDSVESLVKAAQVMLTNSS
<------------------------Type F ECR---------------------><

EKFAGKLKNEHASLGKKDATDDDAKKAILKTHGNTDKGAKELKDLSDSVESLVSTGFTNK
-------------------------Type H ECR----------------><------

LKSGHAELGPVGGNATDENAKQAILKTHGNVTKGAKELKDLSESVEALAKAAQAMSEKFT
-------------------------Type T ECR------------------><----

KKLSESHADIGIQAATDANAKDAILKTNPTKTKGAEELDKLFKAVENLSKAAKKLKEKHT
-------------------------Type U ECR----------------><-------

DLGKKDATDVHAKEAILKTNGTKDKGAAELEKLFESVENLAKAAKEMLSNSNKAFTDKLK
-------------------------Type C ECR---------------><--------

SSHAELGIANGAATDANAKAAILKTNGTKDKGAQELEKLFESVKNLSKAAQETLNNSSTE
-------------------------Type M ECR--------------------><---

FTNKLKSEHAVLGLDNLTDDNAQRAILKKHANKDKGAAELEKLFKAVENLSKAAQDTLKN
-------------------------Type E ECR------------------------

AVKELTSPIVAESPKKP
----------------->
```

Example 8

Evaluation of Immune Response to Chimeric A12CF Protein in Dogs

Ten dogs, approximately two months old, in good health, and not previously vaccinated against Lyme disease, were used in the study. One group (5 dogs) was administered subcutaneously (SC), at the nape of the cervical region/dorsal shoulders, a 1 ml dose of 0.063% PBS on both day 0 and 21. The second group (5 dogs) was similarly administered a 1 ml dose of chimeric A12CF protein adjuvanted with Rehydragel LV, also on day 0 and 21. Serum was collected on days 0, 21, 42 and 63, and analyzed by ELISA and/or Western blots for antibodies to the A12CF chimeric protein.

Dogs receiving the saline administrations remained serologically negative for antibodies to OspC throughout the study, having titers of 41.0 (day 0), 54.1 (day 21), 58.7 (day 42), and 71.4 (day 63). Dogs receiving the A12CF protein adjuvanted with Rehydragel LV, however, mounted a robust serological response to the protein, having titers of 77.6 (day 0), 540.6 (day 21), 16333.0 (day 42), and 8650.2 (day 63).

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Abuodeh R O, Shubitz L F, Siegel E, Snyder S, Peng T, Orsborn K I, et al. Resistance to *Coccidioides immitis* in mice after immunization with recombinant protein or a DNA vaccine of a proline-rich antigen. Infect Immun 1999 June; 67(6):2935-40.

Ahlborg N, Nardin E H, Perlmann P, Berzins K, Andersson R. Immunogenicity of chimeric multiple antigen peptides based on *Plasmodium falciparum* antigens: impact of epitope orientation. Vaccine 1998; 16(1):38-44.

Alghaferi, M. Y., J. M. Anderson, J. Park, P. G. Auwaerter, J. N. Aucott, D. E. Norris, and J. S. Dumler. 2005. *Borrelia burgdorferi* ospC heterogeneity among human and murine isolates from a defined region of Northern Maryland and Southern Pennsylvania: Lack of correlation with invasive and non-invasive genotypes. J. Clin. Microbiol. 43:1879-1884.

Alvarez P, Buscaglia C A, Campetella O. Improving protein pharmacokinetics by genetic fusion to simple amino acid sequences. J Biol Chem 2004 Jan. 30; 279(5):3375-81.

Alverson, J., S. F. Bundle, C. D. Sohaskey, M. C. Lybecker, and D. S. Samuels. 2003. Transcriptional regulation of the ospAB and ospC promoters from *Borrelia burgdorferi*. Mol. Microbiol. 48:1665-1677.

Apta, D., K. Raviprakashb, A. Brinkman, A. Semyonov, S. Yang, C. Skinnera, L. Diehl, R. Lyons, K. Porter, and J. Punnonen. 2006. Tetravalent neutralizing antibody response against four dengue serotypes by a single chimeric dengue envelope antigen. Vaccine 24:335-344.

Asch E S, Bujak D I, Weiss M, Peterson M G, Weinstein A. Lyme disease: an infectious and postinfectious syndrome. J Rheumatol 1994; 21(3):454-61.

Attie, O., J. F. Bruno, Y. Xu, D. Qiu, B. J. Luft, and W. G. Qiu. 2006. Co-evolution of the outer surface protein C gene (ospC) and intraspecific lineages of *Borrelia burgdorferi* sensu stricto in the northeastern United States. Infect Genet Evol E-pub.

Barthold S W, Beck D S, Hansen G M, Terwilliger G A, Moody K D. Lyme borreliosis in selected strains and ages of laboratory mice. J Infect Dis 1990 July; 162(1):133-8.

Barthold S W, Persing D H, Armstrong A L, Peeples R A. Kinetics of *Borrelia burgdorferi* dissemination and evolution of disease after intradermal inoculation of mice. Am J Pathol 1991; 139(2):263-73.

Benach J L, Bosler E M, Hanrahan J P, Coleman J L, Bast T F, Habicht G S, et al. Spirochetes isolated from the blood of two patients with Lyme disease. N Engl J Med 1983; 308: 740-2.

Bockenstedt, L. K., E. Hodzic, S. Feng, K. W. Bourrel, A. de Silva, R. R. Montgomery, E. Fikrig, J. D. Radolf, and S. W. Barthold. 1997. *Borrelia burgdorferi* strain-specific OspC mediated immunity in mice. Infect. Immun. 65:4661-4667.

Bockenstedt L K, Kang I, Chang C, Persing D, Hayday A, Barthold S W. CD4+ T helper 1 cells facilitate regression of murine Lyme carditis. Infect Immun 2001 September; 69(9):5264-9.

Bouche F B, Steinmetz A, Yanagi Y, Muller C P. Induction of broadly neutralizing antibodies against measles virus mutants using a polyepitope vaccine strategy. Vaccine 2005; 23(17-18):2074-7.

Brewer J M, Conacher M, Hunter C A, Mohrs M, Brombacher F, Alexander J. Aluminium hydroxide adjuvant initiates strong antigen-specific Th2 responses in the absence of IL-4- or IL-13-mediated signaling. J Immunol 1999; 163 (12):6448-54.

Brinckerhoff L H, Kalashnikov V V, Thompson L W, Yamshchikov G V, Pierce R A, Galavotti H S, et al. Terminal modifications inhibit proteolytic degradation of an immunogenic MART-1 (27-35) peptide: implications for peptide vaccines. Int J Cancer 1999 Oct. 29; 83(3):326-34.

Brisson D, Dykhuizen D E. ospC diversity in *Borrelia burgdorferi*: Different hosts are different niches. Genetics 2004; 168:713-22.

Brown E L, Kim J H, Reisenbichler E S, Hook M. Multicomponent Lyme vaccine: three is not a crowd. Vaccine 2005; 23(28):3687-96.

Burgdorfer W, Barbour A G, Hayes S F, Benach J L, Grunwaldt E, Davis J P. Lyme disease—a tick-borne spirochetosis? Science 1982; 216:1317-9.

Cai Q L, Wei F, Lin Y H, Shao D D, Wang H. Immunogenicity of polyepitope libraries assembled by epitope shuffling: an approach to the development of chimeric gene vaccination against malaria. Vaccine 2004; 23(2):267-77.

Caro-Aguilar, I., S. Lapp, J. Pohl, M. R. Galinski, and A. Moreno. 2005. Chimeric epitopes delivered by polymeric synthetic linear peptides induce protective immunity to malaria. Microbes Infect. 7:1324-1337.

Christe M, Rutti B, Brossard M. Cytokines (IL-4 and IFN-gamma) and antibodies (IgE and IgG2a) produced in mice infected with *Borrelia burgdorferi* sensu stricto via nymphs of *Ixodes ricinus* ticks or syringe inoculations. Parasitol Res 2000 June; 86(6):491-6.

Coyle P K, Schutzer S E. Neurologic aspects of Lyme disease. Med Clin North Am 2002; 86(2):261-84.

Crasto C J, Feng J A. LINKER: a program to generate linker sequences for fusion proteins. Protein Eng 2000; 13(5): 309-12.

Cribbs D H, Ghochikyan A, Vasilevko V, Tran M, Petrushina I, Sadzikava N, et al. Adjuvant-dependent modulation of Th1 and Th2 responses to immunization with beta-amyloid. Int Immunol 2003 April; 15(4):505-14.

Dale J B, Simmons M, Chiang E C, Chiang E Y. Recombinant, octavalent group A streptococcal M protein vaccine. Vaccine 1996; 14(10):944-8.

Dale J B, Penfound T, Chiang E Y, Long V, Shulman S T, Beall B. Multivalent group A streptococcal vaccine elicits bactericidal antibodies against variant M subtypes. Clin Diagn Lab Immunol 2005; 12(7):833-6.

Dale J B, Chiang E Y, Lederer J W. Recombinant tetravalent group A streptococcal M protein vaccine. J Immunol 1993; 151(4):2188-94.

Dale, J. B. 1999. Mutlivalent group A streptococcal vaccine designed to optimize the immunogenicity of six tandem M protein fragments. Vaccine 17:193-200.

de Silva A M, Zeidner N S, Zhang Y, Dolan M C, Piesman J, Fikrig E. Influence of outer surface protein A antibody on *Borrelia burgdorferi* within feeding ticks. Infect Immun 1999; 67(1):30-5.

Dangl J L, Wensel T G, Morrison S L, Stryer L, Herzenberg L A, Oi V T. Segmental flexibility and complement fixation of genetically engineered chimeric human, rabbit and mouse antibodies. EMBO J. 1988 July; 7(7):1989-94.

Eicken, C., C. Sharma, T. Klabunde, R. T. Owens, D. S. Pikas, M. Hook, and J. C. Sacchettini. 2001. Crystal structure of Lyme disease antigen outer surface protein C from *Borrelia burgdorferi*. J. Biol. Chem. 276:10010-10015.

Eiffert H, Karsten A, Thomssen R, Christen H-J. Characterization of *Borrelia burgdorferi* strains in Lyme arthritis. Scand J Infect Dis 1998; 24:437-9.

Elias A F, Stewart P E, Grimm D, Caimano M J, Eggers C H, Tilly K, et al. Clonal polymorphism of *Borrelia burgdorferi* strain B31 MI: implications for mutagenesis in an infectious strain background. Infect Immun 2002; 70(4): 2139-50.

Elias A F, Bono J L, Carroll J A, Stewart P, Tilly K, Rosa P. Altered stationary-phase response in a *Borrelia burgdorferi* rpoS mutant. J Bacteriol 2000; 182(10):2909-18.

Escudero, R., M. Halluska, P. Backenson, J. Coleman, and J. Benach. 1997. Characterization of the physiological requirements for the bactericidal effects of a monoclonal antibody to OspB of *Borrelia burgdorferi* by confocal microscopy. Infect. Immun. 65:1908-1915.

Fahrer H, van der Linden S M, Sauvian M J, Gem L, Zhioua E, Aeschlimann A. The prevalence and incidence of clinical and asymptomatic Lyme borreliosis in a population at risk. J Infect Dis 1991; 163:305-10.

Fan, C. F., and X. G. Mei. 2005. Co-immunization of BALB/c mice with recombinant immunogens containing G protein fragment and chimeric CTL epitope of respiratory syncytial virus induces enhanced cellular immunity and high level of antibody response. Vaccine 23:4453-4461.

Fingerle, V., U. Hauser, G. Liegl, B. Petko, V. Preac-Mursic, and B. Wilske. 1995. Expression of outer surface proteins A and C of *Borrelia burgdorferi* in *Ixodes ricinus*. J. Clin. Microbiol. 33:1867-1869.

Fraser, C., S. Casjens, W. M. Huang, G. G. Sutton, R. Clayton, R. Lathigra, O. White, K. A. Ketchum, R. Dodson, E. K. Hickey, M. Gwinn, B. Dougherty, J. F. Tomb, R. D. Fleischman, D. Richardson, J. Peterson, A. R. Kerlavage, J. Quackenbush, S. Salzberg, M. Hanson, R. Vugt, N. Palmer, M. D. Adams, J. Gocayne, J. Weidman, T. Utterback, L. Watthey, L. McDonald, P. Artiach, C. Bowman, S. Garland, C. Fujii, M. D. Cotton, K. Horst, K. Roberts, B. Hatch, H. O, Smith, and J. C. Venter. 1997. Genomic sequence of a Lyme disease spirochaete, *Borrelia burgdorferi*. Nature 390:580-586.

Fuchs, R., S. Jauris, F. Lottspeich, V. Preac-Mursic, B. Wilske, and E. Soutschek. 1992. Molecular analysis and expression of a *Borrelia burgdorferi* gene encoding a 22-kDa protein (pC) in *Escherichia coli*. Mol. Microbiol. 6:503-509.

Gasteiger E, Hoogland C, Gattiker A, Duvaud S, Wilkins M R, Appel R D, et al. Protein Identification and Analysis Tools on the ExPASy Server. In: Walker J M, editor. The Proteomics Protocols Handbook. Totowa, N.J.: Humana Press, 2005: 571-608.

Gilmore, R. D., and M. L. Mbow. 1999. Conformational nature of the *Borrelia burgdorferi* B31 outer surface protein C protective epitope. Infect. Immun. 67:5463-5469.

Gilmore R D, Jr., Mbow M L, Stevenson B. Analysis of *Borrelia burgdorferi* gene expression during life cycle phases of the tick vector *Ixodes* scapularis. Microbes Infect 2001; 3(10):799-808.

Gilmore, R. D., R. M. Bacon, A. M. Carpio, J. Piesman, M. C. Dolan, and M. L. Mbow. 2003. Inability of outer-surface protein C (OspC)-primed mice to elicit a protective anamnestic immune response to a tick-transmitted challenge of *Borrelia burgdorferi*. J. Med. Microbiol. 52:551-556.

Gilmore, R. D. J. 1998. A monoclonal antibody generated by antigen inoculation via tick bite is reactive to the *Borrelia burgdorferi* Rev protein, a member of the 2.9 gene family locus. Infect. Immun. 66:980-986.

Gilmore, R. D., K. J. Kappel, M. C. Dolan, T. R. Burkot, and B. J. B. Johnson. 1996. Outer surface protein C (OspC) but not P39 is a protection immunogen against a tick-transmitted *Borrelia burgdorferi* challenge: evidence for a conformational protective epitope in OspC. Infect. Immun. 64:2234-2239.

Golovanov A P, Hautbergue G M, Wilson S A, Lian L Y. A simple method for improving protein solubility and long-term stability. J Am Chem Soc 2004 Jul. 28; 126(29):8933-9.

Grimm, D., K. Tilly, R. Byram, S. P. E, J. G. Krum, D. M. Bueschel, T. G. Schwan, P. F. Policastro, A. F. Elias, and P. A. Rosa. 2004. Outer surface protein C of the Lyme disease spirochetes: A protein induced in ticks for infection in mammals. Proc. Natl. Acad. Sci. USA 101:3142-3147.

Gross D M, Steere A C, Huber B T. T helper 1 response is dominant and localized to the synovial fluid in patients with Lyme arthritis. J Immunol 1998 Jan. 15; 160(2):1022-8.

Guruprasad K, Reddy B V, Pandit M W. Correlation between stability of a protein and its dipeptide composition: a novel approach for predicting in vivo stability of a protein from its primary sequence. Protein Eng 1990; 4(2):155-61.

Guttman D S, Wang P W, Wang I N, Bosler E M, Luft B J, Dykhuizen D E. Multiple infections of *Ixodes* scapularis ticks by *Borrelia burgdorferi* as revealed by single-strand conformation polymorphism analysis. J Clin Microbiol 1996; 34(3):652-6.

Hanson, M. S., and R. Edelman. 2004. Vaccines against Lyme disease, p. 487-498. In M. Levine, J. B. Kaper, R. Rappuoli, M. A. Liu, and M. F. Good (ed.), New generation vaccines, vol. 3. Marcel Dekker A G, New York, N.Y.

Hodzic E, Feng S, Barthold S W. Stability of *Borrelia burgdorferi* outer surface protein C under immune selection pressure. J Infect Dis 2000; 181(2):750-3.

Hofmeister E K, Glass G E, Childs J E, Persing D H. Population dynamics of a naturally occurring heterogeneous mixture of *Borrelia burgdorferi* clones. Infect Immun 1999; 67(11):5709-16.

Horvath, A., L. Karpati, H. K. Sun, M. Good, and I. Toth. 2005. Toward the development of a synthetic group a streptococcal vaccine of high purity and broad protective coverage. J. Med. Chem. 47:4100-4104.

Hovis, K., J. V. McDowell, L. Griffin, and R. T. Marconi. 2004. Identification and characterization of a linear plasmid encoded factor H-binding protein (FhbA) of the relapsing fever spirochete, *Borrelia hermsii*. J. Bacteriol. 186:2612-2618.

Hu C M, Simon M, Kramer M D, Gem L. Tick factors and in vitro cultivation influence the protein profile, antigenicity and pathogenicity of a cloned *Borrelia garinii* isolate from *Ixodes ricinus* hemolymph. Infection 1996; 24(3):251-7.

Hu M C, Walls M A, Stroop S D, Reddish M A, Beall B, Dale J B. Immunogenicity of a 26-valent group A streptococcal vaccine. Infect Immun 2002; 70(4):2171-7.

Hubner, A., X. Yang, D. M. Nolen, T. G. Popova, F. C. Cabello, and M. V. Norgard. 2001. Expression of *Borrelia burgdorferi* OspC and DbpA is controlled by a RpoN-RpoS regulatory pathway. Proc Natl Acad Sci USA 98:12724-12729.

Ikushima, M., K. Matsui, F. Yamada, S. Kawahashi, and A. Nishikawa. 2000. Specific immune response to a synthetic peptide derived from outer surface protein C of *Borrelia burgdorferi* predicts protective borreliacidal antibodies. FEMS Immunol. Med. Microbiol. 29:15-21.

Jiang Y, Lin C, Yin B, He X, Mao Y, Dong M, et al. Effects of the configuration of a multi-epitope chimeric malaria DNA vaccine on its antigenicity to mice. Chin Med J (Engl) 1999; 112(8):686-90.

Jobe, D. A., S. D. Lovrich, R. F. Schell, and S. M. Callister. 2003. C-terminal region of outer surface protein C binds borreliacidal antibodies in sera from patients with Lyme disease. Clin. Diagn. Lab. Immunol. 10:573-578.

Kalish R A, Leong J M, Steere A C. Association of treatment resistant chronic Lyme arthritis with HLA-DR4 and antibody reactivity to OspA and OspB of *Borrelia burgdorferi*. Infect Immun 1993; 61:2774-9.

Kawarasaki Y, Yamada Y, Ichimori M, Shinbata T, Kohda K, Nakano H, et al. Stabilization of affinity-tagged recombinant protein during/after its production in a cell-free system using wheat-germ extract. J Biosci Bioeng 2003; 95(3):209-14.

Keane-Myers A, Maliszewski C R, Finkelman F D, Nickell S P. Recombinant IL-4 treatment augments resistance to *Borrelia burgdorferi* infections in both normal susceptible and antibody-deficient susceptible mice. J Immunol 1996; 156 (7):2488-94.

Keane-Myers A, Nickell S P. T cell subset-dependent modulation of immunity to *Borrelia burgdorferi* in mice. J Immunol 1995; 154(4):1770-6.

Keane-Myers A, Nickell S P. Role of IL-4 and IFN-gamma in modulation of immunity to *Borrelia burgdorferi* in mice. J Immunol 1995; 155(4):2020-8.

Kelleher Doyle M, Telford S R, 3rd, Criscione L, Lin S R, Spielman A, Gravallese E M. Cytokines in murine Lyme carditis: Th1 cytokine expression follows expression of proinflammatory cytokines in a susceptible mouse strain. J Infect Dis 1998 January; 177(1):242-6.

Kjerrulf M, Lowenadler B, Svanholm C, Lycke N. Tandem repeats of T helper epitopes enhance immunogenicity of fusion proteins by promoting processing and presentation. Mol Immunol 1997; 34(8-9):599-608.

Kneller D G, Cohen F E, Langridge R. Improvements in protein secondary structure prediction by an enhanced neural network. J Mol Biol 1990; 214(1):171-82.

Koide S, Yang X, Huang X, Dunn J J, Luft B J. Structure-based design of a second-generation Lyme disease vaccine based on a C-terminal fragment of *Borrelia burgdorferi* OspA. J Mol Biol 2005; 350(2):290-9.

Kotloff, K. L., M. Coretti, K. Palmer, J. D. Campbell, M. A. Reddish, M. C. Hu, S. S. Wasserman, and J. B. Dale. 2005. Safety and immunogenicity of a recombinant multivalent group A streptococcal vaccine in healthy adults: phase 1 trial. JAMA 292:738-739.

Kraiczy P, Hunfeld K P, Peters S, Wurzner R, Ackert G, Wilske B, et al. Borreliacidal activity of early Lyme disease sera against complement-resistant *Borrelia afzelii* FEM1 wild-type and an OspC-lacking FEM1 variant. J Med Microbiol 2000; 49(10):917-28.

Kumaran, D., S. Eswaramoorthy, B. J. Luft, S. Koide, J. J. Dunn, C. L. Lawson, and S. Swaminathan. 2001. Crystal structure of outer surface protein C (OspC) from the Lyme disease spirochete, *Borrelia burgdorferi*. EMBO J. 20:971-978.

Lagal, V., D. Postic, E. Ruzic-Sabljic, and G. Baranton. 2003. Genetic diversity among *Borrelia* strains determine by single-stranded confromation polymorphism analysis of the ospC gene and its association with invasiveness. J. Clin. Microbiol. 41:5059-5065.

Ledin K E, Zeidner N S, Ribeiro J M, Biggerstaff B J, Dolan M C, Dietrich G, et al. Borreliacidal activity of saliva of the tick Amblyomma americanum. Med Vet Entomol 2005; 19(1):90-5.

Lee E N, Kim Y M, Lee H J, Park S W, Jung H Y, Lee J M, et al. Stabilizing peptide fusion for solving the stability and solubility problems of therapeutic proteins. Pharm Res 2005 October; 22(10):1735-46.

Lindblad E B. Aluminium compounds for use in vaccines. Immunol Cell Biol 2004; 82(5):497-505.

Lole, K. S., R. C. Bollinger, R. S. Paranjape, D. Gadkari, S. S. Kulkarni, N. G. Novak, R. Ingersoll, H. W. Sheppard, and S. C. Ray. 1999. Full-length human immunodeficiency virus type 1 genomes from subtype C-infected seroconverters in India, with evidence of intersubtype recombination. J. Virol. 73:152-160.

Lovrich, S. D., D. A. Jobe, R. F. Schell, and S. M. Callister. 2005. Borreliacidal OspC antibodies specific for a highly conserved epitope are immunodominant in human Lyme disease and do not occur in mice or hamsters. Clin. Diagn. Lab. Immunol. 12:746-751.

Marconi R T, Samuels D S, Garon C F. Transcriptional analyses and mapping of the ospC gene in Lyme disease spirochetes. J Bacteriol 1993; 175:926-32.

Marconi, R. T., D. S. Samuels, T. G. Schwan, and C. F. Garon. 1993. Identification of a protein in several *Borrelia* species which is related to OspC of the Lyme disease spirochetes. J. Clin. Microbiol. 31:2577-2583.

Marconi, R. T., D. S. Samuels, and C. F. Garon. 1993. Transcriptional analyses and mapping of the ospC gene in Lyme disease spirochetes. J. Bacteriol. 175:926-932.

Margolis, N., D. Hogan, W. J. Cieplak, T. G. Schwan, and P. A. Rosa. 1994. Homology between *Borrelia burgdorferi* OspC and members of the family of *Borrelia hermsii* variable major proteins. Gene 143:105-110.

Mathiesen, M. J., A. Holm, M. Christiansen, J. Blom, K. Hansen, S. Ostergard, and M. Theisen. 1998. The dominant epitope of *Borrelia garinii* outer surface protein C recognized by sera from patients with neuroborreliosis has a surface exposed conserved structural motif. Infect. Immun. 66:4073-4079.

Mbow, M. L., R. D. Gilmore, Jr., and R. G. Titus. 1999. An OspC-specific monoclonal antibody passively protects mice from tick-transmitted infection by *Borrelia burgdorferi* B31. Infect. Immun. 67:5470-5472.

McDowell, J. V., S. Y. Sung, L. T. Hu, and R. T. Marconi. 2002. Evidence that the variable regions of the central domain of V1sE are antigenic during infection with the Lyme disease spirochetes. Infect. Immun. 70:4196-4203.

McNeela E A, Mills K H. Manipulating the immune system: humoral versus cell-mediated immunity. Adv Drug Deliv Rev 2001; 51(1-3):43-54.

McNeil, S. A., S. A. Halperin, J. M. Langley, B. Smith, A. Warren, G. P. Sharratt, D. M. Baxendale, M. A. Reddish, M. C. Hu, S. D. Stroop, J. Linden, L. F. Fries, P. E. Vink, and J. B. Dale. 2005. Safety and immunogenicity of 26-valent group a *streptococcus* vaccine in healthy adult volunteers. Clin. Infect. Dis. 41:1114-1122.

Meltzer M I, Dennis D T, Orloski K A. The cost effectiveness of vaccinating against Lyme disease. Emerg Infect Dis 1999; 5:321-8.

Metts, S., J. V. McDowell, M. Theisen, P. R. Hansen, and R. T. Marconi. 2003. Analysis of the OspE determinants involved in the binding of factor H and OspE targeting antibodies elicited during infection in mice. Infect. Immun. 71:3587-3596.

Miletic V D, Frank M M. Complement-immunoglobulin interactions. Curr Opin Immunol 1995 February; 7(1):41-7.

Montgomery R R, Schreck K, Wang X, Malawista S E. Human neutrophil calprotectin reduces the susceptibility of *Borrelia burgdorferi* to penicillin. Infect Immun 2006; 74(4):2468-72.

Munson E L, Du Chateau B K, Jobe D A, Lovrich S D, Callister S M, Schell R F. Production of borreliacidal antibody to outer surface protein A in vitro and modulation by interleukin-4. Infect Immun 2000 October; 68(10):5496-501.

Munson E L, Du Chateau B K, Jensen J R, Callister S M, DeCoster D J, Schell R F. Gamma interferon inhibits production of Anti-OspA borreliacidal antibody in vitro. Clin Diagn Lab Immunol 2002 September; 9(5):1095-101.

Nachman S A, Pontrelli L. Central nervous system Lyme disease. Semin Pediatr Infect Dis 2003; 14(2):123-30.

Nagi K S, Joshi R, Thakur R K. Cardiac manifestations of Lyme disease: a review. Can J Cardiol 1996; 12(5):503-6.

Ohnishi, J., J. Piesman, and A. M. de Silva. 2001. Antigenic and genetic heterogeneity of *Borrelia burgdorferi* populations transmitted by ticks. Proc. Natl. Acad. Sci. USA, 98:670-675.

Pal, U., X. Yang, M. Chen, L. K. Bockenstedt, J. F. Anderson, R. A. Flavell, M. V. Norgard, and E. Fikrig. 2004. OspC faciliates *Borrelia burgdorferi* invasion of *Ixodes* scapularis salivary glands. The Journal of Clinical Investigation 113:220-230.

Petrovsky N, Aguilar J C. Vaccine adjuvants: current state and future trends. Immunol Cell Biol 2004; 82(5):488-96.

Potter M R, Noben-Trauth N, Weis J H, Teuscher C, Weis J J. Interleukin-4 (IL-4) and IL-13 signaling pathways do not regulate *Borrelia burgdorferi*-induced arthritis in mice: IgG1 is not required for host control of tissue spirochetes. Infect Immun 2000 October; 68(10):5603-9.

Powell M F, Grey H, Gaeta F, Sette A, Colon S. Peptide stability in drug development: a comparison of peptide reactivity in different biological media. J Pharm Sci 1992 August; 81(8):731-5.

Probert, W. S., M. Crawford, R. B. Cadiz, and R. B. LeFebre. 1997. Immunization with outer surface protein (Osp) A but not OspC provides crossprotection of mice challenged with North American isolates of *Borrelia burgdorferi*. J. Infect. Dis. 175:400-405.

Probert, W. S., and R. B. LeFebvre. 1994. Protection of C3H/HeN mice from challenge with *Borrelia burgdorferi* through active immunization with OspA, OspB, or OspC but not with OspD or the 83-kilodalton antigen. Infect. Immun. 62:1920-1926.

Rammensee H, Bachmann J, Emmerich N P, Bachor O A, Stevanovic S. SYFPEITHI: database for MHC ligands and peptide motifs. Immunogenetics 1999; 50(3-4):213-9.

Remington S J, Breddam K. Carboxypeptidases C and D. Methods Enzymol 1994; 244:231-48.

Rijpkema S G, Tazelaar D J, Molkenboer M J, Noordhoek G T, Plantinga G, Schouls L M, et al. Detection of *Borrelia afzelii*, *Borrelia burgdorferi* sensu stricto, *Borrelia garinii* and group VS116 by PCR in skin biopsies of patients with erythema migrans and acrodermatitis chronica atrophicans. Clin Microbiol Infect 1997; 3(1):109-16.

Roberts, D., M. Caimano, J. McDowell, M. Theisen, A. Holm, E. Orff, D. Nelson, S. Wikel, J. Radolf, and R. Marconi. 2002. Environmental regulation and differential expression of members of the Bdr protein family of *Borrelia burgdorferi*. Infect. Immun. 70:7033-7041.

Rousselle, J. C., S. M. Callister, R. F. Schell, S. D. Lovrich, D. A. Jobe, J. A. Marks, and C. A. Wienke. 1998. Borreliacidal antibody production against outer surface protein C of *Borrelia burgdorferi*. J. Infect. Dis. 178:733-741.

Ruzic-Sabljic E, Lotric-Furlan S, Maraspin V, Cimperman J, Logar M, Jurca T, et al. Comparison of isolation rate of *Borrelia burgdorferi* sensu lato in MKP and BSK-II medium. Int J Med Microbiol 2006; 296(Suppl 40):267-73.

Sadziene, A., B. Wilske, M. S. Ferdows, and A. G. Barbour. 1993. The cryptic ospC gene of *Borrelia burgdorferi* B31 is located on a circular plasmid. Infect. Immun. 61:2192-2195.

Satoskar A R, Elizondo J, Monteforte G M, Stamm L M, Bluethmann H, Katavolos P, et al. Interleukin-4-deficient BALB/c mice develop an enhanced Th1-like response but control cardiac inflammation following *Borrelia burgdorferi* infection. FEMS Microbiol Lett 2000 Feb. 15; 183(2): 319-25.

Scheiblhofer, S., R. Weiss, H. Durnberger, S. Mostbock, M. Breitenbach, I. Livey, and J. Thalhamer. 2003. A DNA vaccine encoding the outer surface protein C from *Borrelia burgdorferi* is able to induce protective immune responses. Microbes Infect. 5:939-946.

Schwan, T. G., and B. J. Hinnebusch. 1998. Bloodstream-versus tick-associated variants of a Relapsing fever bacterium. Science 280:1938-1940.

Schwan T G, Piesman J. Temporal changes in outer surface proteins A and C of the Lyme disease-associated spirochete, *Borrelia burgdorferi*, during the chain of infection in ticks and mice. J Clin Microbiol 2000; 38(1):382-8.

Schwan T G. Temporal regulation of outer surface proteins of the Lyme-disease spirochaete *Borrelia burgdorferi*. Biochem Soc Trans 2003; 31(Pt 1):108-12.

Schwan, T. G., J. Piesman, W. T. Golde, M. C. Dolan, and P. A. Rosa. 1995. Induction of an outer surface protein on *Borrelia burgdorferi* during tick feeding. Proc. Natl. Acad. Sci. USA 92:2909-2913.

Seinost, G., D. E. Dykhuizen, R. J. Dattwyler, W. T. Golde, J. J. Dunn, N. Wang, G. P. Wormser, M. E. Schriefer, and B. J. Luft. 1999. Four clones of *Borrelia burgdorferi* sensu stricto cause invasive infection in humans. Infect. Immun. 67:3518-3524.

Shadick N A, Liang M H, Phillips C B, Fossel K, Kuntz K. The cost-effectiveness of vaccination against Lyme disease. Arch Intern Med 2001; 161:554-61.

Shibaki A, Katz S I. Induction of skewed Th1/Th2 T-cell differentiation via subcutaneous immunization with Freund's adjuvant. Exp Dermatol 2002 April; 11(2):126-34.

Shin J J, Bryksin A V, Godfrey H P, Cabello F C. Localization of BmpA on the exposed outer membrane of *Borrelia burgdorferi* by monospecific anti-recombinant BmpA rabbit antibodies. Infect Immun 2004; 72(4):2280-7.

Spellberg B, Edwards J E, Jr. Type 1/Type 2 immunity in infectious diseases. Clin Infect Dis 2001 January; 32(1): 76-102.

Steere A C, Malawista S E, Snydman D R, Shope R E, Andiman W A, Ross M R, et al. Lyme arthritis: an epidemic of oligoarticular arthritis in children and adults in three Connecticut communities. Arthritis Rheum 1977b; 20:7-17.

Steere A C, Glickstein L. Elucidation of Lyme arthritis. Nat Rev Immunol 2004; 4(2):143-52.

Steere A C, Malawista S E, Hardin J A, Ruddy S, Askenase W, Andiman W A. Erythema chronicum migrans and Lyme arthritis. The enlarging clinical spectrum. Ann Intern Med 1977a; 86:685-98.

Stevenson, B., T. G. Schwan, and P. Rosa. 1995. Temperature—related differential expression of antigens in the Lyme Disase spirochete *Borrelia burgdorferi*. Infect. Immun. 63:4535-4539.

Stevenson B, Bockenstedt L K, Barthold S W. Expression and gene sequence of outer surface protein C of *Borrelia burgdorferi* reisolated from chronically infected mice. Infect Immun 1994; 62(8):3568-71.

Sung, S. Y., J. McDowell, J. A. Carlyon, and R. T. Marconi. 2000. Mutation and recombination in the upstream homology box flanked ospE related genes of the Lyme disease spirochetes results in the development of new antigenic variants during infection. Infect. Immun. 68:1319-1327.

Takayama K, Rothenberg R J, Barbour A G. Absence of lipopolysaccharide in the Lyme disease spirochete, *Borrelia burgdorferi*. Infect Immun 1987 September; 55(9):2311-3.

ten Hagen T L, Sulzer A J, Kidd M R, Lal A A, Hunter R L. Role of adjuvants in the modulation of antibody isotype, specificity, and induction of protection by whole blood-stage *Plasmodium yoelii* vaccines. J Immunol 1993; 151 (12):7077-85.

Theisen D M, Bouche F B, El Kasmi K C, von der Ahe I, Ammerlaan W, Demotz S, et al. Differential antigenicity of recombinant polyepitope-antigens based on loop- and helix-forming B and T cell epitopes. J Immunol Methods 2000; 242(1-2):145-57.

Theisen, M., M. Bone, M. J. Mathiesen, B. Mikkelsen, A. M. Lebech, and K. Hansen. 1995. Evolution of the *Borrelia burgdorferi* outer surface protein OspC. J. Bacteriol. 177: 3036-3044.

Theisen, M., B. Frederiksen, A.-M. Lebech, J. Vuust, and K. Hansen. 1993. Polymorphism in ospC gene of *Borrelia burgdorferi* and immunoreactivity of OspC protein: implications for taxonomy and for use of OspC protein as a diagnostic antigen. J. Clin. Microbiol. 31:2570-2576.

Thompson, J. D., T. J. Gibson, F. Plewniak, F. Jeanmougin, and D. G. Higgins. 1997. The ClustalX windows interface: flexible strategies for multiple sequence alignment aided by quality analysis tools. Nucleic Acids Res. 24:4876-4882.

Tilly K, Elias A F, Errett J, Fischer E, Iyer R, Schwartz I, et al. Genetics and regulation of chitobiose utilization in *Borrelia burgdorferi*. J Bacteriol 2001; 183(19):5544-53.

Tongren J E, Corran P H, Jana W, Langhorne J, Riley E M. Epitope-specific regulation of immunoglobulin class switching in mice immunized with malarial merozoite surface proteins. Infect Immun 2005; 73(12):8119-29.

Walker J R, Altman R K, Warren J W, Altman E. Using protein-based motifs to stabilize peptides. J Pept Res 2003 November; 62(5):214-26.

Wallich R, Siebers A, Jahraus O, Brenner C, Stehle T, Simon M M. DNA vaccines expressing a fusion product of outer surface proteins A and C from *Borrelia burgdorferi* induce protective antibodies suitable for prophylaxis but not for resolution of Lyme disease. Infect Immun 2001; 69(4): 2130-6.

Wang, I. N., D. E. Dykhuizen, W. Qiu, J. J. Dunn, E. M. Bosler, and B. J. Luft. 1999. Genetic diversity of ospC in a local population of *Borrelia burgdorferi* sensu stricto. Genetics 151:15-30.

Wang, X. N., G. P. Zhang, J. Y. Zhou, C. H. Feng, Y. Y. Yang, Q. M. Li, J. Q. Guo, H. X. Qiao, J. Xi, D. Zhao, G. X. Xing, Z. L. Wang, S. H. Wang, Z. J. Xiao, X. W. Li, and R. G. Deng. 2005. Identification of neutralizing epitopes on the VP2 protein of infectious bursal disease virus by phage-displayed heptapeptide library screening and synthetic peptide mapping. Viral Immunol. 18:549-557.

Widhe M, Jarefors S, Ekerfelt C, Vrethem M, Bergstrom S, Forsberg P, et al. *Borrelia*-specific interferon-gamma and interleukin-4 secretion in cerebrospinal fluid and blood during Lyme borreliosis in humans: association with clinical outcome. J Infect Dis 2004; 189(10):1881-91.

Widhe M, Jarefors S, Ekerfelt C, Vrethem M, Bergstrom S, Forsberg P, et al. *Borrelia*-specific interferon-gamma and interleukin-4 secretion in cerebrospinal fluid and blood during Lyme borreliosis in humans: association with clinical outcome. J Infect Dis 2004 May 15; 189(10):1881-91.

Willett T A, Meyer A L, Brown E L, Huber B T. An effective second-generation outer surface protein A-derived Lyme vaccine that eliminates a potentially autoreactive T cell epitope. Proc Natl Acad Sci USA 2004; 101(5):1303-8.

Wilske, B., U. Busch, V. Fingerle, S. Jauris-Heipke, V. Preac-Mursic, D. Robler, and G. Will. 1996. Immunological and molecular variability of OspA and OspC: implications for *Borrelia* vaccine development. Infection 24:208-212.

Wilske, B., V. Preac-Mursic, S. Jauris, A. Hofmann, I. Pradel, E. Soutschek, E. Schwab, G. Will, and G. Wanner. 1993. Immunological and molecular polymorphisms of OspC, an immunodominant major outer surface protein of *Borrelia burgdorferi*. Infect. Immun. 61:2182-2191.

Yang L, Ma Y, Schoenfeld R, Griffiths M, Eichwald E, Araneo B, et al. Evidence for B-lymphocyte mitogen activity in *Borrelia burgdorferi*-infected mice. Infect Immun 1992 August; 60(8):3033-41.

Zhang G L, Khan A M, Srinivasan K N, August J T, Brusic V. MULTIPRED: a computational system for prediction of promiscuous HLA binding peptides. Nucleic Acids Res 2005; 33(W): 172-9.

Zhang, H., A. Raji, M. Theisen, P. R. Hansen, and R. T. Marconi. 2005. bdrF2 of the Lyme disease spirochetes is coexpressed with a series of cytoplasmic proteins and is produced specifically during early infection. J. Bacteriol. 187:175-184.

Zhong W, Stehle T, Museteanu C, Siebers A, Gern L, Kramer M, et al. Therapeutic passive vaccination against chronic Lyme disease in mice. Proc Natl Acad Sci USA 1997; 94(23):12533-8.

Zuckert W R, Kerentseva T A, Lawson C L, Barbour A G. Structural conservation of neurotropism-associated VspA within the variable *Borrelia* Vsp-OspC lipoprotein family. J Biol Chem 2001; 276(1):457-63.

---

We claim:

1. An isolated protein comprising an amino acid sequence having at least 95% sequence identity to SEQ ID NO:263.

2. The isolated protein of claim 1, wherein said isolated protein comprises an amino acid sequence having at least 96% sequence identity to SEQ ID NO:263.

3. The isolated protein of claim 1, wherein said isolated protein comprises an amino acid sequence having at least 97% sequence identity to SEQ ID NO:263.

4. The isolated protein of claim 1, wherein said isolated protein comprises an amino acid sequence having at least 97% sequence identity to SEQ ID NO:263.

5. The isolated protein of claim 1, wherein said isolated protein comprises an amino acid sequence having at least 98% sequence identity to SEQ ID NO:263.

6. The isolated protein of claim 1, wherein said isolated protein comprises an amino acid sequence having at least 99% sequence identity to SEQ ID NO:263.

* * * * *

UNITED STATES PATENT AND TRADEMARK OFFICE
CERTIFICATE OF CORRECTION

| | | |
|---|---|---|
| PATENT NO. | : 8,808,705 B2 | Page 1 of 1 |
| APPLICATION NO. | : 13/879848 | |
| DATED | : August 19, 2014 | |
| INVENTOR(S) | : Richard Thomas Marconi and Christopher Earnhart | |

It is certified that error appears in the above-identified patent and that said Letters Patent is hereby corrected as shown below:

In the Specification,

At Column 1, line 3, insert the following:

--STATEMENT OF GOVERNMENT INTEREST

This invention was made with government support under contract number R01 AI067746 awarded by the National Institutes of Health. The government has certain rights in the invention.--

Signed and Sealed this
Twenty-third Day of December, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,808,705 B2  
APPLICATION NO. : 13/879848  
DATED : August 19, 2014  
INVENTOR(S) : Richard T. Marconi and Christopher Earnhart Page 1 of 1

It is certified that error appears in the above-identified patent and that said Letters Patent is hereby corrected as shown below:

In the claims,

Claim 4 in column 338, lines 57 to 59 should read as follows:

4. The isolated protein of claim 1, wherein said isolated protein comprises an amino acid sequence as set forth in SEQ ID NO:263.

Signed and Sealed this  
Nineteenth Day of April, 2016

Michelle K. Lee  
*Director of the United States Patent and Trademark Office*

SEQUENCE LISTING

```
<160> NUMBER OF SEQ ID NOS: 267

<210> SEQ ID NO 1
<211> LENGTH: 15
<212> TYPE: PRT
<213> ORGANISM: Borrelia burgdorferi

<400> SEQUENCE: 1

Asn Lys Leu Lys Glu Lys His Thr Asp Leu Gly Lys Glu Gly Val
1               5                   10                  15

<210> SEQ ID NO 2
<211> LENGTH: 15
<212> TYPE: PRT
<213> ORGANISM: Borrelia burgdorferi

<400> SEQUENCE: 2

Asn Lys Leu Lys Glu Lys His Thr Asp Leu Gly Lys Arg Gly Val
1               5                   10                  15

<210> SEQ ID NO 3
<211> LENGTH: 16
<212> TYPE: PRT
<213> ORGANISM: Borrelia burgdorferi

<400> SEQUENCE: 3

Asn Lys Leu Lys Glu Lys His Thr Asp Ser Phe Gly Lys Glu Gly Val
1               5                   10                  15

<210> SEQ ID NO 4
<211> LENGTH: 15
<212> TYPE: PRT
<213> ORGANISM: Borrelia burgdorferi
```

```
<400> SEQUENCE: 4

Thr Lys Leu Lys Asp His His Ala Gln Leu Gly Ile Gln Gly Val
1               5                   10                  15

<210> SEQ ID NO 5
<211> LENGTH: 15
<212> TYPE: PRT
<213> ORGANISM: Borrelia burgdorferi

<400> SEQUENCE: 5

Thr Lys Leu Lys Asp Asn Gln Ala Gln Arg Gly Ile Gln Gly Val
1               5                   10                  15

<210> SEQ ID NO 6
<211> LENGTH: 15
<212> TYPE: PRT
<213> ORGANISM: Borrelia burgdorferi

<400> SEQUENCE: 6

Lys Lys Leu Lys Glu Lys His Thr Asp Leu Gly Lys Lys Asp Ala
1               5                   10                  15

<210> SEQ ID NO 7
<211> LENGTH: 15
<212> TYPE: PRT
<213> ORGANISM: Borrelia burgdorferi

<400> SEQUENCE: 7

Lys Lys Leu Ser Asp Asn Gln Ala Glu Leu Gly Ile Glu Asn Ala
1               5                   10                  15

<210> SEQ ID NO 8
<211> LENGTH: 15
<212> TYPE: PRT
<213> ORGANISM: Borrelia burgdorferi

<400> SEQUENCE: 8

Asn Lys Leu Lys Ser Glu His Ala Val Leu Gly Leu Asp Asn Leu
1               5                   10                  15

<210> SEQ ID NO 9
<211> LENGTH: 15
<212> TYPE: PRT
<213> ORGANISM: Borrelia burgdorferi

<400> SEQUENCE: 9

Asn Lys Leu Lys Asn Gly Asn Ala Gln Leu Gly Leu Ala Ala Ala
1               5                   10                  15

<210> SEQ ID NO 10
<211> LENGTH: 17
<212> TYPE: PRT
<213> ORGANISM: Borrelia burgdorferi

<400> SEQUENCE: 10

Lys Lys Leu Ala Asp Ser Asn Ala Asp Leu Gly Val Ala Ala Gly Asn
1               5                   10                  15

Ala

<210> SEQ ID NO 11
<211> LENGTH: 15
<212> TYPE: PRT
<213> ORGANISM: Borrelia burgdorferi
```

<400> SEQUENCE: 11

Gly Lys Leu Lys Asn Glu His Ala Ser Leu Gly Lys Lys Asp Ala
1               5                   10                  15

<210> SEQ ID NO 12
<211> LENGTH: 15
<212> TYPE: PRT
<213> ORGANISM: Borrelia burgdorferi

<400> SEQUENCE: 12

Ala Lys Leu Lys Gly Glu His Thr Asp Leu Gly Lys Glu Gly Val
1               5                   10                  15

<210> SEQ ID NO 13
<211> LENGTH: 15
<212> TYPE: PRT
<213> ORGANISM: Borrelia burgdorferi

<400> SEQUENCE: 13

Lys Lys Leu Lys Asp Ser Arg Ala Glu Leu Gly Lys Lys Asp Ala
1               5                   10                  15

<210> SEQ ID NO 14
<211> LENGTH: 15
<212> TYPE: PRT
<213> ORGANISM: Borrelia burgdorferi

<400> SEQUENCE: 14

Lys Lys Leu Lys Asp Ser His Ala Glu Leu Gly Lys Lys Asp Ala
1               5                   10                  15

<210> SEQ ID NO 15
<211> LENGTH: 15
<212> TYPE: PRT
<213> ORGANISM: Borrelia burgdorferi

<400> SEQUENCE: 15

Lys Lys Leu Glu Gly Glu His Ala Gln Leu Gly Ile Glu Asn Val
1               5                   10                  15

<210> SEQ ID NO 16
<211> LENGTH: 15
<212> TYPE: PRT
<213> ORGANISM: Borrelia burgdorferi

<400> SEQUENCE: 16

Asn Lys Leu Glu Gly Glu His Ala Gln Leu Gly Thr Glu Asn Val
1               5                   10                  15

<210> SEQ ID NO 17
<211> LENGTH: 15
<212> TYPE: PRT
<213> ORGANISM: Borrelia burgdorferi

<400> SEQUENCE: 17

Asp Lys Leu Lys Ser Glu Asn Val Ala Leu Gly Lys Gln Asp Ala
1               5                   10                  15

<210> SEQ ID NO 18
<211> LENGTH: 15
<212> TYPE: PRT
<213> ORGANISM: Borrelia burgdorferi

<400> SEQUENCE: 18

Asp Lys Leu Lys Ser Glu Asn Ala Ala Leu Gly Lys Gln Asp Ala
1               5                   10                  15

<210> SEQ ID NO 19
<211> LENGTH: 17
<212> TYPE: PRT
<213> ORGANISM: Borrelia burgdorferi

<400> SEQUENCE: 19

Asp Lys Leu Lys Ser Ser His Ala Glu Leu Gly Ile Ala Asn Gly Ala
1               5                   10                  15

Ala

<210> SEQ ID NO 20
<211> LENGTH: 17
<212> TYPE: PRT
<213> ORGANISM: Borrelia burgdorferi

<400> SEQUENCE: 20

Lys Lys Leu Gln Ser Ser His Ala Gln Leu Gly Val Ala Gly Gly Ala
1               5                   10                  15

Thr

<210> SEQ ID NO 21
<211> LENGTH: 17
<212> TYPE: PRT
<213> ORGANISM: Borrelia burgdorferi

<400> SEQUENCE: 21

Lys Lys Leu Lys Asp Ser His Gln Glu Leu Gly Val Ala Asn Gly Ala
1               5                   10                  15

Ala

<210> SEQ ID NO 22
<211> LENGTH: 15
<212> TYPE: PRT
<213> ORGANISM: Borrelia burgdorferi

<400> SEQUENCE: 22

Thr Lys Leu Lys Ser Ser Asn Ala Gln Leu Asn Gln Ala Asn Ala
1               5                   10                  15

<210> SEQ ID NO 23
<211> LENGTH: 18
<212> TYPE: PRT
<213> ORGANISM: Borrelia burgdorferi

<400> SEQUENCE: 23

Asn Lys Leu Lys Asn Ser His Ala Glu Leu Gly Val Ala Gly Asn Gly
1               5                   10                  15

Ala Thr

<210> SEQ ID NO 24
<211> LENGTH: 18
<212> TYPE: PRT
<213> ORGANISM: Borrelia burgdorferi

<400> SEQUENCE: 24

Asn Lys Leu Lys Asn Ser His Val Glu Leu Gly Val Ala Gly Asn Gly
1               5                   10                  15

Ala Thr

<210> SEQ ID NO 25
<211> LENGTH: 18
<212> TYPE: PRT
<213> ORGANISM: Borrelia burgdorferi

<400> SEQUENCE: 25

Asn Lys Leu Lys Asn Ser His Ala Glu Leu Gly Val Ala Asn Asn Gly
1               5                   10                  15

Ala Thr

<210> SEQ ID NO 26
<211> LENGTH: 15
<212> TYPE: PRT
<213> ORGANISM: Borrelia burgdorferi

<400> SEQUENCE: 26

Asp Lys Leu Lys Asn Glu His Ala Ser Leu Gly Lys Lys Asp Ala
1               5                   10                  15

<210> SEQ ID NO 27
<211> LENGTH: 17
<212> TYPE: PRT
<213> ORGANISM: Borrelia burgdorferi

<400> SEQUENCE: 27

Asn Lys Leu Lys Thr Ser His Ala Gln Leu Gly Ala Ala Asn Gly Gly
1               5                   10                  15

Ala

<210> SEQ ID NO 28
<211> LENGTH: 18
<212> TYPE: PRT
<213> ORGANISM: Borrelia burgdorferi

<400> SEQUENCE: 28

Asn Lys Leu Lys Asn Ser His Ala Glu Leu Gly Val Ala Ala Asn Gly
1               5                   10                  15

Gly Ala

<210> SEQ ID NO 29
<211> LENGTH: 15
<212> TYPE: PRT
<213> ORGANISM: Borrelia burgdorferi

<400> SEQUENCE: 29

Lys Lys Leu Lys Asp Asn Asn Ala Gln Leu Gly Ile Gln Asn Val
1               5                   10                  15

<210> SEQ ID NO 30
<211> LENGTH: 15
<212> TYPE: PRT
<213> ORGANISM: Borrelia burgdorferi

<400> SEQUENCE: 30

Lys Lys Leu Lys Asp Asn His Ala Gln Phe Gly Ile Gln Asn Val
1               5                   10                  15

<210> SEQ ID NO 31
<211> LENGTH: 17
<212> TYPE: PRT
<213> ORGANISM: Borrelia burgdorferi

<400> SEQUENCE: 31

Asn Lys Leu Lys Ser Gly His Ala Glu Leu Gly Pro Val Gly Gly Asn
1               5                   10                  15

Ala

<210> SEQ ID NO 32
<211> LENGTH: 15
<212> TYPE: PRT
<213> ORGANISM: Borrelia burgdorferi

<400> SEQUENCE: 32

Lys Lys Leu Ser Glu Ser His Ala Asp Ile Gly Ile Gln Ala Ala
1               5                   10                  15

<210> SEQ ID NO 33
<211> LENGTH: 36
<212> TYPE: PRT
<213> ORGANISM: Borrelia burgdorferi

<400> SEQUENCE: 33

Lys Gly Ala Glu Glu Leu Gly Lys Leu Phe Glu Ser Val Glu Val Leu
1               5                   10                  15

Ser Lys Ala Ala Lys Glu Met Leu Ala Asn Ser Val Lys Glu Leu Thr
            20                  25                  30

Ser Pro Val Val
        35

<210> SEQ ID NO 34
<211> LENGTH: 36
<212> TYPE: PRT
<213> ORGANISM: Borrelia burgdorferi

<400> SEQUENCE: 34

Lys Gly Ala Glu Glu Leu Gly Lys Leu Phe Glu Ser Val Glu Val Leu
1               5                   10                  15

Ser Lys Ala Ala Lys Glu Met Leu Ala Asn Ser Val Lys Glu Leu Thr
            20                  25                  30

Asn Pro Val Val
        35

<210> SEQ ID NO 35
<211> LENGTH: 36
<212> TYPE: PRT
<213> ORGANISM: Borrelia burgdorferi

<400> SEQUENCE: 35

Lys Gly Val Glu Glu Leu Glu Lys Leu Ser Gly Ser Leu Glu Ser Leu
1               5                   10                  15

Ser Lys Ala Ala Lys Glu Met Leu Ala Asn Ser Val Lys Glu Leu Thr
            20                  25                  30

Ser Pro Val Val
        35

<210> SEQ ID NO 36
<211> LENGTH: 36
<212> TYPE: PRT
<213> ORGANISM: Borrelia burgdorferi

<400> SEQUENCE: 36

Lys Gly Ala Ala Glu Leu Glu Lys Leu Phe Glu Ser Val Glu Asn Leu
1               5                   10                  15

```
Ala Lys Ala Ala Lys Glu Met Leu Ser Asn Ser Val Lys Glu Leu Thr
            20                  25                  30

Ser Pro Val Val
        35

<210> SEQ ID NO 37
<211> LENGTH: 36
<212> TYPE: PRT
<213> ORGANISM: Borrelia burgdorferi

<400> SEQUENCE: 37

Lys Gly Ala Glu Glu Leu Val Lys Leu Ser Glu Ser Val Ala Gly Leu
1               5                   10                  15

Leu Lys Ala Ala Gln Ala Ile Leu Ala Asn Ser Val Lys Glu Leu Thr
            20                  25                  30

Ser Pro Val Val
        35

<210> SEQ ID NO 38
<211> LENGTH: 36
<212> TYPE: PRT
<213> ORGANISM: Borrelia burgdorferi

<400> SEQUENCE: 38

Lys Gly Ala Ala Glu Leu Glu Lys Leu Phe Lys Ala Val Glu Asn Leu
1               5                   10                  15

Ser Lys Ala Ala Gln Asp Thr Leu Lys Asn Ala Val Lys Glu Leu Thr
            20                  25                  30

Ser Pro Ile Val
        35

<210> SEQ ID NO 39
<211> LENGTH: 36
<212> TYPE: PRT
<213> ORGANISM: Borrelia burgdorferi

<400> SEQUENCE: 39

Lys Gly Ala Lys Glu Leu Lys Asp Leu Ser Asp Ser Val Glu Ser Leu
1               5                   10                  15

Val Lys Ala Ala Gln Val Met Leu Thr Asn Ser Val Lys Glu Leu Thr
            20                  25                  30

Ser Pro Val Val
        35

<210> SEQ ID NO 40
<211> LENGTH: 36
<212> TYPE: PRT
<213> ORGANISM: Borrelia burgdorferi

<400> SEQUENCE: 40

Lys Gly Gly Lys Glu Leu Lys Glu Leu Ser Glu Ala Val Lys Ser Leu
1               5                   10                  15

Leu Lys Ala Ala Gln Ala Ala Leu Ala Asn Ser Val Gln Glu Leu Thr
            20                  25                  30

Ser Pro Val Val
        35

<210> SEQ ID NO 41
<211> LENGTH: 36
<212> TYPE: PRT
<213> ORGANISM: Borrelia burgdorferi
```

```
<400> SEQUENCE: 41

Lys Gly Ala Lys Glu Leu Lys Asp Leu Ser Asp Ser Val Glu Ser Leu
1               5                   10                  15

Val Lys Ala Ala Lys Glu Met Leu Thr Asn Ser Val Lys Glu Leu Thr
            20                  25                  30

Ser Pro Val Val
        35

<210> SEQ ID NO 42
<211> LENGTH: 36
<212> TYPE: PRT
<213> ORGANISM: Borrelia burgdorferi

<400> SEQUENCE: 42

Lys Gly Ala Asp Glu Leu Glu Lys Leu Phe Glu Ser Val Lys Asn Leu
1               5                   10                  15

Ser Lys Ala Ala Lys Glu Met Leu Thr Asn Ser Val Lys Glu Leu Thr
            20                  25                  30

Ser Pro Val Val
        35

<210> SEQ ID NO 43
<211> LENGTH: 24
<212> TYPE: PRT
<213> ORGANISM: Borrelia burgdorferi

<400> SEQUENCE: 43

Lys Gly Ala Lys Glu Leu Lys Glu Leu Phe Glu Ala Val Glu Ser Leu
1               5                   10                  15

Ser Lys Ala Ala Lys Glu Met Leu
            20

<210> SEQ ID NO 44
<211> LENGTH: 36
<212> TYPE: PRT
<213> ORGANISM: Borrelia burgdorferi

<400> SEQUENCE: 44

Lys Gly Ala Ala Glu Leu Glu Lys Leu Phe Lys Ala Val Glu Asn Leu
1               5                   10                  15

Ala Lys Ala Ala Lys Glu Met Leu Ala Asn Ser Val Lys Glu Leu Thr
            20                  25                  30

Ser Pro Ile Val
        35

<210> SEQ ID NO 45
<211> LENGTH: 36
<212> TYPE: PRT
<213> ORGANISM: Borrelia burgdorferi

<400> SEQUENCE: 45

Lys Gly Ala Ala Glu Leu Glu Lys Leu Phe Lys Ala Val Glu Asn Leu
1               5                   10                  15

Pro Lys Ala Ala Lys Glu Met Leu Ala Asn Ser Val Lys Glu Leu Thr
            20                  25                  30

Ser Pro Ile Val
        35

<210> SEQ ID NO 46
```

```
<211> LENGTH: 36
<212> TYPE: PRT
<213> ORGANISM: Borrelia burgdorferi

<400> SEQUENCE: 46

Lys Gly Ala Ala Glu Leu Ala Lys Leu Phe Lys Ala Val Glu Asn Leu
1               5                   10                  15

Pro Gln Ala Ala Lys Glu Met Leu Ala Asn Ser Val Lys Glu Leu Thr
            20                  25                  30

Ser Pro Ile Val
            35

<210> SEQ ID NO 47
<211> LENGTH: 36
<212> TYPE: PRT
<213> ORGANISM: Borrelia burgdorferi

<400> SEQUENCE: 47

Lys Gly Ala Lys Glu Leu Lys Glu Leu Ser Glu Ser Val Glu Thr Leu
1               5                   10                  15

Leu Lys Ala Ala Lys Glu Met Leu Ala Asn Ser Val Lys Glu Leu Thr
            20                  25                  30

Ser Pro Val Val
            35

<210> SEQ ID NO 48
<211> LENGTH: 36
<212> TYPE: PRT
<213> ORGANISM: Borrelia burgdorferi

<400> SEQUENCE: 48

Lys Gly Ala Gln Glu Leu Glu Lys Leu Phe Glu Ser Val Lys Asn Leu
1               5                   10                  15

Ser Lys Ala Ala Gln Glu Thr Leu Asn Asn Ser Val Lys Glu Leu Thr
            20                  25                  30

Ser Pro Val Val
            35

<210> SEQ ID NO 49
<211> LENGTH: 36
<212> TYPE: PRT
<213> ORGANISM: Borrelia burgdorferi

<400> SEQUENCE: 49

Lys Gly Ala Asp Glu Leu Glu Lys Leu Phe Lys Ser Val Glu Ser Leu
1               5                   10                  15

Ala Lys Ala Ala Gln Asp Ala Leu Ala Asn Ser Val Asn Glu Leu Thr
            20                  25                  30

Ser Pro Val Val
            35

<210> SEQ ID NO 50
<211> LENGTH: 36
<212> TYPE: PRT
<213> ORGANISM: Borrelia burgdorferi

<400> SEQUENCE: 50

Lys Gly Ala Glu Glu Leu Glu Lys Leu Phe Lys Ala Val Glu Ser Leu
1               5                   10                  15

Ser Lys Ala Ala Gln Asp Met Leu Thr Asn Ser Val Lys Glu Leu Thr
            20                  25                  30
```

```
Ser Pro Val Val
        35

<210> SEQ ID NO 51
<211> LENGTH: 36
<212> TYPE: PRT
<213> ORGANISM: Borrelia burgdorferi

<400> SEQUENCE: 51

Lys Gly Ala Asp Glu Leu Gly Lys Leu Phe Glu Ser Val Glu Ser Leu
1               5                   10                  15

Ala Lys Ala Ala Lys Glu Met Leu Ala Asn Ser Val Lys Glu Leu Thr
            20                  25                  30

Ser Pro Val Val
        35

<210> SEQ ID NO 52
<211> LENGTH: 36
<212> TYPE: PRT
<213> ORGANISM: Borrelia burgdorferi

<400> SEQUENCE: 52

Lys Gly Ala Glu Glu Leu Val Lys Leu Ala Glu Ser Val Ala Gly Leu
1               5                   10                  15

Phe Lys Val Ala Gln Glu Met Leu Asn Asn Ser Val Lys Glu Leu Thr
            20                  25                  30

Ser Pro Val Val
        35

<210> SEQ ID NO 53
<211> LENGTH: 36
<212> TYPE: PRT
<213> ORGANISM: Borrelia burgdorferi

<400> SEQUENCE: 53

Lys Gly Ala Lys Glu Leu Lys Glu Leu Phe Glu Ser Val Glu Ser Leu
1               5                   10                  15

Ala Lys Ala Ala Lys Glu Ser Leu Thr Asn Ser Val Lys Glu Leu Thr
            20                  25                  30

Ser Pro Val Val
        35

<210> SEQ ID NO 54
<211> LENGTH: 36
<212> TYPE: PRT
<213> ORGANISM: Borrelia burgdorferi

<400> SEQUENCE: 54

Lys Gly Ala Lys Glu Leu Lys Glu Leu Phe Glu Ser Val Glu Ser Leu
1               5                   10                  15

Ala Lys Ala Ala Lys Glu Ala Leu Ser Asn Ser Val Lys Glu Leu Thr
            20                  25                  30

Ser Pro Val Val
        35

<210> SEQ ID NO 55
<211> LENGTH: 36
<212> TYPE: PRT
<213> ORGANISM: Borrelia burgdorferi

<400> SEQUENCE: 55
```

```
Lys Gly Ala Lys Glu Leu Lys Glu Leu Phe Glu Ser Val Glu Ser Leu
1               5                   10                  15

Leu Lys Ala Ala Gln Glu Ala Leu Thr Asn Ser Val Lys Glu Leu Thr
                20                  25                  30

Thr Pro Val Val
        35

<210> SEQ ID NO 56
<211> LENGTH: 36
<212> TYPE: PRT
<213> ORGANISM: Borrelia burgdorferi

<400> SEQUENCE: 56

Lys Gly Ala Asp Glu Leu Ile Lys Leu Ser Gly Ser Leu Glu Ser Leu
1               5                   10                  15

Ser Lys Ala Ala Gln Ala Ile Leu Ala Asn Ser Val Lys Glu Leu Thr
                20                  25                  30

Ser Pro Val Val
        35

<210> SEQ ID NO 57
<211> LENGTH: 36
<212> TYPE: PRT
<213> ORGANISM: Borrelia burgdorferi

<400> SEQUENCE: 57

Lys Gly Val Thr Glu Leu Glu Glu Leu Phe Lys Ser Val Glu Gly Leu
1               5                   10                  15

Ala Lys Ala Ala Lys Glu Ala Ser Ala Asn Ser Val Lys Glu Leu Thr
                20                  25                  30

Ser Pro Val Val
        35

<210> SEQ ID NO 58
<211> LENGTH: 36
<212> TYPE: PRT
<213> ORGANISM: Borrelia burgdorferi

<400> SEQUENCE: 58

Lys Gly Val Thr Glu Leu Glu Glu Leu Phe Lys Ser Val Glu Gly Leu
1               5                   10                  15

Pro Lys Ala Ala Lys Glu Ala Ser Ala Asn Ser Val Lys Glu Leu Thr
                20                  25                  30

Ser Pro Val Val
        35

<210> SEQ ID NO 59
<211> LENGTH: 36
<212> TYPE: PRT
<213> ORGANISM: Borrelia burgdorferi

<400> SEQUENCE: 59

Lys Gly Ala Lys Glu Leu Lys Glu Leu Phe Glu Ser Val Glu Ser Leu
1               5                   10                  15

Ala Lys Ala Ala Gln Ala Ala Leu Ala Asn Ser Val Gln Glu Leu Thr
                20                  25                  30

Asn Pro Val Val
        35
```

```
<210> SEQ ID NO 60
<211> LENGTH: 36
<212> TYPE: PRT
<213> ORGANISM: Borrelia burgdorferi

<400> SEQUENCE: 60

Lys Gly Ala Lys Glu Leu Lys Asp Leu Ser Glu Ser Val Glu Ala Leu
1               5                   10                  15

Ala Lys Ala Ala Gln Ala Met Leu Thr Asn Ser Val Lys Glu Leu Thr
            20                  25                  30

Ser Pro Val Val
        35

<210> SEQ ID NO 61
<211> LENGTH: 36
<212> TYPE: PRT
<213> ORGANISM: Borrelia burgdorferi

<400> SEQUENCE: 61

Lys Gly Ala Glu Glu Leu Asp Lys Leu Phe Lys Ala Val Glu Asn Leu
1               5                   10                  15

Ser Lys Ala Ala Lys Glu Met Leu Ala Asn Ser Val Lys Glu Leu Thr
            20                  25                  30

Ser Pro Val Val
        35

<210> SEQ ID NO 62
<211> LENGTH: 35
<212> TYPE: PRT
<213> ORGANISM: Borrelia burgdorferi

<400> SEQUENCE: 62

Cys Ser Glu Thr Phe Thr Asn Lys Leu Lys Glu Lys His Thr Asp Leu
1               5                   10                  15

Gly Lys Glu Gly Val Thr Asp Ala Asp Ala Lys Glu Ala Ile Leu Lys
            20                  25                  30

Thr Asn Gly
        35

<210> SEQ ID NO 63
<211> LENGTH: 13
<212> TYPE: PRT
<213> ORGANISM: Borrelia burgdorferi

<400> SEQUENCE: 63

Cys Ser Glu Thr Phe Thr Asn Lys Leu Lys Glu Lys His
1               5                   10

<210> SEQ ID NO 64
<211> LENGTH: 13
<212> TYPE: PRT
<213> ORGANISM: Borrelia burgdorferi

<400> SEQUENCE: 64

Glu Thr Phe Thr Asn Lys Leu Lys Glu Lys His Thr Asp
1               5                   10

<210> SEQ ID NO 65
<211> LENGTH: 13
<212> TYPE: PRT
<213> ORGANISM: Borrelia burgdorferi

<400> SEQUENCE: 65
```

Phe Thr Asn Lys Leu Lys Glu Lys His Thr Asp Leu Gly
1               5                   10

<210> SEQ ID NO 66
<211> LENGTH: 13
<212> TYPE: PRT
<213> ORGANISM: Borrelia burgdorferi

<400> SEQUENCE: 66

Asn Lys Leu Lys Glu Lys His Thr Asp Leu Gly Lys Glu
1               5                   10

<210> SEQ ID NO 67
<211> LENGTH: 13
<212> TYPE: PRT
<213> ORGANISM: Borrelia burgdorferi

<400> SEQUENCE: 67

Leu Lys Glu Lys His Thr Asp Leu Gly Lys Glu Gly Val
1               5                   10

<210> SEQ ID NO 68
<211> LENGTH: 13
<212> TYPE: PRT
<213> ORGANISM: Borrelia burgdorferi

<400> SEQUENCE: 68

Glu Lys His Thr Asp Leu Gly Lys Glu Gly Val Thr Asp
1               5                   10

<210> SEQ ID NO 69
<211> LENGTH: 13
<212> TYPE: PRT
<213> ORGANISM: Borrelia burgdorferi

<400> SEQUENCE: 69

His Thr Asp Leu Gly Lys Glu Gly Val Thr Asp Ala Asp
1               5                   10

<210> SEQ ID NO 70
<211> LENGTH: 13
<212> TYPE: PRT
<213> ORGANISM: Borrelia burgdorferi

<400> SEQUENCE: 70

Asp Leu Gly Lys Glu Gly Val Thr Asp Ala Asp Ala Lys
1               5                   10

<210> SEQ ID NO 71
<211> LENGTH: 13
<212> TYPE: PRT
<213> ORGANISM: Borrelia burgdorferi

<400> SEQUENCE: 71

Gly Lys Glu Gly Val Thr Asp Ala Asp Ala Lys Glu Ala
1               5                   10

<210> SEQ ID NO 72
<211> LENGTH: 13
<212> TYPE: PRT
<213> ORGANISM: Borrelia burgdorferi

<400> SEQUENCE: 72

Glu Gly Val Thr Asp Ala Asp Ala Lys Glu Ala Ile Leu

```
1               5                   10
```

<210> SEQ ID NO 73
<211> LENGTH: 13
<212> TYPE: PRT
<213> ORGANISM: Borrelia burgdorferi

<400> SEQUENCE: 73

```
Val Thr Asp Ala Asp Ala Lys Glu Ala Ile Leu Lys Thr
1               5                   10
```

<210> SEQ ID NO 74
<211> LENGTH: 13
<212> TYPE: PRT
<213> ORGANISM: Borrelia burgdorferi

<400> SEQUENCE: 74

```
Asp Ala Asp Ala Lys Glu Ala Ile Leu Lys Thr Asn Gly
1               5                   10
```

<210> SEQ ID NO 75
<211> LENGTH: 169
<212> TYPE: PRT
<213> ORGANISM: Artificial
<220> FEATURE:
<223> OTHER INFORMATION: Chimeric ABKD protein

<400> SEQUENCE: 75

```
Ala His His His His His Val Asp Asp Asp Lys Ile Ser Glu
1               5                   10                  15

Thr Phe Thr Asn Lys Leu Lys Glu His Thr Asp Leu Gly Lys Glu
                20                  25                  30

Gly Ser Met Gly Met Leu Lys Ala Asn Ala Ala Gly Lys Asp Lys Gly
            35                  40                  45

Val Glu Glu Leu Glu Lys Leu Ser Gly Ser Leu Glu Ser Leu Ser Lys
    50                  55                  60

Ala Ala Lys Glu Met Leu Ala Asn Ser Val Lys Glu Leu Thr Ser Thr
65                  70                  75                  80

Asn Gly Asn Leu Ile Thr Asp Ala Ala Lys Asp Lys Gly Ala Ala Glu
                85                  90                  95

Leu Glu Lys Leu Phe Lys Ala Val Glu Asn Leu Ala Lys Ala Ala Lys
            100                 105                 110

Glu Met Leu Ala Asn Ser Val Lys Glu Leu Thr Ser Ser Met Ser Val
        115                 120                 125

Leu Lys Thr His Asn Ala Lys Asp Lys Gly Ala Glu Glu Leu Val Lys
    130                 135                 140

Leu Ser Glu Ser Val Ala Gly Leu Leu Lys Ala Ala Gln Ala Ile Leu
145                 150                 155                 160

Ala Asn Ser Val Lys Glu Leu Thr Ser
                165
```

<210> SEQ ID NO 76
<211> LENGTH: 6
<212> TYPE: PRT
<213> ORGANISM: Borrelia burgdorferi

<400> SEQUENCE: 76

```
Gly Ser Met Gly Met Leu
1               5
```

```
<210> SEQ ID NO 77
<211> LENGTH: 6
<212> TYPE: PRT
<213> ORGANISM: Borrelia burgdorferi

<400> SEQUENCE: 77

Ser Thr Asn Gly Asn Leu
1               5

<210> SEQ ID NO 78
<211> LENGTH: 6
<212> TYPE: PRT
<213> ORGANISM: Borrelia burgdorferi

<400> SEQUENCE: 78

Ser Ser Met Ser Val Leu
1               5

<210> SEQ ID NO 79
<211> LENGTH: 6
<212> TYPE: PRT
<213> ORGANISM: Borrelia burgdorferi

<400> SEQUENCE: 79

Ser Ser Ser Gln Gly Leu
1               5

<210> SEQ ID NO 80
<211> LENGTH: 6
<212> TYPE: PRT
<213> ORGANISM: Borrelia burgdorferi

<400> SEQUENCE: 80

Gly Ala Met Ser Ala Leu
1               5

<210> SEQ ID NO 81
<211> LENGTH: 19
<212> TYPE: PRT
<213> ORGANISM: Borrelia burgdorferi

<400> SEQUENCE: 81

Ser Glu Thr Phe Thr Asn Lys Leu Lys Glu Lys His Thr Asp Leu Gly
1               5                   10                  15

Lys Glu Gly

<210> SEQ ID NO 82
<211> LENGTH: 42
<212> TYPE: PRT
<213> ORGANISM: Borrelia burgdorferi

<400> SEQUENCE: 82

Leu Lys Ala Asn Ala Ala Gly Lys Asp Lys Gly Val Glu Glu Leu Glu
1               5                   10                  15

Lys Leu Ser Gly Ser Leu Glu Ser Leu Ser Lys Ala Ala Lys Glu Met
            20                  25                  30

Leu Ala Asn Ser Val Lys Glu Leu Thr Ser
            35                  40

<210> SEQ ID NO 83
<211> LENGTH: 41
<212> TYPE: PRT
<213> ORGANISM: Borrelia burgdorferi
```

-continued

```
<400> SEQUENCE: 83

Leu Ile Thr Asp Ala Ala Lys Asp Lys Gly Ala Ala Glu Leu Glu Lys
1               5                   10                  15

Leu Phe Lys Ala Val Glu Asn Leu Ala Lys Ala Ala Lys Glu Met Leu
            20                  25                  30

Ala Asn Ser Val Lys Glu Leu Thr Ser
        35                  40

<210> SEQ ID NO 84
<211> LENGTH: 41
<212> TYPE: PRT
<213> ORGANISM: Borrelia burgdorferi

<400> SEQUENCE: 84

Leu Lys Thr His Asn Ala Lys Asp Lys Gly Ala Glu Glu Leu Val Lys
1               5                   10                  15

Leu Ser Glu Ser Val Ala Gly Leu Leu Lys Ala Ala Gln Ala Ile Leu
            20                  25                  30

Ala Asn Ser Val Lys Glu Leu Thr Ser
        35                  40

<210> SEQ ID NO 85
<211> LENGTH: 72
<212> TYPE: PRT
<213> ORGANISM: Borrelia garinii

<400> SEQUENCE: 85

Ser Glu Ala Phe Thr Asn Lys Leu Lys Glu Lys His Ala Glu Leu Gly
1               5                   10                  15

Val Asn Gly Gly Asp Thr Thr Asp Asp Asn Ala Lys Ala Ala Ile Phe
            20                  25                  30

Lys Thr His Pro Thr Lys Asp Lys Gly Val Glu Asp Leu Glu Lys Leu
        35                  40                  45

Ser Glu Ser Val Lys Ser Leu Leu Lys Ala Ala Gln Ala Ala Leu Ser
    50                  55                  60

Asn Ser Val Lys Glu Leu Thr Ser
65                  70

<210> SEQ ID NO 86
<211> LENGTH: 72
<212> TYPE: PRT
<213> ORGANISM: Borrelia garinii

<400> SEQUENCE: 86

Ser Asp Lys Phe Thr Lys Lys Leu Thr Asp Ser His Ala Gln Leu Gly
1               5                   10                  15

Ala Val Gly Gly Ala Ile Asn Asp Asp Arg Ala Lys Glu Ala Ile Leu
            20                  25                  30

Lys Thr His Gly Thr Asn Asp Lys Gly Ala Lys Glu Leu Lys Glu Leu
        35                  40                  45

Ser Glu Ser Val Glu Ser Leu Ala Lys Ala Ala Gln Ala Ala Leu Ala
    50                  55                  60

Asn Ser Val Lys Glu Leu Thr Ser
65                  70

<210> SEQ ID NO 87
<211> LENGTH: 70
<212> TYPE: PRT
<213> ORGANISM: Borrelia burgdorferi
```

```
<400> SEQUENCE: 87

Ser Glu Ala Phe Thr Lys Lys Leu Lys Asp Asn Asn Ala Gln Leu Gly
1               5                   10                  15

Ile Gln Asn Val Gln Asp Val Glu Ala Lys Lys Ala Ile Leu Lys Thr
            20                  25                  30

Asn Gly Asp Ile Ser Lys Gly Ala Lys Glu Leu Lys Glu Leu Phe Glu
        35                  40                  45

Ser Val Glu Ser Leu Ala Lys Ala Ala Gln Ala Ala Leu Ala Asn Ser
    50                  55                  60

Val Gln Glu Leu Thr Asn
65                  70

<210> SEQ ID NO 88
<211> LENGTH: 70
<212> TYPE: PRT
<213> ORGANISM: Borrelia garinii

<400> SEQUENCE: 88

Ser Glu Ala Phe Thr Asn Arg Leu Lys Gly Ser His Ala Gln Leu Gly
1               5                   10                  15

Val Ala Ala Ala Thr Asp Asp His Ala Lys Glu Ala Ile Leu Lys Ser
            20                  25                  30

Asn Pro Thr Lys Asp Lys Gly Ala Lys Glu Leu Lys Asp Leu Ser Glu
        35                  40                  45

Ser Val Glu Ser Leu Ala Lys Ala Ala Gln Gly Ala Leu Ala Asn Ser
    50                  55                  60

Val Lys Glu Leu Thr Asn
65                  70

<210> SEQ ID NO 89
<211> LENGTH: 70
<212> TYPE: PRT
<213> ORGANISM: Borrelia garinii

<400> SEQUENCE: 89

Ser Glu Ala Phe Thr Asn Arg Leu Thr Gly Ser His Ala Gln His Gly
1               5                   10                  15

Val Ala Ala Ala Thr Asp Asp His Ala Lys Glu Ala Ile Leu Lys Ser
            20                  25                  30

Asn Pro Thr Lys Asp Lys Gly Ala Lys Glu Leu Lys Asp Leu Ser Glu
        35                  40                  45

Ser Val Glu Ser Leu Ala Lys Ala Ala Gln Gly Ala Leu Ala Asn Ser
    50                  55                  60

Val Lys Glu Leu Thr Asn
65                  70

<210> SEQ ID NO 90
<211> LENGTH: 72
<212> TYPE: PRT
<213> ORGANISM: Borrelia garinii

<400> SEQUENCE: 90

Ser Glu Ala Phe Thr Asn Lys Leu Lys Glu Lys Thr Gln Glu Leu Ala
1               5                   10                  15

Val Ala Ala Gly Ala Ala Thr Asp Ile Asp Ala Lys Lys Ala Ile Leu
            20                  25                  30

Lys Thr Asn Arg Asp Lys Asp Leu Gly Ala Asp Glu Arg Gly Lys Leu
```

```
                35                  40                  45
Phe Lys Ser Val Glu Ser Leu Ser Lys Ala Ala Gln Glu Ala Ser Ala
    50                  55                  60
Asn Ser Val Lys Glu Leu Thr Ser
65                  70
```

<210> SEQ ID NO 91
<211> LENGTH: 72
<212> TYPE: PRT
<213> ORGANISM: Borrelia garinii

<400> SEQUENCE: 91

```
Ser Val Ala Phe Thr Ser Lys Leu Lys Ser Ser Asn Ala Gln Leu Gly
1               5                   10                  15
Val Ala Asn Gly Asn Ala Thr Asp Asp Asp Ala Lys Lys Ala Ile Leu
                20                  25                  30
Lys Thr Asn Thr Pro Asn Asp Lys Gly Ala Lys Glu Leu Lys Glu Leu
                35                  40                  45
Phe Glu Ser Val Glu Ser Leu Ala Lys Ala Ala Gln Ala Ala Leu Val
    50                  55                  60
Asn Ser Val Gln Glu Leu Thr Asn
65                  70
```

<210> SEQ ID NO 92
<211> LENGTH: 72
<212> TYPE: PRT
<213> ORGANISM: Borrelia garinii

<400> SEQUENCE: 92

```
Ser Glu Ala Phe Thr Lys Lys Leu Lys Asp Ser Asn Ala Gln Leu Gly
1               5                   10                  15
Met Gln Asn Gly Ala Ala Thr Asp Ala His Ala Lys Ala Ala Ile Leu
                20                  25                  30
Lys Thr Asp Ala Thr Lys Asp Lys Gly Ala Thr Glu Leu Gly Glu Leu
                35                  40                  45
Phe Lys Ser Val Glu Ser Leu Ser Lys Ala Ala Gln Glu Ala Ser Ala
    50                  55                  60
Asn Ser Val Lys Glu Leu Thr Ser
65                  70
```

<210> SEQ ID NO 93
<211> LENGTH: 70
<212> TYPE: PRT
<213> ORGANISM: Borrelia garinii

<400> SEQUENCE: 93

```
Ser Ala Ala Phe Thr Lys Lys Leu Gln Asp Gly His Val Asp Leu Gly
1               5                   10                  15
Lys Thr Asp Val Thr Asp Asp Asn Ala Lys Glu Ala Ile Leu Lys Thr
                20                  25                  30
Asn Pro Thr Lys Thr Lys Gly Ala Thr Glu Leu Glu Glu Leu Phe Lys
                35                  40                  45
Ser Val Glu Gly Leu Val Lys Ala Ala Lys Glu Ala Ser Ala Asn Ser
    50                  55                  60
Val Lys Glu Leu Thr Ser
65                  70
```

<210> SEQ ID NO 94

<211> LENGTH: 70
<212> TYPE: PRT
<213> ORGANISM: Borrelia burgdorferi

<400> SEQUENCE: 94

Ser Glu Glu Phe Thr Asn Lys Leu Lys Ser Gly His Ala Asp Leu Gly
1               5                   10                  15

Lys Gln Asp Ala Thr Asp Asp His Ala Lys Ala Ala Ile Leu Lys Thr
            20                  25                  30

His Ala Thr Thr Asp Lys Gly Ala Lys Glu Phe Lys Asp Leu Phe Glu
        35                  40                  45

Ser Val Glu Gly Leu Leu Lys Ala Ala Gln Val Ala Leu Thr Asn Ser
    50                  55                  60

Val Lys Glu Leu Thr Ser
65                  70

<210> SEQ ID NO 95
<211> LENGTH: 70
<212> TYPE: PRT
<213> ORGANISM: Borrelia afzelii

<400> SEQUENCE: 95

Ser Glu Glu Phe Thr Asn Lys Leu Lys Ser Gly His Ala Asp Leu Gly
1               5                   10                  15

Lys Gln Asp Ala Thr Asp Glu His Ala Lys Ala Ala Ile Leu Lys Thr
            20                  25                  30

His Ala Thr Thr Asp Lys Gly Ala Lys Glu Phe Lys Asp Leu Phe Glu
        35                  40                  45

Ser Val Glu Gly Leu Leu Lys Ser Ala Gln Val Ala Leu Thr Asn Ser
    50                  55                  60

Val Lys Glu Leu Thr Asn
65                  70

<210> SEQ ID NO 96
<211> LENGTH: 70
<212> TYPE: PRT
<213> ORGANISM: Borrelia afzelii

<400> SEQUENCE: 96

Ser Glu Glu Phe Thr Asn Lys Leu Lys Gly Gly His Ala Glu Leu Gly
1               5                   10                  15

Leu Ala Ala Ala Thr Asp Glu Asn Ala Lys Lys Ala Ile Leu Lys Thr
            20                  25                  30

Asn Gly Thr Lys Asp Lys Gly Ala Glu Glu Leu Glu Lys Leu Phe Lys
        35                  40                  45

Ser Val Glu Ser Leu Ala Lys Ala Ala Lys Glu Ser Leu Thr Asn Ser
    50                  55                  60

Val Lys Glu Leu Thr Asn
65                  70

<210> SEQ ID NO 97
<211> LENGTH: 70
<212> TYPE: PRT
<213> ORGANISM: Borrelia burgdorferi

<400> SEQUENCE: 97

Ser Glu Ala Phe Thr Lys Lys Leu Gln Asp Ser Asn Ala Asp Leu Gly
1               5                   10                  15

Lys His Asn Ala Thr Asp Ala Asp Ser Lys Glu Ala Ile Leu Lys Thr

```
            20                  25                  30
Asn Gly Thr Lys Thr Lys Gly Ala Lys Glu Leu Glu Glu Leu Phe Lys
         35                  40                  45

Ser Val Glu Ser Leu Ser Lys Ala Ala Lys Glu Ala Leu Ser Asn Ser
    50                  55                  60

Val Lys Glu Leu Thr Ser
65                  70

<210> SEQ ID NO 98
<211> LENGTH: 70
<212> TYPE: PRT
<213> ORGANISM: Borrelia afzelii

<400> SEQUENCE: 98

Ser Glu Ala Phe Thr Lys Lys Leu Gln Asp Ser Asn Ala Asp Leu Gly
1               5                   10                  15

Lys His Asp Ala Thr Asp Ala Asp Ala Lys Lys Ala Ile Leu Lys Thr
            20                  25                  30

Asp Ala Thr Lys Asp Lys Gly Ala Lys Glu Leu Glu Glu Leu Phe Lys
         35                  40                  45

Ser Val Glu Ser Leu Ser Lys Ala Ala Lys Glu Ala Leu Ser Asn Ser
    50                  55                  60

Val Lys Glu Leu Thr Ser
65                  70

<210> SEQ ID NO 99
<211> LENGTH: 70
<212> TYPE: PRT
<213> ORGANISM: Borrelia afzelii

<400> SEQUENCE: 99

Ser Gln Asp Phe Ile Asn Lys Leu Lys Gly Gly His Ala Glu Leu Gly
1               5                   10                  15

Leu Val Ala Ala Thr Asp Ala Asn Ala Lys Ala Ala Ile Leu Lys Thr
            20                  25                  30

Asn Gly Asp Lys Thr Lys Gly Ala Asp Glu Phe Glu Lys Leu Phe Lys
         35                  40                  45

Ser Val Glu Gly Leu Leu Lys Ala Ala Gln Glu Ala Leu Thr Asn Ser
    50                  55                  60

Val Lys Glu Leu Thr Ser
65                  70

<210> SEQ ID NO 100
<211> LENGTH: 70
<212> TYPE: PRT
<213> ORGANISM: Borrelia afzelii

<400> SEQUENCE: 100

Ser Gln Asp Phe Ile Asn Lys Leu Lys Gly Gly His Ala Glu Leu Gly
1               5                   10                  15

Leu Ala Ala Ala Thr Asp Ala Asn Ala Lys Ala Ala Ile Leu Lys Thr
            20                  25                  30

Asn Gly Asp Lys Thr Lys Gly Ala Asp Glu Phe Glu Lys Leu Phe Lys
         35                  40                  45

Ser Val Glu Gly Leu Leu Lys Ala Ala Gln Glu Ala Leu Thr Asn Ser
    50                  55                  60

Val Lys Glu Leu Thr Thr
65                  70
```

<210> SEQ ID NO 101
<211> LENGTH: 70
<212> TYPE: PRT
<213> ORGANISM: Borrelia burgdorferi

<400> SEQUENCE: 101

Ser Glu Thr Phe Thr Asn Lys Leu Lys Glu Lys His Thr Asp Leu Gly
1               5                   10                  15

Lys Glu Gly Val Thr Asp Ala Asp Ala Lys Glu Ala Ile Leu Lys Thr
            20                  25                  30

Asn Gly Thr Lys Thr Lys Gly Ala Glu Glu Leu Gly Lys Leu Phe Glu
        35                  40                  45

Ser Val Glu Val Leu Ser Lys Ala Ala Lys Glu Met Leu Ala Asn Ser
    50                  55                  60

Val Lys Glu Leu Thr Ser
65                  70

<210> SEQ ID NO 102
<211> LENGTH: 72
<212> TYPE: PRT
<213> ORGANISM: Borrelia burgdorferi

<400> SEQUENCE: 102

Ser Ala Ala Phe Thr Lys Lys Leu Ala Asp Ser Asn Ala Asp Leu Gly
1               5                   10                  15

Val Ala Ala Gly Asn Ala Thr Asp Asp Asn Ala Lys Arg Ala Ile Leu
            20                  25                  30

Lys Thr His Gly His Glu Asp Lys Gly Gly Lys Glu Leu Lys Glu Leu
        35                  40                  45

Ser Glu Ala Val Lys Ser Leu Leu Lys Ala Ala Gln Ala Ala Leu Ala
    50                  55                  60

Asn Ser Val Gln Glu Leu Thr Ser
65                  70

<210> SEQ ID NO 103
<211> LENGTH: 70
<212> TYPE: PRT
<213> ORGANISM: Borrelia burgdorferi

<400> SEQUENCE: 103

Ser Glu Asp Phe Thr Asn Lys Leu Lys Asn Gly Asn Ala Gln Leu Gly
1               5                   10                  15

Leu Ala Ala Ala Thr Asp Asp Asn Ala Lys Ala Ala Ile Leu Lys Thr
            20                  25                  30

Asn Gly Thr Asn Asp Lys Gly Ala Lys Glu Leu Lys Asp Leu Ser Asp
        35                  40                  45

Ser Val Glu Ser Leu Val Lys Ala Ala Gln Val Met Leu Thr Asn Ser
    50                  55                  60

Val Lys Glu Leu Thr Ser
65                  70

<210> SEQ ID NO 104
<211> LENGTH: 70
<212> TYPE: PRT
<213> ORGANISM: Borrelia burgdorferi

<400> SEQUENCE: 104

Ser Thr Glu Phe Thr Asn Lys Leu Lys Ser Glu His Ala Val Leu Gly

```
                1               5                  10                 15
Leu Asp Asn Leu Thr Asp Asp Asn Ala Gln Arg Ala Ile Leu Lys Lys
                20                 25                 30

His Ala Asn Lys Asp Lys Gly Ala Ala Glu Leu Glu Lys Leu Phe Lys
            35                 40                 45

Ala Val Glu Asn Leu Ser Lys Ala Ala Gln Asp Thr Leu Lys Asn Ala
        50                 55                 60

Val Lys Glu Leu Thr Ser
65                  70

<210> SEQ ID NO 105
<211> LENGTH: 72
<212> TYPE: PRT
<213> ORGANISM: Borrelia burgdorferi

<400> SEQUENCE: 105

Asn Lys Ala Phe Thr Asp Lys Leu Lys Ser Ser His Ala Glu Leu Gly
1               5                  10                 15

Ile Ala Asn Gly Ala Ala Thr Asp Ala Asn Ala Lys Ala Ala Ile Leu
                20                 25                 30

Lys Thr Asn Gly Thr Lys Asp Lys Gly Ala Gln Glu Leu Glu Lys Leu
            35                 40                 45

Phe Glu Ser Val Lys Asn Leu Ser Lys Ala Ala Gln Glu Thr Leu Asn
        50                 55                 60

Asn Ser Val Lys Glu Leu Thr Ser
65                  70

<210> SEQ ID NO 106
<211> LENGTH: 70
<212> TYPE: PRT
<213> ORGANISM: Borrelia burgdorferi

<400> SEQUENCE: 106

Ser Glu Ser Phe Thr Lys Lys Leu Ser Asp Gln Ala Glu Leu Gly
1               5                  10                 15

Ile Glu Asn Ala Thr Asp Asp Asn Ala Lys Lys Ala Ile Leu Lys Thr
                20                 25                 30

His Asn Ala Lys Asp Lys Gly Ala Glu Glu Leu Val Lys Leu Ser Glu
            35                 40                 45

Ser Val Ala Gly Leu Leu Lys Ala Ala Gln Ala Ile Leu Ala Asn Ser
        50                 55                 60

Val Lys Glu Leu Thr Ser
65                  70

<210> SEQ ID NO 107
<211> LENGTH: 70
<212> TYPE: PRT
<213> ORGANISM: Borrelia burgdorferi

<400> SEQUENCE: 107

Ser Glu Lys Phe Thr Lys Lys Leu Ser Glu Ser His Ala Asp Ile Gly
1               5                  10                 15

Ile Gln Ala Ala Thr Asp Ala Asn Ala Lys Asp Ala Ile Leu Lys Thr
                20                 25                 30

Asn Pro Thr Lys Thr Lys Gly Ala Glu Glu Leu Asp Lys Leu Phe Lys
            35                 40                 45

Ala Val Glu Asn Leu Ser Lys Ala Ala Lys Glu Met Leu Ala Asn Ser
        50                 55                 60
```

Val Lys Asp Leu Gln Val
65              70

<210> SEQ ID NO 108
<211> LENGTH: 70
<212> TYPE: PRT
<213> ORGANISM: Borrelia burgdorferi

<400> SEQUENCE: 108

Ser Glu Lys Phe Thr Lys Leu Ser Glu Ser His Ala Asp Ile Gly
1               5                   10                  15

Ile Gln Ala Ala Thr Asp Ala Asn Ala Lys Asp Ala Ile Leu Lys Thr
                20                  25                  30

Asn Pro Thr Lys Thr Lys Gly Ala Glu Glu Leu Asp Lys Leu Phe Lys
            35                  40                  45

Ala Val Glu Asn Leu Ser Lys Ala Ala Lys Glu Met Leu Ala Asn Ser
        50                  55                  60

Val Lys Glu Leu Thr Ser
65              70

<210> SEQ ID NO 109
<211> LENGTH: 70
<212> TYPE: PRT
<213> ORGANISM: Borrelia burgdorferi

<400> SEQUENCE: 109

Ser Glu Glu Phe Thr Ala Lys Leu Lys Gly Glu His Thr Asp Leu Gly
1               5                   10                  15

Lys Glu Gly Val Thr Asp Asp Asn Ala Lys Ala Ile Leu Lys Thr
                20                  25                  30

Asn Asn Asp Lys Thr Lys Gly Ala Asp Glu Leu Glu Lys Leu Phe Glu
            35                  40                  45

Ser Val Lys Asn Leu Ser Lys Ala Ala Lys Glu Met Leu Thr Asn Ser
        50                  55                  60

Val Lys Glu Leu Thr Ser
65              70

<210> SEQ ID NO 110
<211> LENGTH: 70
<212> TYPE: PRT
<213> ORGANISM: Borrelia burgdorferi

<400> SEQUENCE: 110

Ser Glu Lys Phe Thr Asp Lys Leu Lys Ser Glu Asn Ala Ala Leu Gly
1               5                   10                  15

Lys Gln Asp Ala Ser Asp Asp Ala Lys Lys Ala Ile Leu Lys Thr
                20                  25                  30

His Asn Asp Ile Thr Lys Gly Ala Lys Glu Leu Lys Glu Leu Ser Glu
            35                  40                  45

Ser Val Glu Thr Leu Leu Lys Ala Ala Lys Glu Met Leu Ala Asn Ser
        50                  55                  60

Val Lys Glu Leu Thr Ser
65              70

<210> SEQ ID NO 111
<211> LENGTH: 70
<212> TYPE: PRT
<213> ORGANISM: Borrelia burgdorferi

```
<400> SEQUENCE: 111

Ser Glu Lys Phe Ala Gly Lys Leu Lys Asn Glu His Ala Ser Leu Gly
1               5                   10                  15

Lys Lys Asp Ala Thr Asp Asp Ala Lys Lys Ala Ile Leu Lys Thr
            20                  25                  30

His Gly Asn Thr Asp Lys Gly Ala Lys Glu Leu Lys Asp Leu Ser Asp
            35                  40                  45

Ser Val Glu Ser Leu Val Lys Ala Ala Lys Glu Met Leu Thr Asn Ser
50                  55                  60

Val Lys Glu Leu Thr Ser
65                  70

<210> SEQ ID NO 112
<211> LENGTH: 70
<212> TYPE: PRT
<213> ORGANISM: Borrelia burgdorferi

<400> SEQUENCE: 112

Ser Glu Ala Phe Thr Asp Lys Leu Lys Asn Glu His Ala Ser Leu Gly
1               5                   10                  15

Lys Lys Asp Ala Thr Asp Asp Ala Lys Lys Ala Ile Leu Lys Thr
            20                  25                  30

Asn Val Asp Lys Thr Lys Gly Ala Asp Glu Leu Ile Lys Leu Ser Gly
            35                  40                  45

Ser Leu Glu Ser Leu Ser Lys Ala Ala Gln Ala Ile Leu Ala Asn Ser
50                  55                  60

Val Lys Glu Leu Thr Ser
65                  70

<210> SEQ ID NO 113
<211> LENGTH: 70
<212> TYPE: PRT
<213> ORGANISM: Borrelia garinii

<400> SEQUENCE: 113

Ser Glu Lys Phe Thr Thr Lys Leu Arg Asp Ser His Ala Glu Leu Gly
1               5                   10                  15

Ile Gln Asn Val Gln Asp Asp Asn Ala Lys Arg Ala Ile Leu Lys Thr
            20                  25                  30

His Gly Asn Lys Asp Lys Gly Ala Lys Glu Leu Lys Glu Leu Ser Glu
            35                  40                  45

Ser Leu Glu Lys Leu Ser Lys Ala Ala Gln Ala Ala Leu Ala Asn Ser
50                  55                  60

Val Gln Glu Leu Thr Ser
65                  70

<210> SEQ ID NO 114
<211> LENGTH: 70
<212> TYPE: PRT
<213> ORGANISM: Borrelia garinii

<400> SEQUENCE: 114

Ser Glu Lys Phe Thr Thr Lys Leu Lys Asp Ser His Ala Glu Leu Gly
1               5                   10                  15

Ile Gln Ser Val Gln Asp Asp Asn Ala Lys Lys Ala Ile Leu Lys Thr
            20                  25                  30

His Gly Thr Lys Asp Lys Gly Ala Lys Glu Leu Glu Lys Leu Phe Lys
            35                  40                  45
```

```
Ser Leu Glu Ser Leu Ser Lys Ala Ala Gln Ala Ala Leu Thr Asn Ser
        50                  55                  60

Val Lys Glu Leu Thr Asn
 65                  70

<210> SEQ ID NO 115
<211> LENGTH: 71
<212> TYPE: PRT
<213> ORGANISM: Borrelia burgdorferi

<400> SEQUENCE: 115

Ser Glu Glu Phe Ser Thr Lys Leu Lys Asp Asn His Ala Gln Leu Gly
  1               5                  10                  15

Ile Gln Gly Val Thr Asp Glu Asn Ala Lys Lys Ala Ile Leu Lys Ala
             20                  25                  30

Asn Ala Ala Gly Lys Asp Lys Gly Val Glu Glu Leu Glu Lys Leu Ser
         35                  40                  45

Gly Ser Leu Glu Ser Leu Ser Lys Ala Ala Lys Glu Met Leu Ala Asn
     50                  55                  60

Ser Val Lys Glu Leu Thr Ser
 65                  70

<210> SEQ ID NO 116
<211> LENGTH: 71
<212> TYPE: PRT
<213> ORGANISM: Borrelia burgdorferi

<400> SEQUENCE: 116

Ser Glu Glu Phe Ser Thr Lys Leu Lys Asp Asn His Ala Gln Leu Gly
  1               5                  10                  15

Ile Gln Gly Val Thr Asp Glu Asn Ala Lys Lys Ala Ile Leu Lys Ala
             20                  25                  30

Asn Ala Ala Gly Lys Asp Lys Gly Val Glu Glu Leu Glu Lys Leu Ser
         35                  40                  45

Gly Ser Leu Glu Ser Leu Ser Lys Ala Ala Lys Glu Met Leu Ala Asn
     50                  55                  60

Ser Val Lys Ser Leu Gln Ser
 65                  70

<210> SEQ ID NO 117
<211> LENGTH: 70
<212> TYPE: PRT
<213> ORGANISM: Borrelia burgdorferi

<400> SEQUENCE: 117

Ser Glu Asp Phe Thr Lys Lys Leu Glu Gly Glu His Ala Gln Leu Gly
  1               5                  10                  15

Ile Glu Asn Val Thr Asp Glu Asn Ala Lys Lys Ala Ile Leu Ile Thr
             20                  25                  30

Asp Ala Ala Lys Asp Lys Gly Ala Ala Glu Leu Glu Lys Leu Phe Lys
         35                  40                  45

Ala Val Glu Asn Leu Ala Lys Ala Ala Lys Glu Met Leu Ala Asn Ser
     50                  55                  60

Val Lys Glu Leu Thr Ser
 65                  70

<210> SEQ ID NO 118
<211> LENGTH: 72
```

<212> TYPE: PRT
<213> ORGANISM: Borrelia burgdorferi

<400> SEQUENCE: 118

Ser Asp Asp Phe Thr Lys Lys Leu Gln Ser Ser His Ala Gln Leu Gly
1               5                   10                  15

Val Ala Gly Gly Ala Thr Thr Asp Glu Ala Lys Lys Ala Ile Leu
            20                  25                  30

Arg Thr Asn Ala Ile Lys Asp Lys Gly Ala Asp Glu Leu Glu Lys Leu
            35                  40                  45

Phe Lys Ser Val Glu Ser Leu Ala Lys Ala Ala Gln Asp Ala Leu Ala
        50                  55                  60

Asn Ser Val Asn Glu Leu Thr Ser
65                  70

<210> SEQ ID NO 119
<211> LENGTH: 191
<212> TYPE: PRT
<213> ORGANISM: Borrelia burgdorferi

<400> SEQUENCE: 119

Asn Asn Ser Gly Lys Asp Gly Asn Thr Ser Ala Asn Ser Ala Asp Glu
1               5                   10                  15

Ser Val Lys Gly Pro Asn Leu Thr Glu Ile Ser Lys Lys Ile Thr Asp
            20                  25                  30

Ser Asn Ala Val Leu Leu Ala Val Lys Glu Val Glu Ala Leu Leu Ser
            35                  40                  45

Ser Ile Asp Glu Ile Ala Ala Lys Ala Ile Gly Lys Lys Ile His Gln
        50                  55                  60

Asn Asn Gly Leu Asp Thr Glu Asn Asn His Asn Gly Ser Leu Leu Ala
65                  70                  75                  80

Gly Ala Tyr Ala Ile Ser Thr Leu Ile Lys Gln Lys Leu Asp Gly Leu
                85                  90                  95

Lys Asn Glu Gly Leu Lys Glu Lys Ile Asp Ala Ala Lys Lys Cys Ser
            100                 105                 110

Glu Thr Phe Thr Asn Lys Leu Lys Glu Lys His Thr Asp Leu Gly Lys
            115                 120                 125

Glu Gly Val Thr Asp Ala Asp Ala Lys Glu Ala Ile Leu Lys Thr Asn
        130                 135                 140

Gly Thr Lys Thr Lys Gly Ala Glu Glu Leu Lys Leu Phe Glu Ser
145                 150                 155                 160

Val Glu Val Leu Ser Lys Ala Ala Lys Glu Met Leu Ala Asn Ser Val
                165                 170                 175

Lys Glu Leu Thr Ser Pro Val Val Ala Glu Ser Pro Lys Lys Pro
            180                 185                 190

<210> SEQ ID NO 120
<211> LENGTH: 192
<212> TYPE: PRT
<213> ORGANISM: Borrelia burgdorferi

<400> SEQUENCE: 120

Asn Asn Ser Gly Lys Asp Gly Asn Thr Ser Ala Asn Ser Ala Asp Glu
1               5                   10                  15

Ser Val Lys Gly Pro Asn Leu Thr Glu Ile Ser Lys Lys Ile Thr Asp
            20                  25                  30

Ser Asn Ala Val Leu Leu Ala Val Lys Glu Val Glu Ala Leu Leu Ser

```
                35                  40                  45
Ser Ile Asp Glu Leu Ala Lys Ala Ile Gly Lys Lys Ile Lys Asn Asp
 50                  55                  60

Gly Ser Leu Asp Asn Glu Ala Asn Arg Asn Glu Ser Leu Leu Ala Gly
 65                  70                  75                  80

Ala Tyr Thr Ile Ser Thr Leu Ile Thr Gln Lys Leu Ser Lys Leu Asn
                 85                  90                  95

Gly Ser Glu Gly Leu Lys Glu Lys Ile Ala Ala Lys Lys Cys Ser
                100                 105                 110

Glu Glu Phe Ser Thr Lys Leu Lys Asp Asn His Ala Gln Leu Gly Ile
                115                 120                 125

Gln Gly Val Thr Asp Glu Asn Ala Lys Ala Ile Leu Lys Ala Asn
                130                 135                 140

Ala Ala Gly Lys Asp Lys Gly Val Glu Glu Leu Glu Lys Leu Ser Gly
145                 150                 155                 160

Ser Leu Glu Ser Leu Ser Lys Ala Ala Lys Glu Met Leu Ala Asn Ser
                165                 170                 175

Val Lys Glu Leu Thr Ser Pro Val Val Ala Glu Ser Pro Lys Lys Pro
                180                 185                 190
```

<210> SEQ ID NO 121
<211> LENGTH: 193
<212> TYPE: PRT
<213> ORGANISM: Borrelia burgdorferi

<400> SEQUENCE: 121

```
Asn Asn Ser Gly Lys Asp Gly Asn Thr Ser Ala Asn Ser Ala Asp Glu
 1               5                  10                  15

Ser Val Lys Gly Pro Asn Leu Thr Glu Ile Ser Lys Lys Ile Thr Glu
                20                  25                  30

Ser Asn Ala Val Val Leu Ala Val Lys Glu Ile Glu Thr Leu Leu Ala
                35                  40                  45

Ser Ile Asp Glu Leu Ala Thr Lys Ala Ile Gly Lys Lys Ile Gln Gln
 50                  55                  60

Asn Gly Gly Leu Ala Val Glu Ala Gly His Asn Gly Thr Leu Leu Ala
 65                  70                  75                  80

Gly Ala Tyr Thr Ile Ser Lys Leu Ile Thr Gln Lys Leu Asp Gly Leu
                 85                  90                  95

Lys Asn Ser Glu Lys Leu Lys Glu Lys Ile Glu Asn Ala Lys Lys Cys
                100                 105                 110

Ser Glu Asp Phe Thr Lys Lys Leu Gly Glu His Ala Gln Leu Gly
                115                 120                 125

Ile Glu Asn Ala Thr Asp Ala Glu Asn Ala Lys Lys Ala Ile Leu Ile
                130                 135                 140

Thr Asp Ala Ala Lys Asp Lys Gly Ala Ala Glu Leu Glu Lys Leu Phe
145                 150                 155                 160

Lys Ala Val Glu Asn Leu Ala Lys Ala Ala Lys Glu Met Leu Ala Asn
                165                 170                 175

Ser Val Lys Glu Leu Thr Ser Pro Ile Val Ala Glu Ser Pro Lys Lys
                180                 185                 190

Pro
```

<210> SEQ ID NO 122
<211> LENGTH: 192
<212> TYPE: PRT

<213> ORGANISM: Borrelia burgdorferi

<400> SEQUENCE: 122

```
Asn Asn Ser Gly Lys Asp Gly Asn Thr Ser Ala Asn Ser Ala Asp Glu
1               5                   10                  15

Ser Val Lys Gly Pro Asn Leu Thr Glu Ile Ser Lys Lys Ile Thr Asp
            20                  25                  30

Ser Asn Ala Val Leu Leu Ala Val Lys Glu Val Glu Val Leu Leu Ser
        35                  40                  45

Ser Ile Asp Glu Leu Ala Lys Lys Ala Ile Gly Lys Lys Ile Asp Gln
    50                  55                  60

Asn Asn Ala Leu Gly Thr Leu Asn Asn His Asn Gly Ser Leu Leu Ala
65                  70                  75                  80

Gly Ala Tyr Ala Ile Ser Ala Leu Ile Thr Glu Lys Leu Ser Ser Ile
                85                  90                  95

Lys Asp Ser Gly Glu Leu Lys Ala Glu Ile Glu Lys Ala Lys Lys Cys
            100                 105                 110

Ser Glu Ser Phe Thr Lys Lys Leu Ser Asp Asn Gln Ala Glu Leu Gly
        115                 120                 125

Ile Glu Asn Ala Thr Asp Asp Asn Ala Lys Lys Ala Ile Leu Lys Thr
    130                 135                 140

His Asn Ala Lys Asp Lys Gly Ala Glu Glu Leu Val Lys Leu Ser Glu
145                 150                 155                 160

Ser Val Ala Gly Leu Leu Lys Ala Ala Gln Ala Ile Leu Ala Asn Ser
                165                 170                 175

Val Lys Glu Leu Thr Ser Pro Val Val Ala Glu Ser Pro Lys Lys Pro
            180                 185                 190
```

<210> SEQ ID NO 123
<211> LENGTH: 580
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (429)..(429)
<223> OTHER INFORMATION: Xaa can be any naturally occurring amino acid
<220> FEATURE:
<221> NAME/KEY: misc_feature
<222> LOCATION: (500)..(500)
<223> OTHER INFORMATION: Xaa can be any naturally occurring amino acid

<400> SEQUENCE: 123

Ser Thr Glu Phe Thr Asn Lys Leu Lys Ser Glu His Ala Val Leu Gly

-continued

```
1               5                   10                  15
Leu Asp Asn Leu Thr Asp Asp Asn Ala Gln Arg Ala Ile Leu Lys Lys
                20                  25                  30

His Ala Asn Lys Asp Lys Gly Ala Ala Glu Leu Glu Lys Leu Phe Lys
                35                  40                  45

Ala Val Glu Asn Leu Ser Lys Ala Ala Gln Asp Thr Leu Lys Asn Ala
            50                  55                  60

Val Lys Glu Leu Thr Ser Xaa Ser Asp Asp Phe Thr Lys Lys Leu Gln
65                  70                  75                  80

Ser Ser His Ala Gln Leu Gly Val Ala Gly Ala Thr Thr Asp Glu
                85                  90                  95

Glu Ala Lys Lys Ala Ile Leu Arg Thr Asn Ala Ile Lys Asp Lys Gly
                100                 105                 110

Ala Asp Glu Leu Glu Lys Leu Phe Lys Ser Val Glu Ser Leu Ala Lys
                115                 120                 125

Ala Ala Gln Asp Ala Leu Ala Asn Ser Val Asn Glu Leu Thr Ser Xaa
            130                 135                 140

Ser Glu Glu Phe Thr Ala Lys Leu Lys Gly Glu His Thr Asp Leu Gly
145                 150                 155                 160

Lys Glu Gly Val Thr Asp Asp Asn Ala Lys Lys Ala Ile Leu Lys Thr
                165                 170                 175

Asn Asn Asp Lys Thr Lys Gly Ala Asp Glu Leu Glu Lys Leu Phe Glu
                180                 185                 190

Ser Val Lys Asn Leu Ser Lys Ala Ala Lys Glu Met Leu Thr Asn Ser
            195                 200                 205

Val Lys Glu Leu Thr Ser Xaa Ser Glu Glu Phe Thr Lys Lys Leu Lys
            210                 215                 220

Glu Lys His Thr Asp Leu Gly Lys Lys Asp Ala Thr Asp Val His Ala
225                 230                 235                 240

Lys Glu Ala Ile Leu Lys Thr Asn Gly Thr Lys Asp Lys Gly Ala Ala
                245                 250                 255

Glu Leu Glu Lys Leu Phe Glu Ser Val Glu Asn Leu Ala Lys Ala Ala
            260                 265                 270

Lys Glu Met Leu Ser Asn Ser Val Lys Glu Leu Thr Ser Xaa Ser Glu
            275                 280                 285

Thr Phe Thr Asn Lys Leu Lys Glu Lys His Thr Asp Leu Gly Lys Glu
            290                 295                 300

Gly Val Thr Asp Ala Asp Ala Lys Glu Ala Ile Leu Lys Thr Asn Gly
305                 310                 315                 320

Thr Lys Thr Lys Gly Ala Glu Glu Leu Gly Lys Leu Phe Glu Ser Val
                325                 330                 335

Glu Val Leu Ser Lys Ala Ala Lys Glu Met Leu Ala Asn Ser Val Lys
            340                 345                 350

Glu Leu Thr Ser Xaa Ser Glu Glu Phe Ser Thr Lys Leu Lys Asp Asn
            355                 360                 365

His Ala Gln Leu Gly Ile Gln Gly Val Thr Asp Glu Asn Ala Lys Lys
            370                 375                 380

Ala Ile Leu Lys Ala Asn Ala Gly Lys Asp Lys Gly Val Glu Glu
385                 390                 395                 400

Leu Glu Lys Leu Ser Gly Ser Leu Glu Ser Leu Ser Lys Ala Ala Lys
                405                 410                 415

Glu Met Leu Ala Asn Ser Val Lys Glu Leu Thr Ser Xaa Ser Glu Asp
            420                 425                 430
```

```
Phe Thr Lys Lys Leu Glu Gly Glu His Ala Gln Leu Gly Ile Glu Asn
            435                 440                 445

Val Thr Asp Glu Asn Ala Lys Lys Ala Ile Leu Ile Thr Asp Ala Ala
    450                 455                 460

Lys Asp Lys Gly Ala Ala Glu Leu Glu Lys Leu Phe Lys Ala Val Glu
465                 470                 475                 480

Asn Leu Ala Lys Ala Ala Lys Glu Met Leu Ala Asn Ser Val Lys Glu
                485                 490                 495

Leu Thr Ser Xaa Ser Glu Ser Phe Thr Lys Lys Leu Ser Asp Asn Gln
            500                 505                 510

Ala Glu Leu Gly Ile Glu Asn Ala Thr Asp Asn Ala Lys Lys Ala
            515                 520                 525

Ile Leu Lys Thr His Asn Ala Lys Asp Lys Gly Ala Glu Glu Leu Val
            530                 535                 540

Lys Leu Ser Glu Ser Val Ala Gly Leu Leu Lys Ala Ala Gln Ala Ile
545                 550                 555                 560

Leu Ala Asn Ser Val Lys Glu Leu Thr Ser Pro Val Val Ala Glu Ser
                565                 570                 575

Pro Lys Lys Pro
            580

<210> SEQ ID NO 124
<211> LENGTH: 500
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid

<400> SEQUENCE: 124

Ser Glu Asp Phe Thr Asn Lys Leu Lys Asn Gly Asn Ala Gln Leu Gly
1               5                   10                  15

Leu Ala Ala Ala Thr Asp Asp Asn Ala Lys Ala Ile Leu Lys Thr
                20                  25                  30

Asn Gly Thr Asn Asp Lys Gly Ala Lys Glu Leu Lys Asp Leu Ser Asp
            35                  40                  45

Ser Val Glu Ser Leu Val Lys Ala Ala Gln Val Met Leu Thr Asn Ser
    50                  55                  60

Val Lys Glu Leu Thr Ser Xaa Asn Lys Ala Phe Thr Asp Lys Leu Lys
65              70                  75                  80
```

```
Ser Ser His Ala Glu Leu Gly Ile Ala Asn Gly Ala Ala Thr Asp Ala
            85                  90                  95
Asn Ala Lys Ala Ala Ile Leu Lys Thr Asn Gly Thr Lys Asp Lys Gly
            100                 105                 110
Ala Gln Glu Leu Glu Lys Leu Phe Glu Ser Val Lys Asn Leu Ser Lys
            115                 120                 125
Ala Ala Gln Glu Thr Leu Asn Asn Ser Val Lys Glu Leu Thr Ser Xaa
            130                 135                 140
Ser Glu Lys Phe Thr Lys Lys Leu Ser Glu Ser His Ala Asp Ile Gly
145                 150                 155                 160
Ile Gln Ala Ala Thr Asp Ala Asn Ala Lys Asp Ala Ile Leu Lys Thr
                165                 170                 175
Asn Pro Thr Lys Thr Lys Gly Ala Glu Glu Leu Asp Lys Leu Phe Lys
                180                 185                 190
Ala Val Glu Asn Leu Ser Lys Ala Ala Lys Glu Met Leu Ala Asn Ser
                195                 200                 205
Val Lys Asp Leu Gln Val Xaa Ser Glu Lys Phe Thr Asp Lys Leu Lys
            210                 215                 220
Ser Glu Asn Ala Ala Leu Gly Lys Gln Asp Ala Ser Asp Asp Ala
225                 230                 235                 240
Lys Lys Ala Ile Leu Lys Thr His Asn Asp Ile Thr Lys Gly Ala Lys
                245                 250                 255
Glu Leu Lys Glu Leu Ser Glu Ser Val Glu Thr Leu Leu Lys Ala Ala
                260                 265                 270
Lys Glu Met Leu Ala Asn Ser Val Lys Glu Leu Thr Ser Xaa Ser Glu
            275                 280                 285
Lys Phe Ala Gly Lys Leu Lys Asn Glu His Ala Ser Leu Gly Lys Lys
            290                 295                 300
Asp Ala Thr Asp Asp Ala Lys Lys Ala Ile Leu Lys Thr His Gly
305                 310                 315                 320
Asn Thr Asp Lys Gly Ala Lys Glu Leu Lys Asp Leu Ser Asp Ser Val
                325                 330                 335
Glu Ser Leu Val Lys Ala Ala Lys Glu Met Leu Thr Asn Ser Val Lys
            340                 345                 350
Glu Leu Thr Ser Xaa Ser Glu Ala Phe Thr Asp Lys Leu Lys Asn Glu
            355                 360                 365
His Ala Ser Leu Gly Lys Lys Asp Ala Thr Asp Asp Ala Lys Lys
            370                 375                 380
Ala Ile Leu Lys Thr Asn Val Asp Lys Thr Lys Gly Ala Asp Glu Leu
385                 390                 395                 400
Ile Lys Leu Ser Gly Ser Leu Glu Ser Leu Ser Lys Ala Ala Gln Ala
            405                 410                 415
Ile Leu Ala Asn Ser Val Lys Glu Leu Thr Ser Xaa Ser Ala Ala Phe
            420                 425                 430
Thr Lys Lys Leu Ala Asp Ser Asn Ala Asp Leu Gly Val Ala Ala Gly
            435                 440                 445
Asn Ala Thr Asp Asp Asn Ala Lys Arg Ala Ile Leu Lys Thr His Gly
            450                 455                 460
His Glu Asp Lys Gly Gly Lys Glu Leu Lys Glu Leu Ser Glu Ala Val
465                 470                 475                 480
Lys Ser Leu Leu Lys Ala Ala Gln Ala Ala Leu Ala Asn Ser Val Gln
            485                 490                 495
```

```
<210> SEQ ID NO 125
<211> LENGTH: 573
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (430)..(430)
<223> OTHER INFORMATION: Xaa can be any naturally occurring amino acid
<220> FEATURE:
<221> NAME/KEY: misc_feature
<222> LOCATION: (501)..(501)
<223> OTHER INFORMATION: Xaa can be any naturally occurring amino acid
```

-continued

```
Glu Leu Thr Ser
            500
```

```
<400> SEQUENCE: 125

Ser Glu Lys Phe Thr Thr Lys Leu Arg Asp Ser His Ala Glu Leu Gly
1               5                   10                  15

Ile Gln Asn Val Gln Asp Asp Asn Ala Lys Arg Ala Ile Leu Lys Thr
            20                  25                  30

His Gly Asn Lys Asp Lys Gly Ala Lys Glu Leu Lys Glu Leu Ser Glu
        35                  40                  45

Ser Leu Glu Lys Leu Ser Lys Ala Ala Gln Ala Ala Leu Ala Asn Ser
    50                  55                  60

Val Gln Glu Leu Thr Ser Xaa Ser Glu Lys Phe Thr Thr Lys Leu Lys
65                  70                  75                  80

Asp Ser His Ala Glu Leu Gly Ile Gln Ser Val Gln Asp Asp Asn Ala
                85                  90                  95

Lys Lys Ala Ile Leu Lys Thr His Gly Thr Lys Asp Lys Gly Ala Lys
            100                 105                 110

Glu Leu Glu Glu Leu Phe Lys Ser Leu Glu Ser Leu Ser Lys Ala Ala
        115                 120                 125

Gln Ala Ala Leu Thr Asn Ser Val Lys Glu Leu Thr Asn Xaa Ser Glu
    130                 135                 140

Ala Phe Thr Asn Lys Leu Lys Glu Lys His Ala Glu Leu Gly Val Asn
145                 150                 155                 160

Gly Gly Asp Thr Thr Asp Asp Asn Ala Lys Ala Ala Ile Phe Lys Thr
                165                 170                 175

His Pro Thr Lys Asp Lys Gly Val Glu Asp Leu Glu Lys Leu Ser Glu
            180                 185                 190

Ser Val Lys Ser Leu Leu Lys Ala Ala Gln Ala Ala Leu Ser Asn Ser
        195                 200                 205
```

Val Lys Glu Leu Thr Ser Xaa Ser Asp Lys Phe Thr Lys Leu Thr
210                 215                 220

Asp Ser His Ala Gln Leu Gly Ala Val Gly Ala Ile Asn Asp Asp
225                 230                 235                 240

Arg Ala Lys Glu Ala Ile Leu Lys Thr His Gly Thr Asn Asp Lys Gly
            245                 250                 255

Ala Lys Glu Leu Lys Glu Leu Ser Glu Ser Val Glu Ser Leu Ala Lys
            260                 265                 270

Ala Ala Gln Ala Ala Leu Ala Asn Ser Val Lys Glu Leu Thr Ser Xaa
            275                 280                 285

Ser Glu Ala Phe Thr Lys Lys Leu Lys Asp Asn Ala Gln Leu Gly
290                 295                 300

Ile Gln Asn Val Gln Asp Val Glu Ala Lys Lys Ala Ile Leu Lys Thr
305                 310                 315                 320

Asn Gly Asp Ile Ser Lys Gly Ala Lys Glu Leu Lys Glu Leu Phe Glu
                325                 330                 335

Ser Val Glu Ser Leu Ala Lys Ala Ala Gln Ala Ala Leu Ala Asn Ser
                340                 345                 350

Val Gln Glu Leu Thr Asn Xaa Ser Glu Ala Phe Thr Asn Arg Leu Lys
                355                 360                 365

Gly Ser His Ala Gln Leu Gly Val Ala Ala Thr Asp Asp His Ala
370                 375                 380

Lys Glu Ala Ile Leu Lys Ser Asn Pro Thr Lys Asp Lys Gly Ala Lys
385                 390                 395                 400

Glu Leu Lys Asp Leu Ser Glu Ser Val Glu Ser Leu Ala Lys Ala Ala
                405                 410                 415

Gln Glu Ala Leu Ala Asn Ser Val Lys Glu Leu Thr Asn Xaa Ser Glu
                420                 425                 430

Ala Phe Thr Asn Arg Leu Thr Gly Ser His Ala Gln His Gly Val Ala
                435                 440                 445

Ala Ala Thr Asp Asp His Ala Lys Glu Ala Ile Leu Lys Ser Asn Pro
450                 455                 460

Thr Lys Asp Lys Gly Ala Lys Glu Leu Lys Asp Leu Ser Glu Ser Val
465                 470                 475                 480

Glu Ser Leu Ala Lys Ala Ala Gln Glu Ala Leu Ala Asn Ser Val Lys
                485                 490                 495

Glu Leu Thr Asn Xaa Ser Glu Ala Phe Thr Asn Lys Leu Lys Glu Lys
                500                 505                 510

Thr Gln Glu Leu Ala Val Ala Ala Gly Ala Ala Thr Asp Ile Asp Ala
                515                 520                 525

Lys Lys Ala Ile Leu Lys Thr Asn Arg Asp Lys Asp Leu Gly Ala Asp
530                 535                 540

Glu Arg Gly Lys Leu Phe Lys Ser Val Glu Ser Leu Ser Lys Ala Ala
545                 550                 555                 560

Gln Glu Ala Ser Ala Asn Ser Val Lys Glu Leu Thr Ser
                565                 570

<210> SEQ ID NO 126
<211> LENGTH: 571
<212> TYPE: PRT
<213> ORGANISM: Artificial
<220> FEATURE:
<223> OTHER INFORMATION: Chimeric protein
<220> FEATURE:
<221> NAME/KEY: misc_feature

```
<222> LOCATION: (73)..(73)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (430)..(430)
<223> OTHER INFORMATION: Xaa can be any naturally occurring amino acid
<220> FEATURE:
<221> NAME/KEY: misc_feature
<222> LOCATION: (501)..(501)
<223> OTHER INFORMATION: Xaa can be any naturally occurring amino acid

<400> SEQUENCE: 126

Ser Val Ala Phe Thr Ser Lys Leu Lys Ser Ser Asn Ala Gln Leu Gly
1               5                   10                  15

Val Ala Asn Gly Asn Ala Thr Asp Asp Ala Lys Lys Ala Ile Leu
            20                  25                  30

Lys Thr Asn Thr Pro Asn Asp Lys Gly Ala Lys Glu Leu Lys Glu Leu
        35                  40                  45

Phe Glu Ser Val Glu Ser Leu Ala Lys Ala Ala Gln Ala Ala Leu Val
50                  55                  60

Asn Ser Val Gln Glu Leu Thr Asn Xaa Ser Gly Ala Phe Thr Lys Lys
65                  70                  75                  80

Leu Lys Asp Ser Asn Ala Gln Leu Gly Met Gln Asn Gly Ala Ala Thr
                85                  90                  95

Asp Ala His Ala Lys Ala Ala Ile Leu Lys Thr Asp Ala Thr Lys Asp
            100                 105                 110

Lys Gly Ala Thr Glu Leu Gly Glu Leu Phe Lys Ser Val Glu Ser Leu
        115                 120                 125

Ser Lys Ala Ala Gln Glu Ala Ser Ala Asn Ser Val Lys Glu Leu Thr
130                 135                 140

Ser Xaa Ser Ala Ala Phe Thr Lys Lys Leu Gln Asp Gly His Val Asp
145                 150                 155                 160

Leu Gly Lys Thr Asp Val Thr Asp Asn Ala Lys Glu Ala Ile Leu
            165                 170                 175

Lys Thr Asn Pro Thr Lys Thr Lys Gly Ala Thr Glu Leu Glu Glu Leu
        180                 185                 190

Phe Lys Ser Val Glu Gly Leu Val Lys Ala Lys Glu Ala Ser Ala
            195                 200                 205

Asn Ser Val Lys Glu Leu Thr Ser Xaa Ser Glu Glu Phe Thr Asn Lys
210                 215                 220

Leu Lys Ser Gly His Ala Asp Leu Gly Lys Gln Asp Ala Thr Asp Asp
225                 230                 235                 240

His Ala Lys Ala Ala Ile Leu Lys Thr His Ala Thr Thr Asp Lys Gly
            245                 250                 255

Ala Lys Glu Phe Lys Asp Leu Phe Glu Ser Val Glu Gly Leu Leu Lys
        260                 265                 270
```

```
Ala Ala Gln Val Ala Leu Thr Asn Ser Val Lys Glu Leu Thr Ser Xaa
            275                 280                 285

Ser Glu Glu Phe Thr Asn Lys Leu Lys Gly Gly His Ala Glu Leu Gly
290                 295                 300

Leu Ala Ala Ala Thr Asp Glu Asn Ala Lys Lys Ala Ile Leu Lys Thr
305                 310                 315                 320

Asn Gly Thr Lys Asp Lys Gly Ala Glu Leu Glu Lys Leu Phe Lys
                325                 330                 335

Ser Val Glu Ser Leu Ala Lys Ala Ala Lys Glu Ser Leu Thr Asn Ser
            340                 345                 350

Val Lys Glu Leu Thr Asn Xaa Ser Glu Ala Phe Thr Lys Lys Leu Gln
            355                 360                 365

Asp Ser Asn Ala Asp Leu Gly Lys His Asn Ala Thr Asp Ala Asp Ser
        370                 375                 380

Lys Glu Ala Ile Leu Lys Thr Asn Gly Thr Lys Thr Lys Gly Ala Lys
385                 390                 395                 400

Glu Leu Glu Glu Leu Phe Lys Ser Val Glu Ser Leu Ser Lys Ala Ala
                405                 410                 415

Lys Glu Ala Leu Ser Asn Ser Val Lys Glu Leu Thr Ser Xaa Ser Glu
            420                 425                 430

Ala Phe Thr Lys Lys Leu Gln Asp Ser Asn Ala Asp Leu Gly Lys His
        435                 440                 445

Asp Ala Thr Asp Ala Asp Ala Lys Lys Ala Ile Leu Lys Thr Asp Ala
        450                 455                 460

Thr Lys Asp Lys Gly Ala Lys Glu Leu Glu Glu Leu Phe Lys Ser Val
465                 470                 475                 480

Glu Ser Leu Ser Lys Ala Ala Lys Glu Ala Leu Ser Asn Ser Val Lys
                485                 490                 495

Glu Leu Thr Ser Xaa Ser Gln Asp Phe Ile Asn Lys Leu Lys Gly Gly
            500                 505                 510

His Ala Glu Leu Gly Leu Val Ala Ala Thr Asp Ala Asn Ala Lys Ala
        515                 520                 525

Ala Ile Leu Lys Thr Asn Gly Asp Lys Thr Lys Gly Ala Asp Glu Phe
        530                 535                 540

Glu Lys Leu Phe Lys Ser Val Glu Gly Leu Leu Lys Ala Ala Gln Glu
545                 550                 555                 560

Ala Leu Thr Asn Ser Val Lys Glu Leu Thr Ser
            565                 570

<210> SEQ ID NO 127
<211> LENGTH: 580
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
```

```
<222> LOCATION: (286)..(286)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (429)..(429)
<223> OTHER INFORMATION: Xaa can be any naturally occurring amino acid
<220> FEATURE:
<221> NAME/KEY: misc_feature
<222> LOCATION: (500)..(500)
<223> OTHER INFORMATION: Xaa can be any naturally occurring amino acid

<400> SEQUENCE: 127

Ser Thr Glu Phe Thr Asn Lys Leu Lys Ser Glu His Ala Val Leu Gly
1               5                   10                  15

Leu Asp Asn Leu Thr Asp Asp Asn Ala Gln Arg Ala Ile Leu Lys Lys
            20                  25                  30

His Ala Asn Lys Asp Lys Gly Ala Ala Glu Leu Glu Lys Leu Phe Lys
        35                  40                  45

Ala Val Glu Asn Leu Ser Lys Ala Ala Gln Asp Thr Leu Lys Asn Ala
    50                  55                  60

Val Lys Glu Leu Thr Ser Xaa Ser Asp Asp Phe Thr Lys Lys Leu Gln
65                  70                  75                  80

Ser Ser His Ala Gln Leu Gly Val Ala Gly Ala Thr Thr Asp Glu
                85                  90                  95

Glu Ala Lys Lys Ala Ile Leu Arg Thr Asn Ala Ile Lys Asp Lys Gly
            100                 105                 110

Ala Asp Glu Leu Glu Lys Leu Phe Lys Ser Val Glu Ser Leu Ala Lys
        115                 120                 125

Ala Ala Gln Asp Ala Leu Ala Asn Ser Val Asn Glu Leu Thr Ser Xaa
    130                 135                 140

Ser Glu Glu Phe Thr Ala Lys Leu Lys Gly Glu His Thr Asp Leu Gly
145                 150                 155                 160

Lys Glu Gly Val Thr Asp Asp Asn Ala Lys Lys Ala Ile Leu Lys Thr
                165                 170                 175

Asn Asn Asp Lys Thr Lys Gly Ala Asp Glu Leu Glu Lys Leu Phe Glu
            180                 185                 190

Ser Val Lys Asn Leu Ser Lys Ala Ala Lys Glu Met Leu Thr Asn Ser
        195                 200                 205

Val Lys Glu Leu Thr Ser Xaa Ser Glu Glu Phe Thr Lys Lys Leu Lys
    210                 215                 220

Glu Lys His Thr Asp Leu Gly Lys Lys Asp Ala Thr Asp Val His Ala
225                 230                 235                 240

Lys Glu Ala Ile Leu Lys Thr Asn Gly Thr Lys Asp Lys Gly Ala Ala
                245                 250                 255

Glu Leu Glu Lys Leu Phe Glu Ser Val Glu Asn Leu Ala Lys Ala Ala
            260                 265                 270

Lys Glu Met Leu Ser Asn Ser Val Lys Glu Leu Thr Ser Xaa Ser Glu
        275                 280                 285

Thr Phe Thr Asn Lys Leu Lys Glu Lys His Thr Asp Leu Gly Lys Glu
    290                 295                 300

Gly Val Thr Asp Ala Asp Ala Lys Glu Ala Ile Leu Lys Thr Asn Gly
305                 310                 315                 320

Thr Lys Thr Lys Gly Ala Glu Glu Leu Gly Lys Leu Phe Glu Ser Val
                325                 330                 335
```

```
Glu Val Leu Ser Lys Ala Ala Lys Glu Met Leu Ala Asn Ser Val Lys
            340                 345                 350
Glu Leu Thr Ser Xaa Ser Glu Phe Ser Thr Lys Leu Lys Asp Asn
            355                 360                 365
His Ala Gln Leu Gly Ile Gln Gly Val Thr Asp Glu Asn Ala Lys Lys
            370                 375                 380
Ala Ile Leu Lys Ala Asn Ala Ala Gly Lys Asp Lys Gly Val Glu Glu
385                 390                 395                 400
Leu Glu Lys Leu Ser Gly Ser Leu Glu Ser Leu Ser Lys Ala Ala Lys
                405                 410                 415
Glu Met Leu Ala Asn Ser Val Lys Glu Leu Thr Ser Xaa Ser Glu Asp
                420                 425                 430
Phe Thr Lys Lys Leu Glu Gly Glu His Ala Gln Leu Gly Ile Glu Asn
                435                 440                 445
Val Thr Asp Glu Asn Ala Lys Lys Ala Ile Leu Ile Thr Asp Ala Ala
            450                 455                 460
Lys Asp Lys Gly Ala Ala Glu Leu Glu Lys Leu Phe Lys Ala Val Glu
465                 470                 475                 480
Asn Leu Ala Lys Ala Ala Lys Glu Met Leu Ala Asn Ser Val Lys Glu
                485                 490                 495
Leu Thr Ser Xaa Ser Glu Ser Phe Thr Lys Lys Leu Ser Asp Asn Gln
                500                 505                 510
Ala Glu Leu Gly Ile Glu Asn Ala Thr Asp Asp Asn Ala Lys Lys Ala
                515                 520                 525
Ile Leu Lys Thr His Asn Ala Lys Asp Lys Gly Ala Glu Glu Leu Val
            530                 535                 540
Lys Leu Ser Glu Ser Val Ala Gly Leu Leu Lys Ala Ala Gln Ala Ile
545                 550                 555                 560
Leu Ala Asn Ser Val Lys Glu Leu Thr Ser Pro Val Val Ala Glu Ser
                565                 570                 575
Pro Lys Lys Pro
            580

<210> SEQ ID NO 128
<211> LENGTH: 573
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (430)..(430)
```

```
<223> OTHER INFORMATION: Xaa can be any naturally occurring amino acid
<220> FEATURE:
<221> NAME/KEY: misc_feature
<222> LOCATION: (501)..(501)
<223> OTHER INFORMATION: Xaa can be any naturally occurring amino acid

<400> SEQUENCE: 128
```

Asn Lys Ala Phe Thr Asp Lys Leu Lys Ser Ser His Ala Glu Leu Gly
1               5                   10                  15

Ile Ala Asn Gly Ala Ala Thr Asp Ala Asn Lys Ala Ala Ile Leu
            20                  25                  30

Lys Thr Asn Gly Thr Lys Asp Lys Gly Ala Gln Glu Leu Glu Lys Leu
            35                  40                  45

Phe Glu Ser Val Lys Asn Leu Ser Lys Ala Ala Gln Glu Thr Leu Asn
50                  55                  60

Asn Ser Val Lys Glu Leu Thr Ser Xaa Ser Glu Ala Phe Thr Asn Arg
65                  70                  75                  80

Leu Lys Gly Ser His Ala Gln Leu Gly Val Ala Ala Ala Thr Asp Asp
                85                  90                  95

His Ala Lys Glu Ala Ile Leu Lys Ser Asn Pro Thr Lys Asp Lys Gly
            100                 105                 110

Ala Lys Glu Leu Lys Asp Leu Ser Glu Ser Val Glu Ser Leu Ala Lys
        115                 120                 125

Ala Ala Gln Glu Ala Leu Ala Asn Ser Val Lys Glu Leu Thr Asn Xaa
    130                 135                 140

Ser Glu Ala Phe Thr Lys Lys Leu Gln Asp Ser Asn Ala Asp Leu Gly
145                 150                 155                 160

Lys His Asp Ala Thr Asp Ala Asp Ala Lys Lys Ala Ile Leu Lys Thr
                165                 170                 175

Asp Ala Thr Lys Asp Lys Gly Ala Lys Glu Leu Glu Glu Leu Phe Lys
            180                 185                 190

Ser Val Glu Ser Leu Ser Lys Ala Ala Lys Glu Ala Leu Ser Asn Ser
        195                 200                 205

Val Lys Glu Leu Thr Ser Xaa Ser Glu Lys Phe Thr Asp Lys Leu Lys
    210                 215                 220

Ser Glu Asn Ala Ala Leu Gly Lys Gln Asp Ala Ser Asp Asp Asp Ala
225                 230                 235                 240

Lys Lys Ala Ile Leu Lys Thr His Asn Asp Ile Thr Lys Gly Ala Lys
                245                 250                 255

Glu Leu Lys Glu Leu Ser Glu Ser Val Glu Thr Leu Leu Lys Ala Ala
            260                 265                 270

Lys Glu Met Leu Ala Asn Ser Val Lys Glu Leu Thr Ser Xaa Ser Glu
        275                 280                 285

Ala Phe Thr Asn Arg Leu Thr Gly Ser His Ala Gln His Gly Val Ala
    290                 295                 300

Ala Ala Thr Asp Asp His Ala Lys Glu Ala Ile Leu Lys Ser Asn Pro
305                 310                 315                 320

Thr Lys Asp Lys Gly Ala Lys Glu Leu Lys Asp Leu Ser Glu Ser Val
                325                 330                 335

Glu Ser Leu Ala Lys Ala Ala Gln Glu Ala Leu Ala Asn Ser Val Lys
            340                 345                 350

Glu Leu Thr Asn Xaa Ser Glu Ala Phe Thr Lys Lys Leu Lys Asp Ser
        355                 360                 365

Asn Ala Gln Leu Gly Met Gln Asn Gly Ala Ala Thr Asp Ala His Ala
    370                 375                 380

```
Lys Ala Ala Ile Leu Lys Thr Asp Ala Thr Lys Asp Lys Gly Ala Thr
385                 390                 395                 400

Glu Leu Gly Glu Leu Phe Lys Ser Val Glu Ser Leu Ser Lys Ala Ala
                405                 410                 415

Gln Glu Ala Ser Ala Asn Ser Val Lys Glu Leu Thr Ser Xaa Ser Glu
            420                 425                 430

Ala Phe Thr Asp Lys Leu Lys Asn Glu His Ala Ser Leu Gly Lys Lys
        435                 440                 445

Asp Ala Thr Asp Asp Ala Lys Ala Ile Leu Lys Thr Asn Val
    450                 455                 460

Asp Lys Thr Lys Gly Ala Asp Glu Leu Ile Lys Leu Ser Gly Ser Leu
465                 470                 475                 480

Glu Ser Leu Ser Lys Ala Ala Gln Ala Ile Leu Ala Asn Ser Val Lys
                485                 490                 495

Glu Leu Thr Ser Xaa Ser Asp Lys Phe Thr Lys Lys Leu Thr Asp Ser
                500                 505                 510

His Ala Gln Leu Gly Ala Val Gly Gly Ala Ile Asn Asp Asp Arg Ala
            515                 520                 525

Lys Glu Ala Ile Leu Lys Thr His Gly Thr Asn Asp Lys Gly Ala Lys
530                 535                 540

Glu Leu Lys Glu Leu Ser Glu Ser Val Glu Ser Leu Ala Lys Ala Ala
545                 550                 555                 560

Gln Ala Ala Leu Ala Asn Ser Val Lys Glu Leu Thr Ser
                565                 570

<210> SEQ ID NO 129
<211> LENGTH: 569
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid
<220> FEATURE:
<221> NAME/KEY: misc_feature
<222> LOCATION: (499)..(499)
<223> OTHER INFORMATION: Xaa can be any naturally occurring amino acid

<400> SEQUENCE: 129

Ser Glu Ala Phe Thr Asn Lys Leu Lys Glu Lys His Ala Glu Leu Gly
1               5                   10                  15

Val Asn Gly Gly Asp Thr Asp Asp Asn Ala Lys Ala Ala Ile Phe
```

```
                 20                  25                  30
Lys Thr His Pro Thr Lys Asp Lys Gly Val Glu Asp Leu Glu Lys Leu
                 35                  40                  45
Ser Glu Ser Val Lys Ser Leu Leu Lys Ala Ala Gln Ala Ala Leu Ser
 50                  55                  60
Asn Ser Val Lys Glu Leu Thr Ser Xaa Ser Glu Ala Phe Thr Lys Lys
 65                  70                  75                  80
Leu Gln Asp Ser Asn Ala Asp Leu Gly Lys His Asn Ala Thr Asp Ala
                 85                  90                  95
Asp Ser Lys Glu Ala Ile Leu Lys Thr Asn Gly Thr Lys Thr Lys Gly
                100                 105                 110
Ala Lys Glu Leu Glu Glu Leu Phe Lys Ser Val Glu Ser Leu Ser Lys
                115                 120                 125
Ala Ala Lys Glu Ala Leu Ser Asn Ser Val Lys Glu Leu Thr Ser Xaa
                130                 135                 140
Ser Glu Lys Phe Ala Gly Lys Leu Lys Asn Glu His Ala Ser Leu Gly
145                 150                 155                 160
Lys Lys Asp Ala Thr Asp Asp Ala Lys Lys Ala Ile Leu Lys Thr
                165                 170                 175
His Gly Asn Thr Asp Lys Gly Ala Lys Glu Leu Lys Asp Leu Ser Asp
                180                 185                 190
Ser Val Glu Ser Leu Val Lys Ala Ala Lys Glu Met Leu Thr Asn Ser
                195                 200                 205
Val Lys Glu Leu Thr Ser Xaa Ser Glu Lys Phe Thr Thr Lys Leu Lys
                210                 215                 220
Asp Ser His Ala Glu Leu Gly Ile Gln Ser Val Gln Asp Asp Asn Ala
225                 230                 235                 240
Lys Lys Ala Ile Leu Lys Thr His Gly Thr Lys Asp Lys Gly Ala Lys
                245                 250                 255
Glu Leu Glu Glu Leu Phe Lys Ser Leu Glu Ser Leu Ser Lys Ala Ala
                260                 265                 270
Gln Ala Ala Leu Thr Asn Ser Val Lys Glu Leu Thr Asn Xaa Ser Gln
                275                 280                 285
Asp Phe Ile Asn Lys Leu Lys Gly Gly His Ala Glu Leu Gly Leu Val
                290                 295                 300
Ala Ala Thr Asp Ala Asn Ala Lys Ala Ile Leu Lys Thr Asn Gly
305                 310                 315                 320
Asp Lys Thr Lys Gly Ala Asp Glu Phe Glu Lys Leu Phe Lys Ser Val
                325                 330                 335
Glu Gly Leu Leu Lys Ala Ala Gln Glu Ala Leu Thr Asn Ser Val Lys
                340                 345                 350
Glu Leu Thr Ser Xaa Ser Ala Ala Phe Thr Lys Lys Leu Gln Asp Gly
                355                 360                 365
His Val Asp Leu Gly Lys Thr Asp Val Thr Asp Asp Asn Ala Lys Glu
                370                 375                 380
Ala Ile Leu Lys Thr Asn Pro Thr Lys Thr Lys Gly Ala Thr Glu Leu
385                 390                 395                 400
Glu Glu Leu Phe Lys Ser Val Glu Gly Leu Val Lys Ala Ala Lys Glu
                405                 410                 415
Ala Ser Ala Asn Ser Val Lys Glu Leu Thr Ser Xaa Ser Glu Ala Phe
                420                 425                 430
Thr Lys Lys Leu Lys Asp Asn Asn Ala Gln Leu Gly Ile Gln Asn Val
                435                 440                 445
```

-continued

```
Gln Asp Val Glu Ala Lys Lys Ala Ile Leu Lys Thr Asn Gly Asp Ile
    450                 455                 460
Ser Lys Gly Ala Lys Glu Leu Lys Glu Leu Phe Glu Ser Val Glu Ser
465                 470                 475                 480
Leu Ala Lys Ala Ala Gln Ala Ala Leu Ala Asn Ser Val Gln Glu Leu
                485                 490                 495
Thr Asn Xaa Ser Glu Lys Phe Thr Lys Lys Leu Ser Glu Ser His Ala
            500                 505                 510
Asp Ile Gly Ile Gln Ala Ala Thr Asp Ala Asn Ala Lys Asp Ala Ile
        515                 520                 525
Leu Lys Thr Asn Pro Thr Lys Thr Lys Gly Ala Glu Glu Leu Asp Lys
    530                 535                 540
Leu Phe Lys Ala Val Glu Asn Leu Ser Lys Ala Ala Lys Glu Met Leu
545                 550                 555                 560
Ala Asn Ser Val Lys Asp Leu Gln Val
                565

<210> SEQ ID NO 130
<211> LENGTH: 502
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid
<220> FEATURE:
<221> NAME/KEY: misc_feature
<222> LOCATION: (432)..(432)
<223> OTHER INFORMATION: Xaa can be any naturally occurring amino acid

<400> SEQUENCE: 130

Ser Glu Ala Phe Thr Asn Lys Leu Lys Glu Lys Thr Gln Glu Leu Ala
1               5                   10                  15
Val Ala Ala Gly Ala Ala Thr Asp Ile Asp Ala Lys Lys Ala Ile Leu
                20                  25                  30
Lys Thr Asn Arg Asp Lys Asp Leu Gly Ala Asp Glu Arg Gly Lys Leu
            35                  40                  45
Phe Lys Ser Val Glu Ser Leu Ser Lys Ala Ala Gln Glu Ala Ser Ala
    50                  55                  60
Asn Ser Val Lys Glu Leu Thr Ser Xaa Ser Val Ala Phe Thr Ser Lys
65                  70                  75                  80
Leu Lys Ser Ser Asn Ala Gln Leu Gly Val Ala Asn Gly Asn Ala Thr
                85                  90                  95
Asp Asp Asp Ala Lys Lys Ala Ile Leu Lys Thr Asn Thr Pro Asn Asp
            100                 105                 110
```

```
Lys Gly Ala Lys Glu Leu Lys Glu Leu Phe Glu Ser Val Glu Ser Leu
            115                 120                 125

Ala Lys Ala Ala Gln Ala Ala Leu Val Asn Ser Val Gln Glu Leu Thr
        130                 135                 140

Asn Xaa Ser Glu Glu Phe Thr Asn Lys Leu Lys Ser Gly His Ala Asp
145                 150                 155                 160

Leu Gly Lys Gln Asp Ala Thr Asp His Ala Lys Ala Ala Ile Leu
                165                 170                 175

Lys Thr His Ala Thr Thr Asp Lys Gly Ala Lys Glu Phe Lys Asp Leu
                180                 185                 190

Phe Glu Ser Val Glu Gly Leu Leu Lys Ala Ala Gln Val Ala Leu Thr
            195                 200                 205

Asn Ser Val Lys Glu Leu Thr Ser Xaa Ser Glu Glu Phe Thr Asn Lys
210                 215                 220

Leu Lys Gly Gly His Ala Glu Leu Gly Leu Ala Ala Ala Thr Asp Glu
225                 230                 235                 240

Asn Ala Lys Lys Ala Ile Leu Lys Thr Asn Gly Thr Lys Asp Lys Gly
                245                 250                 255

Ala Glu Glu Leu Glu Lys Leu Phe Lys Ser Val Glu Ser Leu Ala Lys
            260                 265                 270

Ala Ala Lys Glu Ser Leu Thr Asn Ser Val Lys Glu Leu Thr Asn Xaa
        275                 280                 285

Ser Ala Ala Phe Thr Lys Lys Leu Ala Asp Ser Asn Ala Asp Leu Gly
        290                 295                 300

Val Ala Ala Gly Asn Ala Thr Asp Asp Asn Ala Lys Arg Ala Ile Leu
305                 310                 315                 320

Lys Thr His Gly His Glu Asp Lys Gly Gly Lys Glu Leu Lys Glu Leu
                325                 330                 335

Ser Glu Ala Val Lys Ser Leu Leu Lys Ala Ala Gln Ala Ala Leu Ala
            340                 345                 350

Asn Ser Val Gln Glu Leu Thr Ser Xaa Ser Glu Asp Phe Thr Asn Lys
        355                 360                 365

Leu Lys Asn Gly Asn Ala Gln Leu Gly Leu Ala Ala Ala Thr Asp Asp
        370                 375                 380

Asn Ala Lys Ala Ala Ile Leu Lys Thr Asn Gly Thr Asn Asp Lys Gly
385                 390                 395                 400

Ala Lys Glu Leu Lys Asp Leu Ser Asp Ser Val Glu Ser Leu Val Lys
            405                 410                 415

Ala Ala Gln Val Met Leu Thr Asn Ser Val Lys Glu Leu Thr Ser Xaa
        420                 425                 430

Ser Glu Lys Phe Thr Thr Lys Leu Arg Asp Ser His Ala Glu Leu Gly
        435                 440                 445

Ile Gln Asn Val Gln Asp Asp Asn Ala Lys Arg Ala Ile Leu Lys Thr
        450                 455                 460

His Gly Asn Lys Asp Lys Gly Ala Lys Glu Leu Lys Glu Leu Ser Glu
465                 470                 475                 480

Ser Leu Glu Lys Leu Ser Lys Ala Ala Gln Ala Ala Leu Ala Asn Ser
            485                 490                 495

Val Gln Glu Leu Thr Ser
            500

<210> SEQ ID NO 131
<211> LENGTH: 580
```

```
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (356)..(356)
<223> OTHER INFORMATION: Xaa can be any naturally occurring amino acid
<220> FEATURE:
<221> NAME/KEY: misc_feature
<222> LOCATION: (429)..(429)
<223> OTHER INFORMATION: Xaa can be any naturally occurring amino acid
<220> FEATURE:
<221> NAME/KEY: misc_feature
<222> LOCATION: (500)..(500)
<223> OTHER INFORMATION: Xaa can be any naturally occurring amino acid

<400> SEQUENCE: 131

Ser Glu Thr Phe Thr Asn Lys Leu Lys Glu Lys His Thr Asp Leu Gly
1               5                   10                  15

Lys Glu Gly Val Thr Asp Ala Asp Ala Lys Glu Ala Ile Leu Lys Thr
            20                  25                  30

Asn Gly Thr Lys Thr Lys Gly Ala Glu Glu Leu Gly Lys Leu Phe Glu
        35                  40                  45

Ser Val Glu Val Leu Ser Lys Ala Ala Lys Glu Met Leu Ala Asn Ser
    50                  55                  60

Val Lys Glu Leu Thr Ser Xaa Ser Glu Glu Phe Ser Thr Lys Leu Lys
65                  70                  75                  80

Asp Asn His Ala Gln Leu Gly Ile Gln Gly Val Thr Asp Glu Asn Ala
                85                  90                  95

Lys Lys Ala Ile Leu Lys Ala Asn Ala Ala Gly Lys Asp Lys Gly Val
            100                 105                 110

Glu Glu Leu Glu Lys Leu Ser Gly Ser Leu Glu Ser Leu Ser Lys Ala
        115                 120                 125

Ala Lys Glu Met Leu Ala Asn Ser Val Lys Glu Leu Thr Ser Xaa Ser
    130                 135                 140

Glu Asp Phe Thr Lys Lys Leu Glu Gly Glu His Ala Gln Leu Gly Ile
145                 150                 155                 160

Glu Asn Val Thr Asp Glu Asn Ala Lys Lys Ala Ile Leu Ile Thr Asp
                165                 170                 175

Ala Ala Lys Asp Lys Gly Ala Ala Glu Leu Glu Lys Leu Phe Lys Ala
            180                 185                 190

Val Glu Asn Leu Ala Lys Ala Lys Glu Met Leu Ala Asn Ser Val
    195                 200                 205

Lys Glu Leu Thr Ser Xaa Ser Glu Ser Phe Thr Lys Lys Leu Ser Asp
    210                 215                 220

Asn Gln Ala Glu Leu Gly Ile Glu Asn Ala Thr Asp Asp Asn Ala Lys
225                 230                 235                 240
```

```
Lys Ala Ile Leu Lys Thr His Asn Ala Lys Asp Lys Gly Ala Glu Glu
            245                 250                 255

Leu Val Lys Leu Ser Glu Ser Val Ala Gly Leu Leu Lys Ala Ala Gln
            260                 265                 270

Ala Ile Leu Ala Asn Ser Val Lys Glu Leu Thr Ser Xaa Ser Thr Glu
            275                 280                 285

Phe Thr Asn Lys Leu Lys Ser Glu His Ala Val Leu Gly Leu Asp Asn
            290                 295                 300

Leu Thr Asp Asp Asn Ala Gln Arg Ala Ile Leu Lys Lys His Ala Asn
305                 310                 315                 320

Lys Asp Lys Gly Ala Ala Glu Leu Glu Lys Leu Phe Lys Ala Val Glu
            325                 330                 335

Asn Leu Ser Lys Ala Ala Gln Asp Thr Leu Lys Asn Ala Val Lys Glu
            340                 345                 350

Leu Thr Ser Xaa Ser Asp Asp Phe Thr Lys Lys Leu Gln Ser Ser His
            355                 360                 365

Ala Gln Leu Gly Val Ala Gly Gly Ala Thr Thr Asp Glu Glu Ala Lys
            370                 375                 380

Lys Ala Ile Leu Arg Thr Asn Ala Ile Lys Asp Lys Gly Ala Asp Glu
385                 390                 395                 400

Leu Glu Lys Leu Phe Lys Ser Val Glu Ser Leu Ala Lys Ala Ala Gln
            405                 410                 415

Asp Ala Leu Ala Asn Ser Val Asn Glu Leu Thr Ser Xaa Ser Glu Glu
            420                 425                 430

Phe Thr Ala Lys Leu Lys Gly Glu His Thr Asp Leu Gly Lys Glu Gly
            435                 440                 445

Val Thr Asp Asp Asn Ala Lys Lys Ala Ile Leu Lys Thr Asn Asn Asp
            450                 455                 460

Lys Thr Lys Gly Ala Asp Glu Leu Glu Lys Leu Phe Glu Ser Val Lys
465                 470                 475                 480

Asn Leu Ser Lys Ala Ala Lys Glu Met Leu Thr Asn Ser Val Lys Glu
            485                 490                 495

Leu Thr Ser Xaa Ser Glu Glu Phe Thr Lys Leu Lys Glu Lys His
            500                 505                 510

Thr Asp Leu Gly Lys Lys Asp Ala Thr Asp Val His Ala Lys Glu Ala
            515                 520                 525

Ile Leu Lys Thr Asn Gly Thr Lys Asp Lys Gly Ala Ala Glu Leu Glu
            530                 535                 540

Lys Leu Phe Glu Ser Val Glu Asn Leu Ala Lys Ala Ala Lys Glu Met
545                 550                 555                 560

Leu Ser Asn Ser Val Lys Glu Leu Thr Ser Pro Val Val Ala Glu Ser
            565                 570                 575

Pro Lys Lys Pro
            580

<210> SEQ ID NO 132
<211> LENGTH: 571
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (73)..(73)
<223> OTHER INFORMATION: Xaa can be any naturally occurring amino acid
<220> FEATURE:
```

```
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (430)..(430)
<223> OTHER INFORMATION: Xaa can be any naturally occurring amino acid
<220> FEATURE:
<221> NAME/KEY: misc_feature
<222> LOCATION: (501)..(501)
<223> OTHER INFORMATION: Xaa can be any naturally occurring amino acid

<400> SEQUENCE: 132
```

| | | | | | | | | | | | | | | | |
|---|---|---|---|---|---|---|---|---|---|---|---|---|---|---|---|
| Ser | Glu | Ala | Phe | Thr | Asn | Lys | Leu | Lys | Glu | Lys | His | Ala | Glu | Leu | Gly |
| 1 | | | | 5 | | | | | 10 | | | | | 15 | |
| Val | Asn | Gly | Gly | Asp | Thr | Thr | Asp | Asn | Ala | Lys | Ala | Ala | Ile | Phe | |
| | | | 20 | | | | | 25 | | | | | 30 | | |
| Lys | Thr | His | Pro | Thr | Lys | Asp | Lys | Gly | Val | Glu | Asp | Leu | Glu | Lys | Leu |
| | | 35 | | | | | 40 | | | | | 45 | | | |
| Ser | Glu | Ser | Val | Lys | Ser | Leu | Leu | Lys | Ala | Ala | Gln | Ala | Ala | Leu | Ser |
| 50 | | | | | 55 | | | | | 60 | | | | | |
| Asn | Ser | Val | Lys | Glu | Leu | Thr | Ser | Xaa | Ser | Glu | Lys | Phe | Thr | Thr | Lys |
| 65 | | | | | 70 | | | | | 75 | | | | | 80 |
| Leu | Lys | Asp | Ser | His | Ala | Glu | Leu | Gly | Ile | Gln | Ser | Val | Gln | Asp | Asp |
| | | | | 85 | | | | | 90 | | | | | 95 | |
| Asn | Ala | Lys | Lys | Ala | Ile | Leu | Lys | Thr | His | Gly | Thr | Lys | Asp | Lys | Gly |
| | | | 100 | | | | | 105 | | | | | 110 | | |
| Ala | Lys | Glu | Leu | Glu | Glu | Leu | Phe | Lys | Ser | Leu | Glu | Ser | Leu | Ser | Lys |
| | | 115 | | | | | 120 | | | | | 125 | | | |
| Ala | Ala | Gln | Ala | Ala | Leu | Thr | Asn | Ser | Val | Lys | Glu | Leu | Thr | Asn | Xaa |
| 130 | | | | | 135 | | | | | 140 | | | | | |
| Ser | Asp | Lys | Phe | Thr | Lys | Lys | Leu | Thr | Asp | Ser | His | Ala | Gln | Leu | Gly |
| 145 | | | | | 150 | | | | | 155 | | | | | 160 |
| Ala | Val | Gly | Gly | Ala | Ile | Asn | Asp | Asp | Arg | Ala | Lys | Glu | Ala | Ile | Leu |
| | | | | 165 | | | | | 170 | | | | | 175 | |
| Lys | Thr | His | Gly | Thr | Asn | Asp | Lys | Gly | Ala | Lys | Glu | Leu | Lys | Glu | Leu |
| | | | | 180 | | | | | 185 | | | | | 190 | |
| Ser | Glu | Ser | Val | Glu | Ser | Leu | Ala | Lys | Ala | Ala | Gln | Ala | Ala | Leu | Ala |
| | | | 195 | | | | | 200 | | | | | 205 | | |
| Asn | Ser | Val | Lys | Glu | Leu | Thr | Ser | Xaa | Ser | Glu | Lys | Phe | Thr | Thr | Lys |
| | | | 210 | | | | | 215 | | | | | 220 | | |
| Leu | Arg | Asp | Ser | His | Ala | Glu | Leu | Gly | Ile | Gln | Asn | Val | Gln | Asp | Asp |
| 225 | | | | | 230 | | | | | 235 | | | | | 240 |
| Asn | Ala | Lys | Arg | Ala | Ile | Leu | Lys | Thr | His | Gly | Asn | Lys | Asp | Lys | Gly |
| | | | | 245 | | | | | 250 | | | | | 255 | |
| Ala | Lys | Glu | Leu | Lys | Glu | Leu | Ser | Glu | Ser | Leu | Glu | Lys | Leu | Ser | Lys |
| | | | 260 | | | | | 265 | | | | | 270 | | |
| Ala | Ala | Gln | Ala | Ala | Leu | Ala | Asn | Ser | Val | Gln | Glu | Leu | Thr | Ser | Xaa |
| | | | | 275 | | | | | 280 | | | | | 285 | |

-continued

```
Ser Glu Ala Phe Thr Lys Lys Leu Lys Asp Asn Asn Ala Gln Leu Gly
    290                 295                 300

Ile Gln Asn Val Gln Asp Val Glu Ala Lys Lys Ala Ile Leu Lys Thr
305                 310                 315                 320

Asn Gly Asp Ile Ser Lys Gly Ala Lys Glu Leu Lys Glu Leu Phe Glu
                325                 330                 335

Ser Val Glu Ser Leu Ala Lys Ala Ala Gln Ala Ala Leu Ala Asn Ser
            340                 345                 350

Val Gln Glu Leu Thr Asn Xaa Ser Glu Ala Phe Thr Asp Lys Leu Lys
        355                 360                 365

Asn Glu His Ala Ser Leu Gly Lys Lys Asp Ala Thr Asp Asp Ala
    370                 375                 380

Lys Lys Ala Ile Leu Lys Thr Asn Val Asp Lys Thr Lys Gly Ala Asp
385                 390                 395                 400

Glu Leu Ile Lys Leu Ser Gly Ser Leu Glu Ser Leu Ser Lys Ala Ala
                405                 410                 415

Gln Ala Ile Leu Ala Asn Ser Val Lys Glu Leu Thr Ser Xaa Ser Glu
            420                 425                 430

Ala Phe Thr Asn Arg Leu Lys Gly Ser His Ala Gln Leu Gly Val Ala
        435                 440                 445

Ala Ala Thr Asp Asp His Ala Lys Glu Ala Ile Leu Lys Ser Asn Pro
    450                 455                 460

Thr Lys Asp Lys Gly Ala Lys Glu Leu Lys Asp Leu Ser Glu Ser Val
465                 470                 475                 480

Glu Ser Leu Ala Lys Ala Ala Gln Glu Ala Leu Ala Asn Ser Val Lys
                485                 490                 495

Glu Leu Thr Asn Xaa Ser Glu Lys Phe Ala Gly Lys Leu Lys Asn Glu
            500                 505                 510

His Ala Ser Leu Gly Lys Lys Asp Ala Thr Asp Asp Ala Lys Lys
        515                 520                 525

Ala Ile Leu Lys Thr His Gly Asn Thr Asp Lys Gly Ala Lys Glu Leu
    530                 535                 540

Lys Asp Leu Ser Asp Ser Val Glu Ser Leu Val Lys Ala Ala Lys Glu
545                 550                 555                 560

Met Leu Thr Asn Ser Val Lys Glu Leu Thr Ser
                565                 570

<210> SEQ ID NO 133
<211> LENGTH: 575
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
```

```
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (432)..(432)
<223> OTHER INFORMATION: Xaa can be any naturally occurring amino acid
<220> FEATURE:
<221> NAME/KEY: misc_feature
<222> LOCATION: (505)..(505)
<223> OTHER INFORMATION: Xaa can be any naturally occurring amino acid

<400> SEQUENCE: 133
```

| Ser | Glu | Ala | Phe | Thr | Asn | Arg | Leu | Thr | Gly | Ser | His | Ala | Gln | His | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Val Ala Ala Ala Thr Asp Asp His Ala Lys Glu Ala Ile Leu Lys Ser
                20                  25                  30

Asn Pro Thr Lys Asp Lys Gly Ala Lys Glu Leu Lys Asp Leu Ser Glu
            35                  40                  45

Ser Val Glu Ser Leu Ala Lys Ala Ala Gln Glu Ala Leu Ala Asn Ser
 50                  55                  60

Val Lys Glu Leu Thr Asn Xaa Ser Glu Lys Phe Thr Asp Lys Leu Lys
 65                  70                  75                  80

Ser Glu Asn Ala Ala Leu Gly Lys Gln Asp Ala Ser Asp Asp Asp Ala
                85                  90                  95

Lys Lys Ala Ile Leu Lys Thr His Asn Asp Ile Thr Lys Gly Ala Lys
            100                 105                 110

Glu Leu Lys Glu Leu Ser Glu Ser Val Glu Thr Leu Leu Lys Ala Ala
        115                 120                 125

Lys Glu Met Leu Ala Asn Ser Val Lys Glu Leu Thr Ser Xaa Ser Glu
130                 135                 140

Ala Phe Thr Asn Lys Leu Lys Glu Lys Thr Gln Glu Leu Ala Val Ala
145                 150                 155                 160

Ala Gly Ala Ala Thr Asp Ile Asp Ala Lys Lys Ala Ile Leu Lys Thr
                165                 170                 175

Asn Arg Asp Lys Asp Leu Gly Ala Asp Glu Arg Gly Lys Leu Phe Lys
            180                 185                 190

Ser Val Glu Ser Leu Ser Lys Ala Ala Gln Glu Ala Ser Ala Asn Ser
        195                 200                 205

Val Lys Glu Leu Thr Ser Xaa Ser Glu Lys Phe Thr Lys Lys Leu Ser
210                 215                 220

Glu Ser His Ala Asp Ile Gly Ile Gln Ala Ala Thr Asp Ala Asn Ala
225                 230                 235                 240

Lys Asp Ala Ile Leu Lys Thr Asn Pro Thr Lys Thr Lys Gly Ala Glu
                245                 250                 255

Glu Leu Asp Lys Leu Phe Lys Ala Val Glu Asn Leu Ser Lys Ala Ala
            260                 265                 270

Lys Glu Met Leu Ala Asn Ser Val Lys Asp Leu Gln Val Xaa Ser Val
        275                 280                 285

Ala Phe Thr Ser Lys Leu Lys Ser Ser Asn Ala Gln Leu Gly Val Ala
        290                 295                 300

Asn Gly Asn Ala Thr Asp Asp Ala Lys Lys Ala Ile Leu Lys Thr
305                 310                 315                 320

Asn Thr Pro Asn Asp Lys Gly Ala Lys Glu Leu Lys Glu Leu Phe Glu
                325                 330                 335

Ser Val Glu Ser Leu Ala Lys Ala Ala Gln Ala Ala Leu Val Asn Ser
            340                 345                 350

```
Val Gln Glu Leu Thr Asn Xaa Asn Lys Ala Phe Thr Asp Lys Leu Lys
        355                 360                 365

Ser Ser His Ala Glu Leu Gly Ile Ala Asn Gly Ala Ala Thr Asp Ala
370                 375                 380

Asn Ala Lys Ala Ala Ile Leu Lys Thr Asn Gly Thr Lys Asp Lys Gly
385                 390                 395                 400

Ala Gln Glu Leu Glu Lys Leu Phe Glu Ser Val Lys Asn Leu Ser Lys
                405                 410                 415

Ala Ala Gln Glu Thr Leu Asn Asn Ser Val Lys Glu Leu Thr Ser Xaa
                420                 425                 430

Ser Glu Ala Phe Thr Lys Lys Leu Lys Asp Ser Asn Ala Gln Leu Gly
            435                 440                 445

Met Gln Asn Gly Ala Ala Thr Asp Ala His Ala Lys Ala Ala Ile Leu
        450                 455                 460

Lys Thr Asp Ala Thr Lys Asp Lys Gly Ala Thr Glu Leu Gly Glu Leu
465                 470                 475                 480

Phe Lys Ser Val Glu Ser Leu Ser Lys Ala Ala Gln Glu Ala Ser Ala
                485                 490                 495

Asn Ser Val Lys Glu Leu Thr Ser Xaa Ser Glu Asp Phe Thr Asn Lys
                500                 505                 510

Leu Lys Asn Gly Asn Ala Gln Leu Gly Leu Ala Ala Thr Asp Asp
            515                 520                 525

Asn Ala Lys Ala Ala Ile Leu Lys Thr Asn Gly Thr Asn Asp Lys Gly
530                 535                 540

Ala Lys Glu Leu Lys Asp Leu Ser Asp Ser Val Glu Ser Leu Val Lys
545                 550                 555                 560

Ala Ala Gln Val Met Leu Thr Asn Ser Val Lys Glu Leu Thr Ser
                565                 570                 575

<210> SEQ ID NO 134
<211> LENGTH: 498
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid

<400> SEQUENCE: 134

Ser Ala Ala Phe Thr Lys Lys Leu Gln Asp Gly His Val Asp Leu Gly
1               5                   10                  15
```

```
Lys Thr Asp Val Thr Asp Asp Asn Ala Lys Glu Ala Ile Leu Lys Thr
                20                  25                  30

Asn Pro Thr Lys Thr Lys Gly Ala Thr Glu Leu Glu Glu Leu Phe Lys
            35                  40                  45

Ser Val Glu Gly Leu Val Lys Ala Ala Lys Glu Ala Ser Ala Asn Ser
 50                  55                  60

Val Lys Glu Leu Thr Ser Xaa Ser Ala Ala Phe Thr Lys Lys Leu Ala
 65                  70                  75                   80

Asp Ser Asn Ala Asp Leu Gly Val Ala Ala Gly Asn Ala Thr Asp Asp
                 85                  90                  95

Asn Ala Lys Arg Ala Ile Leu Lys Thr His Gly His Glu Asp Lys Gly
                100                 105                 110

Gly Lys Glu Leu Lys Glu Leu Ser Glu Ala Val Lys Ser Leu Leu Lys
            115                 120                 125

Ala Ala Gln Ala Ala Leu Ala Asn Ser Val Gln Glu Leu Thr Ser Xaa
                130                 135                 140

Ser Glu Glu Phe Thr Asn Lys Leu Lys Ser Gly His Ala Asp Leu Gly
145                 150                 155                 160

Lys Gln Asp Ala Thr Asp Asp His Ala Lys Ala Ala Ile Leu Lys Thr
                165                 170                 175

His Ala Thr Thr Asp Lys Gly Ala Lys Glu Phe Lys Asp Leu Phe Glu
                180                 185                 190

Ser Val Glu Gly Leu Leu Lys Ala Ala Gln Val Ala Leu Thr Asn Ser
            195                 200                 205

Val Lys Glu Leu Thr Ser Xaa Ser Gln Asp Phe Ile Asn Lys Leu Lys
210                 215                 220

Gly Gly His Ala Glu Leu Gly Leu Val Ala Ala Thr Asp Ala Asn Ala
225                 230                 235                 240

Lys Ala Ala Ile Leu Lys Thr Asn Gly Asp Lys Thr Lys Gly Ala Asp
                245                 250                 255

Glu Phe Glu Lys Leu Phe Lys Ser Val Glu Gly Leu Leu Lys Ala Ala
                260                 265                 270

Gln Glu Ala Leu Thr Asn Ser Val Lys Glu Leu Thr Ser Xaa Ser Glu
                275                 280                 285

Glu Phe Thr Asn Lys Leu Lys Gly Gly His Ala Glu Leu Gly Leu Ala
                290                 295                 300

Ala Ala Thr Asp Glu Asn Ala Lys Lys Ala Ile Leu Lys Thr Asn Gly
305                 310                 315                 320

Thr Lys Asp Lys Gly Ala Glu Glu Leu Glu Lys Leu Phe Lys Ser Val
                325                 330                 335

Glu Ser Leu Ala Lys Ala Ala Lys Glu Ser Leu Thr Asn Ser Val Lys
                340                 345                 350

Glu Leu Thr Asn Xaa Ser Glu Ala Phe Thr Lys Lys Leu Gln Asp Ser
                355                 360                 365

Asn Ala Asp Leu Gly Lys His Asp Ala Thr Asp Ala Asp Ala Lys Lys
                370                 375                 380

Ala Ile Leu Lys Thr Asp Ala Thr Lys Asp Lys Gly Ala Lys Glu Leu
385                 390                 395                 400

Glu Glu Leu Phe Lys Ser Val Glu Ser Leu Ser Lys Ala Ala Lys Glu
                405                 410                 415

Ala Leu Ser Asn Ser Val Lys Glu Leu Thr Ser Xaa Ser Glu Ala Phe
                420                 425                 430
```

```
Thr Lys Lys Leu Gln Asp Ser Asn Ala Asp Leu Gly Lys His Asn Ala
            435                 440                 445

Thr Asp Ala Asp Ser Lys Glu Ala Ile Leu Lys Thr Asn Gly Thr Lys
    450                 455                 460

Thr Lys Gly Ala Lys Glu Leu Glu Leu Phe Lys Ser Val Glu Ser
465                 470                 475                 480

Leu Ser Lys Ala Ala Lys Glu Ala Leu Ser Asn Ser Val Lys Glu Leu
                485                 490                 495

Thr Ser

<210> SEQ ID NO 135
<211> LENGTH: 436
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (356)..(356)
<223> OTHER INFORMATION: Xaa can be any naturally occurring amino acid

<400> SEQUENCE: 135

Ser Glu Glu Phe Thr Ala Lys Leu Lys Gly Glu His Thr Asp Leu Gly
1               5                   10                  15

Lys Glu Gly Val Thr Asp Asp Asn Ala Lys Lys Ala Ile Leu Lys Thr
                20                  25                  30

Asn Asn Asp Lys Thr Lys Gly Ala Asp Glu Leu Glu Lys Leu Phe Glu
            35                  40                  45

Ser Val Lys Asn Leu Ser Lys Ala Ala Lys Glu Met Leu Thr Asn Ser
        50                  55                  60

Val Lys Glu Leu Thr Ser Xaa Ser Glu Phe Thr Lys Lys Leu Lys
65                  70                  75                  80

Glu Lys His Thr Asp Leu Gly Lys Asp Ala Thr Asp Val His Ala
                85                  90                  95

Lys Glu Ala Ile Leu Lys Thr Asn Gly Thr Lys Asp Lys Gly Ala Ala
            100                 105                 110

Glu Leu Glu Lys Leu Phe Glu Ser Val Glu Asn Leu Ala Lys Ala Ala
        115                 120                 125

Lys Glu Met Leu Ser Asn Ser Val Lys Glu Leu Thr Ser Xaa Ser Glu
    130                 135                 140

Thr Phe Thr Asn Lys Leu Lys Glu Lys His Thr Asp Leu Gly Lys Glu
145                 150                 155                 160

Gly Val Thr Asp Ala Asp Ala Lys Glu Ala Ile Leu Lys Thr Asn Gly
                165                 170                 175

Thr Lys Thr Lys Gly Ala Glu Glu Leu Gly Lys Leu Phe Glu Ser Val
            180                 185                 190
```

```
Glu Val Leu Ser Lys Ala Ala Lys Glu Met Leu Ala Asn Ser Val Lys
        195                 200                 205

Glu Leu Thr Ser Xaa Ser Glu Glu Phe Ser Thr Lys Leu Lys Asp Asn
    210                 215                 220

His Ala Gln Leu Gly Ile Gln Gly Val Thr Asp Glu Asn Ala Lys Lys
225                 230                 235                 240

Ala Ile Leu Lys Ala Asn Ala Ala Gly Lys Asp Lys Gly Val Glu Glu
            245                 250                 255

Leu Glu Lys Leu Ser Gly Ser Leu Glu Ser Leu Ser Lys Ala Ala Lys
        260                 265                 270

Glu Met Leu Ala Asn Ser Val Lys Glu Leu Thr Ser Xaa Ser Glu Asp
    275                 280                 285

Phe Thr Lys Lys Leu Glu Gly Glu His Ala Gln Leu Gly Ile Glu Asn
290                 295                 300

Val Thr Asp Glu Asn Ala Lys Lys Ala Ile Leu Ile Thr Asp Ala Ala
305                 310                 315                 320

Lys Asp Lys Gly Ala Ala Glu Leu Glu Lys Leu Phe Lys Ala Val Glu
            325                 330                 335

Asn Leu Ala Lys Ala Ala Lys Glu Met Leu Ala Asn Ser Val Lys Glu
        340                 345                 350

Leu Thr Ser Xaa Ser Glu Ser Phe Thr Lys Lys Leu Ser Asp Asn Gln
    355                 360                 365

Ala Glu Leu Gly Ile Glu Asn Ala Thr Asp Asp Asn Ala Lys Lys Ala
    370                 375                 380

Ile Leu Lys Thr His Asn Ala Lys Asp Lys Gly Ala Glu Glu Leu Val
385                 390                 395                 400

Lys Leu Ser Glu Ser Val Ala Gly Leu Leu Lys Ala Ala Gln Ala Ile
            405                 410                 415

Leu Ala Asn Ser Val Lys Glu Leu Thr Ser Pro Val Val Ala Glu Ser
        420                 425                 430

Pro Lys Lys Pro
        435

<210> SEQ ID NO 136
<211> LENGTH: 500
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (430)..(430)
```

<223> OTHER INFORMATION: Xaa can be any naturally occurring amino acid

<400> SEQUENCE: 136

```
Ser Thr Glu Phe Thr Asn Lys Leu Lys Ser Glu His Ala Val Leu Gly
1               5                   10                  15
Leu Asp Asn Leu Thr Asp Asp Asn Ala Gln Arg Ala Ile Leu Lys Lys
            20                  25                  30
His Ala Asn Lys Asp Lys Gly Ala Ala Glu Leu Glu Lys Leu Phe Lys
        35                  40                  45
Ala Val Glu Asn Leu Ser Lys Ala Ala Gln Asp Thr Leu Lys Asn Ala
    50                  55                  60
Val Lys Glu Leu Thr Ser Xaa Ser Asp Asp Phe Thr Lys Leu Gln
65                  70                  75                  80
Ser Ser His Ala Gln Leu Gly Val Ala Gly Ala Thr Thr Asp Glu
            85                  90                  95
Glu Ala Lys Lys Ala Ile Leu Arg Thr Asn Ala Ile Lys Asp Lys Gly
        100                 105                 110
Ala Asp Glu Leu Glu Lys Leu Phe Lys Ser Val Glu Ser Leu Ala Lys
    115                 120                 125
Ala Ala Gln Asp Ala Leu Ala Asn Ser Val Asn Glu Leu Thr Ser Xaa
    130                 135                 140
Asn Lys Ala Phe Thr Asp Lys Leu Lys Ser Ser His Ala Glu Leu Gly
145                 150                 155                 160
Ile Ala Asn Gly Ala Ala Thr Asp Ala Asn Ala Lys Ala Ala Ile Leu
            165                 170                 175
Lys Thr Asn Gly Thr Lys Asp Lys Gly Ala Gln Glu Leu Glu Lys Leu
        180                 185                 190
Phe Glu Ser Val Lys Asn Leu Ser Lys Ala Ala Gln Glu Thr Leu Asn
    195                 200                 205
Asn Ser Val Lys Glu Leu Thr Ser Xaa Ser Glu Lys Phe Thr Asp Lys
    210                 215                 220
Leu Lys Ser Glu Asn Ala Ala Leu Gly Lys Gln Asp Ala Ser Asp Asp
225                 230                 235                 240
Asp Ala Lys Lys Ala Ile Leu Lys Thr His Asn Asp Ile Thr Lys Gly
            245                 250                 255
Ala Lys Glu Leu Lys Glu Leu Ser Glu Ser Val Glu Thr Leu Leu Lys
        260                 265                 270
Ala Ala Lys Glu Met Leu Ala Asn Ser Val Lys Glu Leu Thr Ser Xaa
    275                 280                 285
Ser Glu Asp Phe Thr Asn Lys Leu Lys Asn Gly Asn Ala Gln Leu Gly
    290                 295                 300
Leu Ala Ala Ala Thr Asp Asp Asn Ala Lys Ala Ile Leu Lys Thr
305                 310                 315                 320
Asn Gly Thr Asn Asp Lys Gly Ala Lys Glu Leu Lys Asp Leu Ser Asp
            325                 330                 335
Ser Val Glu Ser Leu Val Lys Ala Ala Gln Val Met Leu Thr Asn Ser
        340                 345                 350
Val Lys Glu Leu Thr Ser Xaa Ser Glu Lys Phe Ala Gly Lys Leu Lys
    355                 360                 365
Asn Glu His Ala Ser Leu Gly Lys Lys Asp Ala Thr Asp Asp Ala
    370                 375                 380
Lys Lys Ala Ile Leu Lys Thr His Gly Asn Thr Asp Lys Gly Ala Lys
385                 390                 395                 400
```

```
Glu Leu Lys Asp Leu Ser Asp Ser Val Glu Ser Leu Val Lys Ala Ala
                405                 410                 415

Lys Glu Met Leu Thr Asn Ser Val Lys Glu Leu Thr Ser Xaa Ser Glu
        420                 425                 430

Lys Phe Thr Lys Lys Leu Ser Glu Ser His Ala Asp Ile Gly Ile Gln
            435                 440                 445

Ala Ala Thr Asp Ala Asn Ala Lys Asp Ala Ile Leu Lys Thr Asn Pro
    450                 455                 460

Thr Lys Thr Lys Gly Ala Glu Leu Asp Lys Leu Phe Lys Ala Val
465                 470                 475                 480

Glu Asn Leu Ser Lys Ala Ala Lys Glu Met Leu Ala Asn Ser Val Lys
                485                 490                 495

Asp Leu Gln Val
            500

<210> SEQ ID NO 137
<211> LENGTH: 429
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid

<400> SEQUENCE: 137

Ser Ala Ala Phe Thr Lys Lys Leu Ala Asp Ser Asn Ala Asp Leu Gly
1               5                   10                  15

Val Ala Ala Gly Asn Ala Thr Asp Asp Asn Ala Lys Arg Ala Ile Leu
            20                  25                  30

Lys Thr His Gly His Glu Asp Lys Gly Gly Lys Glu Leu Lys Glu Leu
        35                  40                  45

Ser Glu Ala Val Lys Ser Leu Leu Lys Ala Gln Ala Ala Leu Ala
    50                  55                  60

Asn Ser Val Gln Glu Leu Thr Ser Xaa Ser Glu Ala Phe Thr Asp Lys
65                  70                  75                  80

Leu Lys Asn Glu His Ala Ser Leu Gly Lys Lys Asp Ala Thr Asp Asp
                85                  90                  95

Asp Ala Lys Lys Ala Ile Leu Lys Thr Asn Val Asp Lys Thr Lys Gly
            100                 105                 110

Ala Asp Glu Leu Ile Lys Leu Ser Gly Ser Leu Glu Ser Leu Ser Lys
        115                 120                 125

Ala Ala Gln Ala Ile Leu Ala Asn Ser Val Lys Glu Leu Thr Ser Xaa
    130                 135                 140

Ser Glu Ala Phe Thr Asn Arg Leu Lys Gly Ser His Ala Gln Leu Gly
```

```
                145                 150                 155                 160
Val Ala Ala Thr Asp Asp His Ala Lys Glu Ala Ile Leu Lys Ser
                165                 170                 175

Asn Pro Thr Lys Asp Lys Gly Ala Lys Glu Leu Lys Asp Leu Ser Glu
                180                 185                 190

Ser Val Glu Ser Leu Ala Lys Ala Ala Gln Glu Ala Leu Ala Asn Ser
                195                 200                 205

Val Lys Glu Leu Thr Asn Xaa Ser Glu Ala Phe Thr Lys Lys Leu Gln
210                 215                 220

Asp Ser Asn Ala Asp Leu Gly Lys His Asp Ala Thr Asp Ala Asp Ala
225                 230                 235                 240

Lys Lys Ala Ile Leu Lys Thr Asp Ala Thr Lys Asp Lys Gly Ala Lys
                245                 250                 255

Glu Leu Glu Glu Leu Phe Lys Ser Val Glu Ser Leu Ser Lys Ala Ala
                260                 265                 270

Lys Glu Ala Leu Ser Asn Ser Val Lys Glu Leu Thr Ser Xaa Ser Glu
                275                 280                 285

Ala Phe Thr Asn Arg Leu Thr Gly Ser His Ala Gln His Gly Val Ala
                290                 295                 300

Ala Ala Thr Asp Asp His Ala Lys Glu Ala Ile Leu Lys Ser Asn Pro
305                 310                 315                 320

Thr Lys Asp Lys Gly Ala Lys Glu Leu Lys Asp Leu Ser Glu Ser Val
                325                 330                 335

Glu Ser Leu Ala Lys Ala Ala Gln Glu Ala Leu Ala Asn Ser Val Lys
                340                 345                 350

Glu Leu Thr Asn Xaa Ser Glu Ala Phe Thr Lys Lys Leu Lys Asp Ser
                355                 360                 365

Asn Ala Gln Leu Gly Met Gln Asn Gly Ala Ala Thr Asp Ala His Ala
                370                 375                 380

Lys Ala Ala Ile Leu Lys Thr Asp Ala Thr Lys Asp Lys Gly Ala Thr
385                 390                 395                 400

Glu Leu Gly Glu Leu Phe Lys Ser Val Glu Ser Leu Ser Lys Ala Ala
                405                 410                 415

Gln Glu Ala Ser Ala Asn Ser Val Lys Glu Leu Thr Ser
                420                 425

<210> SEQ ID NO 138
<211> LENGTH: 429
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (359)..(359)
```

<223> OTHER INFORMATION: Xaa can be any naturally occurring amino acid

<400> SEQUENCE: 138

```
Ser Asp Lys Phe Thr Lys Lys Leu Thr Asp Ser His Ala Gln Leu Gly
1               5                   10                  15
Ala Val Gly Gly Ala Ile Asn Asp Asp Arg Ala Lys Glu Ala Ile Leu
            20                  25                  30
Lys Thr His Gly Thr Asn Asp Lys Gly Ala Lys Glu Leu Lys Glu Leu
            35                  40                  45
Ser Glu Ser Val Glu Ser Leu Ala Lys Ala Ala Gln Ala Ala Leu Ala
    50                  55                  60
Asn Ser Val Lys Glu Leu Thr Ser Xaa Ser Glu Ala Phe Thr Asn Lys
65                  70                  75                  80
Leu Lys Glu Lys His Ala Glu Leu Gly Val Asn Gly Gly Asp Thr Thr
                85                  90                  95
Asp Asp Asn Ala Lys Ala Ala Ile Phe Lys Thr His Pro Thr Lys Asp
            100                 105                 110
Lys Gly Val Glu Asp Leu Glu Lys Leu Ser Glu Ser Val Lys Ser Leu
            115                 120                 125
Leu Lys Ala Ala Gln Ala Ala Leu Ser Asn Ser Val Lys Glu Leu Thr
130                 135                 140
Ser Xaa Ser Glu Ala Phe Thr Lys Lys Leu Gln Asp Ser Asn Ala Asp
145                 150                 155                 160
Leu Gly Lys His Asn Ala Thr Asp Ala Asp Ser Lys Glu Ala Ile Leu
                165                 170                 175
Lys Thr Asn Gly Thr Lys Thr Lys Gly Ala Lys Glu Leu Glu Glu Leu
            180                 185                 190
Phe Lys Ser Val Glu Ser Leu Ser Lys Ala Ala Lys Glu Ala Leu Ser
            195                 200                 205
Asn Ser Val Lys Glu Leu Thr Ser Xaa Ser Glu Lys Phe Thr Thr Lys
210                 215                 220
Leu Lys Asp Ser His Ala Glu Leu Gly Ile Gln Ser Val Gln Asp Asp
225                 230                 235                 240
Asn Ala Lys Lys Ala Ile Leu Lys Thr His Gly Thr Lys Asp Lys Gly
                245                 250                 255
Ala Lys Glu Leu Glu Glu Leu Phe Lys Ser Leu Glu Ser Leu Ser Lys
            260                 265                 270
Ala Ala Gln Ala Ala Leu Thr Asn Ser Val Lys Glu Leu Thr Asn Xaa
            275                 280                 285
Ser Gln Asp Phe Ile Asn Lys Leu Lys Gly Gly His Ala Glu Leu Gly
290                 295                 300
Leu Val Ala Ala Thr Asp Ala Asn Ala Lys Ala Ile Leu Lys Thr
305                 310                 315                 320
Asn Gly Asp Lys Thr Lys Gly Ala Asp Glu Phe Glu Lys Leu Phe Lys
            325                 330                 335
Ser Val Glu Gly Leu Leu Lys Ala Ala Gln Glu Ala Leu Thr Asn Ser
            340                 345                 350
Val Lys Glu Leu Thr Ser Xaa Ser Ala Ala Phe Thr Lys Lys Leu Gln
            355                 360                 365
Asp Gly His Val Asp Leu Gly Lys Thr Asp Val Thr Asp Asp Asn Ala
        370                 375                 380
Lys Glu Ala Ile Leu Lys Thr Asn Pro Thr Lys Thr Lys Gly Ala Thr
385                 390                 395                 400
```

```
Glu Leu Glu Glu Leu Phe Lys Ser Val Gly Leu Val Lys Ala Ala
                405                 410                 415

Lys Glu Ala Ser Ala Asn Ser Val Lys Glu Leu Thr Ser
        420                 425

<210> SEQ ID NO 139
<211> LENGTH: 429
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid

<400> SEQUENCE: 139

Ser Glu Ala Phe Thr Lys Lys Leu Lys Asp Asn Asn Ala Gln Leu Gly
1               5                   10                  15

Ile Gln Asn Val Gln Asp Val Glu Ala Lys Lys Ala Ile Leu Lys Thr
            20                  25                  30

Asn Gly Asp Ile Ser Lys Gly Ala Lys Glu Leu Lys Glu Leu Phe Glu
        35                  40                  45

Ser Val Glu Ser Leu Ala Lys Ala Ala Gln Ala Ala Leu Ala Asn Ser
    50                  55                  60

Val Gln Glu Leu Thr Asn Xaa Ser Glu Ala Phe Thr Asn Lys Leu Lys
65                  70                  75                  80

Glu Lys Thr Gln Glu Leu Ala Val Ala Ala Gly Ala Ala Thr Asp Ile
                85                  90                  95

Asp Ala Lys Lys Ala Ile Leu Lys Thr Asn Arg Asp Lys Asp Leu Gly
            100                 105                 110

Ala Asp Glu Arg Gly Lys Leu Phe Lys Ser Val Glu Ser Leu Ser Lys
        115                 120                 125

Ala Ala Gln Glu Ala Ser Ala Asn Ser Val Lys Glu Leu Thr Ser Xaa
    130                 135                 140

Ser Val Ala Phe Thr Ser Lys Leu Lys Ser Ser Asn Ala Gln Leu Gly
145                 150                 155                 160

Val Ala Asn Gly Asn Ala Thr Asp Asp Ala Lys Lys Ala Ile Leu
                165                 170                 175

Lys Thr Asn Thr Pro Asn Asp Lys Gly Ala Lys Glu Leu Lys Glu Leu
            180                 185                 190

Phe Glu Ser Val Glu Ser Leu Ala Lys Ala Ala Gln Ala Ala Leu Val
        195                 200                 205

Asn Ser Val Gln Glu Leu Thr Asn Xaa Ser Glu Glu Phe Thr Asn Lys
    210                 215                 220

Leu Lys Ser Gly His Ala Asp Leu Gly Lys Gln Asp Ala Thr Asp Asp
```

```
                    225                 230                 235                 240

His Ala Lys Ala Ala Ile Leu Lys Thr His Ala Thr Thr Asp Lys Gly
                245                 250                 255

Ala Lys Glu Phe Lys Asp Leu Phe Glu Ser Val Glu Gly Leu Leu Lys
            260                 265                 270

Ala Ala Gln Val Ala Leu Thr Asn Ser Val Lys Glu Leu Thr Ser Xaa
        275                 280                 285

Ser Glu Glu Phe Thr Asn Lys Leu Lys Gly Gly His Ala Glu Leu Gly
    290                 295                 300

Leu Ala Ala Thr Asp Glu Asn Ala Lys Lys Ala Ile Leu Lys Thr
305                 310                 315                 320

Asn Gly Thr Lys Asp Lys Gly Ala Glu Glu Leu Glu Lys Leu Phe Lys
                325                 330                 335

Ser Val Glu Ser Leu Ala Lys Ala Ala Lys Glu Ser Leu Thr Asn Ser
            340                 345                 350

Val Lys Glu Leu Thr Asn Xaa Ser Glu Lys Phe Thr Thr Lys Leu Arg
        355                 360                 365

Asp Ser His Ala Glu Leu Gly Ile Gln Asn Val Gln Asp Asp Asn Ala
    370                 375                 380

Lys Arg Ala Ile Leu Lys Thr His Gly Asn Lys Asp Lys Gly Ala Lys
385                 390                 395                 400

Glu Leu Lys Glu Leu Ser Glu Ser Leu Glu Lys Leu Ser Lys Ala Ala
                405                 410                 415

Gln Ala Ala Leu Ala Asn Ser Val Gln Glu Leu Thr Ser
            420                 425

<210> SEQ ID NO 140
<211> LENGTH: 364
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid

<400> SEQUENCE: 140

Ser Glu Glu Phe Thr Lys Lys Leu Lys Glu Lys His Thr Asp Leu Gly
1               5                   10                  15

Lys Lys Asp Ala Thr Asp Val His Ala Lys Glu Ala Ile Leu Lys Thr
            20                  25                  30

Asn Gly Thr Lys Asp Lys Gly Ala Ala Glu Leu Glu Lys Leu Phe Glu
        35                  40                  45

Ser Val Glu Asn Leu Ala Lys Ala Ala Lys Glu Met Leu Ser Asn Ser
    50                  55                  60

Val Lys Glu Leu Thr Ser Xaa Ser Glu Thr Phe Thr Asn Lys Leu Lys
65                  70                  75                  80
```

```
Glu Lys His Thr Asp Leu Gly Lys Glu Gly Val Thr Asp Ala Asp Ala
                85                  90                  95

Lys Glu Ala Ile Leu Lys Thr Asn Gly Thr Lys Thr Lys Gly Ala Glu
            100                 105                 110

Glu Leu Gly Lys Leu Phe Glu Ser Val Glu Val Leu Ser Lys Ala Ala
        115                 120                 125

Lys Glu Met Leu Ala Asn Ser Val Lys Glu Leu Thr Ser Xaa Ser Glu
    130                 135                 140

Glu Phe Ser Thr Lys Leu Lys Asp Asn His Ala Gln Leu Gly Ile Gln
145                 150                 155                 160

Gly Val Thr Asp Glu Asn Ala Lys Lys Ala Ile Leu Lys Ala Asn Ala
                165                 170                 175

Ala Gly Lys Asp Lys Gly Val Glu Glu Leu Glu Lys Leu Ser Gly Ser
            180                 185                 190

Leu Glu Ser Leu Ser Lys Ala Ala Lys Glu Met Leu Ala Asn Ser Val
        195                 200                 205

Lys Glu Leu Thr Ser Xaa Ser Glu Asp Phe Thr Lys Lys Leu Glu Gly
    210                 215                 220

Glu His Ala Gln Leu Gly Ile Glu Asn Val Thr Asp Glu Asn Ala Lys
225                 230                 235                 240

Lys Ala Ile Leu Ile Thr Asp Ala Ala Lys Asp Lys Gly Ala Ala Glu
                245                 250                 255

Leu Glu Lys Leu Phe Lys Ala Val Glu Asn Leu Ala Lys Ala Ala Lys
            260                 265                 270

Glu Met Leu Ala Asn Ser Val Lys Glu Leu Thr Ser Xaa Ser Glu Ser
        275                 280                 285

Phe Thr Lys Lys Leu Ser Asp Asn Gln Ala Glu Leu Gly Ile Glu Asn
    290                 295                 300

Ala Thr Asp Asp Asn Ala Lys Lys Ala Ile Leu Lys Thr His Asn Ala
305                 310                 315                 320

Lys Asp Lys Gly Ala Glu Glu Leu Val Lys Leu Ser Glu Ser Val Ala
                325                 330                 335

Gly Leu Leu Lys Ala Ala Gln Ala Ile Leu Ala Asn Ser Val Lys Glu
            340                 345                 350

Leu Thr Ser Pro Val Val Ala Glu Ser Pro Lys Lys
        355                 360
```

<210> SEQ ID NO 141
<211> LENGTH: 358
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid

<400> SEQUENCE: 141

Ser Glu Glu Phe Thr Ala Lys Leu Lys Gly Glu His Thr Asp Leu Gly
1               5                   10                  15

Lys Glu Gly Val Thr Asp Asp Asn Ala Lys Ala Ile Leu Lys Thr
            20                  25                  30

Asn Asn Asp Lys Thr Lys Gly Ala Asp Glu Leu Glu Lys Leu Phe Glu
        35                  40                  45

Ser Val Lys Asn Leu Ser Lys Ala Ala Lys Glu Met Leu Thr Asn Ser
    50                  55                  60

Val Lys Glu Leu Thr Ser Xaa Ser Thr Glu Phe Thr Asn Lys Leu Lys
65                  70                  75                  80

Ser Glu His Ala Val Leu Gly Leu Asp Asn Leu Thr Asp Asn Ala
                85                  90                  95

Gln Arg Ala Ile Leu Lys Lys His Ala Asn Lys Asp Lys Gly Ala Ala
                100                 105                 110

Glu Leu Glu Lys Leu Phe Lys Ala Val Glu Asn Leu Ser Lys Ala Ala
                115                 120                 125

Gln Asp Thr Leu Lys Asn Ala Val Lys Glu Leu Thr Ser Xaa Ser Asp
    130                 135                 140

Asp Phe Thr Lys Lys Leu Gln Ser Ser His Ala Gln Leu Gly Val Ala
145                 150                 155                 160

Gly Gly Ala Thr Thr Asp Glu Glu Ala Lys Lys Ala Ile Leu Arg Thr
                165                 170                 175

Asn Ala Ile Lys Asp Lys Gly Ala Asp Glu Leu Glu Lys Leu Phe Lys
                180                 185                 190

Ser Val Glu Ser Leu Ala Lys Ala Ala Gln Asp Ala Leu Ala Asn Ser
                195                 200                 205

Val Asn Glu Leu Thr Ser Xaa Asn Lys Ala Phe Thr Asp Lys Leu Lys
210                 215                 220

Ser Ser His Ala Glu Leu Gly Ile Ala Asn Gly Ala Ala Thr Asp Ala
225                 230                 235                 240

Asn Ala Lys Ala Ala Ile Leu Lys Thr Asn Gly Thr Lys Asp Lys Gly
                245                 250                 255

Ala Gln Glu Leu Glu Lys Leu Phe Glu Ser Val Lys Asn Leu Ser Lys
                260                 265                 270

Ala Ala Gln Glu Thr Leu Asn Asn Ser Val Lys Glu Leu Thr Ser Xaa
    275                 280                 285

Ser Glu Lys Phe Thr Asp Lys Leu Lys Ser Glu Asn Ala Ala Leu Gly
    290                 295                 300

Lys Gln Asp Ala Ser Asp Asp Ala Lys Lys Ala Ile Leu Lys Thr
305                 310                 315                 320

His Asn Asp Ile Thr Lys Gly Ala Lys Glu Leu Lys Glu Leu Ser Glu
                325                 330                 335

Ser Val Glu Thr Leu Leu Lys Ala Ala Lys Glu Met Leu Ala Asn Ser
                340                 345                 350

Val Lys Glu Leu Thr Ser
            355

<210> SEQ ID NO 142
<211> LENGTH: 356
<212> TYPE: PRT
<213> ORGANISM: Artificial
<220> FEATURE:
<223> OTHER INFORMATION: Chimeric protein
<220> FEATURE:
<221> NAME/KEY: misc_feature

```
<222> LOCATION: (71)..(71)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid

<400> SEQUENCE: 142

Ser Glu Asp Phe Thr Asn Lys Leu Lys Asn Gly Asn Ala Gln Leu Gly
1               5                   10                  15

Leu Ala Ala Thr Asp Asp Asn Ala Lys Ala Ile Leu Lys Thr
            20                  25                  30

Asn Gly Thr Asn Asp Lys Gly Ala Lys Glu Leu Lys Asp Leu Ser Asp
            35                  40                  45

Ser Val Glu Ser Leu Val Lys Ala Ala Gln Val Met Leu Thr Asn Ser
50                  55                  60

Val Lys Glu Leu Thr Ser Xaa Ser Glu Lys Phe Ala Gly Lys Leu Lys
65                  70                  75                  80

Asn Glu His Ala Ser Leu Gly Lys Lys Asp Ala Thr Asp Asp Asp Ala
                85                  90                  95

Lys Lys Ala Ile Leu Lys Thr His Gly Asn Thr Asp Lys Gly Ala Lys
                100                 105                 110

Glu Leu Lys Asp Leu Ser Asp Ser Val Glu Ser Leu Val Lys Ala Ala
            115                 120                 125

Lys Glu Met Leu Thr Asn Ser Val Lys Glu Leu Thr Ser Xaa Ser Glu
130                 135                 140

Lys Phe Thr Lys Leu Ser Glu Ser His Ala Asp Ile Gly Ile Gln
145                 150                 155                 160

Ala Ala Thr Asp Ala Asn Ala Lys Asp Ala Ile Leu Lys Thr Asn Pro
                165                 170                 175

Thr Lys Thr Lys Gly Ala Glu Glu Leu Asp Lys Leu Phe Lys Ala Val
            180                 185                 190

Glu Asn Leu Ser Lys Ala Ala Lys Glu Met Leu Ala Asn Ser Val Lys
            195                 200                 205

Asp Leu Gln Val Xaa Ser Ala Ala Phe Thr Lys Lys Leu Ala Asp Ser
        210                 215                 220

Asn Ala Asp Leu Gly Val Ala Ala Gly Asn Ala Thr Asp Asp Asn Ala
225                 230                 235                 240

Lys Arg Ala Ile Leu Lys Thr His Gly His Glu Asp Lys Gly Gly Lys
                245                 250                 255

Glu Leu Lys Glu Leu Ser Glu Ala Val Lys Ser Leu Leu Lys Ala Ala
            260                 265                 270

Gln Ala Ala Leu Ala Asn Ser Val Gln Glu Leu Thr Ser Xaa Ser Glu
        275                 280                 285

Ala Phe Thr Asp Lys Leu Lys Asn Glu His Ala Ser Leu Gly Lys Lys
            290                 295                 300

Asp Ala Thr Asp Asp Ala Lys Lys Ala Ile Leu Lys Thr Asn Val
305                 310                 315                 320

Asp Lys Thr Lys Gly Ala Asp Glu Leu Ile Lys Leu Ser Gly Ser Leu
                325                 330                 335
```

<210> SEQ ID NO 143
<211> LENGTH: 358
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid

<400> SEQUENCE: 143

```
Ser Glu Ala Phe Thr Asn Arg Leu Lys Gly Ser His Ala Gln Leu Gly
1               5                   10                  15

Val Ala Ala Thr Asp Asp His Ala Lys Glu Ala Ile Leu Lys Ser
            20                  25                  30

Asn Pro Thr Lys Asp Lys Gly Ala Lys Glu Leu Lys Asp Leu Ser Glu
        35                  40                  45

Ser Val Glu Ser Leu Ala Lys Ala Ala Gln Glu Ala Leu Ala Asn Ser
    50                  55                  60

Val Lys Glu Leu Thr Asn Xaa Ser Glu Ala Phe Thr Lys Lys Leu Gln
65                  70                  75                  80

Asp Ser Asn Ala Asp Leu Gly Lys His Asp Ala Thr Asp Ala Asp Ala
                85                  90                  95

Lys Lys Ala Ile Leu Lys Thr Asp Ala Thr Lys Asp Lys Gly Ala Lys
            100                 105                 110

Glu Leu Glu Glu Leu Phe Lys Ser Val Glu Ser Leu Ser Lys Ala Ala
        115                 120                 125

Lys Glu Ala Leu Ser Asn Ser Val Lys Glu Leu Thr Ser Xaa Ser Glu
    130                 135                 140

Ala Phe Thr Asn Arg Leu Thr Gly Ser His Ala Gln His Gly Val Ala
145                 150                 155                 160

Ala Ala Thr Asp Asp His Ala Lys Glu Ala Ile Leu Lys Ser Asn Pro
                165                 170                 175

Thr Lys Asp Lys Gly Ala Lys Glu Leu Lys Asp Leu Ser Glu Ser Val
            180                 185                 190

Glu Ser Leu Ala Lys Ala Ala Gln Glu Ala Leu Ala Asn Ser Val Lys
        195                 200                 205

Glu Leu Thr Asn Xaa Ser Glu Ala Phe Thr Lys Lys Leu Lys Asp Ser
    210                 215                 220

Asn Ala Gln Leu Gly Met Gln Asn Gly Ala Ala Thr Asp Ala His Ala
225                 230                 235                 240

Lys Ala Ala Ile Leu Lys Thr Asp Ala Thr Lys Asp Lys Gly Ala Thr
```

```
                        245                 250                 255
Glu Leu Gly Glu Leu Phe Lys Ser Val Glu Ser Leu Ser Lys Ala Ala
            260                 265                 270

Gln Glu Ala Ser Ala Asn Ser Val Lys Glu Leu Thr Ser Xaa Ser Asp
            275                 280                 285

Lys Phe Thr Lys Lys Leu Thr Asp Ser His Ala Gln Leu Gly Ala Val
            290                 295                 300

Gly Gly Ala Ile Asn Asp Asp Arg Ala Lys Glu Ala Ile Leu Lys Thr
305                 310                 315                 320

His Gly Thr Asn Asp Lys Gly Ala Lys Glu Leu Lys Glu Leu Ser Glu
                325                 330                 335

Ser Val Glu Ser Leu Ala Lys Ala Ala Gln Ala Ala Leu Ala Asn Ser
            340                 345                 350

Val Lys Glu Leu Thr Ser
            355

<210> SEQ ID NO 144
<211> LENGTH: 356
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid

<400> SEQUENCE: 144

Ser Glu Ala Phe Thr Asn Lys Leu Lys Glu Lys His Ala Glu Leu Gly
1               5                   10                  15

Val Asn Gly Gly Asp Thr Thr Asp Asn Ala Lys Ala Ala Ile Phe
            20                  25                  30

Lys Thr His Pro Thr Lys Asp Lys Gly Val Glu Asp Leu Glu Lys Leu
            35                  40                  45

Ser Glu Ser Val Lys Ser Leu Leu Lys Ala Ala Gln Ala Ala Leu Ser
50                  55                  60

Asn Ser Val Lys Glu Leu Thr Ser Xaa Ser Gly Ala Phe Thr Lys Lys
65                  70                  75                  80

Leu Gln Asp Ser Asn Ala Asp Leu Gly Lys His Asn Ala Thr Asp Ala
            85                  90                  95

Asp Ser Lys Glu Ala Ile Leu Lys Thr Asn Gly Thr Lys Thr Lys Gly
            100                 105                 110

Ala Lys Glu Leu Glu Glu Leu Phe Lys Ser Val Glu Ser Leu Ser Lys
            115                 120                 125

Ala Ala Lys Glu Ala Leu Ser Asn Ser Val Lys Glu Leu Thr Ser Xaa
            130                 135                 140

Ser Glu Lys Phe Thr Thr Lys Leu Lys Asp Ser His Ala Glu Leu Gly
145                 150                 155                 160
```

Ile Gln Ser Val Gln Asp Asp Asn Ala Lys Lys Ala Ile Leu Lys Thr
            165                 170                 175

His Gly Thr Lys Asp Lys Gly Ala Lys Glu Leu Glu Glu Leu Phe Lys
        180                 185                 190

Ser Leu Glu Ser Leu Ser Lys Ala Ala Gln Ala Ala Leu Thr Asn Ser
        195                 200                 205

Val Lys Glu Leu Thr Asn Xaa Ser Gln Asp Phe Ile Asn Lys Leu Lys
    210                 215                 220

Gly Gly His Ala Glu Leu Gly Leu Val Ala Thr Asp Ala Asn Ala
225                 230                 235                 240

Lys Ala Ala Ile Leu Lys Thr Asn Gly Asp Lys Thr Lys Gly Ala Asp
                245                 250                 255

Glu Phe Glu Lys Leu Phe Lys Ser Val Glu Gly Leu Leu Lys Ala Ala
            260                 265                 270

Gln Glu Ala Leu Thr Asn Ser Val Lys Glu Leu Thr Ser Xaa Ser Ala
        275                 280                 285

Ala Phe Thr Lys Lys Leu Gln Asp Gly His Val Asp Leu Gly Lys Thr
    290                 295                 300

Asp Val Thr Asp Asp Asn Ala Lys Glu Ala Ile Leu Lys Thr Asn Pro
305                 310                 315                 320

Thr Lys Thr Lys Gly Ala Thr Glu Leu Glu Glu Leu Phe Lys Ser Val
                325                 330                 335

Glu Gly Leu Val Lys Ala Ala Lys Glu Ala Ser Ala Asn Ser Val Lys
            340                 345                 350

Glu Leu Thr Ser
        355

<210> SEQ ID NO 145
<211> LENGTH: 429
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid

<400> SEQUENCE: 145

Ser Glu Ala Phe Thr Lys Lys Leu Lys Asp Asn Asn Ala Gln Leu Gly
1               5                   10                  15

Ile Gln Asn Val Gln Asp Val Glu Ala Lys Lys Ala Ile Leu Lys Thr
                20                  25                  30

Asn Gly Asp Ile Ser Lys Gly Ala Lys Glu Leu Lys Glu Leu Phe Glu
            35                  40                  45

Ser Val Glu Ser Leu Ala Lys Ala Ala Gln Ala Ala Leu Ala Asn Ser

```
            50                  55                  60
Val Gln Glu Leu Thr Asn Xaa Ser Glu Ala Phe Thr Asn Lys Leu Lys
 65                  70                  75                  80

Glu Lys Thr Gln Glu Leu Ala Val Ala Ala Gly Ala Ala Thr Asp Ile
                 85                  90                  95

Asp Ala Lys Lys Ala Ile Leu Lys Thr Asn Arg Asp Lys Asp Leu Gly
            100                 105                 110

Ala Asp Glu Arg Gly Lys Leu Phe Lys Ser Val Glu Ser Leu Ser Lys
        115                 120                 125

Ala Ala Gln Glu Ala Ser Ala Asn Ser Val Lys Glu Leu Thr Ser Xaa
    130                 135                 140

Ser Val Ala Phe Thr Ser Lys Leu Lys Ser Ser Asn Ala Gln Leu Gly
145                 150                 155                 160

Val Ala Asn Gly Asn Ala Thr Asp Asp Ala Lys Lys Ala Ile Leu
                165                 170                 175

Lys Thr Asn Thr Pro Asn Asp Lys Gly Ala Lys Glu Leu Lys Glu Leu
                180                 185                 190

Phe Glu Ser Val Glu Ser Leu Ala Lys Ala Gln Ala Ala Leu Val
        195                 200                 205

Asn Ser Val Gln Glu Leu Thr Asn Xaa Ser Glu Glu Phe Thr Asn Lys
210                 215                 220

Leu Lys Ser Gly His Ala Asp Leu Gly Lys Gln Asp Ala Thr Asp Asp
225                 230                 235                 240

His Ala Lys Ala Ala Ile Leu Lys Thr His Ala Thr Thr Asp Lys Gly
                245                 250                 255

Ala Lys Glu Phe Lys Asp Leu Phe Glu Ser Val Glu Gly Leu Leu Lys
                260                 265                 270

Ala Ala Gln Val Ala Leu Thr Asn Ser Val Lys Glu Leu Thr Ser Xaa
        275                 280                 285

Ser Glu Glu Phe Thr Asn Lys Leu Lys Gly Gly His Ala Glu Leu Gly
    290                 295                 300

Leu Ala Ala Ala Thr Asp Glu Asn Ala Lys Lys Ala Ile Leu Lys Thr
305                 310                 315                 320

Asn Gly Thr Lys Asp Lys Gly Ala Glu Glu Leu Glu Lys Leu Phe Lys
                325                 330                 335

Ser Val Glu Ser Leu Ala Lys Ala Lys Glu Ser Leu Thr Asn Ser
        340                 345                 350

Val Lys Glu Leu Thr Asn Xaa Ser Glu Lys Phe Thr Thr Lys Leu Arg
    355                 360                 365

Asp Ser His Ala Glu Leu Gly Ile Gln Asn Val Gln Asp Asp Asn Ala
370                 375                 380

Lys Arg Ala Ile Leu Lys Thr His Gly Asn Lys Asp Lys Gly Ala Lys
385                 390                 395                 400

Glu Leu Lys Glu Leu Ser Glu Ser Leu Glu Lys Leu Ser Lys Ala Ala
                405                 410                 415

Gln Ala Ala Leu Ala Asn Ser Val Gln Glu Leu Thr Ser
            420                 425

<210> SEQ ID NO 146
<211> LENGTH: 580
<212> TYPE: PRT
<213> ORGANISM: Artificial
<220> FEATURE:
<223> OTHER INFORMATION: Chimeric protein
<220> FEATURE:
```

<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (429)..(429)
<223> OTHER INFORMATION: Xaa can be any naturally occurring amino acid
<220> FEATURE:
<221> NAME/KEY: misc_feature
<222> LOCATION: (500)..(500)
<223> OTHER INFORMATION: Xaa can be any naturally occurring amino acid

<400> SEQUENCE: 146

```
Ser Thr Glu Phe Thr Asn Lys Leu Lys Ser Glu His Ala Val Leu Gly
1               5                   10                  15

Leu Asp Asn Leu Thr Asp Asp Asn Ala Gln Arg Ala Ile Leu Lys Lys
            20                  25                  30

His Ala Asn Lys Asp Lys Gly Ala Ala Glu Leu Glu Lys Leu Phe Lys
        35                  40                  45

Ala Val Glu Asn Leu Ser Lys Ala Ala Gln Asp Thr Leu Lys Asn Ala
    50                  55                  60

Val Lys Glu Leu Thr Ser Xaa Ser Asp Asp Phe Thr Lys Lys Leu Gln
65                  70                  75                  80

Ser Ser His Ala Gln Leu Gly Val Ala Gly Ala Thr Thr Asp Glu
                85                  90                  95

Glu Ala Lys Lys Ala Ile Leu Arg Thr Asn Ala Ile Lys Asp Lys Gly
            100                 105                 110

Ala Asp Glu Leu Glu Lys Leu Phe Lys Ser Val Glu Ser Leu Ala Lys
        115                 120                 125

Ala Ala Gln Asp Ala Leu Ala Asn Ser Val Asn Glu Leu Thr Ser Xaa
    130                 135                 140

Ser Glu Glu Phe Thr Ala Lys Leu Lys Gly Glu His Thr Asp Leu Gly
145                 150                 155                 160

Lys Glu Gly Val Thr Asp Asp Asn Ala Lys Lys Ala Ile Leu Lys Thr
                165                 170                 175

Asn Asn Asp Lys Thr Lys Gly Ala Asp Glu Leu Glu Lys Leu Phe Glu
            180                 185                 190

Ser Val Lys Asn Leu Ser Lys Ala Ala Lys Glu Met Leu Thr Asn Ser
        195                 200                 205

Val Lys Glu Leu Thr Ser Xaa Ser Glu Glu Phe Thr Lys Lys Leu Lys
    210                 215                 220

Glu Lys His Thr Asp Leu Gly Lys Lys Asp Ala Thr Asp Val His Ala
225                 230                 235                 240

Lys Glu Ala Ile Leu Lys Thr Asn Gly Thr Lys Asp Lys Gly Ala Ala
                245                 250                 255

Glu Leu Glu Lys Leu Phe Glu Ser Val Glu Asn Leu Ala Lys Ala Ala
```

```
            260                 265                 270
Lys Glu Met Leu Ser Asn Ser Val Lys Glu Leu Thr Ser Xaa Ser Glu
            275                 280                 285

Thr Phe Thr Asn Lys Leu Lys Glu Lys His Thr Asp Leu Gly Lys Glu
            290                 295                 300

Gly Val Thr Asp Ala Asp Ala Lys Glu Ala Ile Leu Lys Thr Asn Gly
305                 310                 315                 320

Thr Lys Thr Lys Gly Ala Glu Glu Leu Gly Lys Leu Phe Glu Ser Val
                325                 330                 335

Glu Val Leu Ser Lys Ala Ala Lys Glu Met Leu Ala Asn Ser Val Lys
                340                 345                 350

Glu Leu Thr Ser Xaa Ser Glu Glu Phe Ser Thr Lys Leu Lys Asp Asn
                355                 360                 365

His Ala Gln Leu Gly Ile Gln Gly Val Thr Asp Glu Asn Ala Lys Lys
                370                 375                 380

Ala Ile Leu Lys Ala Asn Ala Ala Gly Lys Asp Lys Gly Val Glu Glu
385                 390                 395                 400

Leu Glu Lys Leu Ser Gly Ser Leu Glu Ser Leu Ser Lys Ala Ala Lys
                405                 410                 415

Glu Met Leu Ala Asn Ser Val Lys Glu Leu Thr Ser Xaa Ser Glu Asp
                420                 425                 430

Phe Thr Lys Lys Leu Glu Gly Glu His Ala Gln Leu Gly Ile Glu Asn
            435                 440                 445

Val Thr Asp Glu Asn Ala Lys Lys Ala Ile Leu Ile Thr Asp Ala Ala
450                 455                 460

Lys Asp Lys Gly Ala Ala Glu Leu Glu Lys Leu Phe Lys Ala Val Glu
465                 470                 475                 480

Asn Leu Ala Lys Ala Ala Lys Glu Met Leu Ala Asn Ser Val Lys Glu
                485                 490                 495

Leu Thr Ser Xaa Ser Glu Ser Phe Thr Lys Lys Leu Ser Asp Asn Gln
                500                 505                 510

Ala Glu Leu Gly Ile Glu Asn Ala Thr Asp Asp Asn Ala Lys Lys Ala
                515                 520                 525

Ile Leu Lys Thr His Asn Ala Lys Asp Lys Gly Ala Glu Glu Leu Val
                530                 535                 540

Lys Leu Ser Glu Ser Val Ala Gly Leu Leu Lys Ala Ala Gln Ala Ile
545                 550                 555                 560

Leu Ala Asn Ser Val Lys Glu Leu Thr Ser Pro Val Val Ala Glu Ser
                565                 570                 575

Pro Lys Lys Pro
            580

<210> SEQ ID NO 147
<211> LENGTH: 577
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
```

```
<222> LOCATION: (217)..(217)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (432)..(432)
<223> OTHER INFORMATION: Xaa can be any naturally occurring amino acid
<220> FEATURE:
<221> NAME/KEY: misc_feature
<222> LOCATION: (505)..(505)
<223> OTHER INFORMATION: Xaa can be any naturally occurring amino acid

<400> SEQUENCE: 147

Ser Glu Ala Phe Thr Asn Lys Leu Lys Glu Lys His Ala Glu Leu Gly
1               5                   10                  15

Val Asn Gly Gly Asp Thr Thr Asp Asn Ala Lys Ala Ala Ile Phe
            20                  25                  30

Lys Thr His Pro Thr Lys Asp Lys Gly Val Glu Asp Leu Glu Lys Leu
        35                  40                  45

Ser Glu Ser Val Lys Ser Leu Leu Lys Ala Ala Gln Ala Ala Leu Ser
    50                  55                  60

Asn Ser Val Lys Glu Leu Thr Ser Xaa Ser Asp Lys Phe Thr Lys Lys
65                  70                  75                  80

Leu Thr Asp Ser His Ala Gln Leu Gly Ala Val Gly Gly Ala Ile Asn
                85                  90                  95

Asp Asp Arg Ala Lys Glu Ala Ile Leu Lys Thr His Gly Thr Asn Asp
            100                 105                 110

Lys Gly Ala Lys Glu Leu Lys Glu Leu Ser Glu Ser Val Glu Ser Leu
        115                 120                 125

Ala Lys Ala Ala Gln Ala Ala Leu Ala Asn Ser Val Lys Glu Leu Thr
    130                 135                 140

Ser Xaa Ser Glu Ala Phe Thr Lys Lys Leu Lys Asp Asn Asn Ala Gln
145                 150                 155                 160

Leu Gly Ile Gln Asn Val Gln Asp Val Glu Ala Lys Lys Ala Ile Leu
                165                 170                 175

Lys Thr Asn Gly Asp Ile Ser Lys Gly Ala Lys Glu Leu Lys Glu Leu
            180                 185                 190

Phe Glu Ser Val Glu Ser Leu Ala Lys Ala Ala Gln Ala Ala Leu Ala
        195                 200                 205

Asn Ser Val Gln Glu Leu Thr Asn Xaa Ser Glu Ala Phe Thr Asn Arg
    210                 215                 220

Leu Lys Gly Ser His Ala Gln Leu Gly Val Ala Ala Ala Thr Asp Asp
225                 230                 235                 240

His Ala Lys Glu Ala Ile Leu Lys Ser Asn Pro Thr Lys Asp Lys Gly
                245                 250                 255

Ala Lys Glu Leu Lys Asp Leu Ser Glu Ser Val Glu Ser Leu Ala Lys
            260                 265                 270

Ala Ala Gln Glu Ala Leu Ala Asn Ser Val Lys Glu Leu Thr Asn Xaa
        275                 280                 285

Ser Glu Ala Phe Thr Asn Arg Leu Thr Gly Ser His Ala Gln His Gly
    290                 295                 300

Val Ala Ala Ala Thr Asp Asp His Ala Lys Glu Ala Ile Leu Lys Ser
```

```
                305                 310                 315                 320
Asn Pro Thr Lys Asp Lys Gly Ala Lys Glu Leu Lys Asp Leu Ser Glu
                325                 330                 335
Ser Val Glu Ser Leu Ala Lys Ala Ala Gln Glu Ala Leu Ala Asn Ser
            340                 345                 350
Val Lys Glu Leu Thr Asn Xaa Ser Glu Ala Phe Thr Asn Lys Leu Lys
        355                 360                 365
Glu Lys Thr Gln Glu Leu Ala Val Ala Ala Gly Ala Ala Thr Asp Ile
    370                 375                 380
Asp Ala Lys Lys Ala Ile Leu Lys Thr Asn Arg Asp Lys Asp Leu Gly
385                 390                 395                 400
Ala Asp Glu Arg Gly Lys Leu Phe Lys Ser Val Glu Ser Leu Ser Lys
                405                 410                 415
Ala Ala Gln Glu Ala Ser Ala Asn Ser Val Lys Glu Leu Thr Ser Xaa
            420                 425                 430
Ser Val Ala Phe Thr Ser Lys Leu Lys Ser Ser Asn Ala Gln Leu Gly
        435                 440                 445
Val Ala Asn Gly Asn Ala Thr Asp Asp Ala Lys Lys Ala Ile Leu
    450                 455                 460
Lys Thr Asn Thr Pro Asn Asp Lys Gly Ala Lys Glu Leu Lys Glu Leu
465                 470                 475                 480
Phe Glu Ser Val Glu Ser Leu Ala Lys Ala Ala Gln Ala Ala Leu Val
                485                 490                 495
Asn Ser Val Gln Glu Leu Thr Asn Xaa Ser Glu Ala Phe Thr Lys Lys
            500                 505                 510
Leu Lys Asp Ser Asn Ala Gln Leu Gly Met Gln Asn Gly Ala Ala Thr
        515                 520                 525
Asp Ala His Ala Lys Ala Ala Ile Leu Lys Thr Asp Ala Thr Lys Asp
    530                 535                 540
Lys Gly Ala Thr Glu Leu Gly Glu Leu Phe Lys Ser Val Glu Ser Leu
545                 550                 555                 560
Ser Lys Ala Ala Gln Glu Ala Ser Ala Asn Ser Val Lys Glu Leu Thr
                565                 570                 575
Ser
```

<210> SEQ ID NO 148
<211> LENGTH: 569
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (284)..(284)
<223> OTHER INFORMATION: Xaa can be any naturally occurring amino acid
<220> FEATURE:
<221> NAME/KEY: misc_feature
<222> LOCATION: (355)..(355)
<223> OTHER INFORMATION: Xaa can be any naturally occurring amino acid

```
<220> FEATURE:
<221> NAME/KEY: misc_feature
<222> LOCATION: (426)..(426)
<223> OTHER INFORMATION: Xaa can be any naturally occurring amino acid
<220> FEATURE:
<221> NAME/KEY: misc_feature
<222> LOCATION: (499)..(499)
<223> OTHER INFORMATION: Xaa can be any naturally occurring amino acid

<400> SEQUENCE: 148
```

Ser Ala Ala Phe Thr Lys Lys Leu Gln Asp Gly His Val Asp Leu Gly
1               5                   10                  15

Lys Thr Asp Val Thr Asp Asp Asn Ala Lys Glu Ala Ile Leu Lys Thr
            20                  25                  30

Asn Pro Thr Lys Thr Lys Gly Ala Thr Glu Leu Glu Glu Leu Phe Lys
        35                  40                  45

Ser Val Glu Gly Leu Val Lys Ala Ala Lys Glu Ala Ser Ala Asn Ser
    50                  55                  60

Val Lys Glu Leu Thr Ser Xaa Ser Glu Glu Phe Thr Asn Lys Leu Lys
65                  70                  75                  80

Ser Gly His Ala Asp Leu Gly Lys Gln Asp Ala Thr Asp Asp His Ala
                85                  90                  95

Lys Ala Ala Ile Leu Lys Thr His Ala Thr Thr Asp Lys Gly Ala Lys
            100                 105                 110

Glu Phe Lys Asp Leu Phe Glu Ser Val Glu Gly Leu Leu Lys Ala Ala
        115                 120                 125

Gln Val Ala Leu Thr Asn Ser Val Lys Glu Leu Thr Ser Xaa Ser Glu
    130                 135                 140

Glu Phe Thr Asn Lys Leu Lys Gly Gly His Ala Glu Leu Gly Leu Ala
145                 150                 155                 160

Ala Ala Thr Asp Glu Asn Ala Lys Lys Ala Ile Leu Lys Thr Asn Gly
                165                 170                 175

Thr Lys Asp Lys Gly Ala Glu Glu Leu Glu Lys Leu Phe Lys Ser Val
            180                 185                 190

Glu Ser Leu Ala Lys Ala Ala Lys Glu Ser Leu Thr Asn Ser Val Lys
        195                 200                 205

Glu Leu Thr Asn Xaa Ser Glu Ala Phe Thr Lys Lys Leu Gln Asp Ser
    210                 215                 220

Asn Ala Asp Leu Gly Lys His Asn Ala Thr Asp Ala Asp Ser Lys Glu
225                 230                 235                 240

Ala Ile Leu Lys Thr Asn Gly Thr Lys Thr Lys Gly Ala Lys Glu Leu
                245                 250                 255

Glu Glu Leu Phe Lys Ser Val Glu Ser Leu Ser Lys Ala Ala Lys Glu
            260                 265                 270

Ala Leu Ser Asn Ser Val Lys Glu Leu Thr Ser Xaa Ser Glu Ala Phe
        275                 280                 285

Thr Lys Lys Leu Gln Asp Ser Asn Ala Asp Leu Gly Lys His Asp Ala
    290                 295                 300

Thr Asp Ala Asp Ala Lys Lys Ala Ile Leu Lys Thr Asp Ala Thr Lys
305                 310                 315                 320

Asp Lys Gly Ala Lys Glu Leu Glu Glu Leu Phe Lys Ser Val Glu Ser
                325                 330                 335

Leu Ser Lys Ala Ala Lys Glu Ala Leu Ser Asn Ser Val Lys Glu Leu
            340                 345                 350

Thr Ser Xaa Ser Gln Asp Phe Ile Asn Lys Leu Lys Gly Gly His Ala
        355                 360                 365

```
Glu Leu Gly Leu Val Ala Ala Thr Asp Ala Asn Ala Lys Ala Ala Ile
        370                 375                 380

Leu Lys Thr Asn Gly Asp Lys Thr Lys Gly Ala Asp Glu Phe Glu Lys
385                 390                 395                 400

Leu Phe Lys Ser Val Glu Gly Leu Leu Lys Ala Gln Glu Ala Leu
                405                 410                 415

Thr Asn Ser Val Lys Glu Leu Thr Ser Xaa Ser Ala Ala Phe Thr Lys
                420                 425                 430

Lys Leu Ala Asp Ser Asn Ala Asp Leu Gly Val Ala Ala Gly Asn Ala
                435                 440                 445

Thr Asp Asp Asn Ala Lys Arg Ala Ile Leu Lys Thr His Gly His Glu
        450                 455                 460

Asp Lys Gly Gly Lys Glu Leu Lys Glu Leu Ser Glu Ala Val Lys Ser
465                 470                 475                 480

Leu Leu Lys Ala Ala Gln Ala Ala Leu Ala Asn Ser Val Gln Glu Leu
                485                 490                 495

Thr Ser Xaa Ser Glu Asp Phe Thr Asn Lys Leu Lys Asn Gly Asn Ala
                500                 505                 510

Gln Leu Gly Leu Ala Ala Ala Thr Asp Asp Asn Ala Lys Ala Ala Ile
                515                 520                 525

Leu Lys Thr Asn Gly Thr Asn Asp Lys Gly Ala Lys Glu Leu Lys Asp
                530                 535                 540

Leu Ser Asp Ser Val Glu Ser Leu Val Lys Ala Ala Gln Val Met Leu
545                 550                 555                 560

Thr Asn Ser Val Lys Glu Leu Thr Ser
                565

<210> SEQ ID NO 149
<211> LENGTH: 498
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid

<400> SEQUENCE: 149

Asn Lys Ala Phe Thr Asp Lys Leu Lys Ser Ser His Ala Glu Leu Gly
1               5                   10                  15

Ile Ala Asn Gly Ala Ala Thr Asp Ala Asn Ala Lys Ala Ala Ile Leu
                20                  25                  30
```

```
Lys Thr Asn Gly Thr Lys Asp Lys Gly Ala Gln Glu Leu Glu Lys Leu
         35                  40                  45

Phe Glu Ser Val Lys Asn Leu Ser Lys Ala Ala Gln Glu Thr Leu Asn
 50                  55                  60

Asn Ser Val Lys Glu Leu Thr Ser Xaa Ser Glu Lys Phe Thr Lys Lys
 65                  70                  75                  80

Leu Ser Glu Ser His Ala Asp Ile Gly Ile Gln Ala Ala Thr Asp Ala
                 85                  90                  95

Asn Ala Lys Asp Ala Ile Leu Lys Thr Asn Pro Thr Lys Thr Lys Gly
                100                 105                 110

Ala Glu Glu Leu Asp Lys Leu Phe Lys Ala Val Glu Asn Leu Ser Lys
                115                 120                 125

Ala Ala Lys Glu Met Leu Ala Asn Ser Val Lys Asp Leu Gln Val Xaa
            130                 135                 140

Ser Glu Lys Phe Thr Asp Lys Leu Lys Ser Glu Asn Ala Ala Leu Gly
145                 150                 155                 160

Lys Gln Asp Ala Ser Asp Asp Ala Lys Lys Ala Ile Leu Lys Thr
                165                 170                 175

His Asn Asp Ile Thr Lys Gly Ala Lys Glu Leu Lys Glu Leu Ser Glu
                180                 185                 190

Ser Val Glu Thr Leu Leu Lys Ala Ala Lys Glu Met Leu Ala Asn Ser
            195                 200                 205

Val Lys Glu Leu Thr Ser Xaa Ser Glu Lys Phe Ala Gly Lys Leu Lys
        210                 215                 220

Asn Glu His Ala Ser Leu Gly Lys Lys Asp Ala Thr Asp Asp Ala
225                 230                 235                 240

Lys Lys Ala Ile Leu Lys Thr His Gly Asn Thr Asp Lys Gly Ala Lys
                245                 250                 255

Glu Leu Lys Asp Leu Ser Asp Ser Val Glu Ser Leu Val Lys Ala Ala
                260                 265                 270

Lys Glu Met Leu Thr Asn Ser Val Lys Glu Leu Thr Ser Xaa Ser Glu
        275                 280                 285

Ala Phe Thr Asp Lys Leu Lys Asn Glu His Ala Ser Leu Gly Lys Lys
        290                 295                 300

Asp Ala Thr Asp Asp Ala Lys Lys Ala Ile Leu Lys Thr Asn Val
305                 310                 315                 320

Asp Lys Thr Lys Gly Ala Asp Glu Leu Ile Lys Leu Ser Gly Ser Leu
                325                 330                 335

Glu Ser Leu Ser Lys Ala Ala Gln Ala Ile Leu Ala Asn Ser Val Lys
            340                 345                 350

Glu Leu Thr Ser Xaa Ser Glu Lys Phe Thr Thr Lys Leu Arg Asp Ser
        355                 360                 365

His Ala Glu Leu Gly Ile Gln Asn Val Gln Asp Asp Asn Ala Lys Arg
370                 375                 380

Ala Ile Leu Lys Thr His Gly Asn Lys Asp Lys Gly Ala Lys Glu Leu
385                 390                 395                 400

Lys Glu Leu Ser Glu Ser Leu Glu Lys Leu Ser Lys Ala Ala Gln Ala
                405                 410                 415

Ala Leu Ala Asn Ser Val Gln Glu Leu Thr Ser Xaa Ser Glu Lys Phe
                420                 425                 430

Thr Thr Lys Leu Lys Asp Ser His Ala Glu Leu Gly Ile Gln Ser Val
            435                 440                 445
```

```
Gln Asp Asp Asn Ala Lys Lys Ala Ile Leu Lys Thr His Gly Thr Lys
    450                 455                 460

Asp Lys Gly Ala Lys Glu Leu Glu Glu Leu Phe Lys Ser Leu Glu Ser
465                 470                 475                 480

Leu Ser Lys Ala Ala Gln Ala Ala Leu Thr Asn Ser Val Lys Glu Leu
                485                 490                 495

Thr Asn

<210> SEQ ID NO 150
<211> LENGTH: 436
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (356)..(356)
<223> OTHER INFORMATION: Xaa can be any naturally occurring amino acid

<400> SEQUENCE: 150

Ser Glu Glu Phe Thr Ala Lys Leu Lys Gly Glu His Thr Asp Leu Gly
1               5                   10                  15

Lys Glu Gly Val Thr Asp Asp Asn Ala Lys Lys Ala Ile Leu Lys Thr
            20                  25                  30

Asn Asn Asp Lys Thr Lys Gly Ala Asp Glu Leu Glu Lys Leu Phe Glu
        35                  40                  45

Ser Val Lys Asn Leu Ser Lys Ala Ala Lys Glu Met Leu Thr Asn Ser
    50                  55                  60

Val Lys Glu Leu Thr Ser Xaa Ser Glu Glu Phe Thr Lys Lys Leu Lys
65                  70                  75                  80

Glu Lys His Thr Asp Leu Gly Lys Lys Asp Ala Thr Asp Val His Ala
                85                  90                  95

Lys Glu Ala Ile Leu Lys Thr Asn Gly Thr Lys Asp Lys Gly Ala Ala
            100                 105                 110

Glu Leu Glu Lys Leu Phe Glu Ser Val Glu Asn Leu Ala Lys Ala Ala
            115                 120                 125

Lys Glu Met Leu Ser Asn Ser Val Lys Glu Leu Thr Ser Xaa Ser Glu
        130                 135                 140

Thr Phe Thr Asn Lys Leu Lys Glu Lys His Thr Asp Leu Gly Lys Glu
145                 150                 155                 160

Gly Val Thr Asp Ala Asp Ala Lys Glu Ala Ile Leu Lys Thr Asn Gly
                165                 170                 175

Thr Lys Thr Lys Gly Ala Glu Glu Leu Gly Lys Leu Phe Glu Ser Val
            180                 185                 190

Glu Val Leu Ser Lys Ala Ala Lys Glu Met Leu Ala Asn Ser Val Lys
        195                 200                 205
```

Glu Leu Thr Ser Xaa Ser Glu Glu Phe Ser Thr Lys Leu Lys Asp Asn
    210                 215                 220

His Ala Gln Leu Gly Ile Gln Gly Val Thr Asp Glu Asn Ala Lys Lys
225                 230                 235                 240

Ala Ile Leu Lys Ala Asn Ala Ala Gly Lys Asp Lys Gly Val Glu Glu
                245                 250                 255

Leu Glu Lys Leu Ser Gly Ser Leu Glu Ser Leu Ser Lys Ala Ala Lys
            260                 265                 270

Glu Met Leu Ala Asn Ser Val Lys Glu Leu Thr Ser Xaa Ser Glu Asp
        275                 280                 285

Phe Thr Lys Lys Leu Glu Gly Glu His Ala Gln Leu Gly Ile Glu Asn
    290                 295                 300

Val Thr Asp Glu Asn Ala Lys Lys Ala Ile Leu Ile Thr Asp Ala Ala
305                 310                 315                 320

Lys Asp Lys Gly Ala Ala Glu Leu Glu Lys Leu Phe Lys Ala Val Glu
                325                 330                 335

Asn Leu Ala Lys Ala Ala Lys Glu Met Leu Ala Asn Ser Val Lys Glu
            340                 345                 350

Leu Thr Ser Xaa Ser Glu Ser Phe Thr Lys Lys Leu Ser Asp Asn Gln
        355                 360                 365

Ala Glu Leu Gly Ile Glu Asn Ala Thr Asp Asp Asn Ala Lys Lys Ala
    370                 375                 380

Ile Leu Lys Thr His Asn Ala Lys Asp Lys Gly Ala Glu Glu Leu Val
385                 390                 395                 400

Lys Leu Ser Glu Ser Val Ala Gly Leu Leu Lys Ala Ala Gln Ala Ile
                405                 410                 415

Leu Ala Asn Ser Val Lys Glu Leu Thr Ser Pro Val Val Ala Glu Ser
            420                 425                 430

Pro Lys Lys Pro
        435

<210> SEQ ID NO 151
<211> LENGTH: 433
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid

<400> SEQUENCE: 151

Ser Thr Glu Phe Thr Asn Lys Leu Lys Ser Glu His Ala Val Leu Gly
1               5                   10                  15

```
Leu Asp Asn Leu Thr Asp Asp Asn Ala Gln Arg Ala Ile Leu Lys Lys
         20                  25                  30

His Ala Asn Lys Asp Lys Gly Ala Ala Glu Leu Glu Lys Leu Phe Lys
         35                  40                  45

Ala Val Glu Asn Leu Ser Lys Ala Ala Gln Asp Thr Leu Lys Asn Ala
 50                  55                  60

Val Lys Glu Leu Thr Ser Xaa Ser Asp Asp Phe Thr Lys Lys Leu Gln
 65                  70                  75                  80

Ser Ser His Ala Gln Leu Gly Val Ala Gly Ala Thr Thr Asp Glu
             85                  90                  95

Glu Ala Lys Lys Ala Ile Leu Arg Thr Asn Ala Ile Lys Asp Lys Gly
             100                 105                 110

Ala Asp Glu Leu Glu Lys Leu Phe Lys Ser Val Glu Ser Leu Ala Lys
             115                 120                 125

Ala Ala Gln Asp Ala Leu Ala Asn Ser Val Asn Glu Leu Thr Ser Xaa
             130                 135                 140

Ser Glu Ala Phe Thr Asn Lys Leu Lys Glu Lys His Ala Glu Leu Gly
145                 150                 155                 160

Val Asn Gly Gly Asp Thr Thr Asp Asp Asn Ala Lys Ala Ala Ile Phe
                 165                 170                 175

Lys Thr His Pro Thr Lys Asp Lys Gly Val Glu Asp Leu Glu Lys Leu
                 180                 185                 190

Ser Glu Ser Val Lys Ser Leu Leu Lys Ala Ala Gln Ala Ala Leu Ser
             195                 200                 205

Asn Ser Val Lys Glu Leu Thr Ser Xaa Ser Glu Ala Phe Thr Lys Lys
210                 215                 220

Leu Lys Asp Ser Asn Ala Gln Leu Gly Met Gln Asn Gly Ala Ala Thr
225                 230                 235                 240

Asp Ala His Ala Lys Ala Ala Ile Leu Lys Thr Asp Ala Thr Lys Asp
                 245                 250                 255

Lys Gly Ala Thr Glu Leu Gly Glu Leu Phe Lys Ser Val Glu Ser Leu
             260                 265                 270

Ser Lys Ala Ala Gln Glu Ala Ser Ala Asn Ser Val Lys Glu Leu Thr
             275                 280                 285

Ser Xaa Ser Glu Ala Phe Thr Lys Lys Leu Gln Asp Ser Asn Ala Asp
290                 295                 300

Leu Gly Lys His Asp Ala Thr Asp Ala Asp Ala Lys Lys Ala Ile Leu
305                 310                 315                 320

Lys Thr Asp Ala Thr Lys Asp Lys Gly Ala Lys Glu Leu Glu Glu Leu
                 325                 330                 335

Phe Lys Ser Val Glu Ser Leu Ser Lys Ala Lys Glu Ala Leu Ser
             340                 345                 350

Asn Ser Val Lys Glu Leu Thr Ser Xaa Ser Ala Ala Phe Thr Lys Lys
             355                 360                 365

Leu Ala Asp Ser Asn Ala Asp Leu Gly Val Ala Ala Gly Asn Ala Thr
370                 375                 380

Asp Asp Asn Ala Lys Arg Ala Ile Leu Lys Thr His Gly His Glu Asp
385                 390                 395                 400

Lys Gly Gly Lys Glu Leu Lys Glu Leu Ser Glu Ala Val Lys Ser Leu
                 405                 410                 415

Leu Lys Ala Ala Gln Ala Ala Leu Ala Asn Ser Val Gln Glu Leu Thr
             420                 425                 430

Ser
```

```
<210> SEQ ID NO 152
<211> LENGTH: 427
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid

<400> SEQUENCE: 152

Ser Ala Ala Phe Thr Lys Lys Leu Gln Asp Gly His Val Asp Leu Gly
1               5                   10                  15

Lys Thr Asp Val Thr Asp Asp Asn Ala Lys Glu Ala Ile Leu Lys Thr
            20                  25                  30

Asn Pro Thr Lys Thr Lys Gly Ala Thr Glu Leu Glu Gly Leu Phe Lys
        35                  40                  45

Ser Val Glu Gly Leu Val Lys Ala Ala Lys Glu Ala Ser Ala Asn Ser
    50                  55                  60

Val Lys Glu Leu Thr Ser Xaa Asn Lys Ala Phe Thr Asp Lys Leu Lys
65                  70                  75                  80

Ser Ser His Ala Glu Leu Gly Ile Ala Asn Gly Ala Ala Thr Asp Ala
                85                  90                  95

Asn Ala Lys Ala Ala Ile Leu Lys Thr Asn Gly Thr Lys Asp Lys Gly
            100                 105                 110

Ala Gln Glu Leu Glu Lys Leu Phe Glu Ser Val Lys Asn Leu Ser Lys
        115                 120                 125

Ala Ala Gln Glu Thr Leu Asn Asn Ser Val Lys Glu Leu Thr Ser Xaa
    130                 135                 140

Ser Glu Lys Phe Thr Thr Lys Leu Arg Asp Ser His Ala Glu Leu Gly
145                 150                 155                 160

Ile Gln Asn Val Gln Asp Asp Asn Ala Lys Arg Ala Ile Leu Lys Thr
                165                 170                 175

His Gly Asn Lys Asp Lys Gly Ala Lys Glu Leu Lys Glu Leu Ser Glu
            180                 185                 190

Ser Leu Glu Lys Leu Ser Lys Ala Ala Gln Ala Ala Leu Ala Asn Ser
        195                 200                 205

Val Gln Glu Leu Thr Ser Xaa Ser Glu Ala Phe Thr Asn Arg Leu Lys
    210                 215                 220

Gly Ser His Ala Gln Leu Gly Val Ala Ala Thr Asp Asp His Ala
225                 230                 235                 240

Lys Glu Ala Ile Leu Lys Ser Asn Pro Thr Lys Asp Lys Gly Ala Lys
                245                 250                 255
```

```
Glu Leu Lys Asp Leu Ser Glu Ser Val Ser Leu Ala Lys Ala Ala
            260                 265                 270

Gln Glu Ala Leu Ala Asn Ser Val Lys Glu Leu Thr Asn Xaa Ser Glu
        275                 280                 285

Glu Phe Thr Asn Lys Leu Lys Gly Gly His Ala Glu Leu Gly Leu Ala
    290                 295                 300

Ala Ala Thr Asp Glu Asn Ala Lys Lys Ala Ile Leu Lys Thr Asn Gly
305                 310                 315                 320

Thr Lys Asp Lys Gly Ala Glu Glu Leu Lys Leu Phe Lys Ser Val
                325                 330                 335

Glu Ser Leu Ala Lys Ala Ala Lys Glu Ser Leu Thr Asn Ser Val Lys
        340                 345                 350

Glu Leu Thr Asn Xaa Ser Glu Ala Phe Thr Asp Lys Leu Lys Asn Glu
            355                 360                 365

His Ala Ser Leu Gly Lys Lys Asp Ala Thr Asp Asp Ala Lys Lys
        370                 375                 380

Ala Ile Leu Lys Thr Asn Val Asp Lys Thr Lys Gly Ala Asp Glu Leu
385                 390                 395                 400

Ile Lys Leu Ser Gly Ser Leu Glu Ser Leu Ser Lys Ala Ala Gln Ala
        405                 410                 415

Ile Leu Ala Asn Ser Val Lys Glu Leu Thr Ser
        420                 425

<210> SEQ ID NO 153
<211> LENGTH: 429
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid

<400> SEQUENCE: 153

Ser Asp Lys Phe Thr Lys Lys Leu Thr Asp Ser His Ala Gln Leu Gly
1               5                   10                  15

Ala Val Gly Gly Ala Ile Asn Asp Asp Arg Ala Lys Glu Ala Ile Leu
            20                  25                  30

Lys Thr His Gly Thr Asn Asp Lys Gly Ala Lys Glu Leu Lys Glu Leu
        35                  40                  45

Ser Glu Ser Val Glu Ser Leu Ala Lys Ala Ala Gln Ala Ala Leu Ala
    50                  55                  60

Asn Ser Val Lys Glu Leu Thr Ser Xaa Ser Glu Ala Phe Thr Asn Lys
65                  70                  75                  80

Leu Lys Glu Lys Thr Gln Glu Leu Ala Val Ala Ala Gly Ala Ala Thr
```

```
                    85                  90                  95
Asp Ile Asp Ala Lys Ala Ile Leu Lys Thr Asn Arg Asp Lys Asp
                100                 105                 110
Leu Gly Ala Asp Glu Arg Gly Lys Leu Phe Lys Ser Val Glu Ser Leu
                115                 120                 125
Ser Lys Ala Ala Gln Glu Ala Ser Ala Asn Ser Val Lys Glu Leu Thr
            130                 135                 140
Ser Xaa Ser Glu Ala Phe Thr Lys Lys Leu Gln Asp Ser Asn Ala Asp
145                 150                 155                 160
Leu Gly Lys His Asn Ala Thr Asp Ala Asp Ser Lys Glu Ala Ile Leu
                165                 170                 175
Lys Thr Asn Gly Thr Lys Thr Lys Gly Ala Lys Glu Leu Glu Leu
                180                 185                 190
Phe Lys Ser Val Glu Ser Leu Ser Lys Ala Ala Lys Glu Ala Leu Ser
                195                 200                 205
Asn Ser Val Lys Glu Leu Thr Ser Xaa Ser Glu Lys Phe Ala Gly Lys
            210                 215                 220
Leu Lys Asn Glu His Ala Ser Leu Gly Lys Lys Asp Ala Thr Asp Asp
225                 230                 235                 240
Asp Ala Lys Lys Ala Ile Leu Lys Thr His Gly Asn Thr Asp Lys Gly
                245                 250                 255
Ala Lys Glu Leu Lys Asp Leu Ser Asp Ser Val Glu Ser Leu Val Lys
                260                 265                 270
Ala Ala Lys Glu Met Leu Thr Asn Ser Val Lys Glu Leu Thr Ser Xaa
                275                 280                 285
Ser Gln Asp Phe Ile Asn Lys Leu Lys Gly Gly His Ala Glu Leu Gly
            290                 295                 300
Leu Val Ala Ala Thr Asp Ala Asn Ala Lys Ala Ala Ile Leu Lys Thr
305                 310                 315                 320
Asn Gly Asp Lys Thr Lys Gly Ala Asp Glu Phe Glu Lys Leu Phe Lys
                325                 330                 335
Ser Val Glu Gly Leu Leu Lys Ala Ala Gln Glu Ala Leu Thr Asn Ser
            340                 345                 350
Val Lys Glu Leu Thr Ser Xaa Ser Glu Asp Phe Thr Asn Lys Leu Lys
                355                 360                 365
Asn Gly Asn Ala Gln Leu Gly Leu Ala Ala Ala Thr Asp Asp Asn Ala
            370                 375                 380
Lys Ala Ala Ile Leu Lys Thr Asn Gly Thr Asn Asp Lys Gly Ala Lys
385                 390                 395                 400
Glu Leu Lys Asp Leu Ser Asp Ser Val Glu Ser Leu Val Lys Ala Ala
                405                 410                 415
Gln Val Met Leu Thr Asn Ser Val Lys Glu Leu Thr Ser
                420                 425

<210> SEQ ID NO 154
<211> LENGTH: 498
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (142)..(142)
```

```
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid

<400> SEQUENCE: 154

Ser Glu Ala Phe Thr Lys Lys Leu Lys Asp Asn Asn Ala Gln Leu Gly
1               5                   10                  15

Ile Gln Asn Val Gln Asp Val Glu Ala Lys Lys Ala Ile Leu Lys Thr
            20                  25                  30

Asn Gly Asp Ile Ser Lys Gly Ala Lys Glu Leu Lys Glu Leu Phe Glu
        35                  40                  45

Ser Val Glu Ser Leu Ala Lys Ala Ala Gln Ala Ala Leu Ala Asn Ser
    50                  55                  60

Val Gln Glu Leu Thr Asn Xaa Ser Glu Ala Phe Thr Asn Arg Leu Thr
65                  70                  75                  80

Gly Ser His Ala Gln His Gly Val Ala Ala Thr Asp Asp His Ala
                85                  90                  95

Lys Glu Ala Ile Leu Lys Ser Asn Pro Thr Lys Asp Lys Gly Ala Lys
                100                 105                 110

Glu Leu Lys Asp Leu Ser Glu Ser Val Glu Ser Leu Ala Lys Ala Ala
            115                 120                 125

Gln Glu Ala Leu Ala Asn Ser Val Lys Glu Leu Thr Asn Xaa Ser Val
        130                 135                 140

Ala Phe Thr Ser Lys Leu Lys Ser Ser Asn Ala Gln Leu Gly Val Ala
145                 150                 155                 160

Asn Gly Asn Ala Thr Asp Asp Asp Ala Lys Lys Ala Ile Leu Lys Thr
                165                 170                 175

Asn Thr Pro Asn Asp Lys Gly Ala Lys Glu Leu Lys Glu Leu Phe Glu
            180                 185                 190

Ser Val Glu Ser Leu Ala Lys Ala Ala Gln Ala Ala Leu Val Asn Ser
            195                 200                 205

Val Gln Glu Leu Thr Asn Xaa Ser Glu Glu Phe Thr Asn Lys Leu Lys
        210                 215                 220

Ser Gly His Ala Asp Leu Gly Lys Gln Asp Thr Asp Asp His Ala
225                 230                 235                 240

Lys Ala Ala Ile Leu Lys Thr His Ala Thr Thr Asp Lys Gly Ala Lys
                245                 250                 255

Glu Phe Lys Asp Leu Phe Glu Ser Val Glu Gly Leu Leu Lys Ala Ala
            260                 265                 270

Gln Val Ala Leu Thr Asn Ser Val Lys Glu Leu Thr Ser Xaa Ser Glu
        275                 280                 285

Lys Phe Thr Lys Lys Leu Ser Glu Ser His Ala Asp Ile Gly Ile Gln
    290                 295                 300

Ala Ala Thr Asp Ala Asn Ala Lys Asp Ala Ile Leu Lys Thr Asn Pro
305                 310                 315                 320
```

```
Thr Lys Thr Lys Gly Ala Glu Glu Leu Asp Lys Leu Phe Lys Ala Val
            325                 330                 335

Glu Asn Leu Ser Lys Ala Ala Lys Glu Met Leu Ala Asn Ser Val Lys
            340                 345                 350

Asp Leu Gln Val Xaa Ser Glu Lys Phe Thr Asp Lys Leu Lys Ser Glu
            355                 360                 365

Asn Ala Ala Leu Gly Lys Gln Asp Ala Ser Asp Asp Ala Lys Lys
            370                 375                 380

Ala Ile Leu Lys Thr His Asn Asp Ile Thr Lys Gly Ala Lys Glu Leu
385                 390                 395                 400

Lys Glu Leu Ser Glu Ser Val Glu Thr Leu Leu Lys Ala Ala Lys Glu
                405                 410                 415

Met Leu Ala Asn Ser Val Lys Glu Leu Thr Ser Xaa Ser Glu Lys Phe
                420                 425                 430

Thr Thr Lys Leu Lys Asp Ser His Ala Glu Leu Gly Ile Gln Ser Val
                435                 440                 445

Gln Asp Asp Asn Ala Lys Lys Ala Ile Leu Lys Thr His Gly Thr Lys
            450                 455                 460

Asp Lys Gly Ala Lys Glu Leu Glu Glu Leu Phe Lys Ser Leu Glu Ser
465                 470                 475                 480

Leu Ser Lys Ala Ala Gln Ala Ala Leu Thr Asn Ser Val Lys Glu Leu
                485                 490                 495

Thr Asn

<210> SEQ ID NO 155
<211> LENGTH: 580
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (429)..(429)
<223> OTHER INFORMATION: Xaa can be any naturally occurring amino acid
<220> FEATURE:
<221> NAME/KEY: misc_feature
<222> LOCATION: (500)..(500)
<223> OTHER INFORMATION: Xaa can be any naturally occurring amino acid

<400> SEQUENCE: 155

Ser Thr Glu Phe Thr Asn Lys Leu Lys Ser Glu His Ala Val Leu Gly
1               5                   10                  15

Leu Asp Asn Leu Thr Asp Asp Asn Ala Gln Arg Ala Ile Leu Lys Lys
                20                  25                  30
```

```
His Ala Asn Lys Asp Lys Gly Ala Glu Leu Glu Lys Leu Phe Lys
            35                  40                  45
Ala Val Glu Asn Leu Ser Lys Ala Ala Gln Asp Thr Leu Lys Asn Ala
 50                  55                  60
Val Lys Glu Leu Thr Ser Xaa Ser Asp Asp Phe Thr Lys Lys Leu Gln
 65                  70                  75                  80
Ser Ser His Ala Gln Leu Gly Val Ala Gly Ala Thr Thr Asp Glu
                 85                  90                  95
Glu Ala Lys Lys Ala Ile Leu Arg Thr Asn Ala Ile Lys Asp Lys Gly
                100                 105                 110
Ala Asp Glu Leu Glu Lys Leu Phe Lys Ser Val Glu Ser Leu Ala Lys
                115                 120                 125
Ala Ala Gln Asp Ala Leu Ala Asn Ser Val Asn Glu Leu Thr Ser Xaa
                130                 135                 140
Ser Glu Glu Phe Thr Ala Lys Leu Lys Gly Glu His Thr Asp Leu Gly
145                 150                 155                 160
Lys Glu Gly Val Thr Asp Asp Asn Ala Lys Lys Ala Ile Leu Lys Thr
                165                 170                 175
Asn Asn Asp Lys Thr Lys Gly Ala Asp Glu Leu Glu Lys Leu Phe Glu
                180                 185                 190
Ser Val Lys Asn Leu Ser Lys Ala Ala Lys Glu Met Leu Thr Asn Ser
                195                 200                 205
Val Lys Glu Leu Thr Ser Xaa Ser Glu Glu Phe Thr Lys Lys Leu Lys
                210                 215                 220
Glu Lys His Thr Asp Leu Gly Lys Lys Asp Thr Asp Val His Ala
225                 230                 235                 240
Lys Glu Ala Ile Leu Lys Thr Asn Gly Thr Lys Asp Lys Gly Ala Ala
                245                 250                 255
Glu Leu Glu Lys Leu Phe Glu Ser Val Glu Asn Leu Ala Lys Ala Ala
                260                 265                 270
Lys Glu Met Leu Ser Asn Ser Val Lys Glu Leu Thr Ser Xaa Ser Glu
                275                 280                 285
Thr Phe Thr Asn Lys Leu Lys Glu Lys His Thr Asp Leu Gly Lys Glu
                290                 295                 300
Gly Val Thr Asp Ala Asp Ala Lys Glu Ala Ile Leu Lys Thr Asn Gly
305                 310                 315                 320
Thr Lys Thr Lys Gly Ala Glu Glu Leu Gly Lys Leu Phe Glu Ser Val
                325                 330                 335
Glu Val Leu Ser Lys Ala Ala Lys Glu Met Leu Ala Asn Ser Val Lys
                340                 345                 350
Glu Leu Thr Ser Xaa Ser Glu Glu Phe Ser Thr Lys Leu Lys Asp Asn
                355                 360                 365
His Ala Gln Leu Gly Ile Gln Gly Val Thr Asp Glu Asn Ala Lys Lys
                370                 375                 380
Ala Ile Leu Lys Ala Asn Ala Ala Gly Lys Asp Lys Gly Val Glu Glu
385                 390                 395                 400
Leu Glu Lys Leu Ser Gly Ser Leu Glu Ser Leu Ser Lys Ala Ala Lys
                405                 410                 415
Glu Met Leu Ala Asn Ser Val Lys Glu Leu Thr Ser Xaa Ser Glu Asp
                420                 425                 430
Phe Thr Lys Lys Leu Glu Gly Glu His Ala Gln Leu Gly Ile Glu Asn
                435                 440                 445
```

```
Val Thr Asp Glu Asn Ala Lys Lys Ala Ile Leu Ile Thr Asp Ala Ala
        450                 455                 460

Lys Asp Lys Gly Ala Ala Glu Leu Glu Lys Leu Phe Lys Ala Val Glu
465                 470                 475                 480

Asn Leu Ala Lys Ala Ala Lys Glu Met Leu Ala Asn Ser Val Lys Glu
                485                 490                 495

Leu Thr Ser Xaa Ser Glu Ser Phe Thr Lys Lys Leu Ser Asp Asn Gln
            500                 505                 510

Ala Glu Leu Gly Ile Glu Asn Ala Thr Asp Asp Asn Ala Lys Lys Ala
        515                 520                 525

Ile Leu Lys Thr His Asn Ala Lys Asp Lys Gly Ala Glu Glu Leu Val
530                 535                 540

Lys Leu Ser Glu Ser Val Ala Gly Leu Leu Lys Ala Ala Gln Ala Ile
545                 550                 555                 560

Leu Ala Asn Ser Val Lys Glu Leu Thr Ser Pro Val Val Ala Glu Ser
                565                 570                 575

Pro Lys Lys Pro
            580

<210> SEQ ID NO 156
<211> LENGTH: 575
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid
<220> FEATURE:
<221> NAME/KEY: misc_feature
<222> LOCATION: (432)..(432)
<223> OTHER INFORMATION: Xaa can be any naturally occurring amino acid
<220> FEATURE:
<221> NAME/KEY: misc_feature
<222> LOCATION: (505)..(505)
<223> OTHER INFORMATION: Xaa can be any naturally occurring amino acid

<400> SEQUENCE: 156

Ser Asp Lys Phe Thr Lys Lys Leu Thr Asp Ser His Ala Gln Leu Gly
1               5                   10                  15

Ala Val Gly Gly Ala Ile Asn Asp Asp Arg Ala Lys Glu Ala Ile Leu
            20                  25                  30

Lys Thr His Gly Thr Asn Asp Lys Gly Ala Lys Glu Leu Lys Glu Leu
        35                  40                  45

Ser Glu Ser Val Glu Ser Leu Ala Lys Ala Ala Gln Ala Ala Leu Ala
    50                  55                  60

Asn Ser Val Lys Glu Leu Thr Ser Xaa Ser Ala Ala Phe Thr Lys Lys
65                  70                  75                  80
```

```
Leu Ala Asp Ser Asn Ala Asp Leu Gly Val Ala Ala Gly Asn Ala Thr
                85                  90                  95

Asp Asp Asn Ala Lys Arg Ala Ile Leu Lys Thr His Gly His Glu Asp
            100                 105                 110

Lys Gly Gly Lys Glu Leu Lys Glu Leu Ser Glu Ala Val Lys Ser Leu
        115                 120                 125

Leu Lys Ala Ala Gln Ala Leu Ala Asn Ser Val Gln Glu Leu Thr
    130                 135                 140

Ser Xaa Ser Glu Ala Phe Thr Lys Lys Leu Gln Asp Ser Asn Ala Asp
145                 150                 155                 160

Leu Gly Lys His Asn Ala Thr Asp Ala Asp Ser Lys Glu Ala Ile Leu
                165                 170                 175

Lys Thr Asn Gly Thr Lys Thr Lys Gly Ala Lys Glu Leu Glu Leu
            180                 185                 190

Phe Lys Ser Val Glu Ser Leu Ser Lys Ala Lys Glu Ala Leu Ser
        195                 200                 205

Asn Ser Val Lys Glu Leu Thr Ser Xaa Ser Glu Ala Phe Thr Asn Lys
        210                 215                 220

Leu Lys Glu Lys His Ala Glu Leu Gly Val Asn Gly Gly Asp Thr Thr
225                 230                 235                 240

Asp Asp Asn Ala Lys Ala Ala Ile Phe Lys Thr His Pro Thr Lys Asp
                245                 250                 255

Lys Gly Val Glu Asp Leu Glu Lys Leu Ser Glu Ser Val Lys Ser Leu
            260                 265                 270

Leu Lys Ala Ala Gln Ala Ala Leu Ser Asn Ser Val Lys Glu Leu Thr
        275                 280                 285

Ser Xaa Ser Glu Ala Phe Thr Asn Arg Leu Thr Gly Ser His Ala Gln
    290                 295                 300

His Gly Val Ala Ala Thr Asp Asp His Ala Lys Glu Ala Ile Leu
305                 310                 315                 320

Lys Ser Asn Pro Thr Lys Asp Lys Gly Ala Lys Glu Leu Lys Asp Leu
                325                 330                 335

Ser Glu Ser Val Glu Ser Leu Ala Lys Ala Ala Gln Glu Ala Leu Ala
            340                 345                 350

Asn Ser Val Lys Glu Leu Thr Asn Xaa Ser Glu Ala Phe Thr Lys Lys
        355                 360                 365

Leu Gln Asp Ser Asn Ala Asp Leu Gly Lys His Asp Ala Thr Asp Ala
    370                 375                 380

Asp Ala Lys Lys Ala Ile Leu Lys Thr Asp Ala Thr Lys Asp Lys Gly
385                 390                 395                 400

Ala Lys Glu Leu Glu Glu Leu Phe Lys Ser Val Glu Ser Leu Ser Lys
                405                 410                 415

Ala Ala Lys Glu Ala Leu Ser Asn Ser Val Lys Glu Leu Thr Ser Xaa
            420                 425                 430

Ser Glu Ala Phe Thr Lys Lys Leu Lys Asp Ser Asn Ala Gln Leu Gly
        435                 440                 445

Met Gln Asn Gly Ala Ala Thr Asp Ala His Lys Ala Ala Ile Leu
    450                 455                 460

Lys Thr Asp Ala Thr Lys Asp Lys Gly Ala Thr Glu Leu Gly Glu Leu
465                 470                 475                 480

Phe Lys Ser Val Glu Ser Leu Ser Lys Ala Ala Gln Glu Ala Ser Ala
                485                 490                 495
```

-continued

```
Asn Ser Val Lys Glu Leu Thr Ser Xaa Ser Glu Lys Phe Ala Gly Lys
                500                 505                 510

Leu Lys Asn Glu His Ala Ser Leu Gly Lys Lys Asp Ala Thr Asp Asp
        515                 520                 525

Asp Ala Lys Lys Ala Ile Leu Lys Thr His Gly Asn Thr Asp Lys Gly
530                 535                 540

Ala Lys Glu Leu Lys Asp Leu Ser Asp Ser Val Glu Ser Leu Val Lys
545                 550                 555                 560

Ala Ala Lys Glu Met Leu Thr Asn Ser Val Lys Glu Leu Thr Ser
                565                 570                 575
```

<210> SEQ ID NO 157
<211> LENGTH: 571
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (430)..(430)
<223> OTHER INFORMATION: Xaa can be any naturally occurring amino acid
<220> FEATURE:
<221> NAME/KEY: misc_feature
<222> LOCATION: (501)..(501)
<223> OTHER INFORMATION: Xaa can be any naturally occurring amino acid

<400> SEQUENCE: 157

```
Ser Gln Asp Phe Ile Asn Lys Leu Lys Gly Gly His Ala Glu Leu Gly
1               5                   10                  15

Leu Val Ala Ala Thr Asp Ala Asn Ala Lys Ala Ala Ile Leu Lys Thr
                20                  25                  30

Asn Gly Asp Lys Thr Lys Gly Ala Asp Glu Phe Glu Lys Leu Phe Lys
            35                  40                  45

Ser Val Glu Gly Leu Leu Lys Ala Ala Gln Glu Ala Leu Thr Asn Ser
        50                  55                  60

Val Lys Glu Leu Thr Ser Xaa Asn Lys Ala Phe Thr Asp Lys Leu Lys
65                  70                  75                  80

Ser Ser His Ala Glu Leu Gly Ile Ala Asn Gly Ala Ala Thr Asp Ala
                85                  90                  95

Asn Ala Lys Ala Ala Ile Leu Lys Thr Asn Gly Thr Lys Asp Lys Gly
            100                 105                 110

Ala Gln Glu Leu Glu Lys Leu Phe Glu Ser Val Lys Asn Leu Ser Lys
        115                 120                 125

Ala Ala Gln Glu Thr Leu Asn Asn Ser Val Lys Glu Leu Thr Ser Xaa
    130                 135                 140
```

```
Ser Glu Asp Phe Thr Asn Lys Leu Lys Asn Gly Asn Ala Gln Leu Gly
145                 150                 155                 160

Leu Ala Ala Ala Thr Asp Asn Ala Lys Ala Ile Leu Lys Thr
            165                 170                 175

Asn Gly Thr Asn Asp Lys Gly Ala Lys Glu Leu Lys Asp Leu Ser Asp
            180                 185                 190

Ser Val Glu Ser Leu Val Lys Ala Ala Gln Val Met Leu Thr Asn Ser
            195                 200                 205

Val Lys Glu Leu Thr Ser Xaa Ser Glu Lys Phe Thr Thr Lys Leu Lys
210                 215                 220

Asp Ser His Ala Glu Leu Gly Ile Gln Ser Val Gln Asp Asp Asn Ala
225                 230                 235                 240

Lys Lys Ala Ile Leu Lys Thr His Gly Thr Lys Asp Lys Gly Ala Lys
            245                 250                 255

Glu Leu Glu Glu Leu Phe Lys Ser Leu Glu Ser Leu Ser Lys Ala Ala
            260                 265                 270

Gln Ala Ala Leu Thr Asn Ser Val Lys Glu Leu Thr Asn Xaa Ser Glu
            275                 280                 285

Glu Phe Thr Asn Lys Leu Lys Gly Gly His Ala Glu Leu Gly Leu Ala
            290                 295                 300

Ala Ala Thr Asp Glu Asn Ala Lys Lys Ala Ile Leu Lys Thr Asn Gly
305                 310                 315                 320

Thr Lys Asp Lys Gly Ala Glu Leu Glu Lys Leu Phe Lys Ser Val
            325                 330                 335

Glu Ser Leu Ala Lys Ala Ala Lys Glu Ser Leu Thr Asn Ser Val Lys
            340                 345                 350

Glu Leu Thr Asn Xaa Ser Glu Ala Phe Thr Asn Lys Leu Lys Glu Lys
            355                 360                 365

Thr Gln Glu Leu Ala Val Ala Ala Gly Ala Ala Thr Asp Ile Asp Ala
            370                 375                 380

Lys Lys Ala Ile Leu Lys Thr Asn Arg Asp Lys Asp Leu Gly Ala Asp
385                 390                 395                 400

Glu Arg Gly Lys Leu Phe Lys Ser Val Glu Ser Leu Ser Lys Ala Ala
            405                 410                 415

Gln Glu Ala Ser Ala Asn Ser Val Lys Glu Leu Thr Ser Xaa Ser Glu
            420                 425                 430

Lys Phe Thr Thr Lys Leu Arg Asp Ser His Ala Glu Leu Gly Ile Gln
            435                 440                 445

Asn Val Gln Asp Asp Asn Ala Lys Arg Ala Ile Leu Lys Thr His Gly
            450                 455                 460

Asn Lys Asp Lys Gly Ala Lys Glu Leu Lys Glu Leu Ser Glu Ser Leu
465                 470                 475                 480

Glu Lys Leu Ser Lys Ala Ala Gln Ala Ala Leu Ala Asn Ser Val Gln
            485                 490                 495

Glu Leu Thr Ser Xaa Ser Glu Ala Phe Thr Asn Arg Leu Lys Gly Ser
            500                 505                 510

His Ala Gln Leu Gly Val Ala Ala Thr Asp Asp His Ala Lys Glu
            515                 520                 525

Ala Ile Leu Lys Ser Asn Pro Thr Lys Asp Lys Gly Ala Lys Glu Leu
            530                 535                 540

Lys Asp Leu Ser Glu Ser Val Glu Ser Leu Ala Lys Ala Ala Gln Glu
545                 550                 555                 560
```

```
Ala Leu Ala Asn Ser Val Lys Glu Leu Thr Asn
            565                 570
```

<210> SEQ ID NO 158
<211> LENGTH: 498
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (284)..(284)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid

<400> SEQUENCE: 158

```
Ser Glu Lys Phe Thr Asp Lys Leu Lys Ser Glu Asn Ala Ala Leu Gly
1               5                   10                  15

Lys Gln Asp Ala Ser Asp Asp Ala Lys Lys Ala Ile Leu Lys Thr
            20                  25                  30

His Asn Asp Ile Thr Lys Gly Ala Lys Glu Leu Lys Glu Leu Ser Glu
            35                  40                  45

Ser Val Glu Thr Leu Leu Lys Ala Ala Lys Glu Met Leu Ala Asn Ser
        50                  55                  60

Val Lys Glu Leu Thr Ser Xaa Ser Glu Ala Phe Thr Lys Lys Leu Lys
65                  70                  75                  80

Asp Asn Asn Ala Gln Leu Gly Ile Gln Asn Val Gln Asp Val Glu Ala
                85                  90                  95

Lys Lys Ala Ile Leu Lys Thr Asn Gly Asp Ile Ser Lys Gly Ala Lys
            100                 105                 110

Glu Leu Lys Glu Leu Phe Glu Ser Val Glu Ser Leu Ala Lys Ala Ala
        115                 120                 125

Gln Ala Ala Leu Ala Asn Ser Val Gln Glu Leu Thr Asn Xaa Ser Glu
    130                 135                 140

Glu Phe Thr Asn Lys Leu Lys Ser Gly His Ala Asp Leu Gly Lys Gln
145                 150                 155                 160

Asp Ala Thr Asp Asp His Ala Lys Ala Ala Ile Leu Lys Thr His Ala
                165                 170                 175

Thr Thr Asp Lys Gly Ala Lys Glu Phe Lys Asp Leu Phe Glu Ser Val
            180                 185                 190

Glu Gly Leu Leu Lys Ala Ala Gln Val Ala Leu Thr Asn Ser Val Lys
        195                 200                 205

Glu Leu Thr Ser Xaa Ser Glu Ala Phe Thr Asp Lys Leu Lys Asn Glu
    210                 215                 220
```

```
His Ala Ser Leu Gly Lys Lys Asp Ala Thr Asp Asp Ala Lys Lys
225                 230                 235                 240

Ala Ile Leu Lys Thr Asn Val Asp Lys Thr Lys Gly Ala Asp Glu Leu
                245                 250                 255

Ile Lys Leu Ser Gly Ser Leu Glu Ser Leu Ser Lys Ala Ala Gln Ala
            260                 265                 270

Ile Leu Ala Asn Ser Val Lys Glu Leu Thr Ser Xaa Ser Val Ala Phe
        275                 280                 285

Thr Ser Lys Leu Lys Ser Ser Asn Ala Gln Leu Gly Val Ala Asn Gly
    290                 295                 300

Asn Ala Thr Asp Asp Ala Lys Lys Ala Ile Leu Lys Thr Asn Thr
305                 310                 315                 320

Pro Asn Asp Lys Gly Ala Lys Glu Leu Lys Glu Leu Phe Glu Ser Val
                325                 330                 335

Glu Ser Leu Ala Lys Ala Ala Gln Ala Ala Leu Val Asn Ser Val Gln
            340                 345                 350

Glu Leu Thr Asn Xaa Ser Ala Ala Phe Thr Lys Leu Gln Asp Gly
        355                 360                 365

His Val Asp Leu Gly Lys Thr Asp Val Thr Asp Asp Asn Ala Lys Glu
    370                 375                 380

Ala Ile Leu Lys Thr Asn Pro Thr Lys Thr Lys Gly Ala Thr Glu Leu
385                 390                 395                 400

Glu Glu Leu Phe Lys Ser Val Glu Gly Leu Val Lys Ala Ala Lys Glu
                405                 410                 415

Ala Ser Ala Asn Ser Val Lys Glu Leu Thr Ser Xaa Ser Glu Lys Phe
            420                 425                 430

Thr Lys Lys Leu Ser Glu Ser His Ala Asp Ile Gly Ile Gln Ala Ala
        435                 440                 445

Thr Asp Ala Asn Ala Lys Asp Ala Ile Leu Lys Thr Asn Pro Thr Lys
    450                 455                 460

Thr Lys Gly Ala Glu Glu Leu Asp Lys Leu Phe Lys Ala Val Glu Asn
465                 470                 475                 480

Leu Ser Lys Ala Ala Lys Glu Met Leu Ala Asn Ser Val Lys Asp Leu
                485                 490                 495

Gln Val

<210> SEQ ID NO 159
<211> LENGTH: 436
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (356)..(356)
```

<223> OTHER INFORMATION: Xaa can be any naturally occurring amino acid

<400> SEQUENCE: 159

```
Ser Glu Glu Phe Thr Ala Lys Leu Lys Gly Glu His Thr Asp Leu Gly
1               5                   10                  15
Lys Glu Gly Val Thr Asp Asp Asn Ala Lys Lys Ala Ile Leu Lys Thr
            20                  25                  30
Asn Asn Asp Lys Thr Lys Gly Ala Asp Glu Leu Glu Lys Leu Phe Glu
        35                  40                  45
Ser Val Lys Asn Leu Ser Lys Ala Ala Lys Glu Met Leu Thr Asn Ser
    50                  55                  60
Val Lys Glu Leu Thr Ser Xaa Ser Glu Glu Phe Thr Lys Leu Lys
65                  70                  75                  80
Glu Lys His Thr Asp Leu Gly Lys Lys Asp Ala Thr Asp Val His Ala
            85                  90                  95
Lys Glu Ala Ile Leu Lys Thr Asn Gly Thr Lys Asp Lys Gly Ala Ala
            100                 105                 110
Glu Leu Glu Lys Leu Phe Glu Ser Val Glu Asn Leu Ala Lys Ala Ala
            115                 120                 125
Lys Glu Met Leu Ser Asn Ser Val Lys Glu Leu Thr Ser Xaa Ser Glu
130                 135                 140
Thr Phe Thr Asn Lys Leu Lys Glu Lys His Thr Asp Leu Gly Lys Glu
145                 150                 155                 160
Gly Val Thr Asp Ala Asp Ala Lys Glu Ala Ile Leu Lys Thr Asn Gly
            165                 170                 175
Thr Lys Thr Lys Gly Ala Glu Glu Leu Gly Lys Leu Phe Glu Ser Val
            180                 185                 190
Glu Val Leu Ser Lys Ala Ala Lys Glu Met Leu Ala Asn Ser Val Lys
            195                 200                 205
Glu Leu Thr Ser Xaa Ser Glu Glu Phe Ser Thr Lys Leu Lys Asp Asn
            210                 215                 220
His Ala Gln Leu Gly Ile Gln Gly Val Thr Asp Glu Asn Ala Lys Lys
225                 230                 235                 240
Ala Ile Leu Lys Ala Asn Ala Ala Gly Lys Asp Lys Gly Val Glu Glu
            245                 250                 255
Leu Glu Lys Leu Ser Gly Ser Leu Glu Ser Leu Ser Lys Ala Ala Lys
            260                 265                 270
Glu Met Leu Ala Asn Ser Val Lys Glu Leu Thr Ser Xaa Ser Glu Asp
            275                 280                 285
Phe Thr Lys Lys Leu Glu Gly Glu His Ala Gln Leu Gly Ile Glu Asn
            290                 295                 300
Val Thr Asp Glu Asn Ala Lys Lys Ala Ile Leu Ile Thr Asp Ala Ala
305                 310                 315                 320
Lys Asp Lys Gly Ala Ala Glu Leu Glu Lys Leu Phe Lys Ala Val Glu
            325                 330                 335
Asn Leu Ala Lys Ala Ala Lys Glu Met Leu Ala Asn Ser Val Lys Glu
            340                 345                 350
Leu Thr Ser Xaa Ser Glu Ser Phe Thr Lys Lys Leu Ser Asp Asn Gln
            355                 360                 365
Ala Glu Leu Gly Ile Glu Asn Ala Thr Asp Asp Asn Ala Lys Lys Ala
            370                 375                 380
Ile Leu Lys Thr His Asn Ala Lys Asp Lys Gly Ala Glu Glu Leu Val
385                 390                 395                 400
```

-continued

```
Lys Leu Ser Glu Ser Val Ala Gly Leu Leu Lys Ala Ala Gln Ala Ile
                405                 410                 415

Leu Ala Asn Ser Val Lys Glu Leu Thr Ser Pro Val Val Ala Glu Ser
            420                 425                 430

Pro Lys Lys Pro
        435

<210> SEQ ID NO 160
<211> LENGTH: 433
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid

<400> SEQUENCE: 160

Ser Thr Glu Phe Thr Asn Lys Leu Lys Ser Glu His Ala Val Leu Gly
1               5                   10                  15

Leu Asp Asn Leu Thr Asp Asp Asn Ala Gln Arg Ala Ile Leu Lys Lys
            20                  25                  30

His Ala Asn Lys Asp Lys Gly Ala Ala Glu Leu Glu Lys Leu Phe Lys
        35                  40                  45

Ala Val Glu Asn Leu Ser Lys Ala Ala Gln Asp Thr Leu Lys Asn Ala
    50                  55                  60

Val Lys Glu Leu Thr Ser Xaa Ser Asp Asp Phe Thr Lys Lys Leu Gln
65                  70                  75                  80

Ser Ser His Ala Gln Leu Gly Val Ala Gly Ala Thr Thr Asp Glu
                85                  90                  95

Glu Ala Lys Lys Ala Ile Leu Arg Thr Asn Ala Ile Lys Asp Lys Gly
            100                 105                 110

Ala Asp Glu Leu Glu Lys Leu Phe Lys Ser Val Glu Ser Leu Ala Lys
        115                 120                 125

Ala Ala Gln Asp Ala Leu Ala Asn Ser Val Asn Glu Leu Thr Ser Xaa
    130                 135                 140

Ser Asp Lys Phe Thr Lys Lys Leu Thr Asp Ser His Ala Gln Leu Gly
145                 150                 155                 160

Ala Val Gly Gly Ala Ile Asn Asp Asp Arg Ala Lys Glu Ala Ile Leu
                165                 170                 175

Lys Thr His Gly Thr Asn Asp Lys Gly Ala Lys Glu Leu Lys Glu Leu
            180                 185                 190

Ser Glu Ser Val Glu Ser Leu Ala Lys Ala Ala Gln Ala Ala Leu Ala
        195                 200                 205

Asn Ser Val Lys Glu Leu Thr Ser Xaa Ser Ala Ala Phe Thr Lys Lys
```

Leu Ala Asp Ser Asn Ala Asp Leu Gly Val Ala Ala Gly Asn Ala Thr
225                 230                 235                 240

Asp Asp Asn Ala Lys Arg Ala Ile Leu Lys Thr His Gly His Glu Asp
                245                 250                 255

Lys Gly Gly Lys Glu Leu Lys Glu Leu Ser Glu Ala Val Lys Ser Leu
            260                 265                 270

Leu Lys Ala Ala Gln Ala Ala Leu Ala Asn Ser Val Gln Glu Leu Thr
        275                 280                 285

Ser Xaa Ser Glu Ala Phe Thr Lys Lys Leu Gln Asp Ser Asn Ala Asp
    290                 295                 300

Leu Gly Lys His Asn Ala Thr Asp Ala Asp Ser Lys Glu Ala Ile Leu
305                 310                 315                 320

Lys Thr Asn Gly Thr Lys Thr Lys Gly Ala Lys Glu Leu Glu Glu Leu
                325                 330                 335

Phe Lys Ser Val Glu Ser Leu Ser Lys Ala Ala Lys Glu Ala Leu Ser
            340                 345                 350

Asn Ser Val Lys Glu Leu Thr Ser Xaa Ser Glu Ala Phe Thr Asn Lys
        355                 360                 365

Leu Lys Glu Lys His Ala Glu Leu Gly Val Asn Gly Gly Asp Thr Thr
370                 375                 380

Asp Asp Asn Ala Lys Ala Ala Ile Phe Lys Thr His Pro Thr Lys Asp
385                 390                 395                 400

Lys Gly Val Glu Asp Leu Glu Lys Leu Ser Glu Ser Val Lys Ser Leu
            405                 410                 415

Leu Lys Ala Ala Gln Ala Ala Leu Ser Asn Ser Val Lys Glu Leu Thr
        420                 425                 430

Ser

<210> SEQ ID NO 161
<211> LENGTH: 429
<212> TYPE: PRT
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid

<400> SEQUENCE: 161

Ser Glu Ala Phe Thr Asn Arg Leu Thr Gly Ser His Ala Gln His Gly
1               5                   10                  15

Val Ala Ala Thr Asp Asp His Ala Lys Glu Ala Ile Leu Lys Ser
            20                  25                  30

-continued

Asn Pro Thr Lys Asp Lys Gly Ala Lys Glu Leu Lys Asp Leu Ser Glu
            35                  40                  45

Ser Val Glu Ser Leu Ala Lys Ala Ala Gln Glu Ala Leu Ala Asn Ser
 50                  55                  60

Val Lys Glu Leu Thr Asn Xaa Ser Glu Ala Phe Thr Lys Lys Leu Gln
 65                  70                  75                  80

Asp Ser Asn Ala Asp Leu Gly Lys His Asp Ala Thr Asp Ala Asp Ala
                85                  90                  95

Lys Lys Ala Ile Leu Lys Thr Asp Ala Thr Lys Asp Lys Gly Ala Lys
            100                 105                 110

Glu Leu Glu Glu Leu Phe Lys Ser Val Glu Ser Leu Ser Lys Ala Ala
            115                 120                 125

Lys Glu Ala Leu Ser Asn Ser Val Lys Glu Leu Thr Ser Xaa Ser Glu
            130                 135                 140

Ala Phe Thr Lys Lys Leu Lys Asp Ser Asn Ala Gln Leu Gly Met Gln
145                 150                 155                 160

Asn Gly Ala Ala Thr Asp Ala His Ala Lys Ala Ala Ile Leu Lys Thr
                165                 170                 175

Asp Ala Thr Lys Asp Lys Gly Ala Thr Glu Leu Gly Glu Leu Phe Lys
            180                 185                 190

Ser Val Glu Ser Leu Ser Lys Ala Ala Gln Glu Ala Ser Ala Asn Ser
            195                 200                 205

Val Lys Glu Leu Thr Ser Xaa Ser Glu Lys Phe Ala Gly Lys Leu Lys
            210                 215                 220

Asn Glu His Ala Ser Leu Gly Lys Lys Asp Ala Thr Asp Asp Asp Ala
225                 230                 235                 240

Lys Lys Ala Ile Leu Lys Thr His Gly Asn Thr Asp Lys Gly Ala Lys
            245                 250                 255

Glu Leu Lys Asp Leu Ser Asp Ser Val Glu Ser Leu Val Lys Ala Ala
            260                 265                 270

Lys Glu Met Leu Thr Asn Ser Val Lys Glu Leu Thr Ser Xaa Ser Gln
            275                 280                 285

Asp Phe Ile Asn Lys Leu Lys Gly Gly His Ala Glu Leu Gly Leu Val
            290                 295                 300

Ala Ala Thr Asp Ala Asn Ala Lys Ala Ala Ile Leu Lys Thr Asn Gly
305                 310                 315                 320

Asp Lys Thr Lys Gly Ala Asp Glu Phe Glu Lys Leu Phe Lys Ser Val
            325                 330                 335

Glu Gly Leu Leu Lys Ala Ala Gln Glu Ala Leu Thr Asn Ser Val Lys
            340                 345                 350

Glu Leu Thr Ser Xaa Asn Lys Ala Phe Thr Asp Lys Leu Lys Ser Ser
            355                 360                 365

His Ala Glu Leu Gly Ile Ala Asn Gly Ala Thr Asp Ala Asn Ala
            370                 375                 380

Lys Ala Ala Ile Leu Lys Thr Asn Gly Thr Lys Asp Lys Gly Ala Gln
385                 390                 395                 400

Glu Leu Glu Lys Leu Phe Glu Ser Val Lys Asn Leu Ser Lys Ala Ala
            405                 410                 415

Gln Glu Thr Leu Asn Asn Ser Val Lys Glu Leu Thr Ser
            420                 425

<210> SEQ ID NO 162
<211> LENGTH: 498
<212> TYPE: PRT

```
<213> ORGANISM: Artificial
<220> FEATURE:
<223> OTHER INFORMATION: Chimeric protein
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid

<400> SEQUENCE: 162

Ser Glu Asp Phe Thr Asn Lys Leu Lys Asn Gly Asn Ala Gln Leu Gly
1               5                   10                  15

Leu Ala Ala Ala Thr Asp Asp Asn Ala Lys Ala Ile Leu Lys Thr
                20                  25                  30

Asn Gly Thr Asn Asp Lys Gly Ala Lys Glu Leu Lys Asp Leu Ser Asp
            35                  40                  45

Ser Val Glu Ser Leu Val Lys Ala Ala Gln Val Met Leu Thr Asn Ser
50                  55                  60

Val Lys Glu Leu Thr Ser Xaa Ser Glu Lys Phe Thr Thr Lys Leu Lys
65                  70                  75                  80

Asp Ser His Ala Glu Leu Gly Ile Gln Ser Val Gln Asp Asp Asn Ala
                85                  90                  95

Lys Lys Ala Ile Leu Lys Thr His Gly Thr Lys Asp Lys Gly Ala Lys
            100                 105                 110

Glu Leu Glu Glu Leu Phe Lys Ser Leu Glu Ser Leu Ser Lys Ala Ala
        115                 120                 125

Gln Ala Ala Leu Thr Asn Ser Val Lys Glu Leu Thr Asn Xaa Ser Glu
    130                 135                 140

Glu Phe Thr Asn Lys Leu Lys Gly Gly His Ala Glu Leu Gly Leu Ala
145                 150                 155                 160

Ala Ala Thr Asp Glu Asn Ala Lys Lys Ala Ile Leu Lys Thr Asn Gly
                165                 170                 175

Thr Lys Asp Lys Gly Ala Glu Glu Leu Glu Lys Leu Phe Lys Ser Val
            180                 185                 190

Glu Ser Leu Ala Lys Ala Ala Lys Glu Ser Leu Thr Asn Ser Val Lys
        195                 200                 205

Glu Leu Thr Asn Xaa Ser Glu Ala Phe Thr Asn Lys Leu Lys Glu Lys
    210                 215                 220

Thr Gln Glu Leu Ala Val Ala Ala Gly Ala Thr Asp Ile Asp Ala
225                 230                 235                 240

Lys Lys Ala Ile Leu Lys Thr Asn Arg Asp Lys Asp Leu Gly Ala Asp
                245                 250                 255

Glu Arg Gly Lys Leu Phe Lys Ser Val Glu Ser Leu Ser Lys Ala Ala
```

```
                260                 265                 270
Gln Glu Ala Ser Ala Asn Ser Val Lys Glu Leu Thr Ser Xaa Ser Glu
            275                 280                 285

Lys Phe Thr Thr Lys Leu Arg Asp Ser His Ala Glu Leu Gly Ile Gln
        290                 295                 300

Asn Val Gln Asp Asp Asn Ala Lys Arg Ala Ile Leu Lys Thr His Gly
305                 310                 315                 320

Asn Lys Asp Lys Gly Ala Lys Glu Leu Lys Glu Leu Ser Glu Ser Leu
                325                 330                 335

Glu Lys Leu Ser Lys Ala Ala Gln Ala Ala Leu Ala Asn Ser Val Gln
            340                 345                 350

Glu Leu Thr Ser Xaa Ser Glu Ala Phe Thr Asn Arg Leu Lys Gly Ser
        355                 360                 365

His Ala Gln Leu Gly Val Ala Ala Thr Asp His Ala Lys Glu
    370                 375                 380

Ala Ile Leu Lys Ser Asn Pro Thr Lys Asp Lys Gly Ala Lys Glu Leu
385                 390                 395                 400

Lys Asp Leu Ser Glu Ser Val Glu Ser Leu Ala Lys Ala Ala Gln Glu
                405                 410                 415

Ala Leu Ala Asn Ser Val Lys Glu Leu Thr Asn Xaa Ser Glu Lys Phe
            420                 425                 430

Thr Asp Lys Leu Lys Ser Glu Asn Ala Ala Leu Gly Lys Gln Asp Ala
        435                 440                 445

Ser Asp Asp Asp Ala Lys Lys Ala Ile Leu Lys Thr His Asn Asp Ile
450                 455                 460

Thr Lys Gly Ala Lys Glu Leu Lys Glu Leu Ser Glu Ser Val Glu Thr
                470                 475                 480
465

Leu Leu Lys Ala Ala Lys Glu Met Leu Ala Asn Ser Val Lys Glu Leu
            485                 490                 495

Thr Ser

<210> SEQ ID NO 163
<211> LENGTH: 36
<212> TYPE: DNA
<213> ORGANISM: Artificial
<220> FEATURE:
<223> OTHER INFORMATION: Snythetic oligonucleotide primer for PCR

<400> SEQUENCE: 163
gacgacgaca agattaataa ttcagggaaa gatggg                              36

<210> SEQ ID NO 164
<211> LENGTH: 44
<212> TYPE: DNA
<213> ORGANISM: Artificial
<220> FEATURE:
<223> OTHER INFORMATION: Synthetic ologonucleotide primer for PCR

<400> SEQUENCE: 164
gacgacgaca agattcctaa tcttacagaa ataagtaaaa aaat                     44

<210> SEQ ID NO 165
<211> LENGTH: 35
<212> TYPE: DNA
<213> ORGANISM: Artificial
<220> FEATURE:
<223> OTHER INFORMATION: Synthetic oligonucleotide primer for PCR

<400> SEQUENCE: 165
```
gacgacgaca agattaaaga ggttgaagcg ttgct                                    35

<210> SEQ ID NO 166
<211> LENGTH: 39
<212> TYPE: DNA
<213> ORGANISM: Artificial
<220> FEATURE:
<223> OTHER INFORMATION: Synthetic oligonucleotide primer for PCR

<400> SEQUENCE: 166
gacgacgaca agattaaaat acaccaaaat aatggtttg                                39

<210> SEQ ID NO 167
<211> LENGTH: 37
<212> TYPE: DNA
<213> ORGANISM: Artificial
<220> FEATURE:
<223> OTHER INFORMATION: Synthetic oligonucleotide primer for PCR

<400> SEQUENCE: 167
gacgacgaca agattggagc ttatgcaata tcaaccc                                  37

<210> SEQ ID NO 168
<211> LENGTH: 46
<212> TYPE: DNA
<213> ORGANISM: Artificial
<220> FEATURE:
<223> OTHER INFORMATION: Synthetic oligonucleotide primer for PCR

<400> SEQUENCE: 168
gacgacgaca agatttgttc tgaaacattt actaataaat taaaag                        46

<210> SEQ ID NO 169
<211> LENGTH: 46
<212> TYPE: DNA
<213> ORGANISM: Artificial
<220> FEATURE:
<223> OTHER INFORMATION: Synthetic oligonucleotide primer for PCR

<400> SEQUENCE: 169
gacgacgaca agattaataa attaaaagaa aaacacacag atcttg                        46

<210> SEQ ID NO 170
<211> LENGTH: 38
<212> TYPE: DNA
<213> ORGANISM: Artificial
<220> FEATURE:
<223> OTHER INFORMATION: Synthetic oligonucleotide primer for PCR

<400> SEQUENCE: 170
gacgacgaca agattcacac agatcttggt aaagaagg                                 38

<210> SEQ ID NO 171
<211> LENGTH: 37
<212> TYPE: DNA
<213> ORGANISM: Artificial
<220> FEATURE:
<223> OTHER INFORMATION: Synthetic oligonucleotide primer for PCR

<400> SEQUENCE: 171
gacgacgaca agattactga tgctgatgca aaagaag                                  37

<210> SEQ ID NO 172
<211> LENGTH: 41
<212> TYPE: DNA

<213> ORGANISM: Artificial
<220> FEATURE:
<223> OTHER INFORMATION: Synthetic oligonucleotide primer for PCR

<400> SEQUENCE: 172
gacgacgaca agattgaaga acttggaaaa ttatttgaat c          41

<210> SEQ ID NO 173
<211> LENGTH: 41
<212> TYPE: DNA
<213> ORGANISM: Artificial
<220> FEATURE:
<223> OTHER INFORMATION: Synthetic oligonucleotide primer for PCR

<400> SEQUENCE: 173
gacgacgaca agattcttgc taattcagtt aaagagctta c          41

<210> SEQ ID NO 174
<211> LENGTH: 45
<212> TYPE: DNA
<213> ORGANISM: Artificial
<220> FEATURE:
<223> OTHER INFORMATION: Synthetic oligonucleotide primer for PCR

<400> SEQUENCE: 174
gacgacaagc ccggtttaac atttcttagc cgcatcaatt ttttc      45

<210> SEQ ID NO 175
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 175
gacgacaagc ccggtttaaa caccttcttt accaagatct gt         42

<210> SEQ ID NO 176
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 176
gacgacaagc ccggtttaag cacctttagt tttagtacca tt         42

<210> SEQ ID NO 177
<211> LENGTH: 41
<212> TYPE: DNA
<213> ORGANISM: Artificial
<220> FEATURE:
<223> OTHER INFORMATION: Synthetic oligonucleotide primer for PCR

<400> SEQUENCE: 177
gacgacaagc ccggtttaca tctctttagc tgcttttgac a          41

<210> SEQ ID NO 178
<211> LENGTH: 45
<212> TYPE: DNA
<213> ORGANISM: Artificial
<220> FEATURE:
<223> OTHER INFORMATION: Synthetic oligonucleotide primer for PCR

<400> SEQUENCE: 178
gacgacaagc ccggtttagc ttgtaagctc tttaactgaa ttagc      45

<210> SEQ ID NO 179
<211> LENGTH: 39
<212> TYPE: DNA
<213> ORGANISM: Artificial
<220> FEATURE:
<223> OTHER INFORMATION: Synthetic oligonucleotide primer for PCR

<400> SEQUENCE: 179
gacgacaagc ccggtttaag gttttttttgg actttctgc                    39

<210> SEQ ID NO 180
<211> LENGTH: 36
<212> TYPE: DNA
<213> ORGANISM: Artificial
<220> FEATURE:
<223> OTHER INFORMATION: Synthetic oligonucleotide primer for PCR

<400> SEQUENCE: 180
gacgacgaca agattaataa ttcagggaaa gatggg                         36

<210> SEQ ID NO 181
<211> LENGTH: 39
<212> TYPE: DNA
<213> ORGANISM: Artificial
<220> FEATURE:
<223> OTHER INFORMATION: Synthetic oligonucleotide primer for PCR

<400> SEQUENCE: 181
gacgacaagc ccggtttaag gttttttttgg actttctgc                    39

<210> SEQ ID NO 182
<211> LENGTH: 41
<212> TYPE: DNA
<213> ORGANISM: Artificial
<220> FEATURE:
<223> OTHER INFORMATION: Synthetic oligonucleotide primer for PCR

<400> SEQUENCE: 182
gaggagaagc ccggtttatt gtgttattaa ggttgatatt g                   41

<210> SEQ ID NO 183
<211> LENGTH: 43
<212> TYPE: DNA
<213> ORGANISM: Artificial
<220> FEATURE:
<223> OTHER INFORMATION: Synthetic oligonucleotide primer for PCR

<400> SEQUENCE: 183
gacgacgaca agatcttctg aagagtttag tactaaacta aaa                 43

<210> SEQ ID NO 184
<211> LENGTH: 44
<212> TYPE: DNA
<213> ORGANISM: Artificial
<220> FEATURE:
<223> OTHER INFORMATION: Synthetic oligonucleotide primer for PCR

<400> SEQUENCE: 184
gaggagaagc ccggtttatt ttagtttagt actaaactct tcag                44

<210> SEQ ID NO 185
<211> LENGTH: 42
<212> TYPE: DNA
<213> ORGANISM: Artificial
<220> FEATURE:

<223> OTHER INFORMATION: Synthetic oligonucleotide primer for PCR

<400> SEQUENCE: 185
gacgacgaca agatagataa tcatgcacag cttggtatac ag                42

<210> SEQ ID NO 186
<211> LENGTH: 41
<212> TYPE: DNA
<213> ORGANISM: Artificial
<220> FEATURE:
<223> OTHER INFORMATION: Synthetic oligonucleotide primer for PCR

<400> SEQUENCE: 186
gacgacgaca agattataca gggcgttact gatgaaaatg c                 41

<210> SEQ ID NO 187
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 187
gacgacgaca agattgaaaa tgcaaaaaaa gctattttaa aa                42

<210> SEQ ID NO 188
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 188
gaggagaagc ccggtttatg cattttcatc agtaacgccc tg                42

<210> SEQ ID NO 189
<211> LENGTH: 43
<212> TYPE: DNA
<213> ORGANISM: Artificial
<220> FEATURE:
<223> OTHER INFORMATION: Synthetic oligonucleotide primer for PCR

<400> SEQUENCE: 189
gacgacgaca agattgcagc gggtaaagat aagggcgttg aag               43

<210> SEQ ID NO 190
<211> LENGTH: 36
<212> TYPE: DNA
<213> ORGANISM: Artificial
<220> FEATURE:
<223> OTHER INFORMATION: Synthetic oligonucleotide primer for PCR

<400> SEQUENCE: 190
gaggagaagc ccggtttact tatctttacc cgctgc                      36

<210> SEQ ID NO 191
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 191
gacgacgaca agattgaaaa gttgtccgga tcattagaaa gc                42

```
<210> SEQ ID NO 192
<211> LENGTH: 45
<212> TYPE: DNA
<213> ORGANISM: Artificial
<220> FEATURE:
<223> OTHER INFORMATION: Synthetic oligonucleotide primer for PCR

<400> SEQUENCE: 192
gaggagaagc ccggtttatg atccggacaa cttttcaagt tcttc            45

<210> SEQ ID NO 193
<211> LENGTH: 45
<212> TYPE: DNA
<213> ORGANISM: Artificial
<220> FEATURE:
<223> OTHER INFORMATION: Synthetic oligonucleotide primer for PCR

<400> SEQUENCE: 193
gacgacgaca agatcttaga aagcttatcg aaagcagcta aagag            45

<210> SEQ ID NO 194
<211> LENGTH: 44
<212> TYPE: DNA
<213> ORGANISM: Artificial
<220> FEATURE:
<223> OTHER INFORMATION: Synthetic oligonucleotide primer for PCR

<400> SEQUENCE: 194
gaggagaagc ccggtttatg attaagcttt ctaatgatcc ggac             44

<210> SEQ ID NO 195
<211> LENGTH: 44
<212> TYPE: DNA
<213> ORGANISM: Artificial
<220> FEATURE:
<223> OTHER INFORMATION: Synthetic oligonucleotide primer for PCR

<400> SEQUENCE: 195
gaggagaagc ccggtttact ctttagctgc ttttgataag cttc             44

<210> SEQ ID NO 196
<211> LENGTH: 45
<212> TYPE: DNA
<213> ORGANISM: Artificial
<220> FEATURE:
<223> OTHER INFORMATION: Synthetic oligonucleotide primer for PCR

<400> SEQUENCE: 196
gaggagaagc ccggtttatg taagctcttt aactgaatta gcaag            45

<210> SEQ ID NO 197
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 197
gaggagaagc ccggtttaaa tttttttact tatttctgta ag               42

<210> SEQ ID NO 198
<211> LENGTH: 45
<212> TYPE: DNA
<213> ORGANISM: Artificial
<220> FEATURE:
<223> OTHER INFORMATION: Synthetic oligonucleotide primer for PCR
```

<400> SEQUENCE: 198
gaggagaagc ccggtttatt ttttaccaat agctttagca agctc    45

<210> SEQ ID NO 199
<211> LENGTH: 41
<212> TYPE: DNA
<213> ORGANISM: Artificial
<220> FEATURE:
<223> OTHER INFORMATION: Synthetic oligonucleotide primer for PCR

<400> SEQUENCE: 199
gaggagaagc ccggtttata atttttctgt tattagagct g    41

<210> SEQ ID NO 200
<211> LENGTH: 35
<212> TYPE: DNA
<213> ORGANISM: Artificial
<220> FEATURE:
<223> OTHER INFORMATION: Synthetic oligonucleotide primer for PCR

<400> SEQUENCE: 200
gacgacgaca agattaaatg ttctgaaagc tttac    35

<210> SEQ ID NO 201
<211> LENGTH: 43
<212> TYPE: DNA
<213> ORGANISM: Artificial
<220> FEATURE:
<223> OTHER INFORMATION: Synthetic oligonucleotide primer for PCR

<400> SEQUENCE: 201
gaggagaagc ccggtttaaa agctttcaga aacatttctt agc    43

<210> SEQ ID NO 202
<211> LENGTH: 43
<212> TYPE: DNA
<213> ORGANISM: Artificial
<220> FEATURE:
<223> OTHER INFORMATION: Synthetic oligonucleotide primer for PCR

<400> SEQUENCE: 202
gacgacgaca agattactaa aaaactatca gataatcaag cag    43

<210> SEQ ID NO 203
<211> LENGTH: 43
<212> TYPE: DNA
<213> ORGANISM: Artificial
<220> FEATURE:
<223> OTHER INFORMATION: Synthetic oligonucleotide primer for PCR

<400> SEQUENCE: 203
gacgacgaca agattgagct tggtatagag aatgctactg atg    43

<210> SEQ ID NO 204
<211> LENGTH: 41
<212> TYPE: DNA
<213> ORGANISM: Artificial
<220> FEATURE:
<223> OTHER INFORMATION: Synthetic oligonucleotide primer for PCR

<400> SEQUENCE: 204
gacgacgaca agattgctac tgatgataat gcaaaaaagg c    41

<210> SEQ ID NO 205
<211> LENGTH: 45

```
<212> TYPE: DNA
<213> ORGANISM: Artificial
<220> FEATURE:
<223> OTHER INFORMATION: Synthetic oligonucleotide primer for PCR

<400> SEQUENCE: 205
gaggagaagc ccggtttaat tatcatcagt agcattctct atacc            45

<210> SEQ ID NO 206
<211> LENGTH: 43
<212> TYPE: DNA
<213> ORGANISM: Artificial
<220> FEATURE:
<223> OTHER INFORMATION: Synthetic oligonucleotide primer for PCR

<400> SEQUENCE: 206
gaggagaagc ccggtttaag cattatgtgt ttttaaaata gcc              43

<210> SEQ ID NO 207
<211> LENGTH: 40
<212> TYPE: DNA
<213> ORGANISM: Artificial
<220> FEATURE:
<223> OTHER INFORMATION: Synthetic oligonucleotide primer for PCR

<400> SEQUENCE: 207
gacgacgaca agattaaaga caagggtgct gaagaacttg                  40

<210> SEQ ID NO 208
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 208
gaggagaagc ccggtttatg attcagataa ctttacaagt tc               42

<210> SEQ ID NO 209
<211> LENGTH: 43
<212> TYPE: DNA
<213> ORGANISM: Artificial
<220> FEATURE:
<223> OTHER INFORMATION: Synthetic oligonucleotide primer for PCR

<400> SEQUENCE: 209
gacgacgaca agatttcagt agcaggctta ttaaaagcag ctc              43

<210> SEQ ID NO 210
<211> LENGTH: 45
<212> TYPE: DNA
<213> ORGANISM: Artificial
<220> FEATURE:
<223> OTHER INFORMATION: Synthetic oligonucleotide primer for PCR

<400> SEQUENCE: 210
gaggagaagc ccggtttatg aattagccag tatggcttga gctgc            45

<210> SEQ ID NO 211
<211> LENGTH: 40
<212> TYPE: DNA
<213> ORGANISM: Artificial
<220> FEATURE:
<223> OTHER INFORMATION: Synthetic oligonucleotide primer for PCR

<400> SEQUENCE: 211
```
gacgacgaca agatttcagt taaagagctt acaagtcctg        40

<210> SEQ ID NO 212
<211> LENGTH: 37
<212> TYPE: DNA
<213> ORGANISM: Artificial
<220> FEATURE:
<223> OTHER INFORMATION: Synthetic oligonucleotide primer for PCR

<400> SEQUENCE: 212
gaggagaagc ccggtttaat ctattttttt accaata        37

<210> SEQ ID NO 213
<211> LENGTH: 41
<212> TYPE: DNA
<213> ORGANISM: Artificial
<220> FEATURE:
<223> OTHER INFORMATION: Synthetic oligonucleotide primer for PCR

<400> SEQUENCE: 213
gaggagaagc ccggtttatt gtgttattag ttttgatatt g        41

<210> SEQ ID NO 214
<211> LENGTH: 38
<212> TYPE: DNA
<213> ORGANISM: Artificial
<220> FEATURE:
<223> OTHER INFORMATION: Synthetic oligonucleotide primer for PCR

<400> SEQUENCE: 214
gatgacgacg acaagattaa atgttctgaa gattttac        38

<210> SEQ ID NO 215
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 215
gaggagaagc ccggtttaaa aatcttcaga acatttctta gc        42

<210> SEQ ID NO 216
<211> LENGTH: 44
<212> TYPE: DNA
<213> ORGANISM: Artificial
<220> FEATURE:
<223> OTHER INFORMATION: Synthetic oligonucleotide primer for PCR

<400> SEQUENCE: 216
gatgacgacg acaagataat tgaaaatgtt actgatgaga atgc        44

<210> SEQ ID NO 217
<211> LENGTH: 45
<212> TYPE: DNA
<213> ORGANISM: Artificial
<220> FEATURE:
<223> OTHER INFORMATION: Synthetic oligonucleotide primer for PCR

<400> SEQUENCE: 217
gaggagaagc ccggtttaat tttcaattcc aagttgcgca tgttc        45

<210> SEQ ID NO 218
<211> LENGTH: 43
<212> TYPE: DNA
<213> ORGANISM: Artificial

-continued

<220> FEATURE:
<223> OTHER INFORMATION: Synthetic oligonucleotide primer for PCR

<400> SEQUENCE: 218
gatgacgacg acaagattat tttaataaca gatgcagcta aag     43

<210> SEQ ID NO 219
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 219
gaggagaagc ccggtttaag ctgcatctgt tattaaaata gc     42

<210> SEQ ID NO 220
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 220
gaggagaagc ccggtttatt caagctctgc agcgcccta tc     42

<210> SEQ ID NO 221
<211> LENGTH: 45
<212> TYPE: DNA
<213> ORGANISM: Artificial
<220> FEATURE:
<223> OTHER INFORMATION: Synthetic oligonucleotide primer for PCR

<400> SEQUENCE: 221
gaggagaagc ccggtttatg ctttaaatag cttttcaagc tctgc     45

<210> SEQ ID NO 222
<211> LENGTH: 43
<212> TYPE: DNA
<213> ORGANISM: Artificial
<220> FEATURE:
<223> OTHER INFORMATION: Synthetic oligonucleotide primer for PCR

<400> SEQUENCE: 222
gatgacgacg acaagattgc agtagaaact tggcaaaagc agc     43

<210> SEQ ID NO 223
<211> LENGTH: 45
<212> TYPE: DNA
<213> ORGANISM: Artificial
<220> FEATURE:
<223> OTHER INFORMATION: Synthetic oligonucleotide primer for PCR

<400> SEQUENCE: 223
gaggagaagc ccggtttact ctttagctgc ttttgccttg ttttc     45

<210> SEQ ID NO 224
<211> LENGTH: 43
<212> TYPE: DNA
<213> ORGANISM: Artificial
<220> FEATURE:
<223> OTHER INFORMATION: Synthetic oligonucleotide primer for PCR

<400> SEQUENCE: 224
gaggagaagc ccggtttaca tctctttagc tgcttttgcc aag     43

<210> SEQ ID NO 225
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 225
gaggagaagc ccggtttatt ttttaccaat agctttagta gc                           42

<210> SEQ ID NO 226
<211> LENGTH: 49
<212> TYPE: DNA
<213> ORGANISM: Artificial
<220> FEATURE:
<223> OTHER INFORMATION: Synthetic oligonucleotide primer for PCR

<400> SEQUENCE: 226
gacgacgaca agatttctga aacatttact aataaattaa agaaaaac                     49

<210> SEQ ID NO 227
<211> LENGTH: 39
<212> TYPE: DNA
<213> ORGANISM: Artificial
<220> FEATURE:
<223> OTHER INFORMATION: Synthetic oligonucleotide primer for PCR

<400> SEQUENCE: 227
taacataccc atgctacctt ctttaccaag atctgtgtg                               39

<210> SEQ ID NO 228
<211> LENGTH: 35
<212> TYPE: DNA
<213> ORGANISM: Artificial
<220> FEATURE:
<223> OTHER INFORMATION: Synthetic oligonucleotide primer for PCR

<400> SEQUENCE: 228
ggtagcatgg gtatgttaaa agcaaatgca gcggg                                   35

<210> SEQ ID NO 229
<211> LENGTH: 41
<212> TYPE: DNA
<213> ORGANISM: Artificial
<220> FEATURE:
<223> OTHER INFORMATION: Synthetic oligonucleotide primer for PCR

<400> SEQUENCE: 229
taagttaccg tttgtgcttg taagctcttt aactgaatta g                            41

<210> SEQ ID NO 230
<211> LENGTH: 43
<212> TYPE: DNA
<213> ORGANISM: Artificial
<220> FEATURE:
<223> OTHER INFORMATION: Synthetic oligonucleotide primer for PCR

<400> SEQUENCE: 230
agcacaaacg gtaacttaat aacagatgca gctaaagata agg                          43

<210> SEQ ID NO 231
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 231
taaaacgctc atgctacttg taagctcttt aactgaatta gc                42

<210> SEQ ID NO 232
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 232
agtagcatga gcgttttaaa aacacataat gctaaagaca ag                42

<210> SEQ ID NO 233
<211> LENGTH: 44
<212> TYPE: DNA
<213> ORGANISM: Artificial
<220> FEATURE:
<223> OTHER INFORMATION: Synthetic oligonucleotide primer for PCR

<400> SEQUENCE: 233
gaggagaagc ccggtttaac ttgtaagctc tttaactgaa ttag              44

<210> SEQ ID NO 234
<211> LENGTH: 49
<212> TYPE: DNA
<213> ORGANISM: Artificial
<220> FEATURE:
<223> OTHER INFORMATION: Synthetic oligonucleotide primer for PCR

<400> SEQUENCE: 234
gacgacgaca agatttctga aacatttact aataaattaa agaaaaac          49

<210> SEQ ID NO 235
<211> LENGTH: 39
<212> TYPE: DNA
<213> ORGANISM: Artificial
<220> FEATURE:
<223> OTHER INFORMATION: Synthetic oligonucleotide primer for PCR

<400> SEQUENCE: 235
taaagctgac atagcacctt ctttaccaag atctgtgtg                    39

<210> SEQ ID NO 236
<211> LENGTH: 35
<212> TYPE: DNA
<213> ORGANISM: Artificial
<220> FEATURE:
<223> OTHER INFORMATION: Synthetic oligonucleotide primer for PCR

<400> SEQUENCE: 236
ggtagcatgg gtatgttaaa agcaaatgca gcggg                        35

<210> SEQ ID NO 237
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 237
taaaacgctc atgctacttg taagctcttt aactgaatta gc                42

<210> SEQ ID NO 238

```
<211> LENGTH: 45
<212> TYPE: DNA
<213> ORGANISM: Artificial
<220> FEATURE:
<223> OTHER INFORMATION: Synthetic oligonucleotide primer for PCR

<400> SEQUENCE: 238
gaggagaagc ccggtttaac ttgtaagctc tttaactgaa ttagc          45

<210> SEQ ID NO 239
<211> LENGTH: 44
<212> TYPE: DNA
<213> ORGANISM: Artificial
<220> FEATURE:
<223> OTHER INFORMATION: Synthetic oligonucleotide primer for PCR

<400> SEQUENCE: 239
gaggagaagc ccggtttaac ttgtaagctc tttaactgaa ttag           44

<210> SEQ ID NO 240
<211> LENGTH: 53
<212> TYPE: DNA
<213> ORGANISM: Artificial
<220> FEATURE:
<223> OTHER INFORMATION: Synthetic oligonucleotide primer for PCR

<400> SEQUENCE: 240
gaggagaagc ccggtttatg caggaggact tgtaagctct taactgaat tag  53

<210> SEQ ID NO 241
<211> LENGTH: 50
<212> TYPE: DNA
<213> ORGANISM: Artificial
<220> FEATURE:
<223> OTHER INFORMATION: Synthetic oligonucleotide primer for PCR

<400> SEQUENCE: 241
gaggagaagc ccggtttatc ctccacttgt aagctcttta actgaattag     50

<210> SEQ ID NO 242
<211> LENGTH: 44
<212> TYPE: DNA
<213> ORGANISM: Artificial
<220> FEATURE:
<223> OTHER INFORMATION: Synthetic oligonucleotide primer for PCR

<400> SEQUENCE: 242
taacataccc atgctaccac ttgtaagctc tttaactgaa ttag           44

<210> SEQ ID NO 243
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 243
agttcaagcc aaggcttaaa aacacataat gctaaagaca ag             42

<210> SEQ ID NO 244
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 244
```
taagccttgg cttgaacttg taagctctttt aactgaatta gc  42

<210> SEQ ID NO 245
<211> LENGTH: 42
<212> TYPE: DNA
<213> ORGANISM: Artificial
<220> FEATURE:
<223> OTHER INFORMATION: Synthetic oligonucleotide primer for PCR

<400> SEQUENCE: 245
ggtgctatgt cagcttttaaa aacacataat gctaaagaca ag  42

<210> SEQ ID NO 246
<211> LENGTH: 15
<212> TYPE: DNA
<213> ORGANISM: Artificial
<220> FEATURE:
<223> OTHER INFORMATION: Synthetic oligonucleotide primer for PCR

<400> SEQUENCE: 246
gaggagaagc ccggt  15

<210> SEQ ID NO 247
<211> LENGTH: 27
<212> TYPE: DNA
<213> ORGANISM: Artificial
<220> FEATURE:
<223> OTHER INFORMATION: Synthetic oligonucleotide primer for PCR

<400> SEQUENCE: 247
cgaaattaat acgactcact atagggg  27

<210> SEQ ID NO 248
<211> LENGTH: 19
<212> TYPE: DNA
<213> ORGANISM: Artificial
<220> FEATURE:
<223> OTHER INFORMATION: Synthetic oligonucleotide primer for PCR

<400> SEQUENCE: 248
gctagttatt gctcagcgg  19

<210> SEQ ID NO 249
<211> LENGTH: 384
<212> TYPE: PRT
<213> ORGANISM: Artificial
<220> FEATURE:
<223> OTHER INFORMATION: Chimeric protein

<400> SEQUENCE: 249

Ala His His His His His His Val Asp Asp Asp Lys Ile Thr Gly
1               5                   10                  15

Leu Lys Ser Glu His Ala Val Leu Gly Leu Asp Asn Leu Thr Asp Asp
            20                  25                  30

Asn Ala Gln Arg Ala Ile Leu Lys Lys His Ala Asn Lys Asp Lys Gly
        35                  40                  45

Ala Ala Glu Leu Glu Lys Leu Phe Lys Ala Val Glu Asn Leu Ser Lys
    50                  55                  60

Ala Ala Gln Asp Thr Leu Lys Asn Ala Pro Gly Val Gly Ala Thr Thr
65                  70                  75                  80

Asp Glu Glu Ala Lys Lys Ala Ile Leu Arg Thr Asn Ala Ile Lys Asp
                85                  90                  95

```
Lys Gly Ala Asp Glu Leu Glu Lys Leu Phe Lys Ser Val Glu Ser Leu
            100                 105                 110

Ala Lys Ala Ala Gln Asp Ala Thr Gln Met Leu Lys Thr Asn Asn Asp
        115                 120                 125

Lys Thr Lys Gly Ala Asp Glu Leu Glu Lys Leu Phe Glu Ser Val Lys
    130                 135                 140

Asn Leu Ser Lys Ala Ala Lys Glu Met Leu Thr Asn Ser Val Lys Glu
145                 150                 155                 160

Leu Thr Ser Thr Glu Pro Ser Glu Glu Phe Thr Lys Lys Leu Lys Glu
                165                 170                 175

Lys His Thr Asp Leu Gly Lys Lys Asp Ala Thr Asp Val His Ala Lys
            180                 185                 190

Glu Ala Ile Leu Lys Thr Asn Gly Thr Lys Asp Lys Gly Ala Ala Glu
        195                 200                 205

Leu Glu Lys Leu Phe Glu Ser Gly Glu Asp Val Ser Glu Thr Phe Thr
    210                 215                 220

Asn Lys Leu Lys Glu Lys His Thr Asp Leu Gly Lys Glu Gly Ser Met
225                 230                 235                 240

Gly Met Leu Lys Ala Asn Ala Ala Gly Lys Asp Lys Gly Val Glu Glu
                245                 250                 255

Leu Glu Lys Leu Ser Gly Ser Leu Glu Ser Leu Ser Lys Ala Ala Lys
            260                 265                 270

Glu Met Leu Ala Asn Ser Val Lys Glu Leu Thr Ser Thr Asn Gly Asn
        275                 280                 285

Leu Ile Thr Asp Ala Ala Lys Asp Lys Gly Ala Ala Glu Leu Glu Lys
    290                 295                 300

Leu Phe Lys Ala Val Glu Asn Leu Ala Lys Ala Lys Glu Met Leu
305                 310                 315                 320

Ala Asn Ser Val Lys Glu Leu Thr Ser Met Ser Val Leu Lys Thr
                325                 330                 335

His Asn Ala Lys Asp Lys Gly Ala Glu Glu Leu Val Lys Leu Ser Glu
            340                 345                 350

Ser Val Ala Gly Leu Leu Lys Ala Ala Gln Ala Ile Leu Ala Asn Ser
        355                 360                 365

Val Lys Glu Leu Thr Ser Pro Val Val Ala Glu Ser Pro Lys Lys Pro
    370                 375                 380

<210> SEQ ID NO 250
<211> LENGTH: 569
<212> TYPE: PRT
<213> ORGANISM: Artificial Sequence
<220> FEATURE:
<223> OTHER INFORMATION: Chimeric protein

<400> SEQUENCE: 250

Ser Glu Thr Phe Thr Asn Lys Leu Lys Glu Lys His Thr Asp Leu Gly
1               5                   10                  15

Lys Glu Gly Val Thr Asp Ala Asp Ala Lys Glu Ala Ile Leu Lys Thr
            20                  25                  30

Asn Gly Thr Lys Thr Lys Gly Ala Glu Glu Leu Gly Lys Leu Phe Glu
        35                  40                  45

Ser Val Glu Val Leu Ser Lys Ala Ala Lys Glu Met Leu Ala Asn Ser
    50                  55                  60

Val Lys Glu Leu Thr Ser Ser Glu Glu Phe Ser Thr Lys Leu Lys Asp
65                  70                  75                  80
```

```
Asn His Ala Gln Leu Gly Ile Gln Gly Val Thr Asp Glu Asn Ala Lys
            85                  90                  95
Lys Ala Ile Leu Lys Ala Asn Ala Ala Gly Lys Asp Lys Gly Val Glu
        100                 105                 110
Glu Leu Glu Lys Leu Ser Gly Ser Leu Glu Ser Leu Ser Ser Glu Asp
    115                 120                 125
Phe Thr Lys Lys Leu Glu Gly Glu His Ala Gln Leu Gly Ile Glu Asn
130                 135                 140
Val Thr Asp Glu Asn Ala Lys Lys Ala Ile Leu Ile Thr Asp Ala Ala
145                 150                 155                 160
Lys Asp Lys Gly Ala Ala Glu Leu Glu Lys Leu Phe Lys Ala Val Glu
                165                 170                 175
Asn Leu Ala Ala Lys Leu Lys Gly Glu His Thr Asp Leu Gly Lys Glu
            180                 185                 190
Gly Val Thr Asp Asp Asn Ala Lys Lys Ala Ile Leu Lys Thr Asn Asn
        195                 200                 205
Asp Lys Thr Lys Gly Ala Asp Glu Leu Glu Lys Leu Phe Glu Ser Val
    210                 215                 220
Lys Asn Leu Ser Lys Ala Ala Lys Glu Met Leu Thr Asn Ser Ser Glu
225                 230                 235                 240
Lys Phe Ala Gly Lys Leu Lys Asn Glu His Ala Ser Leu Gly Lys Lys
                245                 250                 255
Asp Ala Thr Asp Asp Ala Lys Lys Ala Ile Leu Lys Thr His Lys Gly
            260                 265                 270
Asn Thr Asp Lys Gly Ala Lys Glu Leu Lys Asp Leu Ser Asp Ser Val
        275                 280                 285
Glu Ser Leu Val Ser Asp Asp Phe Thr Lys Lys Leu Gln Ser Ser His
    290                 295                 300
Ala Gln Leu Gly Val Ala Gly Gly Ala Thr Thr Asp Glu Glu Ala Lys
305                 310                 315                 320
Lys Ala Ile Leu Arg Thr Asn Ala Ile Lys Asp Lys Gly Ala Asp Glu
                325                 330                 335
Leu Glu Lys Leu Phe Lys Ser Val Glu Ser Leu Ala Lys Ala Ala Gln
            340                 345                 350
Asp Ala Leu Ala Asn Ser Val Asn Glu Leu Thr Ser Lys Lys Leu Lys
        355                 360                 365
Glu Lys His Thr Asp Leu Gly Lys Lys Asp Ala Thr Asp Val His Ala
    370                 375                 380
Lys Glu Ala Ile Leu Lys Thr Asn Gly Thr Lys Asp Lys Gly Ala Ala
385                 390                 395                 400
Glu Leu Glu Lys Leu Phe Glu Ser Val Glu Asn Leu Ala Lys Ala Ala
                405                 410                 415
Lys Glu Met Leu Ser Asn Ser Asn Lys Ala Phe Thr Asp Lys Leu Lys
            420                 425                 430
Ser Ser His Ala Glu Leu Gly Ile Ala Asn Gly Ala Ala Thr Asp Ala
        435                 440                 445
Asn Ala Lys Ala Ala Ile Leu Lys Thr Asn Gly Thr Lys Asp Lys Gly
    450                 455                 460
Ala Gln Glu Leu Glu Lys Leu Phe Glu Ser Val Lys Asn Leu Ser Lys
465                 470                 475                 480
Ala Ala Gln Glu Thr Leu Asn Asn Ser Ser Glu Ser Phe Thr Lys Lys
                485                 490                 495
Leu Ser Asp Asn Gln Ala Glu Leu Gly Ile Glu Asn Ala Thr Asp Asp
```

```
              500                 505                 510
Asn Ala Lys Lys Ala Ile Leu Lys Thr His Asn Ala Lys Asp Lys Gly
            515                 520                 525

Ala Glu Glu Leu Val Lys Leu Ser Glu Ser Val Ala Gly Leu Leu Lys
    530                 535                 540

Ala Ala Gln Ala Ile Leu Ala Asn Ser Val Lys Glu Leu Thr Ser Pro
545                 550                 555                 560

Val Val Ala Glu Ser Pro Lys Lys Pro
                565

<210> SEQ ID NO 251
<211> LENGTH: 431
<212> TYPE: PRT
<213> ORGANISM: Artificial Sequence
<220> FEATURE:
<223> OTHER INFORMATION: Chimeric protein

<400> SEQUENCE: 251

Ser Glu Thr Phe Thr Asn Lys Leu Lys Glu Lys His Thr Asp Leu Gly
1               5                   10                  15

Lys Glu Gly Val Thr Lys Gly Ala Glu Leu Gly Lys Leu Phe Glu
            20                  25                  30

Ser Val Glu Val Leu Ser Lys Ala Ala Lys Glu Met Leu Ala Asn Ser
        35                  40                  45

Val Lys Glu Leu Thr Ser Ser Glu Glu Phe Ser Thr Lys Leu Lys Asp
    50                  55                  60

Asn His Ala Gln Leu Gly Ile Gln Gly Val Thr Lys Gly Val Glu Glu
65                  70                  75                  80

Leu Glu Lys Leu Ser Gly Ser Leu Glu Ser Leu Ser Ser Glu Asp Phe
                85                  90                  95

Thr Lys Lys Leu Glu Gly Glu His Ala Gln Leu Gly Ile Glu Asn Val
            100                 105                 110

Thr Ala Ala Glu Leu Glu Lys Leu Phe Lys Ala Val Glu Asn Leu Ala
        115                 120                 125

Lys Ala Ala Lys Glu Met Ala Lys Leu Lys Gly Glu His Thr Asp Leu
    130                 135                 140

Gly Lys Glu Gly Val Thr Lys Gly Ala Asp Glu Leu Glu Lys Leu Phe
145                 150                 155                 160

Glu Ser Val Lys Asn Leu Ser Lys Ala Ala Lys Glu Met Leu Thr Asn
                165                 170                 175

Ser Lys Glu Ser Glu Lys Phe Ala Gly Lys Leu Lys Asn Glu His Ala
            180                 185                 190

Ser Leu Gly Lys Lys Asp Ala Thr Lys Gly Ala Lys Glu Leu Lys Asp
        195                 200                 205

Leu Ser Asp Ser Val Glu Ser Leu Val Lys Ala Ser Asp Asp Phe Thr
    210                 215                 220

Lys Lys Leu Gln Ser Ser His Ala Gln Leu Gly Val Ala Gly Gly Ala
225                 230                 235                 240

Thr Thr Ala Asp Glu Leu Glu Lys Leu Phe Lys Ser Val Glu Ser Leu
                245                 250                 255

Ala Lys Ala Ala Gln Asp Ala Leu Ala Asn Ser Val Asn Glu Leu Thr
            260                 265                 270

Ser Lys Lys Leu Lys Glu Lys His Thr Asp Leu Gly Lys Lys Asp Ala
        275                 280                 285

Thr Ala Ala Glu Leu Glu Lys Leu Phe Glu Ser Val Glu Asn Leu Ala
```

```
        290                 295                 300
Lys Ala Ala Lys Glu Met Leu Ser Asn Ser Asn Lys Ala Phe Thr Asp
305                 310                 315                 320

Lys Leu Lys Ser Ser His Ala Glu Leu Gly Ile Ala Asn Gly Ala Ala
                325                 330                 335

Thr Lys Gly Ala Gln Glu Leu Glu Lys Leu Phe Glu Ser Val Lys Asn
            340                 345                 350

Leu Ser Lys Ala Ala Gln Glu Thr Leu Asn Asn Ser Val Lys Glu Ser
        355                 360                 365

Glu Ser Phe Thr Lys Lys Leu Ser Asp Asn Gln Ala Glu Leu Gly Ile
    370                 375                 380

Glu Asn Ala Thr Lys Gly Ala Glu Glu Leu Val Lys Leu Ser Glu Ser
385                 390                 395                 400

Val Ala Gly Leu Leu Lys Ala Ala Gln Ala Ile Leu Ala Asn Ser Val
                405                 410                 415

Lys Glu Leu Thr Ser Pro Val Val Ala Glu Ser Pro Lys Lys Pro
            420                 425                 430

<210> SEQ ID NO 252
<211> LENGTH: 432
<212> TYPE: PRT
<213> ORGANISM: Artificial Sequence
<220> FEATURE:
<223> OTHER INFORMATION: Chimeric protein

<400> SEQUENCE: 252

Ser Glu Thr Phe Thr Asn Lys Leu Lys Glu Lys His Thr Asp Leu Gly
1               5                   10                  15

Lys Glu Gly Val Thr Lys Gly Ala Glu Glu Leu Gly Lys Leu Phe Glu
            20                  25                  30

Ser Val Glu Val Leu Ser Lys Ala Ala Lys Glu Met Leu Ala Asn Ser
        35                  40                  45

Val Lys Glu Leu Thr Ser Lys Gly Val Glu Glu Leu Glu Lys Leu Ser
    50                  55                  60

Gly Ser Leu Glu Ser Leu Ser Asn Lys Ala Phe Thr Asp Lys Leu Lys
65                  70                  75                  80

Ser Ser His Ala Glu Leu Gly Ile Ala Asn Gly Ala Ala Thr Lys Lys
                85                  90                  95

Leu Lys Glu Lys His Thr Asp Leu Gly Lys Lys Asp Ala Thr Lys Gly
            100                 105                 110

Ala Asp Glu Leu Glu Lys Leu Phe Glu Ser Val Lys Asn Leu Ser Lys
        115                 120                 125

Ala Ala Lys Glu Met Leu Thr Asn Ser Lys Glu Ile Ala Ala Glu Leu
    130                 135                 140

Glu Lys Leu Phe Lys Ala Val Glu Asn Leu Ala Lys Ala Ala Lys Glu
145                 150                 155                 160

Met Ala Lys Leu Lys Gly Glu His Thr Asp Leu Gly Lys Glu Gly Val
                165                 170                 175

Thr Ser Glu Glu Phe Ser Thr Lys Leu Lys Asp Asn His Ala Gln Leu
            180                 185                 190

Gly Ile Gln Gly Val Thr Lys Gly Ala Lys Glu Leu Lys Asp Leu Ser
        195                 200                 205

Asp Ser Val Glu Ser Leu Val Lys Ala Ala Glu Leu Glu Lys Leu
    210                 215                 220

Phe Glu Ser Val Glu Asn Leu Ala Lys Ala Ala Lys Glu Met Leu Ser
```

```
             225                 230                 235                 240
        Asn Ser Ser Glu Lys Phe Ala Gly Lys Leu Lys Asn Glu His Ala Ser
                         245                 250                 255
        Leu Gly Lys Lys Asp Ala Thr Ser Glu Asp Phe Thr Lys Lys Leu Glu
                         260                 265                 270
        Gly Glu His Ala Gln Leu Gly Ile Glu Asn Val Thr Lys Gly Ala Gln
                         275                 280                 285
        Glu Leu Glu Lys Leu Phe Glu Ser Val Lys Asn Leu Ser Lys Ala Ala
                         290                 295                 300
        Gln Glu Thr Leu Asn Asn Ser Val Lys Glu Ala Asp Glu Leu Glu Lys
        305                 310                 315                 320
        Leu Phe Lys Ser Val Glu Ser Leu Ala Lys Ala Ala Gln Asp Ala Leu
                         325                 330                 335
        Ala Asn Ser Val Asn Glu Leu Thr Ser Ser Gly Ser Phe Thr Lys Lys
                         340                 345                 350
        Leu Ser Asp Asn Gln Ala Glu Leu Gly Ile Glu Asn Ala Thr Ser Asp
                         355                 360                 365
        Asp Phe Thr Lys Lys Leu Gln Ser Ser His Ala Gln Leu Gly Val Ala
                         370                 375                 380
        Gly Gly Ala Thr Thr Lys Gly Ala Glu Glu Leu Val Lys Leu Ser Glu
        385                 390                 395                 400
        Ser Val Ala Gly Leu Leu Lys Ala Ala Gln Ala Ile Leu Ala Asn Ser
                         405                 410                 415
        Val Lys Glu Leu Thr Ser Pro Val Val Ala Glu Ser Pro Lys Lys Pro
                         420                 425                 430

<210> SEQ ID NO 253
<211> LENGTH: 503
<212> TYPE: PRT
<213> ORGANISM: Artificial Sequence
<220> FEATURE:
<223> OTHER INFORMATION: Chimeric protein

<400> SEQUENCE: 253

Ser Glu Lys Phe Thr Thr Lys Leu Lys Asp Ser His Ala Glu Leu Gly
1               5                   10                  15

Ile Gln Ser Val Gln Asp Asp Asn Ala Lys Lys Ala Ile Leu Lys Thr
                20                  25                  30

His Gly Thr Lys Asp Lys Gly Ala Lys Glu Leu Glu Leu Phe Lys
                35                  40                  45

Ser Leu Glu Ser Leu Ser Lys Ala Ala Gln Ala Ala Leu Thr Asn Ser
    50                  55                  60

Val Lys Glu Leu Thr Asn Ser Asp Lys Phe Thr Lys Lys Leu Thr Asp
65                  70                  75                  80

Ser His Ala Gln Leu Gly Ala Val Gly Gly Ala Ile Asn Asp Asp Arg
                85                  90                  95

Ala Lys Glu Ala Ile Leu Lys Thr His Gly Thr Asn Asp Lys Gly Ala
                100                 105                 110

Lys Glu Leu Lys Glu Leu Ser Glu Ser Val Glu Ser Leu Ala Lys Ala
                115                 120                 125

Ala Gln Ala Ala Leu Ala Asn Ser Ser Glu Ala Phe Thr Lys Lys Leu
                130                 135                 140

Lys Asp Ser Asn Ala Gln Leu Gly Met Gln Asn Gly Ala Ala Thr Asp
145                 150                 155                 160

Ala His Ala Lys Ala Ala Ile Leu Lys Thr Asp Ala Thr Lys Asp Lys
```

165                 170                 175
Gly Ala Thr Glu Leu Gly Glu Leu Phe Lys Ser Val Glu Ser Leu Ser
                180                 185                 190

Lys Ala Ala Gln Glu Ala Ser Val Ala Phe Thr Ser Lys Leu Lys Ser
            195                 200                 205

Ser Asn Ala Gln Leu Gly Val Ala Asn Gly Asn Ala Thr Asp Asp Asp
        210                 215                 220

Ala Lys Lys Ala Ile Leu Lys Thr Asn Thr Pro Asn Asp Lys Gly Ala
225                 230                 235                 240

Lys Glu Leu Lys Glu Leu Phe Glu Ser Val Glu Ser Leu Ala Lys Ala
                245                 250                 255

Ala Gln Ala Ala Leu Val Asn Ser Val Gln Glu Leu Thr Asn Ser Glu
            260                 265                 270

Ala Phe Thr Asn Arg Leu Lys Gly Ser His Ala Gln Leu Gly Val Ala
        275                 280                 285

Ala Ala Thr Asp Asp His Ala Lys Glu Ala Ile Leu Lys Ser Asn Pro
290                 295                 300

Thr Lys Asp Lys Gly Ala Lys Glu Leu Lys Asp Leu Ser Glu Ser Val
305                 310                 315                 320

Glu Ser Leu Ala Lys Ala Ala Gln Glu Ala Leu Ala Asn Ser Val Lys
                325                 330                 335

Glu Leu Thr Asn Ser Glu Ala Phe Thr Lys Lys Leu Lys Asp Asn Asn
            340                 345                 350

Ala Gln Leu Gly Ile Gln Asn Val Gln Asp Val Glu Ala Lys Lys Ala
        355                 360                 365

Ile Leu Lys Thr Asn Gly Asp Ile Ser Lys Ser Glu Ala Phe Thr Asn
370                 375                 380

Lys Leu Lys Glu Lys His Ala Glu Leu Gly Val Asn Gly Gly Asp Thr
385                 390                 395                 400

Thr Asp Asp Asn Ala Lys Ala Ala Ile Phe Lys Thr His Pro Thr Lys
                405                 410                 415

Asp Lys Gly Val Glu Asp Leu Glu Lys Leu Ser Glu Ser Val Lys Ser
            420                 425                 430

Leu Leu Lys Ala Ala Gln Ala Ala Leu Ser Asn Ser Ala Ala Phe Thr
        435                 440                 445

Lys Lys Leu Gln Asp Gly His Val Asp Leu Gly Lys Thr Asp Val Thr
450                 455                 460

Asp Asp Asn Ala Lys Glu Ala Ile Leu Lys Thr Asn Pro Thr Lys Thr
465                 470                 475                 480

Lys Gly Ala Thr Glu Leu Glu Glu Leu Phe Lys Ser Val Glu Gly Leu
                485                 490                 495

Val Lys Ala Ala Lys Glu Ala
            500

<210> SEQ ID NO 254
<211> LENGTH: 381
<212> TYPE: PRT
<213> ORGANISM: Artificial Sequence
<220> FEATURE:
<223> OTHER INFORMATION: Chimeric protein

<400> SEQUENCE: 254

Ser Glu Lys Phe Thr Thr Lys Leu Lys Asp Ser His Ala Glu Leu Gly
1               5                   10                  15

Ile Gln Ser Val Gln Asp Lys Gly Ala Lys Glu Leu Glu Glu Leu Phe

```
            20                  25                  30
Lys Ser Leu Glu Ser Leu Ser Lys Ala Ala Gln Ala Ala Leu Thr Asn
        35                  40                  45

Ser Val Lys Glu Leu Thr Asn Ser Asp Lys Phe Thr Lys Lys Leu Thr
    50                  55                  60

Asp Ser His Ala Gln Leu Gly Ala Val Gly Ala Ile Asn Asp Lys
65                  70                  75                  80

Gly Ala Lys Glu Leu Lys Glu Leu Ser Glu Ser Val Glu Ser Leu Ala
                85                  90                  95

Lys Ala Ala Gln Ala Ala Leu Ala Asn Ser Ser Glu Ala Phe Thr Lys
            100                 105                 110

Lys Leu Lys Asp Ser Asn Ala Gln Leu Gly Met Gln Asn Gly Ala Ala
            115                 120                 125

Thr Asp Lys Gly Ala Thr Glu Leu Gly Glu Leu Phe Lys Ser Val Glu
            130                 135                 140

Ser Leu Ser Lys Ala Ala Gln Glu Ala Ser Val Ala Phe Thr Ser Lys
145                 150                 155                 160

Leu Lys Ser Ser Asn Ala Gln Leu Gly Val Ala Asn Gly Asn Ala Thr
                165                 170                 175

Asp Lys Gly Ala Lys Glu Leu Lys Glu Leu Phe Glu Ser Val Glu Ser
            180                 185                 190

Leu Ala Lys Ala Ala Gln Ala Ala Leu Val Asn Ser Val Gln Glu Leu
            195                 200                 205

Thr Asn Ser Glu Ala Phe Thr Asn Arg Leu Lys Gly Ser His Ala Gln
            210                 215                 220

Leu Gly Val Ala Ala Thr Asp Lys Gly Ala Lys Glu Leu Lys Asp
225                 230                 235                 240

Leu Ser Glu Ser Val Glu Ser Leu Ala Lys Ala Ala Gln Glu Ala Leu
                245                 250                 255

Ala Asn Ser Val Lys Glu Leu Thr Asn Ser Glu Ala Phe Thr Lys Lys
            260                 265                 270

Leu Lys Asp Asn Asn Ala Gln Leu Gly Ile Gln Asn Val Gln Ser Glu
            275                 280                 285

Ala Phe Thr Asn Lys Leu Lys Glu Lys His Ala Glu Leu Gly Val Asn
            290                 295                 300

Gly Gly Asp Thr Thr Asp Lys Gly Val Glu Asp Leu Glu Lys Leu Ser
305                 310                 315                 320

Glu Ser Val Lys Ser Leu Leu Lys Ala Ala Gln Ala Ala Leu Ser Asn
                325                 330                 335

Ser Ala Ala Phe Thr Lys Lys Leu Gln Asp Gly His Val Asp Leu Gly
            340                 345                 350

Lys Thr Asp Val Thr Thr Lys Gly Ala Thr Glu Leu Glu Glu Leu Phe
            355                 360                 365

Lys Ser Val Glu Gly Leu Val Lys Ala Ala Lys Glu Ala
            370                 375                 380

<210> SEQ ID NO 255
<211> LENGTH: 382
<212> TYPE: PRT
<213> ORGANISM: Artificial Sequence
<220> FEATURE:
<223> OTHER INFORMATION: Chimeric protein

<400> SEQUENCE: 255

Ser Glu Ala Phe Thr Lys Lys Leu Lys Asp Ser Asn Ala Gln Leu Gly
```

```
1               5                   10                  15
Met Gln Asn Gly Ala Ala Thr Asp Lys Gly Ala Lys Glu Leu Glu Glu
                20                  25                  30
Leu Phe Lys Ser Leu Glu Ser Leu Ser Lys Ala Ala Gln Ala Ala Leu
                35                  40                  45
Thr Asn Ser Val Lys Glu Leu Thr Asn Lys Asp Lys Gly Ala Lys Glu
        50                  55                  60
Leu Lys Glu Leu Phe Glu Ser Val Glu Ser Leu Ala Lys Ala Ala Gln
65                  70                  75                  80
Ala Ala Leu Val Asn Ser Val Gln Glu Leu Thr Asn Ser Glu Lys Phe
                85                  90                  95
Thr Thr Lys Leu Lys Asp Ser His Ala Glu Leu Gly Ile Gln Ser Val
                100                 105                 110
Gln Ser Asp Lys Phe Thr Lys Lys Leu Thr Asp Ser His Ala Gln Leu
            115                 120                 125
Gly Ala Val Gly Gly Ala Ile Asn Asp Lys Gly Ala Lys Glu Leu Lys
        130                 135                 140
Glu Leu Ser Glu Ser Val Glu Ser Leu Ala Lys Ala Ala Gln Ala Ala
145                 150                 155                 160
Leu Ala Asn Ser Asp Lys Gly Ala Lys Glu Leu Lys Asp Leu Ser Glu
                165                 170                 175
Ser Val Glu Ser Leu Ala Lys Ala Ala Gln Glu Ala Leu Ala Asn Ser
                180                 185                 190
Val Lys Glu Leu Thr Asn Ser Val Ala Phe Thr Ser Lys Leu Lys Ser
                195                 200                 205
Ser Asn Ala Gln Leu Gly Val Ala Asn Gly Asn Ala Thr Ser Glu Ala
        210                 215                 220
Phe Thr Lys Lys Leu Lys Asp Asn Asn Ala Gln Leu Gly Ile Gln Asn
225                 230                 235                 240
Val Gln Thr Lys Gly Ala Thr Glu Leu Glu Glu Leu Phe Lys Ser Val
                245                 250                 255
Glu Gly Leu Val Lys Ala Ala Lys Glu Ala Asp Lys Gly Val Glu Asp
                260                 265                 270
Leu Glu Lys Leu Ser Glu Ser Val Lys Ser Leu Leu Lys Ala Ala Gln
                275                 280                 285
Ala Ala Leu Ser Asn Ser Ala Ala Phe Thr Lys Lys Leu Gln Asp Gly
        290                 295                 300
His Val Asp Leu Gly Lys Thr Asp Val Thr Ser Glu Ala Phe Thr Asn
305                 310                 315                 320
Arg Leu Lys Gly Ser His Ala Gln Leu Gly Val Ala Ala Thr Asp
                325                 330                 335
Lys Gly Ala Thr Glu Leu Gly Glu Leu Phe Lys Ser Val Glu Ser Leu
                340                 345                 350
Ser Lys Ala Ala Gln Glu Ala Ser Glu Ala Phe Thr Asn Lys Leu Lys
                355                 360                 365
Glu Lys His Ala Glu Leu Gly Val Asn Gly Gly Asp Thr Thr
                370                 375                 380

<210> SEQ ID NO 256
<211> LENGTH: 512
<212> TYPE: PRT
<213> ORGANISM: Artificial Sequence
<220> FEATURE:
<223> OTHER INFORMATION: Chimeric protein
```

<400> SEQUENCE: 256

```
Ser Glu Glu Phe Thr Asn Lys Leu Lys Ser Gly His Ala Asp Leu Gly
1               5                   10                  15

Lys Gln Asp Ala Thr Asp His Ala Lys Ala Ile Leu Lys Thr
            20                  25                  30

His Ala Thr Thr Asp Lys Gly Ala Lys Glu Phe Lys Asp Leu Phe Glu
                35                  40                  45

Ser Val Glu Gly Leu Leu Lys Ala Ala Gln Val Ala Leu Thr Asn Ser
    50                  55                  60

Val Lys Glu Leu Thr Ser Lys Leu Lys Gly Gly His Ala Glu Leu Gly
65                  70                  75                  80

Leu Ala Ala Ala Thr Asp Glu Asn Ala Lys Lys Ala Ile Leu Lys Thr
                85                  90                  95

Asn Gly Thr Lys Asp Lys Gly Ala Glu Glu Leu Glu Lys Leu Phe Lys
                100                 105                 110

Ser Val Glu Ser Leu Ala Lys Ala Ala Lys Glu Ser Leu Thr Asn Ser
            115                 120                 125

Val Lys Glu Leu Thr Asn Thr Lys Leu Arg Asp Ser His Ala Glu Leu
130                 135                 140

Gly Ile Gln Asn Val Gln Asp Asp Asn Ala Lys Arg Ala Ile Leu Lys
145                 150                 155                 160

Thr His Gly Asn Lys Asp Lys Gly Ala Lys Glu Leu Lys Glu Leu Ser
                165                 170                 175

Glu Ser Leu Glu Lys Leu Ser Lys Ala Ala Gln Ala Ala Leu Ala Asn
            180                 185                 190

Ser Val Gln Glu Leu Thr Ser Ser Glu Ala Phe Thr Asn Lys Leu Lys
            195                 200                 205

Glu Lys Thr Gln Glu Leu Ala Val Ala Ala Gly Ala Ala Thr Asp Ile
210                 215                 220

Asp Ala Lys Lys Ala Ile Leu Lys Thr Asn Arg Asp Lys Asp Leu Gly
225                 230                 235                 240

Ala Asp Glu Arg Gly Lys Leu Phe Lys Ser Val Glu Ser Leu Ser Lys
                245                 250                 255

Ala Ala Gln Glu Ala Ser Ala Asn Ser Val Lys Glu Leu Thr Ser Ser
            260                 265                 270

Glu Ala Phe Thr Asp Lys Leu Lys Asn Glu His Ala Ser Leu Gly Lys
            275                 280                 285

Lys Asp Ala Thr Asp Asp Ala Lys Ala Ile Leu Lys Thr Asn
290                 295                 300

Val Asp Lys Thr Lys Gly Ala Asp Glu Leu Ile Lys Leu Ser Gly Ser
305                 310                 315                 320

Leu Glu Ser Leu Ser Lys Ala Ala Gln Ala Ile Leu Ala Asn Ser Glu
                325                 330                 335

Ala Phe Thr Lys Lys Leu Gln Asp Ser Asn Ala Asp Leu Gly Lys His
            340                 345                 350

Asn Ala Thr Asp Ala Asp Ser Lys Glu Ala Ile Leu Lys Thr Asn Gly
            355                 360                 365

Thr Lys Thr Lys Gly Ala Lys Glu Leu Glu Glu Leu Phe Lys Ser Val
            370                 375                 380

Glu Ser Leu Ser Lys Ala Ala Lys Glu Ala Leu Ser Asn Ser Val Lys
385                 390                 395                 400

Glu Leu Thr Ser Ser Gln Asp Phe Ile Asn Lys Leu Lys Gly Gly His
                405                 410                 415
```

```
Ala Glu Leu Gly Leu Val Ala Ala Thr Asp Ala Asn Ala Lys Ala Ala
            420                 425                 430

Ile Leu Lys Thr Asn Gly Asp Lys Thr Lys Gly Ala Asp Glu Phe Glu
            435                 440                 445

Lys Leu Phe Lys Ser Val Glu Gly Leu Leu Lys Ala Ala Gln Glu Ala
        450                 455                 460

Leu Thr Asn Ser Val Lys Glu Leu Thr Ser Ser Glu Ala Phe Thr Lys
465                 470                 475                 480

Lys Leu Gln Asp Ser Asn Ala Asp Leu Gly Lys His Asp Ala Thr Asp
                485                 490                 495

Ala Asp Ala Lys Lys Ala Ile Leu Lys Thr Asp Ala Thr Lys Asp Lys
            500                 505                 510

<210> SEQ ID NO 257
<211> LENGTH: 383
<212> TYPE: PRT
<213> ORGANISM: Artificial Sequence
<220> FEATURE:
<223> OTHER INFORMATION: Chimeric protein

<400> SEQUENCE: 257

Ser Glu Glu Phe Thr Asn Lys Leu Lys Ser Gly His Ala Asp Leu Gly
1               5                   10                  15

Lys Gln Asp Ala Thr Lys Gly Ala Lys Glu Phe Lys Asp Leu Phe Glu
            20                  25                  30

Ser Val Glu Gly Leu Leu Lys Ala Ala Gln Val Ala Leu Thr Asn Ser
        35                  40                  45

Val Lys Glu Leu Thr Ser Lys Leu Lys Gly Gly His Ala Glu Leu Gly
    50                  55                  60

Leu Ala Ala Ala Thr Lys Gly Ala Glu Glu Leu Glu Lys Leu Phe Lys
65                  70                  75                  80

Ser Val Glu Ser Leu Ala Lys Ala Ala Lys Glu Ser Leu Thr Asn Ser
                85                  90                  95

Val Lys Glu Leu Thr Asn Thr Lys Leu Arg Asp Ser His Ala Glu Leu
            100                 105                 110

Gly Ile Gln Asn Val Gln Lys Gly Ala Lys Glu Leu Lys Glu Leu Ser
        115                 120                 125

Glu Ser Leu Glu Lys Leu Ser Lys Ala Ala Gln Ala Ala Leu Ala Asn
    130                 135                 140

Ser Val Gln Glu Leu Thr Ser Ser Glu Ala Phe Thr Asn Lys Leu Lys
145                 150                 155                 160

Glu Lys Thr Gln Glu Leu Ala Val Ala Ala Gly Ala Ala Thr Leu Gly
                165                 170                 175

Ala Asp Glu Arg Gly Lys Leu Phe Lys Ser Val Glu Ser Leu Ser Lys
            180                 185                 190

Ala Ala Gln Glu Ala Ser Ala Asn Ser Val Lys Glu Leu Thr Ser Ser
        195                 200                 205

Glu Ala Phe Thr Asp Lys Leu Lys Asn Glu His Ala Ser Leu Gly Lys
    210                 215                 220

Lys Asp Ala Thr Lys Gly Ala Asp Glu Leu Ile Lys Leu Ser Gly Ser
225                 230                 235                 240

Leu Glu Ser Leu Ser Lys Ala Ala Gln Ala Ile Leu Ala Asn Ser Glu
                245                 250                 255

Ala Phe Thr Lys Lys Leu Gln Asp Ser Asn Ala Asp Leu Gly Lys His
            260                 265                 270
```

```
Asn Ala Thr Lys Gly Ala Lys Glu Leu Glu Glu Leu Phe Lys Ser Val
            275                 280                 285

Glu Ser Leu Ser Lys Ala Ala Lys Glu Ala Leu Ser Asn Ser Val Lys
        290                 295                 300

Glu Leu Thr Ser Ser Gln Asp Phe Ile Asn Lys Leu Lys Gly Gly His
305                 310                 315                 320

Ala Glu Leu Gly Leu Val Ala Ala Thr Lys Gly Ala Asp Glu Phe Glu
            325                 330                 335

Lys Leu Phe Lys Ser Val Glu Gly Leu Leu Lys Ala Ala Gln Glu Ala
            340                 345                 350

Leu Thr Asn Ser Val Lys Glu Leu Thr Ser Ser Glu Ala Phe Thr Lys
            355                 360                 365

Lys Leu Gln Asp Ser Asn Ala Asp Leu Gly Lys His Asp Ala Thr
            370                 375                 380

<210> SEQ ID NO 258
<211> LENGTH: 383
<212> TYPE: PRT
<213> ORGANISM: Artificial Sequence
<220> FEATURE:
<223> OTHER INFORMATION: Chimeric protein

<400> SEQUENCE: 258

Ser Glu Glu Phe Thr Asn Lys Leu Lys Ser Gly His Ala Asp Leu Gly
1               5                   10                  15

Lys Gln Asp Ala Thr Lys Gly Ala Lys Glu Phe Lys Asp Leu Phe Glu
            20                  25                  30

Ser Val Glu Gly Leu Leu Lys Ala Ala Gln Val Ala Leu Thr Asn Ser
        35                  40                  45

Val Lys Glu Leu Thr Ser Lys Glu Lys Gly Ala Glu Glu Leu Glu Lys
    50                  55                  60

Leu Phe Lys Ser Val Glu Ser Leu Ala Lys Ala Ala Lys Glu Ser Leu
65                  70                  75                  80

Thr Asn Ser Val Lys Glu Leu Thr Asn Ser Glu Ala Phe Thr Asp Lys
                85                  90                  95

Leu Lys Asn Glu His Ala Ser Leu Gly Lys Lys Asp Ala Thr Thr Lys
            100                 105                 110

Leu Arg Asp Ser His Ala Glu Leu Gly Ile Gln Asn Val Gln Leu Gly
        115                 120                 125

Ala Asp Glu Arg Gly Lys Leu Phe Lys Ser Val Glu Ser Leu Ser Lys
130                 135                 140

Ala Ala Gln Glu Ala Ser Ala Asn Ser Val Lys Glu Leu Thr Ser Lys
145                 150                 155                 160

Glu Lys Gly Ala Lys Glu Leu Glu Glu Leu Phe Lys Ser Val Glu Ser
                165                 170                 175

Leu Ser Lys Ala Ala Lys Glu Ala Leu Ser Asn Ser Val Lys Glu Leu
            180                 185                 190

Thr Ser Ser Glu Ala Phe Thr Lys Lys Leu Gln Asp Ser Asn Ala Asp
        195                 200                 205

Leu Gly Lys His Asn Ala Thr Ser Glu Ala Phe Thr Lys Lys Leu Gln
    210                 215                 220

Asp Ser Asn Ala Asp Leu Gly Lys His Asp Ala Thr Lys Gly Ala Asp
225                 230                 235                 240

Glu Phe Glu Lys Leu Phe Lys Ser Val Glu Gly Leu Leu Lys Ala Ala
                245                 250                 255
```

```
Gln Glu Ala Leu Thr Asn Ser Val Lys Glu Leu Thr Ser Glu Leu Lys
            260                 265                 270

Glu Leu Ser Glu Ser Leu Glu Lys Leu Ser Lys Ala Ala Gln Ala Ala
        275                 280                 285

Leu Ala Asn Ser Val Gln Glu Leu Thr Ser Ser Glu Ala Phe Thr Asn
    290                 295                 300

Lys Leu Lys Glu Lys Thr Gln Glu Leu Ala Val Ala Ala Gly Ala Ala
305                 310                 315                 320

Thr Lys Leu Lys Gly Gly His Ala Glu Leu Gly Leu Ala Ala Ala Thr
                325                 330                 335

Lys Gly Ala Asp Glu Leu Ile Lys Leu Ser Gly Ser Leu Glu Ser Leu
                340                 345                 350

Ser Lys Ala Ala Gln Ala Ile Leu Ala Asn Ser Gln Asp Phe Ile Asn
        355                 360                 365

Lys Leu Lys Gly Gly His Ala Glu Leu Gly Leu Val Ala Ala Thr
    370                 375                 380

<210> SEQ ID NO 259
<211> LENGTH: 823
<212> TYPE: PRT
<213> ORGANISM: Artificial Sequence
<220> FEATURE:
<223> OTHER INFORMATION: Chimeric protein

<400> SEQUENCE: 259

Ser Glu Asp Phe Thr Asn Lys Leu Lys Asn Gly Asn Ala Gln Leu Gly
1               5                   10                  15

Leu Ala Ala Ala Thr Lys Gly Ala Lys Glu Leu Lys Asp Leu Ser Asp
            20                  25                  30

Ser Val Glu Ser Leu Val Lys Ala Ala Gln Val Met Leu Thr Asn Ser
        35                  40                  45

Ser Thr Gly Phe Thr Asn Lys Leu Lys Ser Gly His Ala Glu Leu Gly
    50                  55                  60

Pro Val Gly Gly Asn Ala Thr Lys Gly Ala Lys Glu Leu Lys Asp Leu
65                  70                  75                  80

Ser Glu Ser Val Glu Ala Leu Ala Lys Ala Ala Gln Ala Met Leu Thr
                85                  90                  95

Asn Ser Glu Lys Phe Thr Lys Leu Ser Glu Ser His Ala Asp
            100                 105                 110

Ile Gly Ile Gln Ala Ala Thr Lys Gly Ala Glu Glu Leu Asp Lys Leu
        115                 120                 125

Phe Lys Ala Val Glu Asn Leu Ser Lys Ser Thr Glu Phe Thr Asn Lys
    130                 135                 140

Leu Lys Ser Glu His Ala Val Leu Gly Leu Asp Asn Leu Thr Lys Gly
145                 150                 155                 160

Ala Ala Glu Leu Glu Lys Leu Phe Lys Ala Val Glu Asn Leu Ser Lys
                165                 170                 175

Ala Ala Gln Asp Thr Leu Lys Asn Ala Val Lys Glu Leu Thr Ser Pro
            180                 185                 190

Ile Val Ala Glu Ser Pro Lys Lys Pro Ser Glu Thr Phe Thr Asn Lys
        195                 200                 205

Leu Lys Glu Lys His Thr Asp Leu Gly Lys Glu Gly Val Thr Lys Gly
    210                 215                 220

Ala Glu Glu Leu Gly Lys Leu Phe Glu Ser Val Glu Val Leu Ser Lys
225                 230                 235                 240
```

```
Ala Ala Lys Glu Met Leu Ala Asn Ser Val Lys Glu Leu Thr Ser Ser
                245                 250                 255
Glu Glu Phe Ser Thr Lys Leu Lys Asp Asn His Ala Gln Leu Gly Ile
            260                 265                 270
Gln Gly Val Thr Lys Gly Val Glu Glu Leu Lys Leu Ser Gly Ser
        275                 280                 285
Leu Glu Ser Leu Ser Ser Glu Asp Phe Thr Lys Lys Leu Glu Gly Glu
            290                 295                 300
His Ala Gln Leu Gly Ile Glu Asn Val Thr Ala Ala Glu Leu Glu Lys
305                 310                 315                 320
Leu Phe Lys Ala Val Glu Asn Leu Ala Lys Ala Lys Glu Met Ala
                325                 330                 335
Lys Leu Lys Gly Glu His Thr Asp Leu Gly Lys Glu Gly Val Thr Lys
            340                 345                 350
Gly Ala Asp Glu Leu Glu Lys Leu Phe Glu Ser Val Lys Asn Leu Ser
        355                 360                 365
Lys Ala Ala Lys Glu Met Leu Thr Asn Ser Val Lys Glu Ser Glu Lys
        370                 375                 380
Phe Ala Gly Lys Leu Lys Asn Glu His Ala Ser Leu Gly Lys Lys Asp
385                 390                 395                 400
Ala Thr Lys Gly Ala Lys Glu Leu Lys Asp Leu Ser Asp Ser Val Glu
                405                 410                 415
Ser Leu Val Lys Ala Ser Asp Phe Thr Lys Lys Leu Gln Ser Ser
                420                 425                 430
His Ala Gln Leu Gly Val Ala Gly Ala Thr Thr Ala Asp Glu Leu
        435                 440                 445
Glu Lys Leu Phe Lys Ser Val Glu Ser Leu Ala Lys Ala Ala Gln Asp
450                 455                 460
Ala Leu Ala Asn Ser Val Asn Glu Leu Thr Ser Lys Lys Leu Lys Glu
465                 470                 475                 480
Lys His Thr Asp Leu Gly Lys Lys Asp Ala Thr Ala Ala Glu Leu Glu
            485                 490                 495
Lys Leu Phe Glu Ser Val Glu Asn Leu Ala Lys Ala Ala Lys Glu Met
                500                 505                 510
Leu Ser Asn Ser Asn Lys Ala Phe Thr Asp Lys Leu Lys Ser Ser His
            515                 520                 525
Ala Glu Leu Gly Ile Ala Asn Gly Ala Ala Thr Lys Gly Ala Gln Glu
            530                 535                 540
Leu Glu Lys Leu Phe Glu Ser Val Lys Asn Leu Ser Lys Ala Ala Gln
545                 550                 555                 560
Glu Thr Leu Asn Asn Ser Val Lys Glu Ser Glu Ser Phe Thr Lys Lys
                565                 570                 575
Leu Ser Asp Asn Gln Ala Glu Leu Gly Ile Glu Asn Ala Thr Lys Gly
            580                 585                 590
Ala Glu Glu Leu Val Lys Leu Ser Glu Ser Val Ala Gly Leu Leu Lys
        595                 600                 605
Ala Ala Gln Ala Ile Leu Ala Asn Ser Val Lys Glu Leu Thr Ser Pro
        610                 615                 620
Val Val Ala Glu Ser Pro Lys Lys Pro Asn Asn Ser Gly Lys Asp Gly
625                 630                 635                 640
Asn Thr Ser Ala Asn Ser Ala Asp Glu Ser Val Lys Gly Pro Asn Leu
                645                 650                 655
```

```
Thr Glu Ile Ser Lys Lys Ile Thr Glu Ser Asn Ala Val Val Leu Ala
            660                 665                 670

Val Lys Glu Ile Glu Thr Leu Leu Ser Ser Ile Asp Glu Leu Ala Thr
            675                 680                 685

Lys Ala Ile Gly Gln Lys Ile Asp Ala Asn Gly Leu Gly Val Gln Ala
            690                 695                 700

Asn Gln Asn Gly Ser Leu Leu Ala Gly Ala Tyr Ala Ile Ser Thr Leu
705                 710                 715                 720

Ile Thr Gln Lys Leu Ser Ala Leu Asn Ser Glu Asp Leu Lys Glu Lys
            725                 730                 735

Val Ala Lys Val Lys Lys Cys Ser Glu Asp Phe Thr Asn Lys Leu Lys
            740                 745                 750

Asn Gly Asn Ala Gln Leu Gly Leu Ala Ala Thr Asp Asp Asn Ala
            755                 760                 765

Lys Ala Ala Ile Leu Lys Thr Asn Gly Thr Asn Asp Lys Gly Ala Lys
            770                 775                 780

Glu Leu Lys Asp Leu Ser Asp Ser Val Glu Ser Leu Val Lys Ala Ala
785                 790                 795                 800

Gln Val Met Leu Thr Asn Ser Val Lys Glu Leu Thr Ser Pro Val Val
            805                 810                 815

Ala Glu Ser Pro Lys Lys Pro
            820

<210> SEQ ID NO 260
<211> LENGTH: 335
<212> TYPE: PRT
<213> ORGANISM: Artificial Sequence
<220> FEATURE:
<223> OTHER INFORMATION: Chimeric protein

<400> SEQUENCE: 260

Ser Glu Asp Phe Thr Asn Lys Leu Lys Asn Gly Asn Ala Gln Leu Gly
1               5                   10                  15

Leu Ala Ala Ala Thr Lys Gly Ala Lys Glu Leu Lys Asp Leu Ser Asp
            20                  25                  30

Ser Val Glu Ser Leu Val Lys Ala Ala Gln Val Met Leu Thr Asn Ser
            35                  40                  45

Ser Thr Gly Phe Thr Asn Lys Leu Lys Ser Gly His Ala Glu Leu Gly
            50                  55                  60

Pro Val Gly Gly Asn Ala Thr Lys Gly Ala Lys Glu Leu Lys Asp Leu
65                  70                  75                  80

Ser Glu Ser Val Glu Ala Leu Ala Lys Ala Ala Gln Ala Met Leu Thr
            85                  90                  95

Asn Ser Glu Lys Phe Thr Lys Leu Ser Glu Ser His Ala Asp
            100                 105                 110

Ile Gly Ile Gln Ala Ala Thr Lys Gly Ala Glu Glu Leu Asp Lys Leu
            115                 120                 125

Phe Lys Ala Val Glu Asn Leu Ser Lys Ser Thr Glu Phe Thr Asn Lys
            130                 135                 140

Leu Lys Ser Glu His Ala Val Leu Gly Leu Asp Asn Leu Thr Lys Gly
145                 150                 155                 160

Ala Ala Glu Leu Glu Lys Leu Phe Lys Ala Val Glu Asn Leu Ser Lys
            165                 170                 175

Ala Ala Gln Asp Thr Leu Lys Asn Ala Val Lys Glu Leu Thr Ser Pro
            180                 185                 190
```

```
Ile Val Ala Glu Ser Pro Lys Lys Pro Ser Glu Thr Phe Thr Asn Lys
            195                 200                 205

Leu Lys Glu Lys His Thr Asp Leu Gly Lys Glu Gly Val Thr Lys Gly
    210                 215                 220

Ala Glu Glu Leu Gly Lys Leu Phe Glu Ser Val Glu Val Leu Ser Lys
225                 230                 235                 240

Ala Ala Lys Glu Met Leu Ala Asn Ser Val Lys Glu Leu Thr Ser Ser
                245                 250                 255

Glu Glu Phe Ser Thr Lys Leu Lys Asp Asn His Ala Gln Leu Gly Ile
                260                 265                 270

Gln Gly Val Thr Lys Gly Val Glu Glu Leu Gly Lys Leu Ser Gly Ser
            275                 280                 285

Leu Glu Ser Leu Ser Ser Glu Asp Phe Thr Lys Lys Leu Glu Gly Glu
    290                 295                 300

His Ala Gln Leu Gly Ile Glu Asn Val Thr Ala Ala Glu Leu Glu Lys
305                 310                 315                 320

Leu Phe Lys Ala Val Glu Asn Leu Ala Lys Ala Ala Lys Glu Met
                325                 330                 335
```

<210> SEQ ID NO 261
<211> LENGTH: 298
<212> TYPE: PRT
<213> ORGANISM: Artificial Sequence
<220> FEATURE:
<223> OTHER INFORMATION: Chimeric protein

<400> SEQUENCE: 261

```
Ala Lys Leu Lys Gly Glu His Thr Asp Leu Gly Lys Glu Gly Val Thr
1               5                   10                  15

Lys Gly Ala Asp Glu Leu Glu Lys Leu Phe Glu Ser Val Lys Asn Leu
            20                  25                  30

Ser Lys Ala Ala Lys Glu Met Leu Thr Asn Ser Val Lys Glu Ser Glu
        35                  40                  45

Lys Phe Ala Gly Lys Leu Lys Asn Glu His Ala Ser Leu Gly Lys Lys
    50                  55                  60

Asp Ala Thr Lys Gly Ala Lys Glu Leu Lys Asp Leu Ser Asp Ser Val
65                  70                  75                  80

Glu Ser Leu Val Lys Ala Ser Asp Asp Phe Thr Lys Lys Leu Gln Ser
                85                  90                  95

Ser His Ala Gln Leu Gly Val Ala Gly Gly Ala Thr Thr Ala Asp Glu
            100                 105                 110

Leu Glu Lys Leu Phe Lys Ser Val Glu Ser Leu Ala Lys Ala Ala Gln
        115                 120                 125

Asp Ala Leu Ala Asn Ser Val Asn Glu Leu Thr Ser Lys Lys Leu Lys
    130                 135                 140

Glu Lys His Thr Asp Leu Gly Lys Lys Asp Ala Thr Ala Ala Glu Leu
145                 150                 155                 160

Glu Lys Leu Phe Glu Ser Val Glu Asn Leu Ala Lys Ala Ala Lys Glu
                165                 170                 175

Met Leu Ser Asn Ser Asn Lys Ala Phe Thr Asp Lys Leu Lys Ser Ser
            180                 185                 190

His Ala Glu Leu Gly Ile Ala Asn Gly Ala Ala Thr Lys Gly Ala Gln
        195                 200                 205

Glu Leu Glu Lys Leu Phe Glu Ser Val Lys Asn Leu Ser Lys Ala Ala
    210                 215                 220
```

```
Gln Glu Thr Leu Asn Asn Ser Val Lys Glu Ser Glu Ser Phe Thr Lys
225                 230                 235                 240

Lys Leu Ser Asp Asn Gln Ala Glu Leu Gly Ile Glu Asn Ala Thr Lys
                245                 250                 255

Gly Ala Glu Glu Leu Val Lys Leu Ser Glu Ser Val Ala Gly Leu Leu
            260                 265                 270

Lys Ala Ala Gln Ala Ile Leu Ala Asn Ser Val Lys Glu Leu Thr Ser
        275                 280                 285

Pro Val Val Ala Glu Ser Pro Lys Lys Pro
    290                 295
```

<210> SEQ ID NO 262
<211> LENGTH: 451
<212> TYPE: PRT
<213> ORGANISM: Artificial Sequence
<220> FEATURE:
<223> OTHER INFORMATION: Chimeric protein

<400> SEQUENCE: 262

```
Ala Lys Leu Lys Gly Glu His Thr Asp Leu Gly Lys Glu Gly Val Thr
1               5                   10                  15

Lys Gly Ala Asp Glu Leu Glu Lys Leu Phe Glu Ser Val Lys Asn Leu
            20                  25                  30

Ser Lys Ala Ala Lys Glu Met Leu Thr Asn Ser Val Lys Glu Ser Glu
        35                  40                  45

Lys Phe Ala Gly Lys Leu Lys Asn Glu His Ala Ser Leu Gly Lys Lys
    50                  55                  60

Asp Ala Thr Lys Gly Ala Lys Glu Leu Lys Asp Leu Ser Asp Ser Val
65                  70                  75                  80

Glu Ser Leu Val Lys Ala Ser Asp Asp Phe Thr Lys Lys Leu Gln Ser
                85                  90                  95

Ser His Ala Gln Leu Gly Val Ala Gly Gly Ala Thr Thr Ala Asp Glu
            100                 105                 110

Leu Glu Lys Leu Phe Lys Ser Val Glu Ser Leu Ala Lys Ala Ala Gln
        115                 120                 125

Asp Ala Leu Ala Asn Ser Val Asn Glu Leu Thr Ser Lys Lys Leu Lys
    130                 135                 140

Glu Lys His Thr Asp Leu Gly Lys Lys Asp Ala Thr Ala Ala Glu Leu
145                 150                 155                 160

Glu Lys Leu Phe Glu Ser Val Glu Asn Leu Ala Lys Ala Ala Lys Glu
                165                 170                 175

Met Leu Ser Asn Ser Asn Lys Ala Phe Thr Asp Lys Leu Lys Ser Ser
            180                 185                 190

His Ala Glu Leu Gly Ile Ala Asn Gly Ala Ala Thr Lys Gly Ala Gln
        195                 200                 205

Glu Leu Glu Lys Leu Phe Glu Ser Val Lys Asn Leu Ser Lys Ala Ala
    210                 215                 220

Gln Glu Thr Leu Asn Asn Ser Val Lys Glu Ser Glu Ser Phe Thr Lys
225                 230                 235                 240

Lys Leu Ser Asp Asn Gln Ala Glu Leu Gly Ile Glu Asn Ala Thr Lys
                245                 250                 255

Gly Ala Glu Glu Leu Val Lys Leu Ser Glu Ser Val Ala Gly Leu Leu
            260                 265                 270

Lys Ala Ala Gln Ala Ile Leu Ala Asn Ser Val Lys Glu Leu Thr Ser
        275                 280                 285
```

```
Pro Val Val Ala Glu Ser Pro Lys Lys Pro Ser Thr Glu Glu Lys Phe
    290                 295                 300

Asn Glu Lys Gly Glu Val Ser Glu Lys Ile Ile Thr Arg Ala Asp Gly
305                 310                 315                 320

Thr Arg Leu Glu Tyr Thr Gly Ile Lys Ser Asp Gly Ser Gly Lys Ala
                325                 330                 335

Lys Glu Val Leu Lys Gly Tyr Val Leu Glu Gly Thr Leu Thr Ala Glu
            340                 345                 350

Lys Thr Thr Leu Val Val Lys Glu Gly Thr Val Thr Leu Ser Lys Asn
        355                 360                 365

Ile Ser Lys Ser Gly Glu Val Ser Val Glu Leu Asn Asp Thr Asp Ser
    370                 375                 380

Ser Ala Ala Thr Lys Lys Thr Ala Ala Trp Asn Ser Gly Thr Ser Thr
385                 390                 395                 400

Leu Thr Ile Thr Val Asn Ser Lys Lys Thr Lys Asp Leu Val Phe Thr
                405                 410                 415

Lys Glu Asn Thr Ile Thr Val Gln Gln Tyr Asp Ser Asn Gly Thr Lys
            420                 425                 430

Leu Glu Gly Ser Ala Val Glu Ile Thr Lys Leu Asp Glu Ile Lys Asn
        435                 440                 445

Ala Leu Lys
    450

<210> SEQ ID NO 263
<211> LENGTH: 488
<212> TYPE: PRT
<213> ORGANISM: Artificial Sequence
<220> FEATURE:
<223> OTHER INFORMATION: Chimeric protein

<400> SEQUENCE: 263

Ala Lys Leu Lys Gly Glu His Thr Asp Leu Gly Lys Glu Gly Val Thr
1               5                   10                  15

Lys Gly Ala Asp Glu Leu Glu Lys Leu Phe Glu Ser Val Lys Asn Leu
            20                  25                  30

Ser Lys Ala Ala Lys Glu Met Leu Thr Asn Ser Val Lys Glu Ser Glu
        35                  40                  45

Lys Phe Ala Gly Lys Leu Lys Asn Glu His Ala Ser Leu Gly Lys Lys
    50                  55                  60

Asp Ala Thr Lys Gly Ala Lys Glu Leu Lys Asp Leu Ser Asp Ser Val
65                  70                  75                  80

Glu Ser Leu Val Lys Ala Ser Asp Asp Phe Thr Lys Lys Leu Gln Ser
                85                  90                  95

Ser His Ala Gln Leu Gly Val Ala Gly Gly Ala Thr Thr Ala Asp Glu
            100                 105                 110

Leu Glu Lys Leu Phe Lys Ser Val Glu Ser Leu Ala Lys Ala Ala Gln
        115                 120                 125

Asp Ala Leu Ala Asn Ser Val Asn Glu Leu Thr Ser Lys Lys Leu Lys
    130                 135                 140

Glu Lys His Thr Asp Leu Gly Lys Lys Asp Ala Thr Ala Ala Glu Leu
145                 150                 155                 160

Glu Lys Leu Phe Glu Ser Val Glu Asn Leu Ala Lys Ala Ala Lys Glu
                165                 170                 175

Met Leu Ser Asn Ser Asn Lys Ala Phe Thr Asp Lys Leu Lys Ser Ser
            180                 185                 190
```

His Ala Glu Leu Gly Ile Ala Asn Gly Ala Ala Thr Lys Gly Ala Gln
            195                 200                 205

Glu Leu Glu Lys Leu Phe Glu Ser Val Lys Asn Leu Ser Lys Ala Ala
        210                 215                 220

Gln Glu Thr Leu Asn Asn Ser Val Lys Glu Ser Glu Ser Phe Thr Lys
225                 230                 235                 240

Lys Leu Ser Asp Asn Gln Ala Glu Leu Gly Ile Glu Asn Ala Thr Lys
                245                 250                 255

Gly Ala Glu Glu Leu Val Lys Leu Ser Glu Ser Val Ala Gly Leu Leu
            260                 265                 270

Lys Ala Ala Gln Ala Ile Leu Ala Asn Ser Val Lys Glu Leu Thr Ser
        275                 280                 285

Pro Val Val Ala Glu Ser Pro Lys Lys Pro Asn Asn Ser Gly Lys Asp
    290                 295                 300

Gly Asn Thr Ser Ala Asn Ser Ala Asp Glu Ser Val Lys Gly Pro Asn
305                 310                 315                 320

Leu Thr Glu Ile Ser Lys Lys Ile Thr Glu Ser Asn Ala Val Val Leu
                325                 330                 335

Ala Val Lys Glu Ile Glu Thr Leu Leu Ser Ser Ile Asp Glu Leu Ala
            340                 345                 350

Thr Lys Ala Ile Gly Gln Lys Ile Asp Ala Asn Gly Leu Gly Val Gln
        355                 360                 365

Ala Asn Gln Asn Gly Ser Leu Leu Ala Gly Ala Tyr Ala Ile Ser Thr
    370                 375                 380

Leu Ile Thr Gln Lys Leu Ser Ala Leu Asn Ser Glu Asp Leu Lys Glu
385                 390                 395                 400

Lys Val Ala Lys Val Lys Lys Cys Ser Glu Asp Phe Thr Asn Lys Leu
                405                 410                 415

Lys Asn Gly Asn Ala Gln Leu Gly Leu Ala Ala Ala Thr Asp Asp Asn
            420                 425                 430

Ala Lys Ala Ala Ile Leu Lys Thr Asn Gly Thr Asn Asp Lys Gly Ala
        435                 440                 445

Lys Glu Leu Lys Asp Leu Ser Asp Ser Val Glu Ser Leu Val Lys Ala
    450                 455                 460

Ala Gln Val Met Leu Thr Asn Ser Val Lys Glu Leu Thr Ser Pro Val
465                 470                 475                 480

Val Ala Glu Ser Pro Lys Lys Pro
                485

<210> SEQ ID NO 264
<211> LENGTH: 511
<212> TYPE: PRT
<213> ORGANISM: Artificial Sequence
<220> FEATURE:
<223> OTHER INFORMATION: Chimeric protein

<400> SEQUENCE: 264

Asn Asn Ser Gly Lys Asp Gly Asn Thr Ser Ala Asn Ser Ala Asp Glu
1               5                   10                  15

Ser Val Lys Gly Pro Asn Leu Thr Glu Ile Ser Lys Lys Ile Thr Asp
            20                  25                  30

Ser Asn Ala Val Leu Leu Ala Val Lys Glu Val Glu Ala Leu Leu Ser
        35                  40                  45

Ser Ile Asp Glu Ile Ala Ala Lys Ala Ile Gly Lys Lys Ile His Gln
    50                  55                  60

```
Asn Asn Gly Leu Asp Thr Glu Asn Asn His Asn Gly Ser Leu Leu Ala
 65                  70                  75                  80

Gly Ala Tyr Ala Ile Ser Thr Leu Ile Lys Gln Lys Leu Asp Gly Leu
                 85                  90                  95

Lys Asn Glu Gly Leu Lys Glu Lys Ile Asp Ala Ala Lys Lys Cys Ser
            100                 105                 110

Glu Thr Phe Thr Asn Lys Leu Lys Glu Lys His Thr Asp Leu Gly Lys
        115                 120                 125

Glu Gly Val Thr Asp Ala Asp Ala Lys Glu Ala Ile Leu Lys Thr Asn
    130                 135                 140

Gly Thr Lys Thr Lys Gly Ala Glu Glu Leu Gly Lys Leu Phe Glu Ser
145                 150                 155                 160

Val Glu Val Leu Ser Lys Ala Ala Lys Glu Met Leu Ala Asn Ser Val
                165                 170                 175

Lys Glu Leu Thr Ser Pro Val Val Ala Glu Ser Pro Lys Lys Pro Ser
            180                 185                 190

Glu Asp Phe Thr Lys Lys Leu Glu Gly Glu His Ala Gln Leu Gly Ile
        195                 200                 205

Glu Asn Val Thr Asp Glu Asn Ala Lys Lys Ala Ile Leu Ile Thr Asp
    210                 215                 220

Ala Ala Lys Asp Lys Gly Ala Ala Glu Leu Glu Lys Leu Phe Lys Ala
225                 230                 235                 240

Val Glu Asn Leu Ala Ala Lys Leu Lys Gly Glu His Thr Asp Leu Gly
                245                 250                 255

Lys Glu Gly Val Thr Asp Asp Asn Ala Lys Lys Ala Ile Leu Lys Thr
            260                 265                 270

Asn Asn Asp Lys Thr Lys Gly Ala Asp Glu Leu Glu Lys Leu Phe Glu
        275                 280                 285

Ser Val Lys Asn Leu Ser Lys Ala Ala Lys Glu Met Leu Thr Asn Ser
    290                 295                 300

Ser Glu Glu Phe Ser Thr Lys Leu Lys Asp Asn His Ala Gln Leu Gly
305                 310                 315                 320

Ile Gln Gly Val Thr Asp Glu Asn Ala Lys Lys Ala Ile Leu Lys Ala
                325                 330                 335

Asn Ala Ala Gly Lys Asp Lys Gly Val Glu Glu Leu Glu Lys Leu Ser
            340                 345                 350

Gly Ser Leu Glu Ser Leu Ser Ser Asp Phe Thr Lys Lys Leu Gln
        355                 360                 365

Ser Ser His Ala Gln Leu Gly Val Ala Gly Ala Thr Thr Asp Glu
    370                 375                 380

Glu Ala Lys Lys Ala Ile Leu Arg Thr Asn Ala Ile Lys Asp Lys Gly
385                 390                 395                 400

Ala Asp Glu Leu Glu Lys Leu Phe Lys Ser Val Glu Ser Leu Ala Lys
                405                 410                 415

Ala Ala Gln Asp Ala Leu Ala Asn Ser Val Asn Glu Leu Thr Ser Ser
            420                 425                 430

Glu Ser Phe Thr Lys Lys Leu Ser Asp Asn Gln Ala Glu Leu Gly Ile
        435                 440                 445

Glu Asn Ala Thr Asp Asp Asn Ala Lys Ala Ile Leu Lys Thr His
    450                 455                 460

Asn Ala Lys Asp Lys Gly Ala Glu Glu Leu Val Lys Leu Ser Glu Ser
465                 470                 475                 480
```

```
Val Ala Gly Leu Leu Lys Ala Gln Ala Ile Leu Ala Asn Ser Val
            485                 490                 495
Lys Glu Leu Thr Ser Pro Val Val Ala Glu Ser Pro Lys Lys Pro
            500                 505                 510

<210> SEQ ID NO 265
<211> LENGTH: 390
<212> TYPE: PRT
<213> ORGANISM: Artificial Sequence
<220> FEATURE:
<223> OTHER INFORMATION: Chimeric protein

<400> SEQUENCE: 265

Ser Glu Thr Phe Thr Asn Lys Leu Lys Glu Lys His Thr Asp Leu Gly
1               5                   10                  15
Lys Glu Gly Val Thr Asp Ala Asp Ala Lys Glu Ala Ile Leu Lys Thr
                20                  25                  30
Asn Gly Thr Lys Thr Lys Gly Ala Glu Glu Leu Gly Lys Leu Phe Glu
            35                  40                  45
Ser Val Glu Val Leu Ser Lys Ala Ala Lys Glu Met Leu Ala Asn Ser
        50                  55                  60
Val Lys Glu Leu Thr Ser Ser Glu Asp Phe Thr Lys Lys Leu Glu Gly
65                  70                  75                  80
Glu His Ala Gln Leu Gly Ile Glu Asn Val Thr Asp Glu Asn Ala Lys
                85                  90                  95
Lys Ala Ile Leu Ile Thr Asp Ala Ala Lys Asp Lys Gly Ala Ala Glu
            100                 105                 110
Leu Glu Lys Leu Phe Lys Ala Val Glu Asn Leu Ala Ala Lys Leu Lys
        115                 120                 125
Gly Glu His Thr Asp Leu Gly Lys Glu Gly Val Thr Asp Asp Asn Ala
    130                 135                 140
Lys Lys Ala Ile Leu Lys Thr Asn Asn Asp Lys Thr Lys Gly Ala Asp
145                 150                 155                 160
Glu Leu Glu Lys Leu Phe Glu Ser Val Lys Asn Leu Ser Lys Ala Ala
                165                 170                 175
Lys Glu Met Leu Thr Asn Ser Ser Glu Glu Phe Ser Thr Lys Leu Lys
            180                 185                 190
Asp Asn His Ala Gln Leu Gly Ile Gln Gly Val Thr Asp Glu Asn Ala
        195                 200                 205
Lys Lys Ala Ile Leu Lys Ala Asn Ala Ala Gly Lys Asp Lys Gly Val
    210                 215                 220
Glu Glu Leu Glu Lys Leu Ser Gly Ser Leu Glu Ser Leu Ser Ser Asp
225                 230                 235                 240
Asp Phe Thr Lys Lys Leu Gln Ser Ser His Ala Gln Leu Gly Val Ala
                245                 250                 255
Gly Gly Ala Thr Thr Asp Glu Glu Ala Lys Lys Ala Ile Leu Arg Thr
            260                 265                 270
Asn Ala Ile Lys Asp Lys Gly Ala Asp Glu Leu Glu Lys Leu Phe Lys
        275                 280                 285
Ser Val Glu Ser Leu Ala Lys Ala Ala Gln Asp Ala Leu Ala Asn Ser
    290                 295                 300
Val Asn Glu Leu Thr Ser Ser Glu Ser Phe Thr Lys Lys Leu Ser Asp
305                 310                 315                 320
Asn Gln Ala Glu Leu Gly Ile Glu Asn Ala Thr Asp Asp Asn Ala Lys
                325                 330                 335
```

```
Lys Ala Ile Leu Lys Thr His Asn Ala Lys Asp Lys Gly Ala Glu Glu
            340                 345                 350

Leu Val Lys Leu Ser Glu Ser Val Ala Gly Leu Leu Lys Ala Ala Gln
            355                 360                 365

Ala Ile Leu Ala Asn Ser Val Lys Glu Leu Thr Ser Pro Val Val Ala
            370                 375                 380

Glu Ser Pro Lys Lys Pro
385                 390

<210> SEQ ID NO 266
<211> LENGTH: 568
<212> TYPE: PRT
<213> ORGANISM: Artificial Sequence
<220> FEATURE:
<223> OTHER INFORMATION: Chimeric protein

<400> SEQUENCE: 266

Asn Asn Ser Gly Lys Asp Gly Asn Thr Ser Ala Asn Ser Ala Asp Glu
1               5                   10                  15

Ser Val Lys Gly Pro Asn Leu Thr Glu Ile Ser Lys Lys Ile Thr Glu
            20                  25                  30

Ser Asn Ala Val Val Leu Ala Val Lys Glu Ile Glu Thr Leu Leu Ser
        35                  40                  45

Ser Ile Asp Glu Leu Ala Thr Lys Ala Ile Gly Gln Lys Ile Asp Ala
    50                  55                  60

Asn Gly Leu Gly Val Gln Ala Asn Gln Asn Gly Ser Leu Leu Ala Gly
65                  70                  75                  80

Ala Tyr Ala Ile Ser Thr Leu Ile Thr Gln Lys Leu Ser Ala Leu Asn
                85                  90                  95

Ser Glu Asp Leu Lys Glu Lys Val Ala Lys Val Lys Lys Cys Ser Glu
            100                 105                 110

Asp Phe Thr Asn Lys Leu Lys Asn Gly Asn Ala Gln Leu Gly Leu Ala
            115                 120                 125

Ala Ala Thr Asp Asp Asn Ala Lys Ala Ala Ile Leu Lys Thr Asn Gly
        130                 135                 140

Thr Asn Asp Lys Gly Ala Lys Glu Leu Lys Asp Leu Ser Asp Ser Val
145                 150                 155                 160

Glu Ser Leu Val Lys Ala Ala Gln Val Met Leu Thr Asn Ser Val Lys
                165                 170                 175

Glu Leu Thr Ser Pro Val Val Ala Glu Ser Pro Lys Lys Pro Ser Glu
            180                 185                 190

Lys Phe Ala Gly Lys Leu Lys Asn Glu His Ala Ser Leu Gly Lys Lys
            195                 200                 205

Asp Ala Thr Asp Asp Ala Lys Lys Ala Ile Leu Lys Thr His Gly
        210                 215                 220

Asn Thr Asp Lys Gly Ala Lys Glu Leu Lys Asp Leu Ser Asp Ser Val
225                 230                 235                 240

Glu Ser Leu Val Ser Thr Gly Phe Thr Asn Lys Leu Lys Ser Gly His
                245                 250                 255

Ala Glu Leu Gly Pro Val Gly Gly Asn Ala Thr Asp Glu Asn Ala Lys
            260                 265                 270

Gln Ala Ile Leu Lys Thr His Gly Asn Val Thr Lys Gly Ala Lys Glu
            275                 280                 285

Leu Lys Asp Leu Ser Glu Ser Val Glu Ala Leu Ala Lys Ala Ala Gln
            290                 295                 300
```

```
Ala Met Ser Glu Lys Phe Thr Lys Lys Leu Ser Glu His Ala Asp
305                 310                 315                 320

Ile Gly Ile Gln Ala Ala Thr Asp Ala Asn Ala Lys Asp Ala Ile Leu
                325                 330                 335

Lys Thr Asn Pro Thr Lys Thr Lys Gly Ala Glu Glu Leu Asp Lys Leu
            340                 345                 350

Phe Lys Ala Val Glu Asn Leu Ser Lys Ala Lys Lys Leu Lys Glu
                355                 360                 365

Lys His Thr Asp Leu Gly Lys Lys Asp Ala Thr Asp Val His Ala Lys
    370                 375                 380

Glu Ala Ile Leu Lys Thr Asn Gly Thr Lys Asp Lys Gly Ala Ala Glu
385                 390                 395                 400

Leu Glu Lys Leu Phe Glu Ser Val Glu Asn Leu Ala Lys Ala Ala Lys
                405                 410                 415

Glu Met Leu Ser Asn Ser Asn Lys Ala Phe Thr Asp Lys Leu Lys Ser
                420                 425                 430

Ser His Ala Glu Leu Gly Ile Ala Asn Gly Ala Ala Thr Asp Ala Asn
            435                 440                 445

Ala Lys Ala Ala Ile Leu Lys Thr Asn Gly Thr Lys Asp Lys Gly Ala
450                 455                 460

Gln Glu Leu Glu Lys Leu Phe Glu Ser Val Lys Asn Leu Ser Lys Ala
465                 470                 475                 480

Ala Gln Glu Thr Leu Asn Asn Ser Ser Thr Glu Phe Thr Asn Lys Leu
                485                 490                 495

Lys Ser Glu His Ala Val Leu Gly Leu Asp Asn Leu Thr Asp Asp Asn
                500                 505                 510

Ala Gln Arg Ala Ile Leu Lys Lys His Ala Asn Lys Asp Lys Gly Ala
                515                 520                 525

Ala Glu Leu Glu Lys Leu Phe Lys Ala Val Glu Asn Leu Ser Lys Ala
                530                 535                 540

Ala Gln Asp Thr Leu Lys Asn Ala Val Lys Glu Leu Thr Ser Pro Ile
545                 550                 555                 560

Val Ala Glu Ser Pro Lys Lys Pro
                565

<210> SEQ ID NO 267
<211> LENGTH: 437
<212> TYPE: PRT
<213> ORGANISM: Artificial Sequence
<220> FEATURE:
<223> OTHER INFORMATION: Chimeric protein

<400> SEQUENCE: 267

Asn Lys Leu Lys Asn Gly Asn Ala Gln Leu Gly Leu Ala Ala Thr
1               5                   10                  15

Asp Asp Asn Ala Lys Ala Ala Ile Leu Lys Thr Asn Gly Thr Asn Asp
                20                  25                  30

Lys Gly Ala Lys Glu Leu Lys Asp Leu Ser Asp Ser Val Glu Ser Leu
            35                  40                  45

Val Lys Ala Ala Gln Val Met Leu Thr Asn Ser Ser Glu Lys Phe Ala
50                  55                  60

Gly Lys Leu Lys Asn Glu His Ala Ser Leu Gly Lys Lys Asp Ala Thr
65                  70                  75                  80

Asp Asp Asp Ala Lys Lys Ala Ile Leu Lys Thr His Gly Asn Thr Asp
                85                  90                  95
```

-continued

```
Lys Gly Ala Lys Glu Leu Lys Asp Leu Ser Asp Ser Val Glu Ser Leu
            100                 105                 110

Val Ser Thr Gly Phe Thr Asn Lys Leu Lys Ser Gly His Ala Glu Leu
            115                 120                 125

Gly Pro Val Gly Gly Asn Ala Thr Asp Glu Asn Ala Lys Gln Ala Ile
            130                 135                 140

Leu Lys Thr His Gly Asn Val Thr Lys Gly Ala Lys Glu Leu Lys Asp
145                 150                 155                 160

Leu Ser Glu Ser Val Glu Ala Leu Ala Lys Ala Ala Gln Ala Met Ser
                    165                 170                 175

Glu Lys Phe Thr Lys Lys Leu Ser Glu Ser His Ala Asp Ile Gly Ile
            180                 185                 190

Gln Ala Ala Thr Asp Ala Asn Ala Lys Asp Ala Ile Leu Lys Thr Asn
            195                 200                 205

Pro Thr Lys Thr Lys Gly Ala Glu Glu Leu Asp Lys Leu Phe Lys Ala
            210                 215                 220

Val Glu Asn Leu Ser Lys Ala Ala Lys Lys Leu Lys Glu Lys His Thr
225                 230                 235                 240

Asp Leu Gly Lys Lys Asp Ala Thr Asp Val His Ala Lys Glu Ala Ile
                    245                 250                 255

Leu Lys Thr Asn Gly Thr Lys Asp Lys Gly Ala Ala Glu Leu Glu Lys
            260                 265                 270

Leu Phe Glu Ser Val Glu Asn Leu Ala Lys Ala Ala Lys Glu Met Leu
            275                 280                 285

Ser Asn Ser Asn Lys Ala Phe Thr Asp Lys Leu Lys Ser Ser His Ala
290                 295                 300

Glu Leu Gly Ile Ala Asn Gly Ala Ala Thr Asp Ala Asn Ala Lys Ala
305                 310                 315                 320

Ala Ile Leu Lys Thr Asn Gly Thr Lys Asp Lys Gly Ala Gln Glu Leu
            325                 330                 335

Glu Lys Leu Phe Glu Ser Val Lys Asn Leu Ser Lys Ala Ala Gln Glu
            340                 345                 350

Thr Leu Asn Asn Ser Ser Thr Glu Phe Thr Asn Lys Leu Lys Ser Glu
            355                 360                 365

His Ala Val Leu Gly Leu Asp Asn Leu Thr Asp Asp Asn Ala Gln Arg
            370                 375                 380

Ala Ile Leu Lys Lys His Ala Asn Lys Asp Lys Gly Ala Ala Glu Leu
385                 390                 395                 400

Glu Lys Leu Phe Lys Ala Val Glu Asn Leu Ser Lys Ala Ala Gln Asp
            405                 410                 415

Thr Leu Lys Asn Ala Val Lys Glu Leu Thr Ser Pro Ile Val Ala Glu
            420                 425                 430

Ser Pro Lys Lys Pro
            435
```